US009556110B2

(12) United States Patent
Mahon et al.

(10) Patent No.: US 9,556,110 B2
(45) Date of Patent: Jan. 31, 2017

(54) AMINOALCOHOL LIPIDOIDS AND USES THEREOF

(71) Applicant: Massachusetts Institute of Technology, Cambridge, MA (US)

(72) Inventors: Kerry Peter Mahon, Cambridge, MA (US); Kevin Thomas Love, Boston, MA (US); Christopher G. Levins, Flemington, NJ (US); Kathryn Ann Whitehead, Pittsburgh, PA (US); Robert S. Langer, Newton, MA (US); Daniel Griffith Anderson, Framingham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/599,004

(22) Filed: Jan. 16, 2015

(65) Prior Publication Data

US 2015/0203439 A1   Jul. 23, 2015

Related U.S. Application Data

(62) Division of application No. 13/128,020, filed as application No. PCT/US2009/006018 on Nov. 6, 2009, now Pat. No. 8,969,353.

(60) Provisional application No. 61/166,518, filed on Apr. 3, 2009, provisional application No. 61/112,414, filed on Nov. 7, 2008.

(51) Int. Cl.

| | | |
|---|---|---|
| *C07C 217/08* | (2006.01) | |
| *A61K 9/127* | (2006.01) | |
| *A61K 9/51* | (2006.01) | |
| *A61K 47/16* | (2006.01) | |
| *A61K 48/00* | (2006.01) | |
| *C07C 215/14* | (2006.01) | |
| *C07D 295/13* | (2006.01) | |
| *C12N 15/11* | (2006.01) | |
| *C12N 15/88* | (2006.01) | |
| *A61K 31/7088* | (2006.01) | |
| *A61K 38/02* | (2006.01) | |

(52) U.S. Cl.

CPC ........... *C07C 217/08* (2013.01); *A61K 9/1271* (2013.01); *A61K 9/5123* (2013.01); *A61K 31/7088* (2013.01); *A61K 38/02* (2013.01); *A61K 47/16* (2013.01); *A61K 48/0025* (2013.01); *C07C 215/14* (2013.01); *C07D 295/13* (2013.01); *C12N 15/111* (2013.01); *C12N 15/88* (2013.01); *B01J 2531/0252* (2013.01); *B01J 2531/845* (2013.01); *C12N 2310/14* (2013.01); *C12N 2310/3515* (2013.01); *C12N 2320/32* (2013.01)

(58) Field of Classification Search
CPC ..... C07C 217/08; C07D 295/13; A61K 9/1271
USPC .................................................. 544/358, 401
See application file for complete search history.

(56) References Cited

U.S. PATENT DOCUMENTS

| | | | |
|---|---|---|---|
| 2,647,121 A | 7/1953 | Jacoby | |
| 2,717,909 A | 9/1955 | Kosmin | |
| 2,819,718 A | 1/1958 | Goldman | |
| 2,844,629 A | 7/1958 | William et al. | |
| 3,096,560 A | 7/1963 | Liebig | |
| 3,350,325 A | 10/1967 | Ashby et al. | |
| 3,535,289 A | 10/1970 | Yoshihara et al. | |
| 3,614,954 A | 10/1971 | Mirowski et al. | |
| 3,614,955 A | 10/1971 | Mirowski | |
| 3,656,185 A | 4/1972 | Carpentier | |
| 3,805,301 A | 4/1974 | Liebig | |
| 3,945,052 A | 3/1976 | Liebig | |
| 3,956,502 A | 5/1976 | Slovinsky et al. | |
| 3,995,623 A | 12/1976 | Blake et al. | |
| 4,013,507 A | 3/1977 | Rembaum | |
| 4,022,833 A | 5/1977 | Diana et al. | |
| 4,072,146 A | 2/1978 | Howes | |

(Continued)

FOREIGN PATENT DOCUMENTS

| | | |
|---|---|---|
| CA | 2518132 A1 | 3/2006 |
| CA | 2 769 408 A1 | 2/2011 |

(Continued)

OTHER PUBLICATIONS

Invitation to Pay Additional Fees, mailed Dec. 14, 2012, in connection with Application No. PCT/US2012/062222.

(Continued)

*Primary Examiner* — Golam M M Shameem
(74) *Attorney, Agent, or Firm* — Wolf, Greenfield & Sacks, P.C.

(57) ABSTRACT

Aminoalcohol lipidoids are prepared by reacting an amine with an epoxide-terminated compound are described. Methods of preparing aminoalcohol lipidoids from commercially available starting materials are also provided. Aminoalcohol lipidoids may be prepared from racemic or stereochemically pure epoxides. Aminoalcohol lipidoids or salts forms thereof are preferably biodegradable and biocompatible and may be used in a variety of drug delivery systems. Given the amino moiety of these aminoalcohol lipidoid compounds, they are particularly suited for the delivery of polynucleotides. Complexes, micelles, liposomes or particles containing the inventive lipidoids and polynucleotide have been prepared. The inventive lipidoids may also be used in preparing microparticles for drug delivery. They are particularly useful in delivering labile agents given their ability to buffer the pH of their surroundings.

25 Claims, 28 Drawing Sheets

(56) References Cited

U.S. PATENT DOCUMENTS

| | | |
|---|---|---|
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,873,370 A | 10/1989 | Chiu |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,197,977 A | 3/1993 | Hoffman, Jr. et al. |
| 5,200,395 A | 4/1993 | Eto et al. |
| 5,201,998 A | 4/1993 | Topfl et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,352,461 A | 10/1994 | Feldstein et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,736,573 A | 4/1998 | Galat |
| 5,772,694 A | 6/1998 | Bokros et al. |
| 5,776,165 A | 7/1998 | Ripart |
| 5,776,747 A | 7/1998 | Schinstine et al. |
| 5,817,873 A | 10/1998 | Meyer et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,976,569 A | 11/1999 | Milstein |
| 6,034,056 A | 3/2000 | Dutta |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,318 B1 | 12/2001 | Milstein |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,696,424 B1 | 2/2004 | Wheeler |
| 6,756,055 B2 | 6/2004 | McDonald et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,287,849 B2 | 10/2012 | Langer et al. |
| 8,361,555 B2 | 1/2013 | Paquet, Jr. |
| 8,450,298 B2 * | 5/2013 | Mahon .............. A61K 9/1271 514/80 |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 * | 3/2015 | Mahon .............. A61K 9/1271 514/252.12 |
| 9,006,487 B2 | 4/2015 | Anderson et al. |
| 9,193,827 B2 | 11/2015 | Ma et al. |
| 9,315,472 B2 | 4/2016 | Dong et al. |
| 2002/0022721 A1 | 2/2002 | Trulson et al. |
| 2002/0094528 A1 | 7/2002 | Salafsky |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0181077 A1 | 9/2004 | Raymond et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0223939 A1 | 10/2006 | Lange et al. |
| 2006/0228404 A1 | 10/2006 | Anderson et al. |
| 2007/0185128 A1 | 8/2007 | Conde-Frieboes et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |

(56) References Cited

U.S. PATENT DOCUMENTS

| | | |
|---|---|---|
| 2010/0240072 A1 | 9/2010 | Wester et al. |
| 2010/0331234 A1 | 12/2010 | Mahon et al. |
| 2011/0009641 A1 | 1/2011 | Anderson et al. |
| 2011/0158935 A1 | 6/2011 | Kraft |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0196923 A1 | 8/2012 | Rege et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0161830 A1 | 6/2014 | Anderson et al. |
| 2014/0329884 A1 | 11/2014 | Dong et al. |
| 2016/0009657 A1 | 1/2016 | Anderson et al. |

FOREIGN PATENT DOCUMENTS

| | | |
|---|---|---|
| CN | 101506196 A | 8/2009 |
| CN | 100 569 877 C | 12/2009 |
| CN | 101 863 544 B | 9/2011 |
| DE | 2430998 A1 | 1/1975 |
| DE | 2520814 A1 | 11/1976 |
| DE | 2 530 243 A1 | 1/1977 |
| DE | 2 903 979 A1 | 8/1980 |
| EP | 0 211 305 A2 | 2/1987 |
| EP | 0 673 637 A1 | 9/1995 |
| EP | 0 959 092 A1 | 11/1999 |
| EP | 1 277 829 A2 | 1/2003 |
| EP | 1 912 679 A2 | 4/2008 |
| EP | 2 045 251 A1 | 4/2009 |
| EP | 2 476 756 A1 | 7/2012 |
| EP | 2 532 649 | 12/2012 |
| FR | 1 378 382 | 11/1964 |
| FR | 2235112 A1 | 1/1975 |
| GB | 1072118 A | 6/1967 |
| GB | 1 602 085 A | 11/1981 |
| JP | S48-022365 A | 3/1973 |
| JP | S49-127908 A | 12/1974 |
| JP | 50-24216 A | 3/1975 |
| JP | S51-023537 A | 2/1976 |
| JP | 51-125144 | 11/1976 |
| JP | S52-010847 A | 1/1977 |
| JP | 52078924 A2 | 7/1977 |
| JP | 63-125144 A | 5/1988 |
| JP | 63-154788 A | 6/1988 |
| JP | 1099679 A2 | 4/1989 |
| JP | 4-108173 A | 4/1992 |
| JP | H06-200073 A | 7/1994 |
| JP | H06-211978 A | 8/1994 |
| JP | H07-053535 A | 2/1995 |
| JP | H09-505593 A | 6/1997 |
| JP | H10-197978 A | 7/1998 |
| JP | 11-005786 A | 1/1999 |
| JP | 11-080142 A | 3/1999 |
| JP | 2001-523215 A | 11/2001 |
| JP | 2002-167368 A | 6/2002 |
| JP | 2003-519199 A | 6/2003 |
| JP | 2008-247749 A | 10/2008 |
| JP | 2014172827 | 9/2014 |
| WO | WO 93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 96/26179 A1 | 8/1996 |
| WO | WO 96/36314 A2 | 11/1996 |
| WO | WO 97/23457 A1 | 7/1997 |
| WO | WO 98/16202 A1 | 4/1998 |
| WO | WO 00/03044 A1 | 1/2000 |
| WO | WO 01/15726 A2 | 3/2001 |
| WO | WO 02/22709 A1 | 3/2002 |
| WO | WO 02/31025 A2 | 4/2002 |
| WO | WO 02/097068 A2 | 12/2002 |
| WO | WO 03/040288 A2 | 5/2003 |
| WO | WO 03/070735 A2 | 8/2003 |
| WO | WO 2004/043588 A2 | 5/2004 |
| WO | WO 2004/048345 A2 | 6/2004 |
| WO | WO 2004/106411 | 12/2004 |
| WO | WO 2005/028619 A2 | 3/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/096662 | 8/2007 |
| WO | WO 2007/143659 | 12/2007 |
| WO | WO 2008/011561 | 1/2008 |
| WO | WO 2008/036168 A2 | 3/2008 |
| WO | WO 2008/113364 A2 | 9/2008 |
| WO | WO 2008/119741 A2 | 10/2008 |
| WO | WO 2009/046220 A2 | 4/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/099387 A1 | 9/2010 |
| WO | WO 2010/114789 A1 | 10/2010 |
| WO | WO 2010/129709 A1 | 11/2010 |
| WO | WO 2010/144789 A2 | 12/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/179562 A1 | 11/2014 |
| WO | WO 2014/210356 A1 | 12/2014 |

OTHER PUBLICATIONS

International Search Report and Written Opinion, mailed Mar. 27, 2013 in connection with Application No. PCT/US2012/062222.

International Preliminary Report on Patentability, mailed May 8, 2014, in connection with Application No. PCT/US2012/062222.

Extended European Search Report, mailed Jun. 29, 2009, in connection with Application No. European Application No. 06784878.8.

Extended European Search Report, mailed Jun. 19, 2012, in connection with Application No. European Application No. 11186795.8.

International Search Report and Written Opinion, mailed May 29, 2008, in connection with Application No. PCT/US2006/023171.

International Preliminary Report on Patentability, mailed Jul. 3, 2008, in connection with Application No. PCT/US2006/023171.

Extended European Search Report, mailed Jan. 28, 2008, in connection with Application No. EP 07013193.3.

Invitation to Pay Additional Fees, mailed Sep. 29, 2004, in connection with Application No. PCT/U52004/016521.

International Search Report and Written Opinion, mailed Dec. 8, 2004, in connection with Application No. PCT/US2004/016521.

International Preliminary Report on Patentability, mailed Dec. 15, 2005, in connection with Application No. PCT/US2004/016521.

International Search Report, mailed May 22, 2002, in connection with Application No. PCT/US2001/031270.

Written Opinion, mailed Jan. 2, 2003, in connection with Application No. PCT/US2001/031270.

International Preliminary Examination Report, mailed Aug. 19, 2003, in connection with Application No. PCT/US2001/031270.

Extended European Search Report, mailed Oct. 5, 2009, in connection with Application No. EP 07813156.2.

International Search Report and Written Opinion, mailed Sep. 29, 2008, in connection with Application No. PCT/US2007/073976.

International Preliminary Report on Patentability, mailed Feb. 5, 2009, in connection with Application No. PCT/US2007/073976.

Extended European Search Report, mailed Jul. 18, 2011, in connection with Application No. EP 07798132.2.

(56) References Cited

OTHER PUBLICATIONS

International Search Report and Written Opinion, mailed Dec. 13, 2007, in connection with Application No. PCT/US2007/070430.
International Preliminary Report on Patentability, mailed Dec. 24, 2008, in connection with Application No. PCT/US2007/070430.
International Search Report and Written Opinion, mailed Jun. 16, 2010, in connection with Application No. PCT/US2009/005810.
International Preliminary Report on Patentability, mailed May 12, 2011, in connection with Application No. PCT/US2009/005810.
International Search Report and Written Opinion, mailed Mar. 20, 2012, in connection with Application No. PCT/US2011/049360.
International Preliminary Report on Patentability, mailed Mar. 7, 2013, in connection with Application No. PCT/US2011/049360.
Partial Supplementary European Search Report, mailed Nov. 26, 2014, in connection with Application No. European Application No. 11820727.3.
Extended European Search Report, mailed Apr. 22, 2015, in connection with Application No. European Application No. 11820727.3.
Invitation to Pay Additional Fees, mailed on Jul. 24, 2012, in connection with Application No. PCT/US2012/030349.
International Search Report and Written Opinion, mailed on Oct. 5, 2012, in connection with Application No. PCT/US2012/030349.
International Preliminary Report on Patentability, mailed on Oct. 10, 2013, in connection with Application No. PCT/US2012/030349.
Invitation to Pay Additional Fees, mailed Oct. 31, 2013, in connection with Application No. PCT/US2013/054726.
International Search Report and Written Opinion, mailed Jan. 7, 2014, in connection with Application No. PCT/US2013/054726.
International Preliminary Report on Patentability, mailed Feb. 26, 2015, in connection with Application No. PCT/US2013/054726.
International Search Report and Written Opinion, mailed Aug. 5, 2014, in connection with Application No. PCT/US2014/036355.
International Search Report and Written Opinion, mailed Oct. 24, 2014, in connection with Application No. PCT/US2014/044408.
STN-CAS database Registry No. 1071084-05-3. Entered STN-CAS database on Nov. 6, 2008.
STN-CAS database Registry No. 1056016. Entered STN-CAS database on Oct. 1, 2008.
STN-CAS database Registry No. 1044533-56-3. Entered STN-CAS database on Aug. 28, 2008.
STN-CAS database Registry No. 1043632-07-0. Entered STN-CAS database on Aug. 26, 2008.
STN-CAS database Registry No. 1030297-62-1. Entered STN-CAS database on Jun. 24, 2008.
STN-CAS database Registry No. 1030297-42-7. Entered STN-CAS database on Jun. 24, 2008.
STN-CAS database Registry No. 1030297-07-4. Entered STN-CAS database on Jun. 24, 2008.
STN-CAS database Registry No. 1016794-08-3. Entered STN-CAS database on Apr. 23, 2008.
STN-CAS database Registry No. 909784-14-1. Entered STN-CAS database on Oct. 6, 2006.
STN-CAS database Registry No. 909784-08-3. Entered STN-CAS database on Oct. 6, 2006.
STN-CAS database Registry No. 909783-96-6. Entered STN-CAS database on Oct. 6, 2006.
STN-CAS database Registry No. 757226-26-9. Entered STN-CAS database on Oct. 6, 2004.
STN-CAS database Registry No. 698698-42-9. Entered STN-CAS database on Jun. 24, 2004.
STN-CAS database Registry No. 490035-26-2. Entered STN-CAS database on Feb. 14, 2003.
STN-CAS database Registry No. 488783-17-1. Entered STN-CAS database on Feb. 12, 2003.
STN-CAS database Registry No. 302899-57-6. Entered STN-CAS database on Nov. 15, 2000.
STN-CAS database Registry No. 295781-15-6. Entered STN-CAS database on Oct. 19, 2000.
STN-CAS database Registry No. 136581-83-4. Entered STN-CAS database on Oct. 4, 1991.
STN-CAS database Registry No. 116071-63-7. Entered STN-CAS database on Aug. 27, 1988.
STN-CAS database Registry No. 105317-96-2. Entered STN-CAS database on Nov. 22, 1986.
STN-CAS database Registry No. 104538-56-9. Entered STN-CAS database on Oct. 4, 1986.
STN-CAS database Registry No. 94159-80-5. Entered STN-CAS database on Sep. 8, 1985.
STN-CAS database Registry No. 85438-36-4. Entered STN-CAS database on Nov. 16, 1984.
STN-CAS database Registry No. 63888-73-3. Entered STN-CAS database on Nov. 16, 1984.
STN-CAS database Registry No. 63888-70-0. Entered STN-CAS database on Nov. 16, 1984.
STN-CAS database Registry No. 63888-69-7. Entered STN-CAS database on Nov. 16, 1984.
STN-CAS database Registry No. 63888-68-6. Entered STN-CAS database on Nov. 16, 1984.
STN-CAS database Registry No. 90018-95-4. Entered STN-CAS database on Nov. 16, 1984.
STN-CAS database Registry No. 56619-89-7. Entered STN-CAS database on Nov. 16, 1984.
STN-CAS database Registry No. 51750-80-2. Entered STN-CAS database on Nov. 16, 1984.
STN-CAS database Registry No. 42381-51-1. Entered STN-CAS database on Nov. 16, 1984.
STN-CAS database Registry No. 1030297-62-1. Entered STN-CAS database on Jun. 24, 2008. With chemical structure.
STN-CAS database Registry No. 60068-44-2. Entered STN-CAS database on Nov. 16, 1984.
STN-CAS database Registry No. 60068-43-1. Entered STN-CAS database on Nov. 16, 1984.
Adami et al., An amino acid-based amphoteric liposomal delivery system for systemic administration of siRNA. Mol Ther. Jun. 2011;19(6):1141-51.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Akinc et al., Exploring polyethylenimine-mediated DNA transfection and the proton sponge hypothesis. J Gene Med. May 2005;7(5):657-63.
Akinc et al., Parallel synthesis and biophysical characterization of a degradable polymer library for gene delivery. J Am Chem Soc. May 7, 2003;125(18):5316-23.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Akira et al., Functions of toll-like receptors: lessons from KO mice. C R Biol. Jun. 2004;327(6):581-9.
Ali et al., Derivation of type II alveolar epithelial cells from murine embryonic stem cells. Tissue Eng. Aug. 2002;8(4):541-50.
Allison, The mode of action of immunological adjuvants. Dev Biol Stand. 1998;92:3-11. Review.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
Anderson et al., Nanoliter-scale synthesis of arrayed biomaterials and application to human embryonic stem cells. Nat. Biotechnol. Jul. 2004;22(7):863-6. Epub Jun. 13, 2004.
Anderson et al., Structure/property studies of polymeric gene delivery using a library of poly(beta-amino esters). Mol Ther. Mar. 2005;11(3):426-34.
Anderson, Biological Responses to Materials. Annu Rev Mater Res. 2001;31:81-110.
Anderson, Chapter 4. Mechanisms of Inflammation and Infection With Implanted Devices. Cardiovasc Pathol. 1993;2:33S-41S.
Anderson, Human gene therapy. Nature. Apr. 30, 1998;392(6679 Suppl):25-30. Review.

(56) References Cited

OTHER PUBLICATIONS

Asokan et al., Cytosolic delivery of macromolecules. 3. Synthesis and characterization of acid-sensitive bis-detergents. Bioconjug Chem. Nov.-Dec. 2004;15(6):1166-73.
Astle et al., A VEGFR2 Antagonist and Other Peptoids Evade Immune Recognition. Int J Pept Res Ther. 2008;14(3):223-227.
Bajaj et al., Synthesis and gene transfection efficacies of PEI-cholesterol-based lipopolymers. Bioconjug Chem. Aug. 2008;19(8):1640-51. Epub Jul. 11, 2008.
Ballermann et al., Shear stress and the endothelium. Kidney Int Suppl. Sep. 1998;67:S100-8.
Bartel, MicroRNAs: Genomics, Biogenesis, Mechanism, and Function. Cell. 2004;116:281-97.
Behr et al., Efficient gene transfer into mammalian primary endocrine cells with lipopolyaminecoated DNA. Proc Natl Acad Sci U S A. Sep. 1989;86(18):6982-6.
Behr, Synthetic gene-transfer vectors. Acc Chem Res. 1993;26:274-278.
Berge et al., Pharmaceutical salts. J Pharm Sci. Jan. 1977;66(1):1-19.
Boudou et al., Multiple functionalities of polyelectrolyte multilayer films: new biomedical applications. Adv Mater. Jan. 26, 2010;22(4):441-67.
Bourque et al., Hydroformylation Reactions Using Recyclable Rhodium-Complexed Dendrimers on Silica. J Am Chem Soc. 2000;122(5):956-957.
Boussif et al., A versatile vector for gene and oligonucleotide transfer into cells in culture and in vivo: polyethylenimine. Proc Natl Acad Sci U S A. Aug. 1, 1995;92(16):7297-301.
Bratlie et al., Rapid biocompatibility analysis of materials via in vivo fluorescence imaging of mouse models. PLoS One. Apr. 6, 2010;5(4):e10032.
Braun et al., Structure/function relationships of polyamidoamine/DNA dendrimers as gene delivery vehicles. J Pharm Sci. Feb. 2005;94(2):423-36.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):5763. Epub May 24, 2008.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Brodbeck et al., Biomaterial surface chemistry dictates adherent monocyte/macrophage cytokine expression in vitro. Cytokine. Jun. 21, 2002;18(6):311-9.
Burnett et al., Current progress of siRNA/shRNA therapeutics in clinical trials. Biotechnol J. Sep. 2011;6(9):1130-46. doi: 10.1002/biot.201100054. Epub Jul. 11, 2011.
Byk et al., Synthesis, activity, and structure-activity relationship studies of novel cationic lipids for DNA transfer. J Med Chem. 1998;41(2):224-235.
Campbell et al., Application of cytokeratin 7 and 20 immunohistochemistry to diagnostic pathology. Current Diagnostic Pathology. 2001;7:113-22.
Carter et al., Mechanobiology of skeletal regeneration. Clin Orthop Relat Res. Oct. 1998;(355 Suppl):S41-55.
Castanotto et al.,. The promises and pitfalls of RNA-interference-based therapeutics. Nature. Jan. 22, 2009;457(7228):426-33. doi: 10.1038/nature07758.
Chakraborty, Potentiality of Small Interfering RNAs (siRNA) as Recent Therapeutic Targets for Gene-Silencing. Curr Drug Targets. 2007;8:469-82.
Chan et al., Triplex DNA: fundamentals, advances, and potential applications for gene therapy. J Mol Med. Apr. 1997;75(4):267-82. Review.
Chang, Therapeutic applications of polymeric artificial cells. Nat Rev Drug Discov. Mar. 2005;4(3):221-35.
Chen et al., Polymeric growth factor delivery strategies for tissue engineering. Pharm Res. Aug. 2003;20(8):1103-12.
Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.
Chen et al., Tumor-targeted delivery of siRNA by non-viral vector: safe and effective cancer therapy. Expert Opin Drug Deliv. Dec. 2008;5(12):1301-11. doi: 10.1517/17425240802568505.
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Chu et al., Cytokeratin 7 and cytokeratin 20 expression in epithelial neoplasms: a survey of 435 cases. Mod Pathol. Sep. 2000;13(9):962-72.
Conley et al., Derivation, propagation and differentiation of human embryonic stem cells. Int J Biochem Cell Biol. Apr. 2004;36(4):555-67.
Conte et al., Regioselective ring opening of [(perfluoroalkyl)methyl] oxiranes with N-nucleophiles. J Fluorine Chem. 2005;126(9-10):1274-80.
Cotten et al., Receptor-mediated transport of DNA into eukaryotic cells. Methods Enzymol. 1993;217:618-44.
Creusat et al., Proton sponge trick for pH-sensitive disassembly of polyethylenimine-based siRNA delivery systems. Bioconjug Chem. May 19, 2010;21(5):994-1002.
Cristofaro et al., Role of Toll-like receptors in infection and immunity: clinical implications. Drugs. 2006;66(1):15-29.
Crooke, Evaluating the mechanism of action of antiproliferative antisense drugs. Antisense Nucleic Acid Drug Dev. Apr. 2000;10(2):123-6.
Crooke, Molecular mechanisms of action of antisense drugs. Biochim Biophys Acta. Dec. 10, 1999;1489(1):31-44. Review.
Crystal, Transfer of genes to humans: early lessons and obstacles to success. Science. Oct. 20, 1995;270(5235):404-10. Review.
Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.
Davis et al., Evidence of RNAi in humans from systemically administered siRNA via targeted nanoparticles. Nature. Apr. 15, 2010;464(7291):1067-70. Epub Mar. 21, 2010.
Davis, The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.
Decher, Fuzzy Nanoassemblies: Toward Layered Polymeric Multicomposites. Science. 1997;277;1232-37.
Dern et al., Toxicity studies of pyrimethamine (daraprim). Am J Trop Med Hyg. Mar. 1955;4(2):217-20.
Deshmukh et al., Liposome and polylysine mediated gene therapy. New J Chem. 1997;21:113-124.
Diebold et al., Innate antiviral responses by means of TLR7-mediated recognition of single-stranded RNA. Science. Mar. 5, 2004;303(5663):1529-31. Epub Feb. 19, 2004.
Discher et al., Polymer vesicles. Science. Aug. 9, 2002;297(5583):967-73. Review.
Discher et al., Polymersomes: tough vesicles made from diblock copolymers. Science. May 14, 1999;284(5417):1143-6.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.
Dushnik-Levinson et al., Embryogenesis in vitro: study of differentiation of embryonic stem cells. Biol Neonate. 1995;67(2):77-83.
Eberle et al., Modifications in small interfering RNA that separate immunostimulation from RNA interference. J Immunol. Mar. 1, 2008;180(5):3229-37.

(56) References Cited

OTHER PUBLICATIONS

Elbashir et al., Duplexes of 21-nucleotide RNAs mediate RNA interference in cultured mammalian cells. Nature. May 24, 2001;411(6836):494-8.

Elbashir et al., RNA interference is mediated by 21- and 22-nucleotide RNAs. Genes Dev. 2001;15:188-200.

Ewert et al., Cationic lipid-DNA complexes for gene therapy: understanding the relationship between complex structure and gene delivery pathways at the molecular level. Curr Med Chem. Jan. 2004;11(2):133-49.

Lelgner et al., Lipofection: a highly efficient, lipid-mediated DNA-transfection procedure. Proc Natl Acad Sci U S A. Nov. 1987;84(21):7413-7.

Fenske et al., Liposomal nanomedicines. Expert Opin Drug Deliv. Jan. 2008;5(1):25-44.

Ferruti et al., A novel modification of poly(1-lysine) leading to a soluble cationic polymer with reduced toxicity and with potential as a transfection agent. Macromol Chem Phys 1998;199:2565-75.

Ferruti et al., Linear amino polymers: Synthesis, protonation and complex formation. Advances in Polymer Science. 1984;58:55-92.

Fire et al., Potent and specific genetic interference by double-stranded RNA in Caenorhabditis elegans. Nature. Feb. 19, 1998;391(6669):806-11.

Fisher et al., Photoinitiated Polymerization of Biomaterials. Annu Rev Mater Res. 2001;31:171-81.

Forsbach et al., Identification of RNA sequence motifs stimulating sequence-specific TLR8-dependent immune responses. J Immunol. Mar. 15, 2008;180(6):3729-38.

Fourneau et al., Two new series of local anesthetics derived from piperazine. Bulletin de la Societe Chimique de France. 1930;47:1003-16. French.

Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. doi: 10.1073/pnas.0805434105. Epub Aug. 11, 2008.

Friedmann, Human gene therapy—an immature genie, but certainly out of the bottle. Nat Med. Feb. 1996;2(2):144-7.

Furgeson et al., Modified linear polyethylenimine-cholesterol conjugates for DNA complexation. Bioconjug Chem. Jul.-Aug. 2003;14(4):840-7.

Furgeson et al., Novel water insoluble lipoparticulates for gene delivery. Pharm Res. Apr. 2002;19(4):382-90.

Gademann et al., The fourth helical secondary structure of beta-peptides: the (P)-28-helix of a beta-hexapeptide consisting of (2R,3S)-3-amino-2-hydroxy acid residues. Angew Chem Int Ed Engl. Apr. 4, 2003;42(13):1534-7.

Gardner, Stem cells and regenerative medicine: principles, prospects and problems. C R Biol. Jun.-Jul. 2007;330(6-7):465-73. Epub Feb. 15, 2007.

Geisbert et al., Postexposure protection of non-human primates against a lethal Ebola virus challenge with RNA interference: a proof-of-concept study. Lancet. May 29, 2010;375(9729):1896-905. doi:10.1016/50140-6736(10)60357-1.

Geissmann et al., Development of monocytes, macrophages, and dendritic cells. Science. Feb. 5, 2010;327(5966):656-61. doi: 10.1126/science.1178331.

Geng et al., Hydrolytic degradation of poly(ethylene oxide)-block-polycaprolactone worm micelles. J Am Chem Soc. Sep. 21, 2005;127(37):12780-1.

Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.

Giuliani et al., Beyond natural antimicrobial peptides: multimeric peptides and other peptidomimetic approaches. Cell Mol Life Sci. Jul. 2011;68(13):2255-66. doi: 10.1007/s00018011-0717-3. Epub May 20, 2011.

Godbey et al., Size matters: molecular weight affects the efficiency of poly(ethylenimine) as a gene delivery vehicle. J Biomed Mater Res. Jun. 5, 1999;45(3):268-75.

Gonzalez et al., New class of polymers for the delivery of macromolecular therapeutics. Bioconjug Chem. Nov.-Dec. 1999;10(6):1068-74.

Grayson et al., Biophysical and structural characterization of polyethylenimine-mediated siRNA delivery in vitro. Pharm Res. Aug. 2006;23(8):1868-76.

Grivennikov et al., Immunity, inflammation, and cancer. Cell. Mar. 19, 2010;140(6):883-99. doi: 10.1016/j.cell.2010.01.025.

Gross et al., Bioluminescence imaging of myeloperoxidase activity in vivo. Nat Med. Apr. 2009;15(4):455-61. Epub Mar. 22, 2009.

Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.

Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.

Guan et al., Embryonic stem cell-derived neurogenesis. Retinoic acid induction and lineage selection of neuronal cells. Cell Tissue Res. Aug. 2001;305(2):171-6.

Guan et al., Surface photo-grafting of polyurethane with 2-hydroxyethyl acrylate for promotion of human endothelial cell adhesion and growth. J Biomater Sci Polym Ed. 2000;11(5):523-36.

Gunatillake et al., Recent developments in biodegradable synthetic polymers. Biotechnol Annu Rev. 2006;12:301-47.

Gupta et al., A review of in vitro-in vivo investigations on dendrimers: the novel nanoscopic drug carriers. Nanomedicine. Jun. 2006;2(2):66-73.

Haensler et al., Polyamidoamine cascade polymers mediate efficient transfection of cells in culture. Bioconjug Chem. Sep.-Oct. 1993;4(5):372-9.

Hammond et al., An RNA-directed nuclease mediates post-transcriptional gene silencing in *Drosophila* cells. Nature. 2000;404:293-96.

Harder et al., Molecular Conformation in Oligo(ethylene glycol)-Terminated Self-Assembled Monolayers on Gold and Silver Surfaces Determines Their Ability to Resist Protein Adsorpotion. J Phys Chem B. 1998;102:426-36.

Hasan et al., Identification of cytokeratin 1 as a binding protein and presentation receptor for kininogens on endothelial cells. Proc Natl Acad Sci U S A. Mar. 31, 1998;95(7):3615-20.

Heil et al., Species-specific recognition of single-stranded RNA via toll-like receptor 7 and 8. Science. Mar. 5, 2004;303(5663):1526-9. Epub Feb. 19, 2004.

Hemmi et al, Small anti-viral compounds activate immune cells via the TLR7 MyD88-dependent signaling pathway. Nat Immunol. Feb. 2002;3(2):196-200. Epub Jan. 22, 2002.

Heyes et al., Cationic lipid saturation influences intracellular delivery of encapsulated nucleic acids. J Control Release. Oct. 3, 2005;107(2):276-87.

Hill et al., Enantioselective Epoxidation of Allylic Alcohols: (2S,3S)-3-Propyloxiranemethanol. Org Syn. 1990;7:461.

Hill et al., in vitro cytotoxicity of poly(amidoamine)s: relevance to DNA delivery. Biochim Biophys Acta. Apr. 19, 1999;1427(2):161-74.

Hoekenga, The treatment of malaria with hydroxychloroquine. Am J Trop Med Hyg. Mar. 1955;4(2): 221-3.

Hofland et al., Formation of stable cationic lipid/DNA complexes for gene transfer. Proc Natl Acad Sci USA. Jul. 9, 1996;93(14):7305-9.

Holmlin et al., Zwitterionic SAMs that Resist Nonspecific Adsorption of Protein from Aqueous Buffer. Langmuir. 2001;17:2841-50.

Hope et al., Cationic Lipids, Phosphatidylethanolamine and the Intracellular Delivery of Polymeric, Nucleic Acid-Based Drugs. Molecular Membrane Technology. 1998;15:1-14.

Hornung et al., Quantitative expression of toll-like receptor 1-10 mRNA in cellular subsets of human peripheral blood mononuclear cells and sensitivity to CpG oligodeoxynucleotides. J Immunol. May 1, 2002;168(9):4531-7.

(56) References Cited

OTHER PUBLICATIONS

Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Howard, Delivery of RNA interference therapeutics using polycation-based nanoparticles. Adv Drug Deliv Rev. Jul. 25, 2009;61(9):710-20. Epub Apr. 5, 2009.
Huang et al., Claudin-3 gene silencing with siRNA suppresses ovarian tumor growth and metastasis. Proc Natl Acad Sci U S A. Mar. 3, 2009;106(9):3426-30. doi: 10.1073/pnas.0813348106. Epub Feb. 10, 2009.
Hunt et al., Effect of biomaterial surface charge on the inflammatory response: evaluation of cellular infiltration and TNF alpha production. J Biomed Mater Res. May 1996;31(1):139-44.
Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.
Ikeda et al., Role of micafungin in the antifungal armamentarium. Curr Med Chem. 2007;14(11):1263-75.
Incani et al., Lipid and hydrophobic modification of cationic carriers on route to superior gene vectors. Soft Matter. 2010;6:2124-38.
Ingber et al., Mechanochemical switching between growth and differentiation during fibroblast growth factor-stimulated angiogenesis in vitro: role of extracellular matrix. J Cell Biol. Jul. 1989;109(1):317-30.
Irwin et al., Modulus-dependent macrophage adhesion and behavior. J Biomater Sci Polym Ed. 2008;19(10):1363-82.
Ito, Surface micropatterning to regulate cell functions. Biomaterials. Dec. 1999;20(23-24):2333-42.
Itskovitz-Eldor et al., Differentiation of human embryonic stem cells into embryoid bodies compromising the three embryonic germ layers. Mol Med. Feb. 2000;6(2):88-95.
Iwasaki et al., Toll-like receptor control of the adaptive immune responses. Nat Immunol. Oct. 2004;5(10):987-95.
Jarrossay et al., Specialization and complementarity in microbial molecule recognition by human myeloid and plasmacytoid dendritic cells. Eur J Immunol. Nov. 2001;31(11):3388-93.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.
Jia et al., Demonstration of two novel methods for predicting functional siRNA efficiency. BMC Bioinformatics. 2006;7:271.
Jiang et al., Electrochemically controlled release of lipid/DNA complexes: a new tool for synthetic gene delivery system. Electrochem Commun. 2004;6:576-82.
Jiang et al., Hyaluronic acid-polyethyleneimine conjugate for target specific intracellular delivery of siRNA. Biopolymers. Jul. 2008;89(7):635-42.
Jiang et al., Ultralow-fouling, functionalizable, and hydrolyzable zwitterionic materials and their derivatives for biological applications. Adv Mater. Mar. 5, 2010;22(9):920-32.
Johansson et al., Evidence for involvement of activin A and bone morphogenetic protein 4 in mammalian mesoderm and hematopoietic development. Mol Cell Biol. Jan. 1995;15(1):141-51.
John et al. Effective RNAi-mediated gene silencing without interruption of the endogenous microRNA pathway. Nature. Oct. 11, 2007;449(7163):745-7. Epub Sep. 26, 2007.
Jolck et al., Solid-phase synthesis of PEGylated lipopeptides using click chemistry. Bioconjug Chem. May 19, 2010;21(5):807-10.
Jon et al., Degradable poly(amino alcohol esters) as potential DNA vectors with low cytotoxicity. Biomacromolecules. Nov.-Dec. 2003;4(6):1759-62.
Judge et al., Design of noninflammatory synthetic siRNA mediating potent gene silencing in vivo. Mol Ther. Mar. 2006;13(3):494-505. Epub Dec. 15, 2005.
Juliano et al., Biological barriers to therapy with antisense and siRNA oligonucleotides. Mol Pharm. May-Jun. 2009;6(3):686-95. doi:10.1021/mp900093r.
Kabanov et al., DNA complexes with polycations for the delivery of genetic material into cells. Bioconjug Chem. Jan.-Feb. 1995;6(1):7-20.
Kamath et al., Surface chemistry influences implant-mediated host tissue responses. J Biomed Mater Res A. Sep. 2008;86(3):617-26.
Kanetani et al., Synthesis, and physicochemical and antimicrobial properties of 3-(3-alkyl-1-piperazinyl)-1-propanesulfonic acids and some related compounds. The Chemical Society of Japan. 1983(12):1783-91.
Katsuki et al., Chapter 1. Asymmetric Epoxidation of Allylic Alcohols: The Katsuki-Sharpless Epoxidation Reaction. Org React 1996;48:1-299.
Katsuki et al., the First Practical Method for Asymmetric Epoxidation. J Am Chem Soc. 1980:102;5974-76.
Kaufman et al., Hematopoietic colony-forming cells derived from human embryonic stem cells. Proc Natl Acad Sci USA. Sep. 11, 2001;98(19):10716-21. Epub Sep. 4, 2001.
Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.
Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.
Kim et al., Efficient siRNA delivery using water soluble lipopolymer for anti-angiogenic gene therapy. J Control Release. Apr. 23, 2007;118(3):357-63. Epub Jan. 9, 2007.
Kim et al., Local and systemic delivery of VEGF siRNA using polyelectrolyte complex micelles for effective treatment of cancer. J Control Release. Jul. 14, 2008;129(2):107-16. Epub Mar. 14, 2008.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Kleinman et al., Sequence- and target-independent angiogenesis suppression by siRNA via TLR3. Nature. Apr. 3, 2008;452(7187):591-7. Epub Mar. 26, 2008.
Klibanov et al., Amphipathic polyethyleneglycols effectively prolong the circulation time of liposomes. FEBS Lett. Jul. 30, 1990;268(1):235-7.
Krieg et al., CpG motifs in bacterial DNA trigger direct B-cell activation. Nature. Apr. 6, 1995;374(6522):546-9.
Krieg et al., Toll-like receptors 7, 8, and 9: linking innate immunity to autoimmunity. Immunol Rev. Dec. 2007;220:251-69.
Krieg, The toll of too much TLR7. Immunity. Nov. 2007;27(5):695-7.
Kukowska-Latallo et al., Efficient transfer of genetic material into mammalian cells using Starburst polyamidoamine dendrimers. Proc Natl Acad Sci USA. May 14, 1996;93(10):4897-902.
Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.
Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.
Langer, Perspectives and challenges in tissue engineering and regenerative medicine. Adv Mater. Sep. 4, 2009;21(32-33):3235-6.
Lee et al., Rapid pharmacokinetic and biodistribution studies using cholorotoxin-conjugated iron oxide nanoparticles: a novel non-radioactive method. PLoS One. Mar. 4, 2010;5(3):e9536. doi: 10.1371/journal.pone.0009536.
Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.
Leuschner et al., Therapeutic siRNA silencing in inflammatory monocytes in mice. Nat Biotechnol. Oct. 9, 2011;29(11):1005-10. doi: 10.1038/nbt.1989.

(56) References Cited

OTHER PUBLICATIONS

Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Li et al., Defining the optimal parameters for hairpin-based knockdown constructs. RNA. 2007;13:1765-74.
Li et al., Plasticity of the urothelial phenotype: effects of gastrointestinal mesenchyme/stroma and implications for urinary tract reconstruction. Differentiation. Oct. 2000;66(2-3):126-35.
Li et al., Reverse Atom Transfer Radical Polymerization in Miniemulsion. Macromolecules. 2003;36(16):6028-6035.
Lim, et al., A self-destroying polycationic polymer: biodegradable poly(4-hydroxy-1-proline ester. J. Am. Chem. Soc. 1999;121:5633-5639.
Love et al., Lipid-like materials for low-dose, in vivo gene silencing. Proc Natl Acad Sci U S A. Feb. 2, 2010;107(5):1864-9. Epub Jan. 11, 2010.
Lukyanov et al., Micelles from lipid derivatives of water-soluble polymers as delivery systems for poorly soluble drugs. Adv Drug Deliv Rev. May 7, 2004;56(9):1273-89.
Luo et al., Synthetic DNA delivery systems. Nat Biotechnol. Jan. 2000;18(1):33-7. Review.
Lyle et al., Cytokeratin 15 (K15) as an Epithelial Stem Cell Marker: Implications for Aging and Carcinogenesis. J Invest Derma. 1999;112(4):623. Abstract #606.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly((β-amino esters): Synthesis, Characterization, and Self-Assembly with Plasmid DNA. J. Am. Chem. Soc. 2000;122 (44): 10761-8.
Lynn et al., pH-Responsive Polymer Microspheres: Rapid Release of Encapsulated Material within the Range of Intracellular pH. Angew Chem Int Ed Engl. May 4, 2001;40(9):1707-10.
Ma et al., Development of Cationic Polymer Coatings to Regulate Foreign Body Responses. Adv Mater. 2011;23:H189-94.
Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.
Marques et al., Activation of the mammalian immune system by siRNAs. Nat Biotechnol. Nov. 2005;23(11):1399-405.
Marshak-Rothstein, Toll-like receptors in systemic autoimmune disease. Nat Rev Immunol. Nov. 2006;6(11):823-35.
Martell et al., the Preparation and the Properties of Some N,N'-Disubstituted-ethylenediaminedipropionic Acids. J Am Chem Soc. 1950;72:5357-61.
Mathiowitz et al., Novel microcapsules for delivery systems. Reactive Polymers. 1987;6:275-283.
Mathiowitz et al., Polyanhydride microspheres as drug carriers I. Hot-melt microencapsulation. J Control Release. 1987;5:13-22.
Mathiowitz et al., Polyanhydride Microspheres as Drug Carriers. II. Microencapsulation by Solvent Removal. J Appl Polymer Sci. 1988;35:755-774.
Mattey et al., Demonstration of cytokeratin in endothelial cells of the synovial microvasculature in situ and in vitro. Br J Rheumatol. Aug. 1993;32(8):676-82.
Mendelsohn et al., Rational design of cytophilic and cytophobic polyelectrolyte multilayer thin films. Biomacromolecules. Jan.-Feb. 2003;4(1):96-106.
Miller, Cationic Liposomes for Gene Therapy. Angew. Chem. Int. Ed. 1998;37:1769-1785.
Mintzer et al., Nonviral vectors for gene delivery. Chem Rev. Feb. 2009;109(2):259-302.
Moll et al., the human keratins: biology and pathology. Histochem Cell Biol. 2008 Jun;129(6):705-33. Epub May 7, 2008.
Moll, [Cytokeratins as markers of differentiation. Expression profiles in epithelia and epithelial tumors] Veroff Pathol. 1993;142:1-197. German.
Morris et al., Lentiviral-mediated delivery of siRNAs for antiviral therapy. Gene Ther. 2006;13:553-58.
Morrissey et al., Potent and persistent in vivo anti-HBV activity of chemically modified siRNAs. Nat Biotechnol. Aug. 2005;23(8):1002-7. Epub Jul. 24, 2005.
Mulligan, The basic science of gene therapy. Science. May 14, 1993;260(5110):926-32. Review.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Naito et al., siVirus: web-based antiviral siRNA design software for highly divergent viral sequences. Nucleic Acids Res. 2006;34:W448-450.
Narang et al., Cationic lipids with increased DNA binding affinity for nonviral gene transfer in dividing and nondividing cells. Bioconjug Chem. Jan.-Feb. 2005;16(1):156-68.
Navarro et al., Phospholipid-polyethylenimine conjugate-based micelle-like nanoparticles for siRNA delivery. Drug Deliv and Trans Res. 2011; 25-33.
Neamnark et al., Aliphatic lipid substitution on 2 kDa polyethylenimine improves plasmid delivery and transgene expression. Mol Pharm. Nov.-Dec. 2009;6(6):1798-815.
Nguyen et al., A novel high-throughput cell-based method for integrated quantification of type I interferons and in vitro screening of immunostimulatory RNA drug delivery. Biotechnol Bioeng. Jul. 1, 2009;103(4):664-75.
Nguyen et al., Drug delivery-mediated control of RNA immunostimulation. Mol Ther. Sep. 2009;17(9):1555-62. Epub Jul. 7, 2009.
Nolan et al., Quantification of mRNA using real-time RT-PCR. Nat Protoc. 2006;1(3):1559-82.
Novak et al., Biomimetic strategies based on viruses and bacteria for the development of immune evasive biomaterials. Biomaterials. Apr. 2009;30(11):1989-2005. Epub Jan. 29, 2009.
Novina et al., The RNAi revolution. Nature. 2004;430:161-64.
Novobrantseva et al., Systemic RNAi-mediated Gene Silencing in Nonhuman Primate and Rodent Myeloid Cells. Mol Ther Nucleic Acids. Jan. 24, 2012;1:e4. doi: 10.1038/mtna.2011.3.
Odorico et al., Multilineage differentiation from human embryonic stem cell lines. Stem Cells. 2001;19(3):193-204.
Onuki et al., A review of the biocompatibility of implantable devices: current challenges to overcome foreign body response. J Diabetes Sci Technol. Nov. 2008;2(6):1003-15.
Orive et al., Cell encapsulation: promise and progress. Nat Med. Jan. 2003;9(1):104-7.
Ostuni et al., A Survey of Structure-Property Relationships of Surfaces that Resist the Adsorption of Protein . Langmuir. 2001;17:5605-20.
Parrish et al., Five- and six-membered ring opening of pyroglutamic diketopiperazine. J Org Chem. Mar. 22, 2002;67(6):1820-6.
Pashine et al., Targeting the innate immune response with improved vaccine adjuvants. Nat Med. Apr. 2005;11(4 Suppl):S63-8.
Paul et al., Topographical control of human macrophages by a regularly microstructured polyvinylidene fluoride surface. Biomaterials. Oct. 2008;29(30):4056-64. Epub Jul. 29, 2008.
Peer et al., Nanocarriers as an emerging platform for cancer therapy. Nat Nanotechnol. Dec. 2007;2(12):751-60.
Peppas et al., Hydrogels in Biology and Medicine: From Molecular Principles to Bionanotechnology. Mater. 2006;18:1345-60.
Pera et al., Human embryonic stem cells. J Cell Sci. Jan. 2000;113 ( Pt 1):5-10.
Philipp et al., Hydrophobically modified oligoethylenimines as highly efficient transfection agents for siRNA delivery. Bioconjug Chem. Nov. 2009;20(11):2055-61.
Phillips et al., Enhanced antibody response to liposome-associated protein antigens: preferential stimulation of IgG2a/b production. Vaccine. 1992;10(3):151-8.
Pollard et al., Ether amino alcohols. II. J Org Chem. 1952;17:1-3.
Prata et al., Lipophilic peptides for gene delivery. Bioconjug Chem. Feb. 2008;19(2):418-20.
Putnam et al., Poly(4-hydroxy-l-proline ester): Low-Temperature Polycondensation and Plasmid DNA Complexation. Macromolecules 1999;32:3658-62.

(56) References Cited

OTHER PUBLICATIONS

Putnam, Polymers for gene delivery across length scales. Nat Mater. Jun. 2006;5(6):439-51.
Ratner et al., Biomaterials: where we have been and where we are going. Annu Rev Biomed Eng. 2004;6:41-75.
Refai et al., Effect of titanium surface topography on macrophage activation and secretion of proinflammatory cytokines and chemokines. J Biomed Mater Res A. Aug. 1, 2004;70(2):194-205.
Reynolds et al., Rational siRNA design for RNA interference. Nat Biotechnol. 2004;22(3):326-30.
Robbins et al., 2'-O-methyl-modified RNAs act as TLR7 antagonists. Mol Ther. Sep. 2007;15(9):1663-9. Epub Jun. 19, 2007.
Robbins et al., siRNA and innate immunity. Oligonucleotides. Jun. 2009;19(2):89-102.
Sahay et al., Endocytosis of nanomedicines. J Control Release. Aug. 3, 2010;145(3):182-95. Epub Mar. 10, 2010.
Sakiyama-Elbert et al., Functional Biomaterials: Design of Novel Biomaterials. Ann Rev Mater Res. 2001;31:183-201.
Saltzman, Chapter 19. Cell Interactions with Polymers. In: Principles of Tissue Engineering, 2d ed., 2000:221-35.
Sanford, The biolistic process. Trends Biotechnol. 1988;6:299-302.
Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.
Sawaf et al., [Cytokeratins, markers of epithelial cell differentiation: expression in normal epithelia.] Pathol Biol (Paris). 1992;40:655-65. French.
Schaus et al., Highly Selective Hydrolytic Kinetic Resolution of Terminal Epoxides Catalyzed by Chiral (salen)CoIII Complexes. Practical Synthesis of Enantioenriched Terminal Epoxides and 1,2-Biols. J Am Chem Soc. 2002;124(7):1307-15.
Scheel et al., Therapeutic anti-tumor immunity triggered by injections of immunostimulating single-stranded RNA. Eur J Immunol. Oct. 2006;36(10):2807-16.
Schena et al., Quantitative monitoring of gene expression patterns with a complementary DNA microarray. Science. Oct. 20, 1995;270(5235):467-70.
Schon et al., TLR7 and TLR8 as targets in cancer therapy. Oncogene. Jan. 7, 2008;27(2):190-9.
Schuldiner et al., Effects of eight growth factors on the differentiation of cells derived from human embryonic stem cells. Proc Natl Acad Sci U S A. Oct. 10, 2000;97(21):11307-12.
Schutte et al., Cytokine profiling using monocytes/macrophages cultured on common biomaterials with a range of surface chemistries. J Biomed Mater Res A. Jan. 2009;88(1):128-39.
Schweizer et al., Synthetic Studies towards the Total Synthesis of Providencin. Synthesis. 2007;24:3807-14.
Semple et al., Rational design of cationic lipids for siRNA delivery. Nat Biotechnol. Feb. 2010;28(2):172-6. doi:10.1038/nbt.1602. Epub Jan. 17, 2010.
Sen, Surfactin: biosynthesis, genetics and potential applications. Adv Exp Med Biol. 2010;672:316-23.
Shchori, Poly(secondary Amine)s from Diacrylates and Diamines. J Polym Sci Polymer. Jun. 1983;21(6):413-15.
Siegwart et al., Combinatorial synthesis of chemically diverse core-shell nanoparticles for intracellular delivery. Proc Natl Acad Sci U S A. Aug. 9, 2011;108(32):12996-3001. doi: 10.1073/pnas. 1106379108. Epub Jul. 22, 2011.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Sioud, Innate sensing of self and non-self RNAs by Toll-like receptors. Trends Mol Med. Apr. 2006;12(4):167-76. Epub Mar. 10, 2006.
Sioud, Single-stranded small interfering RNA are more immunostimulatory than their double-stranded counterparts: a central role for 2'-hydroxyl uridines in immune responses. Eur J Immunol. May 2006;36(5):1222-30.
Spradling et al., Stem cells find their niche. Nature. Nov. 1, 2001;414(6859):98-104.
Staubli et al., Hydrolytically degradable amino acid containing polymers. J Am Chem Soc. 1990;45:4419-24.
Steinman et al., Taking dendritic cells into medicine. Nature. Sep. 27, 2007;449(7161):419-26.
Stocum, Stem cells in regenerative biology and medicine. Wound Repair Regen. Nov.-Dec. 2001;9(6):429-42.
Streuli, Extracellular matrix remodeling and cellular differentiation. Curr Opin Cell Biol. 1999;11:634-40.
Suh et al., Ionization of Poly(ethylenimine) and Poly(allylamine) at Various PHS. Bioorg Chem. 1994;22:318-27.
Swali et al., Solid-Phase Dendrimer Synthesis and the Generation of Super-High-Loading Resin Beads for Combinatorial Chemistry. J Org Chem Am Chem Soc. 1997;62:4902-03.
Szoka et al., Comparative properties and methods of preparation of lipid vesicles (liposomes). Annu Rev Biophys Bioeng. 1980;9:467-508.
Tabara et al., The rde-1 Gene, RNA Interference, and Transposon Silencing in C. elegans. Cell. 1999;99:123-32.
Tan et al., Engineering Nanocarriers for siRNA Delivery. Small. Apr. 4, 2011;7(7):841-56. doi: 10.1002/sm11.201001389. Epub Feb. 25, 2011.
Tang et al., In vitro gene delivery by degraded polyamidoamine dendrimers. Bioconjug Chem. Nov.-Dec. 1996;7(6):703-14.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Thiel et al., Therapeutic applications of DNA and RNA aptamers. Oligonucleotides. Sep. 2009;19(3):209-22. doi: 10.1089/oli.2009.0199.
Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.
Thomson et al., Embryonic stem cell lines derived from human blastocysts. Science. Nov. 6, 1998;282(5391):1145-7.
Toom et al., Synthesis of amphiphilic amino alcohols. Synthetic Communication. 2008;38(23):4295-4313.
Tranchant et al., Physicochemical optimisation of plasmid delivery by cationic lipids. J Gene Med. Feb. 2004;6 Suppl 1:S24-35.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.
Unkeless et al., Structure and function of human and murine receptors for IgG. Annu Rev Immunol. 1988;6:251-81.
Urban-Klein et al., RNAi-mediated gene-targeting through systemic application of polyethylenimine (PEI)-complexed siRNA in vivo. Gene Ther. Mar. 2005;12(5):461-6.
Van Balen et al., Liposome/water lipophilicity: methods, information content, and pharmaceutical applications. Med Res Rev. May 2004;24(3):299-324.
Van De Wetering et al., Structure-activity relationships of water-soluble cationic methacrylate/methacrylamide polymers for nonviral gene delivery. Bioconjug Chem. Jul.-Aug. 1999;10(4):589-97.
Van Dijkhuizen-Radersma et al., Biocompatibility and degradation of poly(ether-ester) microspheres: in vitro and in vivo evaluation. Biomaterials. Dec. 2002;23(24):4719-29.
Vandenbroucke et al., Prolonged gene silencing in hepatoma cells and primary hepatocytes after small interfering RNA delivery with biodegradable poly(beta-amino esters). J Gene Med. Jul. 2008;10(7):783-94.
Von Harpe et al., Characterization of commercially available and synthesized polyethylenimines for gene delivery. J Control Release. Nov. 3, 2000;69(2):309-22.
Walde et al., Preparation of Vesicles (Liposomes). In: Encyclopedia of Nanoscience and Nanotechnology. Nalwa, ed. American Scientific Publishers: Los Angeles. 2004;9:43-79.
Wang et al, The functions of microRNAs in plants. Front Biosci. 2007;12:3975-82.

(56) References Cited

OTHER PUBLICATIONS

Ward, A Review of the Foreign-body Response to Subcutaneously-implanted Devices: The Role of Macrophages and Cytokines in Biofouling and Fibrosis. J Diabetes Sci Technol. 2008;2:768-77.
Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.
Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., in vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012.
Whitehead et al., Knocking down barriers: advances in siRNA delivery. Nat Rev Drug Discov. Feb. 2009;8(2):129-38.
Wilen et al., Strategies in Optical Resolutions. Tetrahedron. 1977;33:2725-36.
Williams, on the mechanisms of biocompatibility. Biomaterials. Jul. 2008;29(20):2941-53. Epub Apr. 28, 2008.
Wintermantel et al., Blocked polyurethane prepolymers as component A in reactive adhesives. STN International HCAPLUS Database. 2006. Accession No. 2006:215601.
Wobus, Potential of embryonic stem cells. Mol Aspects Med. Jun. 2001;22(3):149-64.
Wu et al., Cationic lipid polymerization as a novel approach for constructing new DNA delivery agents. Bioconjug Chem. Mar.-Apr. 2001;12(2):251-7.
Yaffee et al., Serial passaging and differentiation of myogenic cells isolated from dystrophic mouse muscle. Nature. 1977;270:725-27.
Yiu et al., Filtering of Ineffective siRNAs and Improved siRNA Design Tool. Bioinformatics. 2005;21(2):144-51.
Yoshioka et al., Epoxy-based Electroactive Polymer Gels. Experimental Mechanics. 2002;42:404-08.
Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.
Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.
Zamore et al., RNAi: Double-Stranded RNA Directs the ATP-Dependent Cleavage of mRNA at 21 to 23 Nucleotide Intervals. Cell. 2000;101:25-33.
Zaugg et al., 3-Carboxy-2,5-piperazinedione and Derivatives. J Amer Chem Soc. Jun. 5, 1956;78(11):2626-2631.
Zauner et al., Polylysine-based transfection systems utilizing receptor-mediated delivery. Adv Drug Deliv Rev. Mar. 2, 1998;30(1-3):97-113.
Zhang et al., Human Toll-like receptor-dependent induction of interferons in protective immunity to viruses. Immunol Rev. Dec. 2007;220:225-36.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/la104590k. Epub Jan. 20, 2011.
Zhao et al., A developmental view of microRNA function. Trends Biochem. 2007;32(4):189-97.
Zintchenko et al., Simple modifications of branched PEI lead to highly efficient siRNA carriers with low toxicity. Bioconjug Chem. Jul. 2008;19(7):1448-55. Epub Jun. 14, 2008.
U.S. Appl. No. 14/941,384, filed Nov. 13, 2015, Ma et al.
U.S. Appl. No. 14/995,842, filed Jan. 14, 2016, Dahlman et al.
U.S. Appl. No. 14/987,717, filed Jan. 4, 2016, Anderson et al.
U.S. Appl. No. 14/900,869, filed Dec. 22, 2015, Alibi et al.
PCT/US2014/036355, Nov. 12, 2015, International Preliminary Report on Patentability.
PCT/US2014/044408, Jan. 7, 2016, International Preliminary Report on Patentability.
International Preliminary Report on Patentability for PCT/US2014/036355, mailed Nov. 12, 2015.
International Preliminary Report on Patentability for PCT/US2014/044408, mailed Jan. 7, 2016.
STN-CAS database Registry No. 1067642-37-8. Entered STN-CAS database on Oct. 29, 2008.
Hsu et al., Diethanolamine (DEA) degradation under gas-treating conditions. Industrial and Engineering Chemistry Product Research and Development. 1985;24(4):630-35.
Moure et al. Chemical modulation of peptoids: synthesis and conformational studies on partially constrained derivatives. Chemistry. Jul. 4, 2011;17(28):7927-39. doi: 10.1002/chem.201100216. Epub May 24, 2011.
Rogers et al., Synthetic Experiments in the Ferrichrome Series. Biochemistry. Dec. 1964;3:1850-5.
STN-CAS database Registry No. 6302-30-3. Entered STN-CAS database on Nov. 16, 1984.
STN-CAS database Registry No. 3768-41-0. Entered STN-CAS database on Nov. 16, 1984.
STN-CAS database Registry No. 21282-28-0. Entered STN-CAS database on Nov. 16, 1984.
STN-CAS database Registry No. 28549-91-9. Entered STN-CAS database on Nov. 16, 1984.
STN-CAS database Registry No. 53731-96-7. Entered STN-CAS database on Nov. 16, 1984.
STN-CAS database Registry No. 53731-98-9. Entered STN-CAS database on Nov. 16, 1984.
STN-CAS database Registry No. 54736-47-9. Entered STN-CAS database on Nov. 16, 1984.
STN-CAS database Registry No. 57018-25-4. Entered STN-CAS database on Nov. 16, 1984.
STN-CAS database Registry No. 57273-30-0. Entered STN-CAS database on Nov. 16, 1984.
STN-CAS database Registry No. 68310-64-5. Entered STN-CAS database on Nov. 16, 1984.
STN-CAS database Registry No. 89038-30-2. Entered STN-CAS database on Nov. 16, 1984.
STN-CAS database Registry No. 103745-33-1. Entered STN-CAS database on Aug. 18, 1986.
STN-CAS database Registry No. 128351-30-4. Entered STN-CAS database on Jul. 20, 1990.
STN-CAS database Registry No. 129257-51-8. Entered STN-CAS database on Sep. 7, 1990.
STN-CAS database Registry No. 129257-52-9. Entered STN-CAS database on Sep. 7, 1990.
STN-CAS database Registry No. 635749-38-1. Entered STN-CAS database on Jan. 9, 2004.
STN-CAS database Registry No. 785789-76-6. Entered STN-CAS database on Nov. 22, 2004.
STN-CAS database Registry No. 883453-96-1. Entered STN-CAS database on May 9, 2006.
STN-CAS database Registry No. 956464-55-4. Entered STN-CAS database on Dec. 3, 2007.
STN-CAS database Registry No. 956465-28-4. Entered STN-CAS database on Dec. 3, 2007.
STN-CAS database Registry No. 1100276-71-8. Entered STN-CAS database on Feb. 3, 2009.
U.S. Appl. No. 13/662,002, filed Oct. 26, 2012, Dong et al.
U.S. Appl. No. 11/453,222, filed Jul. 14, 2006, Anderson et al.
U.S. Appl. No. 12/716,732, filed Mar. 3, 2010, Mahon et al.
U.S. Appl. No. 13/128,020, filed Aug. 16, 2011, Mahon et al.
U.S. Appl. No. 13/126,260, filed Apr. 27, 2011, Nguyen et al.
U.S. Appl. No. 13/819,280, filed Feb. 26, 2013, Ma et al.
U.S. Appl. No. 13/428,695, filed Mar. 23, 2012, Dahlman et al.
U.S. Appl. No. 14/089,603, filed Nov. 25, 2013, Anderson et al.
EP 09825132.5, Jul. 16, 2013, Extended European Search Report.

(56) References Cited

OTHER PUBLICATIONS

PCT/US2009/006018, May 25, 2010, International Search Report and Written Opinion.
PCT/US2009/006018, May 19, 2011, International Preliminary Report on Patentability.
Extended European Search Report for European Application No. 09825132.5, dated Jul. 16, 2013.
International Search Report and Written Opinion for PCT/US2009/006018, mailed May 25, 2010.
International Preliminary Report on Patentability for PCT/US2009/006018, mailed May 19, 2011.
Akinc et al., A combinatorial library of lipid-like materials for delivery of RNAi therapeutics. Nat Biotech. 2008;26(5):561-69.
Bossle et al., Synthesis and biological activity of new 2-substituted analogs of fluphenazine. J Med Chem. Mar. 1, 1976;19(3):370-3.
Ryng et al., Synthesis and Structure Elucidation of 5-Aminomethinimino-3-methyl-4-isoxazolecarboxylic Acid Phenylamides and Their Immunological Activity. Archiv der Pharmazie. Jan. 1, 1997;330(11):319-26.

* cited by examiner

Figure 2

| Identifier | Structure | Identifier | Structure |
|---|---|---|---|
| C6 | (epoxide with butyl chain) | 113 | $H_2N$-CH$_2$CH$_2$-N(CH$_3$)-CH$_2$CH$_2$-$NH_2$ |
| C8 | (epoxide with hexyl chain) | 114 | $H_2N$-CH$_2$CH$_2$-NH-CH$_2$CH$_2$-$NH_2$ |
| C8b | (glycidyl 2-ethylhexyl ether) | 116 | trans-1,2-diaminocyclohexane |
| C10 | (epoxide with octyl chain) | 117 | cis-1,2-diaminocyclohexane |
| C10d | (epoxide with octenyl chain) | | |
| C12 | (epoxide with decyl chain) | | |
| C14 | (epoxide with dodecyl chain) | | |
| C16 | (epoxide with tetradecyl chain) | | |
| C18 | (epoxide with hexadecyl chain) | | |
| C11f | (epoxide with perfluorinated chain) | | |
| 62 | CH$_3$NH-(CH$_2$)$_3$-NHCH$_3$ | | |
| 96 | CH$_3$NH-(CH$_2$)$_3$-NH$_2$ | | |
| 98 | $H_2N$-CH$_2$CH$_2$-NH-CH$_2$CH$_2$-NH-CH$_2$CH$_2$-$NH_2$ | | |
| 99 | $H_2N$-CH$_2$CH$_2$-$NH_2$ | | |
| 100 | $H_2N$-CH$_2$CH$_2$CH$_2$-$NH_2$ | | |
| 103 | HO-CH$_2$CH$_2$-NH-CH$_2$CH$_2$-NH-CH$_2$CH$_2$-OH | | |
| 109 | $H_2N$-CH$_2$CH$_2$-NH-CH$_2$CH$_2$-OH | | |
| 110 | $H_2N$-CH$_2$CH$_2$-N(CH$_2$CH$_2$NH$_2$)-CH$_2$CH$_2$-$NH_2$ | | |
| 111 | $H_2N$-CH$_2$CH$_2$-NH-CH$_2$CH$_2$-NH-CH$_2$CH$_2$-NH-CH$_2$CH$_2$-$NH_2$ | | |
| 112 | $H_2N$-CH$_2$CH$_2$CH$_2$-NH-CH$_2$CH$_2$-$NH_2$ | | |

Figure 3
| Structure | $^1$H NMR | MW calculated | MW observed |
|---|---|---|---|
| 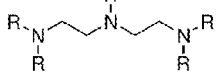 | Confirmed | 1024.8 | 1024.8 |
| 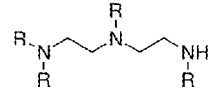 | Confirmed | 840.4 | 840.52 |
| 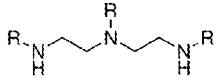 | Confirmed | 656.1 | 656.62 |
| R =  | | | |

AMINOALCOHOL LIPIDOIDS AND USES THEREOF

RELATED APPLICATIONS

The present application is a divisional of and claims priority under 35 U.S.C. §120 to U.S. Application, U.S. Ser. No. 13/128,020, filed Aug. 16, 2011, now issued as U.S. Pat. No. 8,969,353, which is a national stage filing under 35 U.S.C. §371 of international PCT application, PCT/US2009/006018, filed Nov. 6, 2009, which claims priority under 35 U.S.C. §119(e) to U.S. provisional applications, U.S. Ser. No. 61/112,414, filed Nov. 7, 2008, and U.S. Ser. No. 61/166,518, filed Apr. 3, 2009; each of which is incorporated herein by reference.

GOVERNMENT SUPPORT

This invention was made with Government support under Grant No. 5-U54-CA119349-03, 5-R01-EB000244-27; and EB00244, awarded by the National Institutes of Health; and Grant No. 1154-CA-119349, awarded by the Center of Cancer Nanotechnology Excellence. The Government has certain rights in this invention.

BACKGROUND OF THE INVENTION

Despite promise in the laboratory, the potential of genetic therapies for the treatment of disease has yet to be realized. Initial attempts to translate genetic materials into cures led to cancer and, in some cases, death to patients involved in the clinical trials. Such deleterious outcomes were attributed not to the genetic material, but to the viral delivery systems utilized in these trials. As a result, there has been intense interest in developing synthetic materials that have the delivery efficiencies of viral vectors but circumvent the mutagenesis that led to the observed side effects (e.g., cancer).

Synthetic materials, or nonviral delivery vectors, come in a variety of forms that work in unique ways. Polymeric materials such as polyethylenimine or poly(beta-amino ester)s have been shown to efficiently complex DNA for delivery into the cell. Polymers in these classes of delivery agents typically contain amine functionalities that serve to electrostatically bind to DNA to form nanoparticles that are then taken up by the cell via endocytosis. Once in the cell, these amine groups serve to buffer the endosome and cause an influx of ions due to the proton-sponge mechanism. The resulting burst of the endocytic vesicle leads to the release of the payload of the particle, which is then free to travel to the nucleus where the DNA is expressed.

While the mechanism of RNA-based therapies is different, the objective of the delivery system remains the same. The RNA must be complexed and internalized by the cell in order to exhibit activity. In many cases, polymeric materials do not work as efficiently for RNA delivery. This is likely due to the difference in chemical structure of the therapeutic RNA being delivered, which are generally short, linear fragments containing additional hydroxyl moieties on each ribose ring. These differences necessitate an alternative nonviral approach that is suited for complexation with short RNA strands. Promising results have been achieved with materials that form liposomes or lipoplexes that entrap the RNA or form nanoparticles, which are efficiently internalized by the cell.

The materials utilized to form a lipid-based delivery system generally consist of a positively charged headgroup and a hydrophobic tail. The charged portion serves to electrostatically bind the negatively charged RNA, while the hydrophobic tail leads to self-assembly into lipophilic particles. Such cationic lipids are promising but still fall short of the transfection efficiency achieved by viral vectors.

Few advances have been made in the field, in part due to the limited structural diversity of these lipid-like molecules, which is a result of the difficult synthetic procedures required to access these structures. Therefore, in order to push the area of nonviral lipid particle delivery systems forward, it is necessary to investigate chemical transformations that can lead to diverse molecules capable of complexing RNA and shuttling the material across the cell membrane. The most successful approach to date has been the contribution by Anderson and coworkers, who generated a library of lipid-like materials using straightforward simple chemical transformations. This set of materials was based on the well-known and efficient reaction known as the Michael addition of an amine to an acrylamide or acrylate to yield a beta-amino amide or a beta-amino ester, respectively. These structures consist of an amine core linked to long, hydrophobic alkyl chains. Starting with a set of amines and Michael acceptors, the team generated over 1000 compounds that were tested for their ability to complex and deliver RNA in a high throughput assay. This screen led to the identification of a number of lead compounds that were more efficient in vitro than the current industry standard, Lipofectamine 2000, and are currently being tested in vivo for potential use in therapeutic applications (Akinc et al., *Nat. Biotech.* 2008, (26) 561).

There exists a continuing need for a new set of lipid-like molecules that feature similar properties to the existing amine-containing lipidoid materials, but accessed through an entirely different chemical reaction and having the ability to deliver RNA as well as other nucleic acids and other diagnostic, therapeutic, and prophylactic agents to cells.

SUMMARY OF THE INVENTION

The present invention originates from the discovery that aminoalcohol lipidoid compounds for drug delivery may be prepared by reacting an amine with a terminal epoxide or an aldehyde.

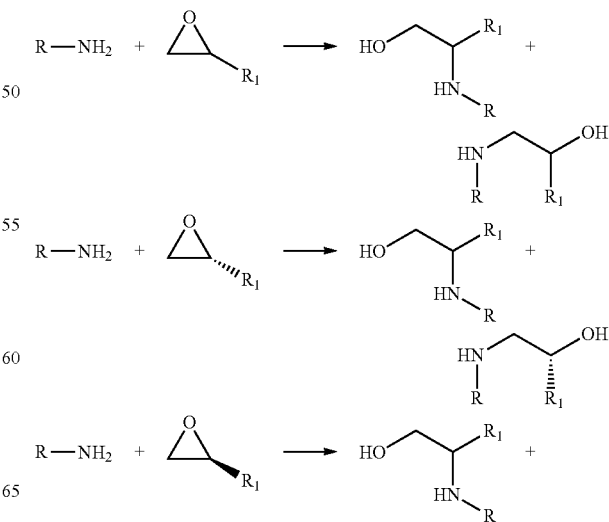

-continued

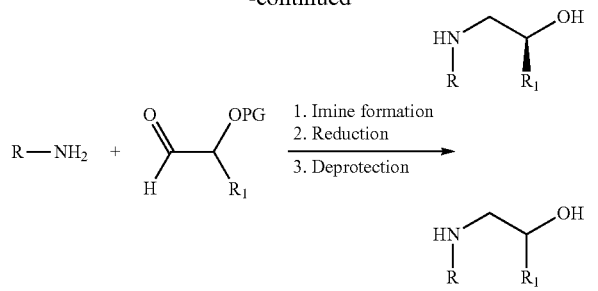

The inventive lipidoid compounds are particularly useful in the administration of polynucleotides. The aminoalcohol lipidoid compounds of the present invention are amenable to combinatorial synthesis and screening to generate libraries of compounds for use as nonviral drug delivery agents. The inventive compounds may be used for other purposes as well such as, for example, coatings, additives, excipients.

In one aspect, the present invention provides novel aminoalcohol lipidoid compounds of the formulae:

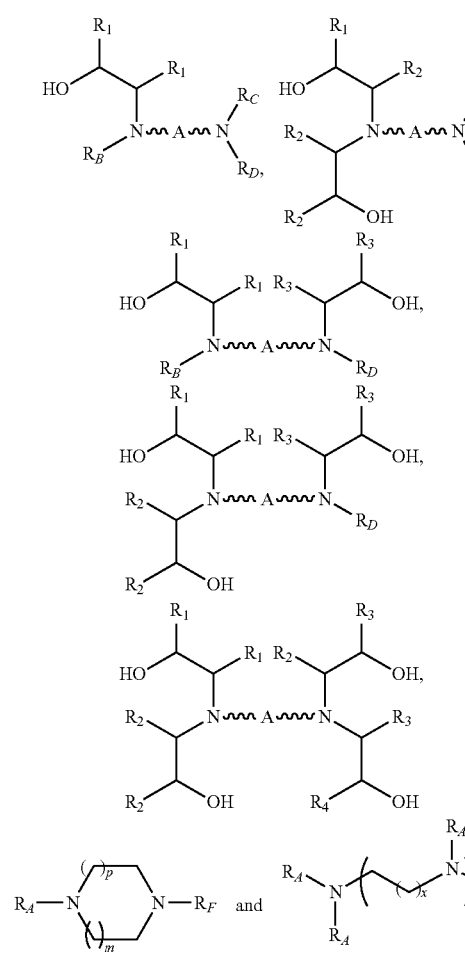

These aminoalcohol lipidoid compounds may be prepared by reacting an amine with an epoxide-terminated compound. In certain embodiments, the epoxide is stereochemically pure (e.g., enantiomerically pure). In certain embodiments, the amine is stereochemically pure (e.g., enantiomerically pure). In certain embodiments, the lipidoid is prepared from the reductive amination of an imine which is derived from the condensation of an amine and an aldehyde. In certain embodiments, each

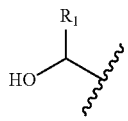

is independently

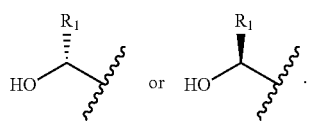

In certain embodiments, each

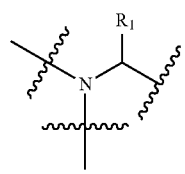

is independently

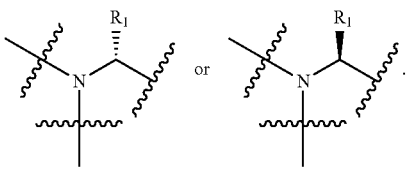

In certain embodiments, each

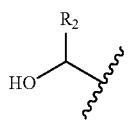

is independently

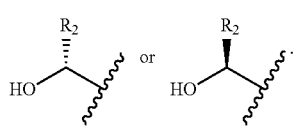

In certain embodiments, each

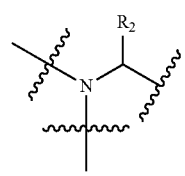

is independently

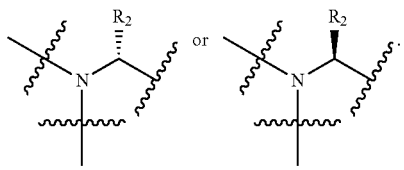

In certain embodiments, each

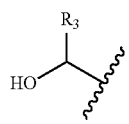

is independently

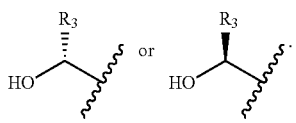

In certain embodiments, each

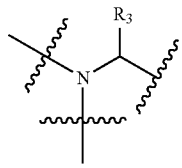

is independently

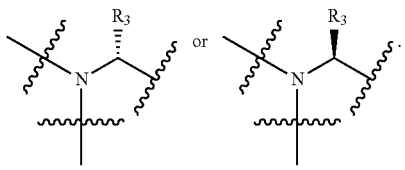

In certain embodiments, each

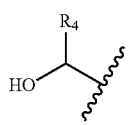

is independently

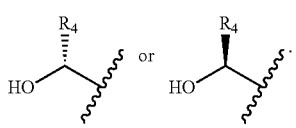

In certain embodiments, and each

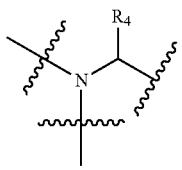

is independently

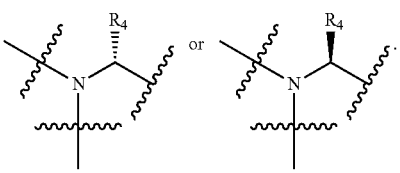

In certain embodiments, an amine and an epoxide-terminated compound are reacted at elevated temperatures in the absence of solvent to prepare the inventive aminoalcohol lipidoids as shown in FIG. 1. In certain embodiments, the aminoalcohol lipidoid compounds include a hydrophilic portion resulting from the opening of the epoxide by the amine and a hydrophobic aliphatic tail.

Typically, the amines chosen contain between two and five amine moieties and the epoxide-terminated compounds include a tail of varying chain lengths and optionally feature various functional groups and varying degrees of saturation. The inventive aminoalcohol lipidoid compounds may be used in the delivery of therapeutic agents (e.g., polynucleotide, small molecule, protein, peptide) to a subject. The inventive aminoalcohol lipidoid compounds are particularly useful in delivering negatively charged agents given the tertiary amines available for protonation thus forming a cationic moiety. For example, the aminoalcohol lipidoid compounds may be used to delivery DNA, RNA, or other polynucleotides to a subject or to a cell. As would be appreciated by one of skill in the art, the above reaction may result in a mixture with lipidoid compounds having one tail, some having two tails, some having three tails, and yet others having four or more tails. Also, two different epoxide compounds may be used in the reaction mixture to prepare an aminoalcohol lipidoid compound with two different tails.

In another aspect, novel aminoalcohol lipidoid compounds for drug delivery may be prepared by reacting a polyamine with a terminal epoxide.

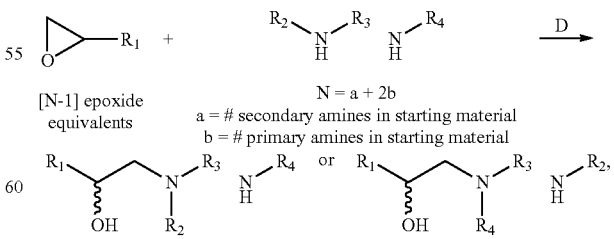

wherein, $R_1$ represents alkyl chains of varying lengths, while $R_2$ through $R_4$ generally represent various combinations of alkyl chains, polyamines, and hydrogen atoms. Reactions are set up by adding [N−1] equivalents of epoxide to polyamine (where N is the number of 2° amines plus 2× number of 1° amines in the polyamine starting material). This generates a mixture enriched in compounds with [N−1] tails. Typically, these compounds are a mixture of various constitutional isomers, are usually isolable by chromatography on silica gel; the identity and purity of the products may be confirmed through $^1H/^{13}C$ NMR spectroscopy and/or by MALDI-MS (with 2,5-dihydroxybenzoic acid matrix). As described herein, the epoxide, the amine, or both the epoxide and the amine may be stereochemically pure.

These inventive lipidoid compounds are also particularly useful in the administration of polynucleotides. The aminoalcohol lipidoid compounds of the present invention are amenable to combinatorial synthesis and screening to generate libraries of compounds for use as nonviral drug delivery agents. The inventive compounds may be used for other purposes as well such as coatings, additives, materials, and excipients.

In one aspect, the present invention provides a novel aminoalcohol lipidoid compound of the formula:

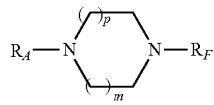

as described herein. In another aspect, the present invention provides a novel aminoalcohol lipidoid compound of the formula:

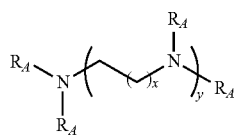

as described herein.

In one aspect, the present invention provides novel aminoalcohol lipidoid compounds based upon reacting a polyamine with a suitable terminal epoxide as described herein. In certain embodiments, the polyamine is "amine 111" of the formula:

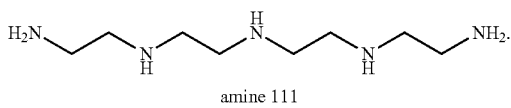 [SMILES: NCCNCCNCCNCCN]

amine 111

In certain embodiments, the polyamine is "amine 200" of the formula:

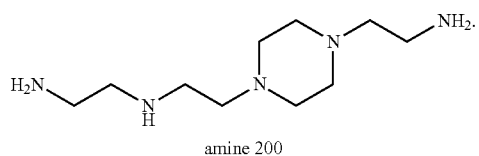 [SMILES: NCCNCCN1CCN(CCN)CC1]

amine 200

In certain embodiments, the polyamine is "amine 205" of the formula:

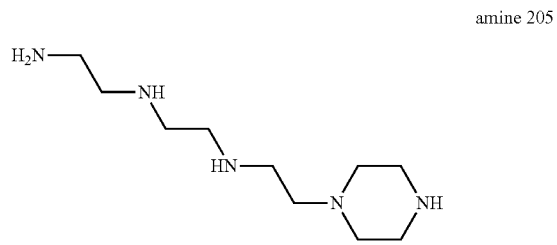 [SMILES: NCCNCCNCCN1CCNCC1]

amine 205

In certain embodiments, the polyamine is "amine 96" of the formula:

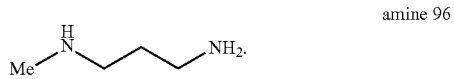

amine 96

Materials based on amine 96 are generated through systematic variation around the amine 96 core structure (see Example 15, Part 2) Aminoalcohol lipidoid compounds based upon amine 111 resulted from performing MALDI-MS analyses on the products of the amine 111 and epoxide reaction (see Example 14, Part 1).

In one aspect of the invention, the inventive aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The inventive aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

The invention also provides methods of preparing the inventive aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30° C.-100° C., preferably at approximately 50° C.-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

The invention also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess.

For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-di methyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5- dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), p-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of diseases or disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like.

The term "alkynyl" as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like.

The term "alkoxy," or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "carboxylic acid" as used herein refers to a group of formula —$CO_2H$.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl) amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl," as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle," as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle," as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

The terms "halo" and "halogen" as used herein refer to an atom selected from fluorine, chlorine, bromine, and iodine.

The term "heterocyclic," as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "heteroaryl", as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl) amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-di azacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacycloocctane, decahydroquinoline, piperazine, piperidine, pyrrolidine, thiomorpholine, and triazole.

The term "substituted," whether preceded by the term "optionally" or not, and "substituent," as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc. In certain embodiments, an aninoalcohol lipidoid compound is associated with a polynucleotide through electrostatic interactions.

"Biocompatible": The term "biocompatible," as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable compounds are uncatalyzed.

"Effective amount": In general, the "effective amount" of an active agent or composition refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. In certain embodiments, the small molecule is uncharged. In certain embodiments, the small molecule is negatively charged. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

BRIEF DESCRIPTION OF THE DRAWING

FIG. 2 depicts exemplary amines containing between two and five amine functionalities and racemic epoxides of varying tails, unique functional groups and varying degrees of saturation that may be used for preparing aminoalcohol lipidoids.

FIG. 3 depicts characterization data of aminoalcohol lipidoids derived from amine 114.

DETAILED DESCRIPTION OF CERTAIN EMBODIMENTS OF THE INVENTION

Figure 1:
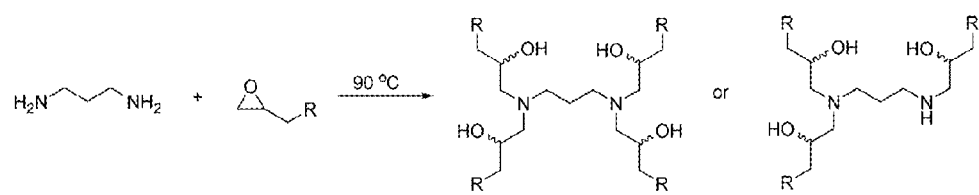
FIG. 1 depicts a general synthetic scheme for preparing aminoalcohol lipidoids by combining amines and epoxides, and reacting them at approximately 90° C.

The present invention provides novel aminoalcohol lipidoid compounds and drug delivery systems based on the use of such aminoalcohol lipidoid compounds. The system may be used in the pharmaceutical/drug delivery arts to delivery polynucleotides, proteins, small molecules, peptides, antigen, drugs, etc. to a patient, tissue, organ, cell, etc. These novel compounds may also be used as materials for coating, additives, excipients, materials, bioengineering, etc.

The aminoalcohol lipidoid compounds of the present invention provide for several different uses in the drug delivery art. The amine-containing portion of the aminoalcohol lipidoid compounds may be used to complex polynucleotides, thereby enhancing the delivery of polynucleotide and preventing their degradation. The aminoalcohol lipidoid compounds may also be used in the formation of picoparticles, nanoparticles, microparticles, liposomes, and micelles containing the agent to be delivered. Preferably, the aminoalcohol lipidoid compounds are biocompatible and biodegradable, and the formed particles are also biodegradable and biocompatible and may be used to provide controlled, sustained release of the agent to be delivered. These lipidoids and their corresponding particles may also be responsive to pH changes given that these lipidoids are protonated at lower pH. The lipidoids may also act as proton sponges in the delivery of an agent to a cell to cause endosome lysis.

1. Aminoalcohol Lipidoid Compounds

The aminoalcohol lipidoid compounds of the present invention are aminoalcohol lipidoid compounds containing primary, secondary, tertiary, and/or quaternary amines, and salts thereof. The amines may be cyclic or acyclic amines. In certain embodiments, the inventive aminoalcohol lipidoid compounds are relatively non-cytotoxic. In another embodiment, the inventive aminoalcohol lipidoid compounds are biocompatible and biodegradable. In certain embodiments, the aminoalcohol lipidoids of the present invention have $pK_a$s in the range of approximately 5.5 to approximately 7.5, more preferably between approximately 6.0 and approximately 7.0. In another embodiment, the aminoalcohol lipidoid compounds may be designed to have a desired $pK_a$ between approximately 3.0 and approximately 9.0, or between approximately 5.0 and approximately 8.0. The inventive aminoalcohol lipidoid compounds are particularly attractive for drug delivery for several reasons: 1) they contain amino groups for interacting with DNA, RNA, other polynucleotides, and other negatively charged agents, for buffering the pH, for causing endosomolysis, for protecting the agent to be delivered, etc.; 2) they can be synthesized from commercially available starting materials; and/or 3) they are pH responsive and can be engineered with a desired $pK_a$.

In certain embodiments, the aminoalcohol lipidoid compound or composition containing aminoalcohol lipidoid compound(s), are those derived from terminated epoxides of 14 carbons or greater coupled with monomers of three or more amine functional groups. In certain embodiments, the composition containing an aminoalcohol lipidoid compound is about 40-60% lipidoid, about 40-60% cholesterol, and about 5-20% PEG. In certain embodiments, the composition containing an aminoalcohol lipidoid compound is about 50-60% lipidoid, about 40-50% cholesterol, and about 5-10% PEG. In certain embodiments, the composition containing an aminoalcohol lipidoid compound is 52% lipidoid, 48% cholesterol, and 10% PEG. In certain embodiments, the composition containing an aminoalcohol lipidoid is about 50-75% lipidoid, about 20-40% cholesterol, and about 1-10% PEG. In certain embodiments, the composition containing an aminoalcohol lipidoid compound is about 60-70% lipidoid, about 25-35% cholesterol, and about 5-10% PEG.

In certain embodiments, the aminoalcohol lipidoid compounds may be prepared by reacting an amine with a terminal epoxide or an aldehyde according to the following schemes.

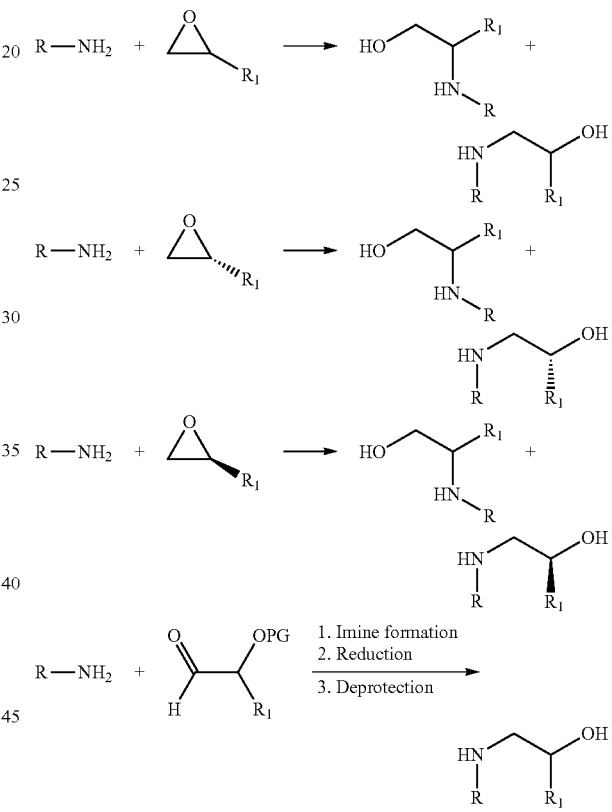

In certain embodiments, the epoxide is stereochemically pure (e.g., enantiomerically pure). In certain embodiments, the amine is stereochemically pure (e.g., enantiomerically pure). In certain embodiments, the lipidoid is prepared from the reductive amination of an imine which derived from the condensation of an amine and an aldehyde. In certain embodiments, the aminoalcohol lipidoid compounds of the present invention are of one of the formulae:

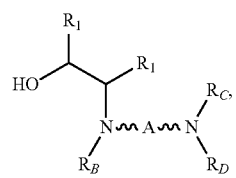

-continued

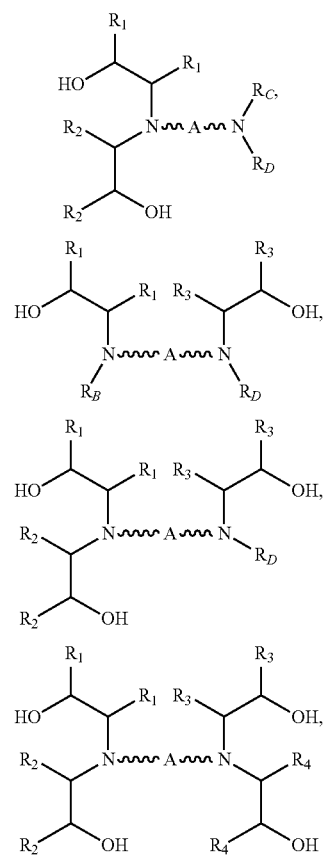

wherein each occurrence of A, $R_1$, $R_2$, $R_3$, $R_4$, $R_B$, $R_C$, $R_D$, $R_A$, $R_F$, m, p, x, and y are as defined herein. As will be appreciated by one of skill in the art, the amine may be reacted with an excess of epoxide to form a fully functionalized aminoalcohol lipidoid compound. Or, the lipidoid may have fewer epoxide-derived tails than when fully functionalized. In certain embodiments, each

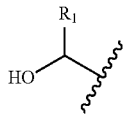

is independently

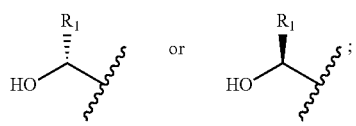

each

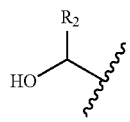

is independently

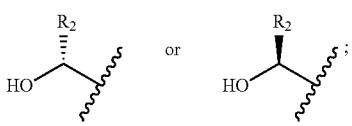

each

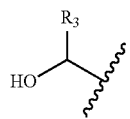

is independently

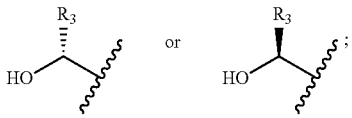

and each

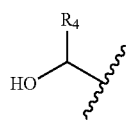

is independently

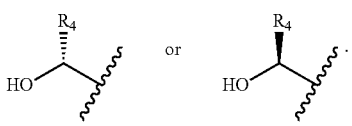

In certain embodiments, the aminoalcohol lipidoid compound of the present invention is of the formula:

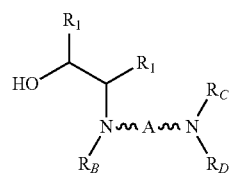

wherein:

A is a substituted or unsubstituted, branched or unbranched, cyclic or acyclic $C_{2-20}$ alkylene, optionally interrupted by 1 or more heteroatoms independently selected from O, S and N, or A is a substituted or unsubstituted, saturated or unsaturated 4-6-membered ring;

$R_1$ is hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen;

$R_B$, $R_C$, and $R_D$ are, independently, hydrogen, a substituted, unsubstituted, branched or unbranched $C_{1-20}$-aliphatic, or a substituted, unsubstituted, branched or unbranched $C_{1-20}$-heteroaliphatic or —CH$_2$CH(OH)R$_E$;

$R_B$ and $R_D$ together may optionally form a cyclic structure;

$R_C$ and $R_D$ together may optionally form a cyclic structure; and $R_E$ is a substituted, unsubstituted, branched or unbranched $C_{1-20}$ aliphatic or a substituted, unsubstituted, branched or unbranched $C_{1-20}$ heteroaliphatic; or a pharmaceutically acceptable salt thereof.

In certain embodiments, A is an unsubstituted, unbranched, and acyclic $C_{2-20}$ alkylene. In certain embodiments, A is a substituted or unsubstituted, branched or unbranched, cyclic or acyclic $C_{2-20}$, alkylene, optionally interrupted by 1 or more nitrogen atoms. In certain embodiments, A is a substituted, unbranched, and acyclic $C_{2-10}$ alkylene, optionally interrupted, by 1 oxygen atom. In certain embodiments, A is of the

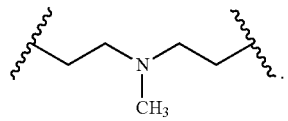 [SMILES: *CCN(C)CC*]

In certain embodiments, A is a substituted or unsubstituted, branched or unbranched, cyclic or acyclic $C_{2-20}$ alkylene, optionally interrupted, by 1 or more oxygen atoms. In certain embodiments A is an unsubstituted, unbranched, and acyclic $C_{2-10}$ alkylene, optionally interrupted by 1 or more oxygen atoms. In certain embodiments A is an unsubstituted, unbranched, and acyclic $C_{2-10}$ alkylene, optionally interrupted by 2 oxygen atoms. In certain embodiments, A is of the formula

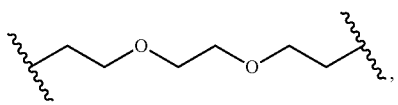 [SMILES: *CCOCCOCC*]

In certain embodiments, A is of the formula

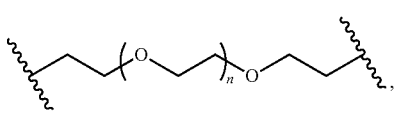

wherein n is an integer between 1 and 10, inclusive. In certain embodiments, A is a substituted or unsubstituted, branched or unbranched, cyclic or acyclic $C_{2-20}$ alkylene, optionally interrupted by 1 or more nitrogen atoms. In certain embodiments A is an unsubstituted, unbranched, and acyclic $C_{2-10}$ alkylene, optionally interrupted by 1 or more nitrogen atoms. In certain embodiments A is an unsubstituted, unbranched, and acyclic $C_{2-10}$ alkylene, optionally interrupted by 2 nitrogen atoms. In certain embodiments, A is of the formula

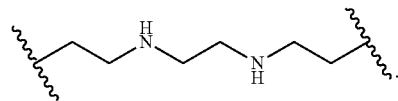 [SMILES: *CCNCCNCC*]

In certain embodiments, A is of the formula

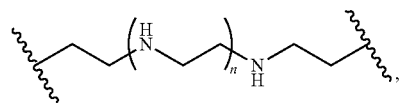

wherein n is an integer between 1 and 10, inclusive.

In certain embodiments, A is selected from the following formulae:

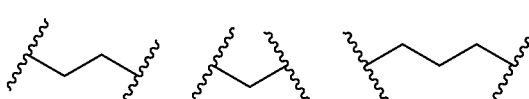

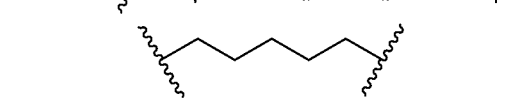

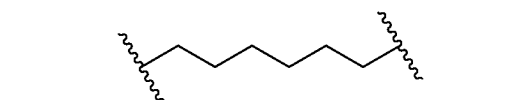

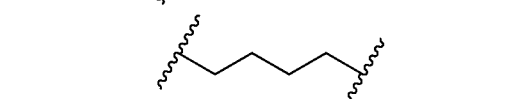

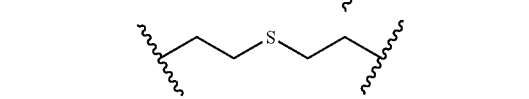

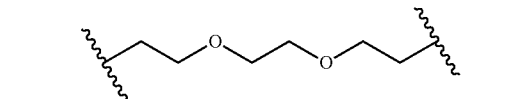

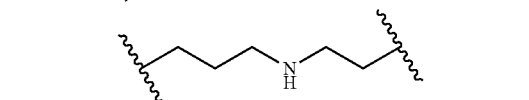

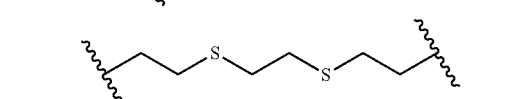

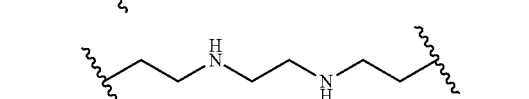

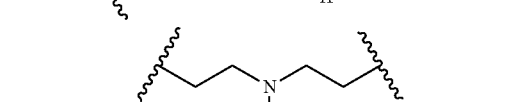

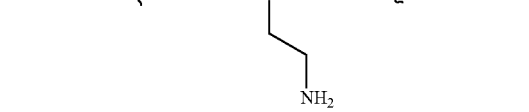

-continued

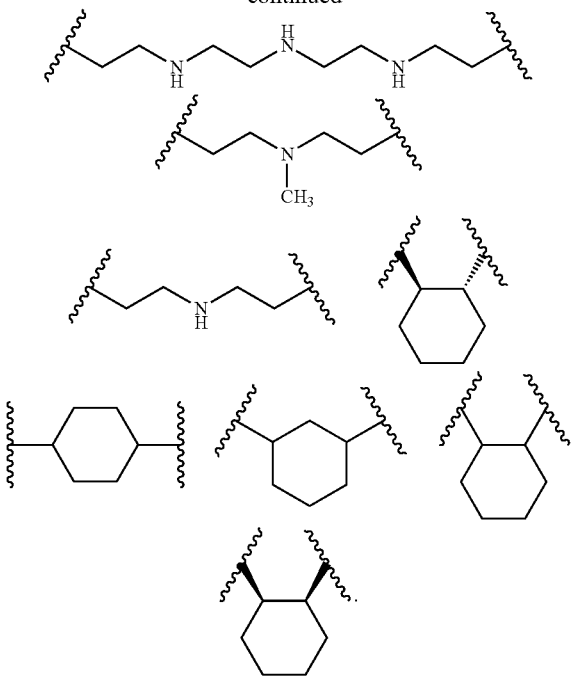

In certain embodiments, $R_1$ is hydrogen. In certain embodiments, $R_1$ is an unsubstituted and unbranched, $C_{1-20}$-aliphatic or $C_{1-20}$ heteroaliphatic moiety. In some embodiments, $R_1$ is an unsubstituted and unbranched, $C_{10-12}$-aliphatic group. In some embodiments, $R_1$ is

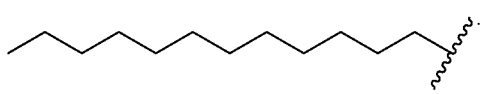 [SMILES: *CCCCCCCCCCCC]

In some embodiments, $R_1$ is an unsubstituted and unbranched, $C_{13}$ heteroaliphatic group. In some embodiments, $R_1$

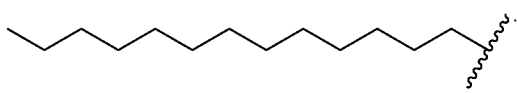 [SMILES: *CCCCCCCCCCCCC]

In some embodiments, $R_1$ is an unsubstituted and unbranched, $C_{14}$ heteroaliphatic group. In some embodiments, $R_1$ is

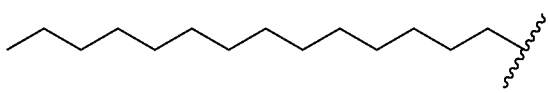

In certain embodiments, $R_1$ is selected from the following formulae:

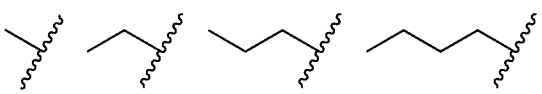

-continued

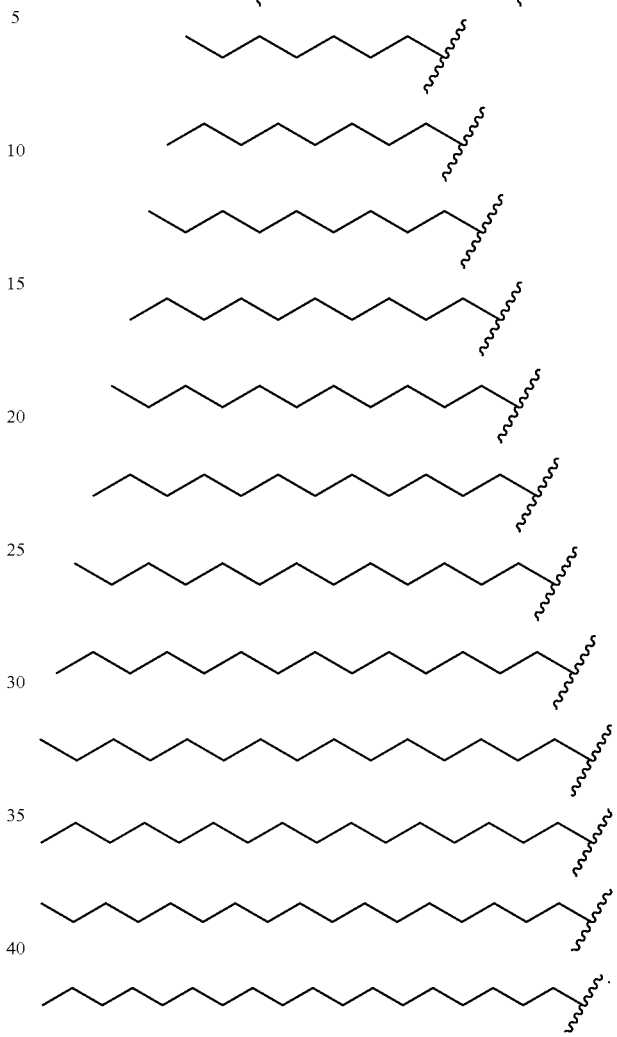

In certain embodiments, $R_1$ is a $C_{1-20}$ alkenyl moiety, optionally substituted. In certain embodiments, $R_1$ is selected from the following formulae:

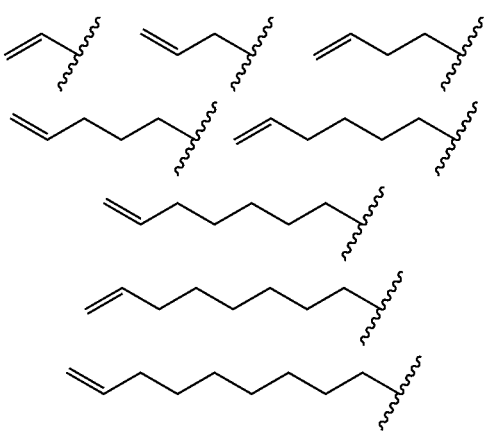

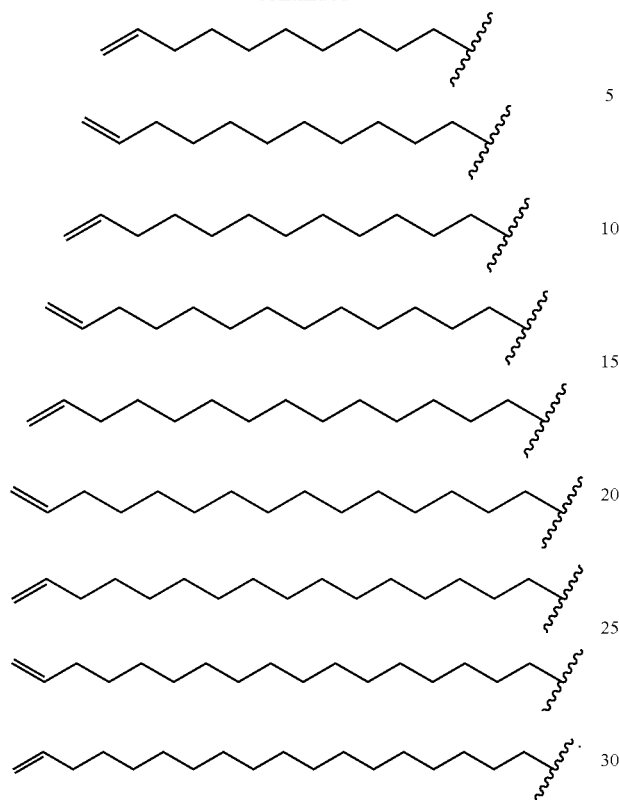
It will be appreciated by one of ordinary skill in the art that the above substituents may have multiple sites of unsaturation, and could be so at any position within the substituent.
In certain embodiments, each
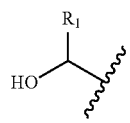
is independently
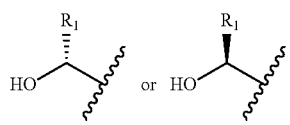
In certain embodiments, $R_1$ is:
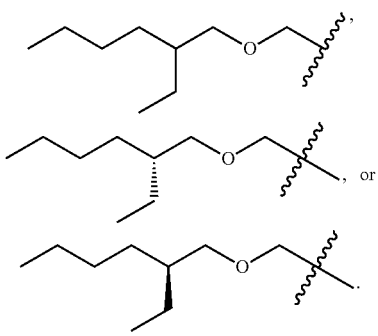
In certain embodiments, $R_1$ is selected from the following formulae:
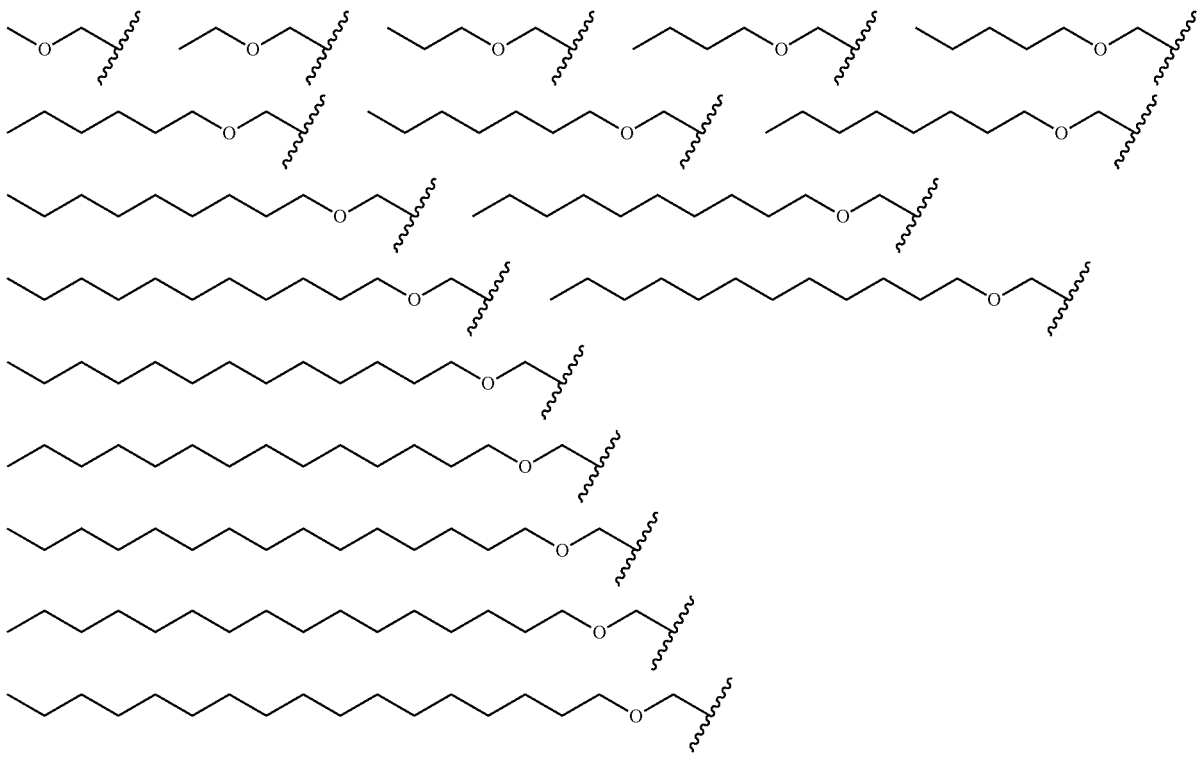

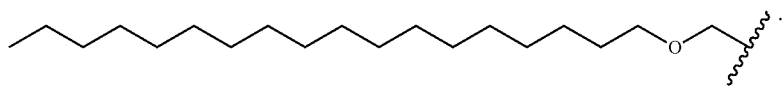

In certain embodiments, $R_1$ is selected from the following formulae:

In certain embodiments, $R_1$ is fluorinated. In certain embodiments $R_1$ is a fluorinated aliphatic moiety. In certain embodiments $R_1$ is perfluorinated. In certain embodiments $R_1$ is a perfluorinated aliphatic moiety. In certain embodiments, $R_1$ is a perfluorinated $C_{1-20}$ alkyl group. In certain embodiments, $R_1$ is selected from the following formulae:

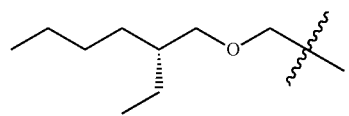

-continued

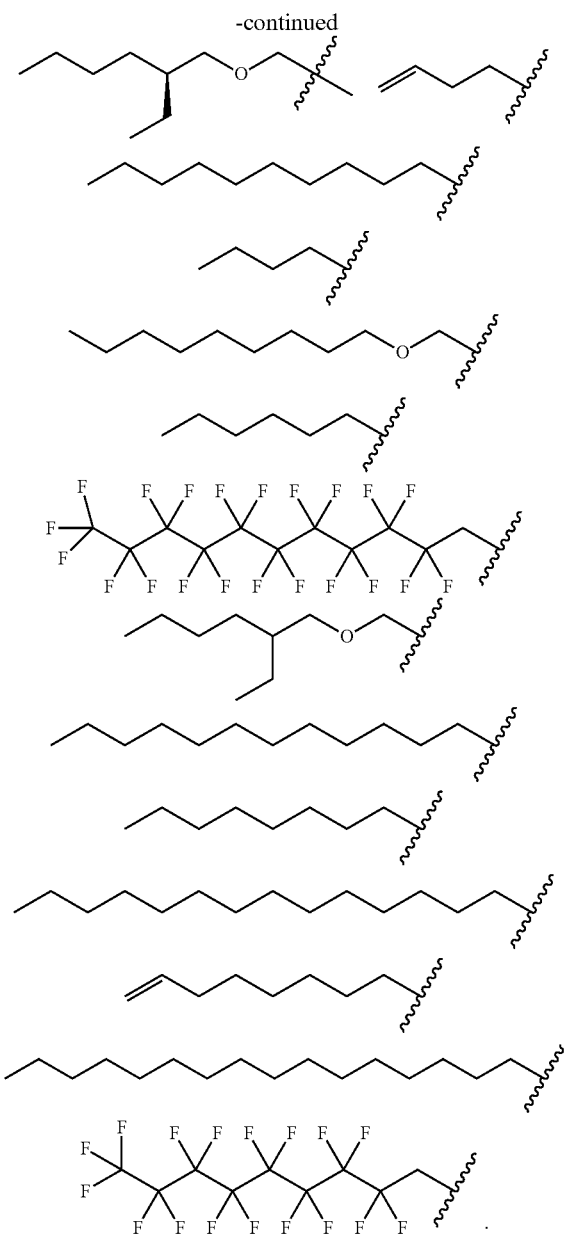

In certain embodiments, R₁ is selected from the following formulae:

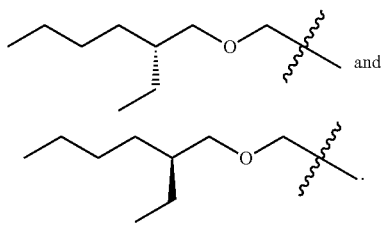

In certain embodiments, $R_B$ is hydrogen. In certain embodiments, $R_B$ is an unsubstituted and unbranched $C_{1-20}$-aliphatic. In certain embodiments $R_B$ is $C_{1-6}$-alkyl. In certain embodiments $R_B$ is methyl. In certain embodiments $R_B$ is ethyl. In certain embodiments $R_B$ is propyl. In certain embodiments $R_B$ is butyl. In certain embodiments, $R_B$ is an unsubstituted and unbranched $C_{1-20}$-heteroaliphatic. In certain embodiments $R_B$ is $C_{1-6}$-heteroalkyl. In certain embodiments, $R_B$ is —$CH_2CH(OH)R_E$.

In certain embodiments, $R_C$ is hydrogen. In certain embodiments, $R_C$ is an unsubstituted and unbranched $C_{1-20}$-aliphatic. In certain embodiments $R_C$ is $C_{1-6}$-alkyl. In certain embodiments $R_C$ is methyl. In certain embodiments $R_C$ is ethyl. In certain embodiments $R_C$ is propyl. In certain embodiments $R_C$ is butyl. In certain embodiments, $R_C$ is an unsubstituted and unbranched $C_{1-20}$-heteroaliphatic. In certain embodiments $R_C$ is $C_{1-6}$-heteroalkyl. In certain embodiments, $R_C$ is —$CH_2CH(OH)R_E$.

In certain embodiments, $R_D$ is hydrogen. In certain embodiments, $R_D$ is an unsubstituted and unbranched $C_{1-20}$-aliphatic. In certain embodiments $R_D$ is $C_{1-6}$-alkyl. In certain embodiments $R_D$ is methyl. In certain embodiments $R_D$ is ethyl. In certain embodiments $R_D$ is propyl. In certain embodiments $R_D$ is butyl. In certain embodiments, $R_D$ is an unsubstituted and unbranched $C_{1-20}$-heteroaliphatic. In certain embodiments $R_D$ is $C_{1-6}$-heteroalkyl. In certain embodiments, $R_D$ is —$CH_2CH(OH)R_E$.

In certain embodiments, $R_B$, $R_C$, and $R_D$ are all the same. In certain embodiments, $R_B$, $R_C$, and $R_D$ are all hydrogen or all $C_1$-$C_6$ alkyl. In certain embodiments, $R_B$, $R_C$, and $R_D$ are all hydrogen. In certain embodiments, $R_B$, $R_C$, and $R_D$ are all $C_1$-$C_6$ alkyl. In certain embodiments, $R_B$, $R_C$, and $R_D$ are all hydroxyalkyl. In certain embodiments, $R_B$, $R_C$, and $R_D$ are all aminoalkyl. In certain embodiments, $R_B$, $R_C$, and $R_D$ are hydrogen or methyl. In certain embodiments, at least two of $R_B$, $R_C$, and $R_D$ are the same. In certain embodiments, $R_B$, $R_C$, and $R_D$ are all different.

In certain embodiments, $R_E$ is hydrogen. In certain embodiments, $R_E$ is an unsubstituted and unbranched $C_{1-20}$-aliphatic. In certain embodiments $R_E$ is $C_{1-6}$-alkyl. In certain embodiments $R_E$ is methyl. In certain embodiments $R_E$ is ethyl. In certain embodiments $R_E$ is propyl. In certain embodiments $R_E$ is butyl. In certain embodiments, $R_E$ is an unsubstituted and unbranched $C_{1-20}$-heteroaliphatic. In certain embodiments $R_E$ is $C_{1-6}$-heteroalkyl.

Particular exemplary compounds include:

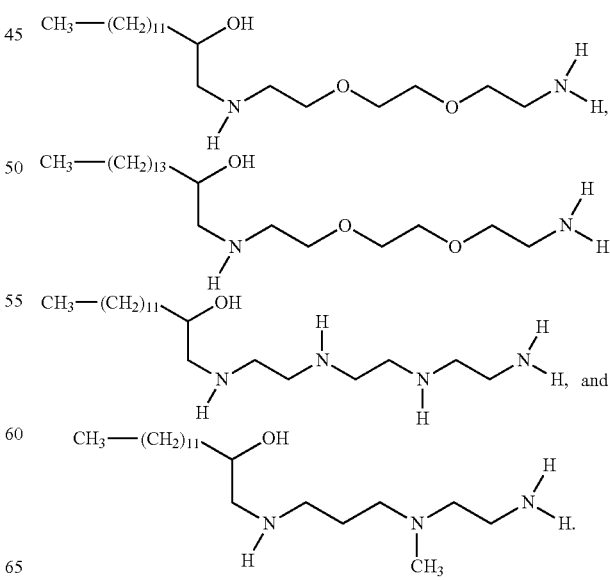

In certain embodiments, the aminoalcohol lipidoid compound of the present invention is of the formula:

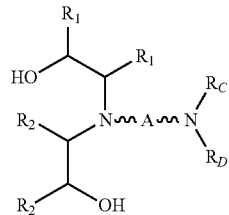

A is a substituted or unsubstituted, branched or unbranched, cyclic or acyclic $C_{2-20}$ alkylene, optionally interrupted by 1 or more heteroatoms independently selected from O, S and N, or A is a substituted or unsubstituted, saturated or unsaturated 4-6-membered ring;

$R_1$ and $R_2$ are, independently, hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen and at least one occurrence of $R_2$ is hydrogen;

$R_C$ and $R_D$ are, independently, hydrogen, a substituted, unsubstituted, branched or unbranched $C_{1-20}$-aliphatic, or a substituted, unsubstituted, branched or unbranched $C_{1-20}$-heteroaliphatic or —CH$_2$CH(OH)R$_E$;

$R_C$ and $R_D$ together may optionally form a cyclic structure; and $R_E$ is a substituted, unsubstituted, branched or unbranched $C_{1-20}$ aliphatic or a substituted, unsubstituted, branched or unbranched $C_{1-20}$ heteroaliphatic; or a pharmaceutically acceptable salt thereof.

In certain embodiments, A is an unsubstituted, unbranched, and acyclic $C_{2-20}$ alkylene. In certain embodiments, A is a substituted or unsubstituted, branched or unbranched, cyclic or acyclic $C_{2-20}$ alkylene, optionally interrupted by 1 or more nitrogen atoms. In certain embodiments A is a substituted, unbranched, and acyclic $C_{2-10}$ alkylene, optionally interrupted by 1 oxygen atom. In certain embodiments, A is of the formula

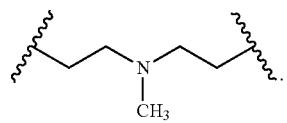

In certain embodiments, A is a substituted or unsubstituted, branched or unbranched, cyclic or acyclic $C_{2-20}$ alkylene, optionally interrupted by 1 or more oxygen atoms. In certain embodiments A is an unsubstituted, unbranched, and acyclic $C_{2-10}$ alkylene, optionally interrupted by 1 or more oxygen atoms. In certain embodiments A is an unsubstituted, unbranched, and acyclic $C_{2-10}$ alkylene, optionally interrupted by 2 oxygen atoms. In certain embodiments, A is of the formula

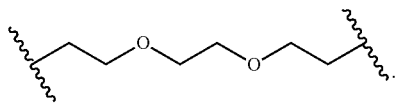 [SMILES: *CCOCCOCC*]

In certain embodiments, A is of the formula

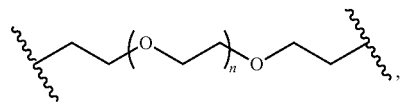

wherein n is an integer between 1 and 10, inclusive. In certain embodiments, A is a substituted or unsubstituted, branched or unbranched, cyclic or acyclic $C_{2-20}$ alkylene, optionally interrupted by 1 or more nitrogen atoms. In certain embodiments A is an unsubstituted, unbranched, and acyclic $C_{2-10}$ alkylene, optionally interrupted by 1 or more nitrogen atoms. In certain embodiments A is an unsubstituted, unbranched, and acyclic $C_{2-10}$ alkylene, optionally interrupted by 2 nitrogen atoms. In certain embodiments, A is of the formula

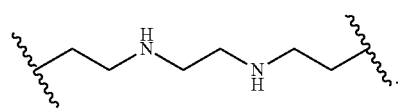 [SMILES: *CCNCCNCC*]

In certain embodiments, A is of the formula

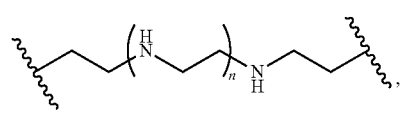

wherein n is an integer between 1 and 10, inclusive.

In certain embodiments, A is selected from the following formulae:

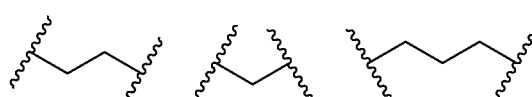
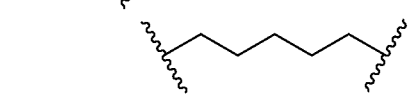
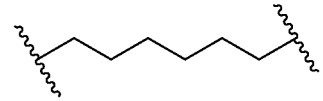
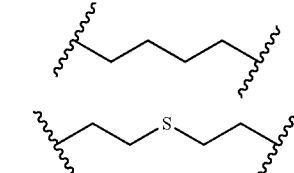
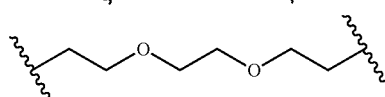
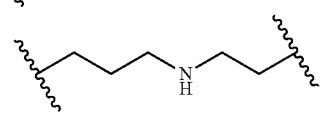

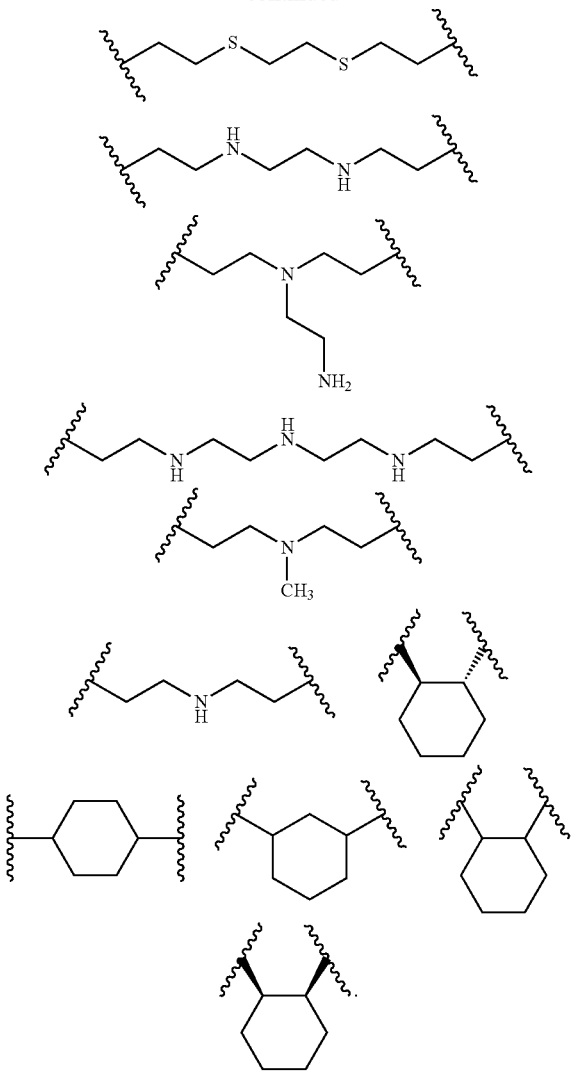

In certain embodiments, $R_1$ and $R_2$ are hydrogen. In certain embodiments, $R_1$ and $R_2$ are, independently, an unsubstituted and unbranched, $C_{1-20}$-aliphatic or $C_{1-20}$ heteroaliphatic moiety. In some embodiments, $R_1$ and $R_2$ are, independently, an unsubstituted and unbranched, $C_{10-12}$-aliphatic group. In some embodiments, $R_1$ and $R_2$ are

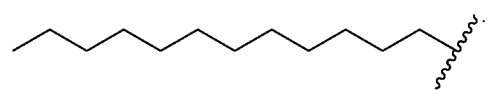 [SMILES: *CCCCCCCCCCCC]

In some embodiments, $R_1$ and $R_2$ are, independently, an unsubstituted and unbranched, $C_{13}$ heteroaliphatic group. In some embodiments, $R_1$ and $R_2$ are

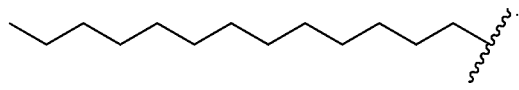 [SMILES: *CCCCCCCCCCCCC]

In some embodiments, $R_1$ and $R_2$ are, independently, an unsubstituted and unbranched, $C_{14}$ heteroaliphatic group. In some embodiments, $R_1$ and $R_2$ are

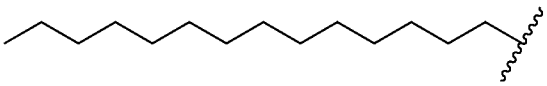

In certain embodiments, $R_1$ and $R_2$ are, independently, selected from the following formulae:

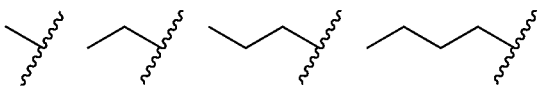
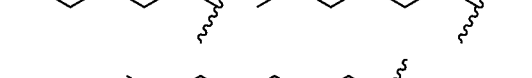
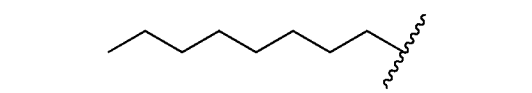
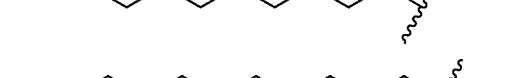
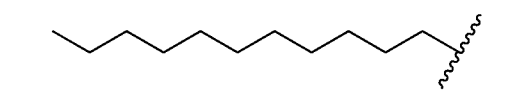
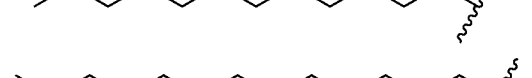
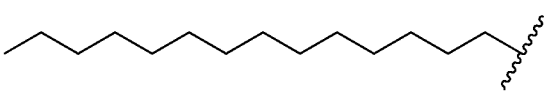
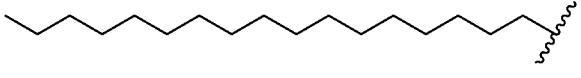

In certain embodiments, $R_1$ and $R_2$ are, a $C_{1-20}$ alkenyl moiety, optionally substituted. In certain embodiments, $R_1$ and $R_2$ are, independently, selected from the following formulae:

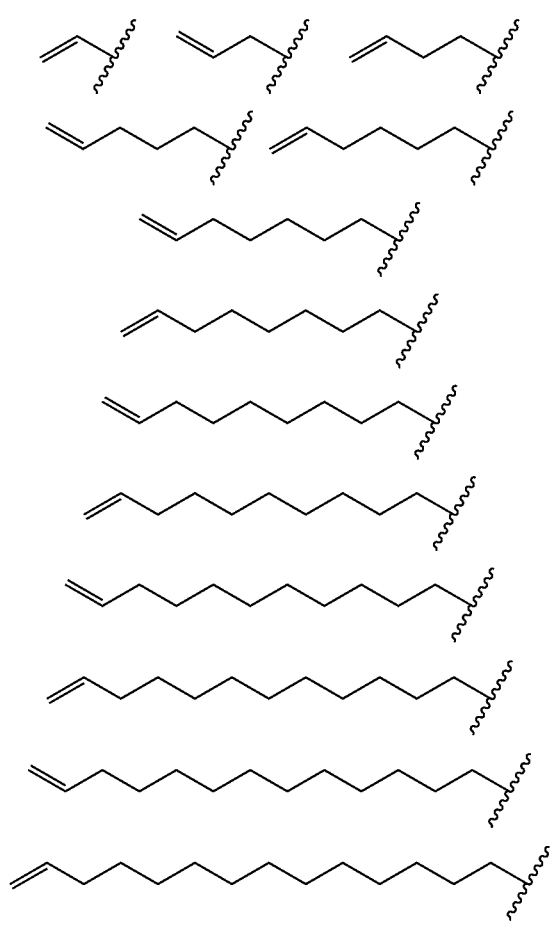
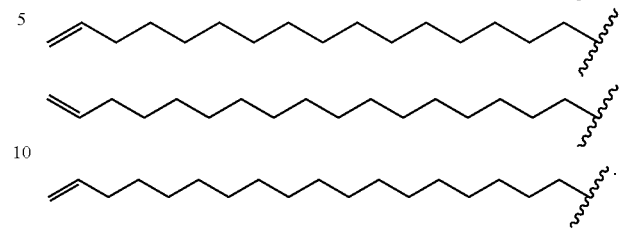
It will be appreciated by one of ordinary skill in the art that the above substituents may have multiple sites of unsaturation, and could be so at any position within the substituent.
In certain embodiments, $R_1$ and $R_2$ are:
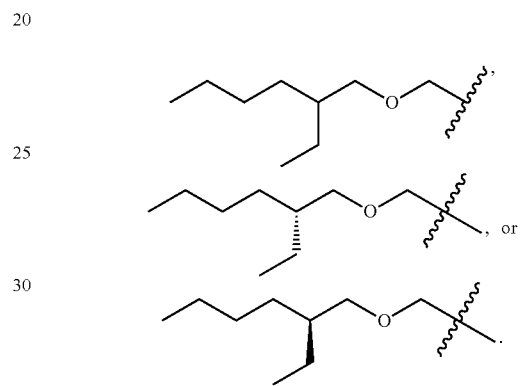
In certain embodiments, $R_1$ and $R_3$ are, independently, selected from the following formulae:
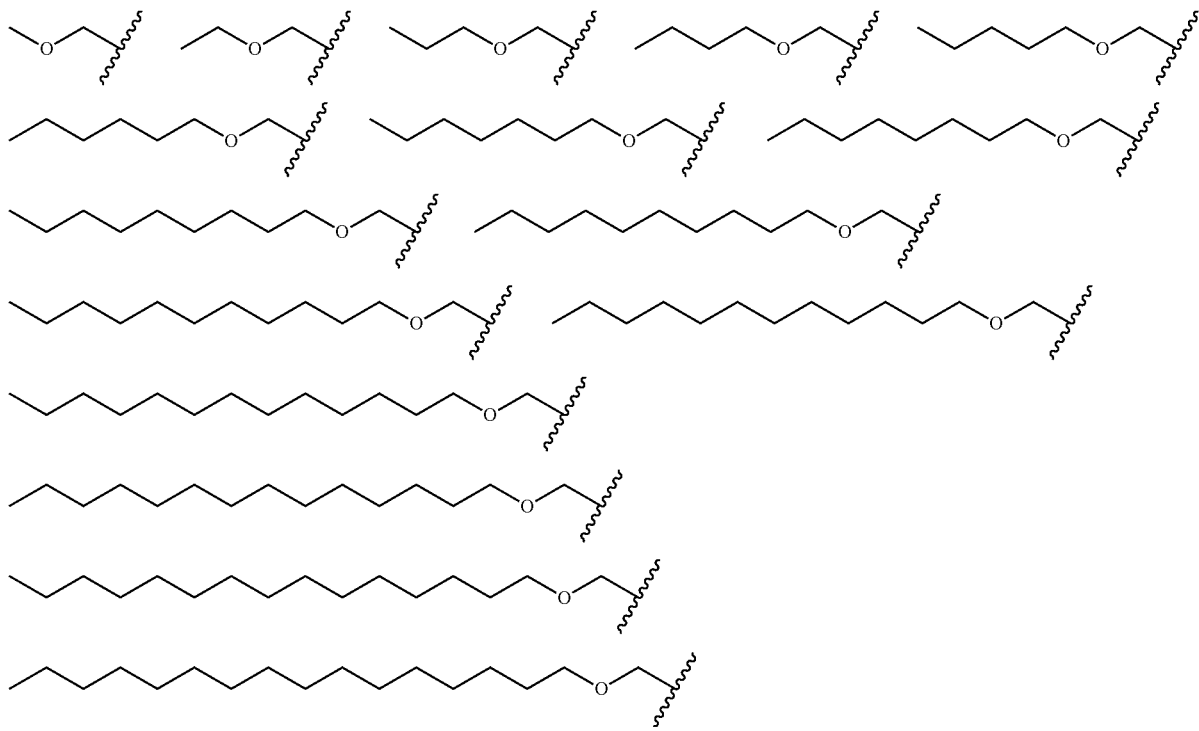

-continued

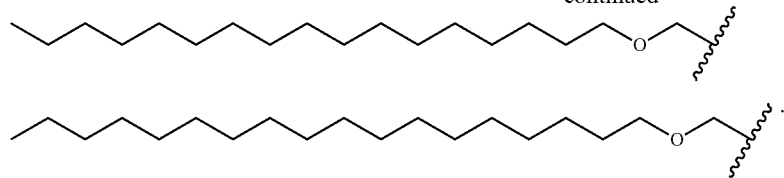

In certain embodiments, $R_1$ and $R_2$ are fluorinated. In certain embodiments $R_1$ and $R_2$ are a fluorinated aliphatic moiety. In certain embodiments $R_1$ and $R_2$ are perfluorinated. In certain embodiments $R_1$ and $R_2$ are a perfluorinated aliphatic moiety. In certain embodiments, $R_1$ and $R_2$ are a perfluorinated $C_{1-20}$ alkyl group. In certain embodiments, $R_1$ and $R_2$ are selected from the following formulae:

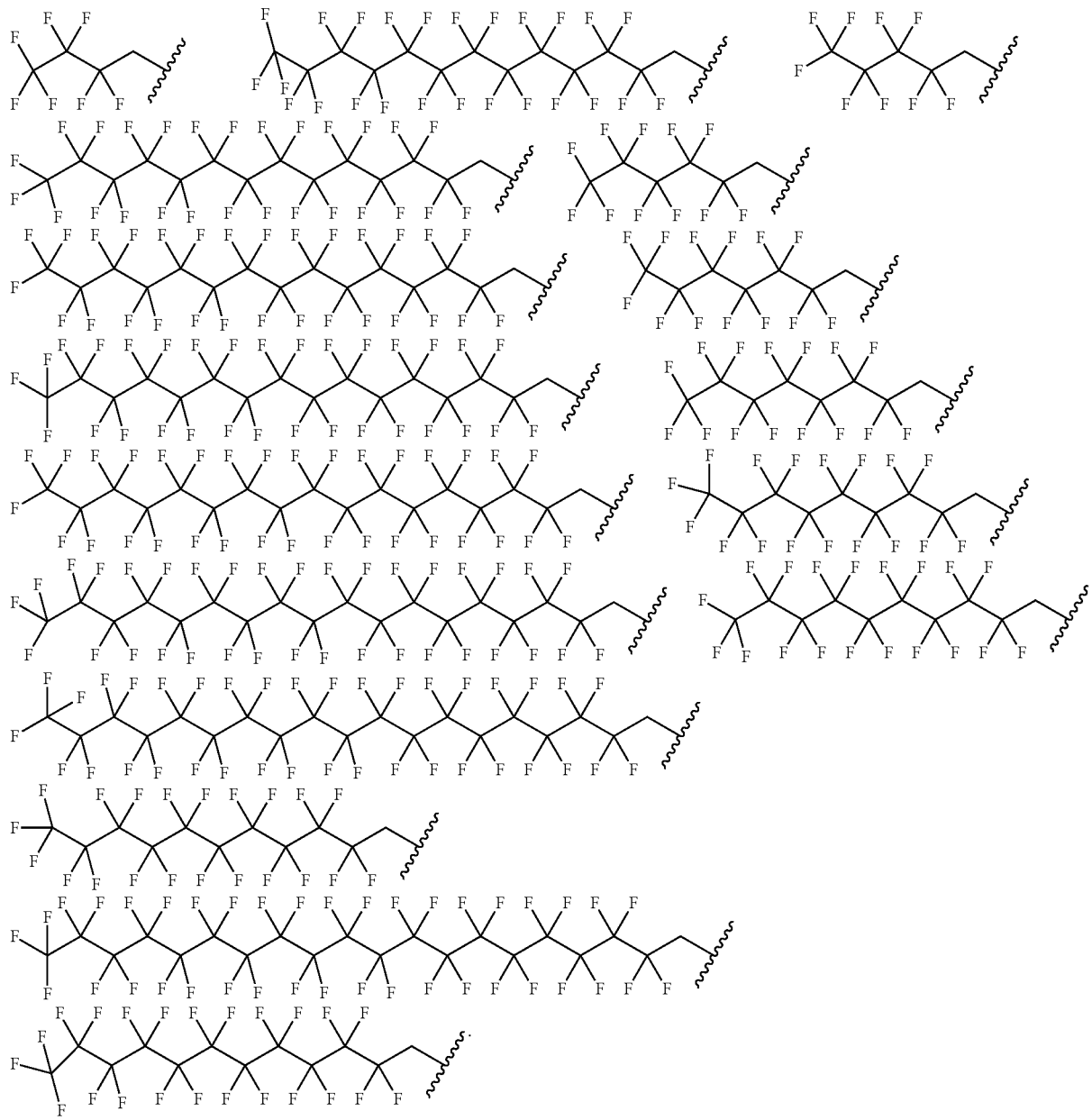

In certain embodiments, $R_1$ and $R_2$ are, independently, selected from the following formulae:

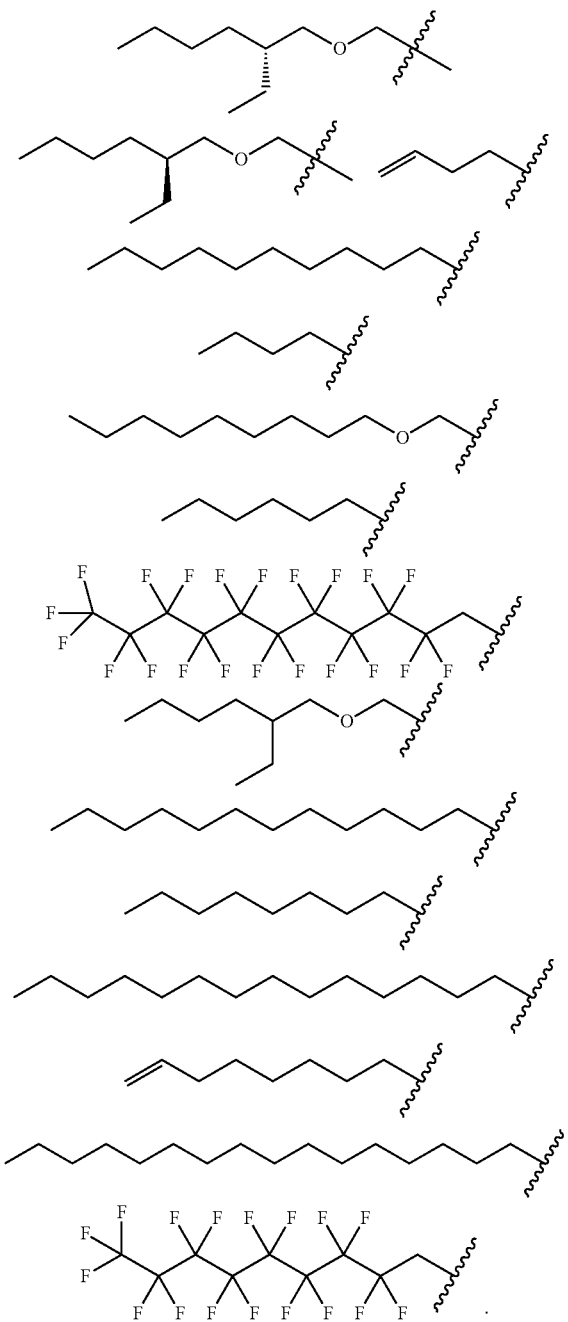

In certain embodiments, $R_1$ and $R_2$ are both the same. In certain embodiments, each of $R_1$ and $R_2$ are independently hydrogen or $C_1$-$C_6$ alkyl. In certain embodiments, $R_1$ and $R_2$ are both hydrogen. In certain embodiments, $R_1$ and $R_2$ are both $C_1$-$C_6$ alkyl. In certain embodiments, $R_1$ and $R_2$ are both hydroxyalkyl. In certain embodiments, $R_1$ and $R_2$ are both aminoalkyl. In certain embodiments, $R_1$ and $R_2$ are different.

In certain embodiments, $R_C$ is hydrogen. In certain embodiments, $R_C$ is an unsubstituted and unbranched $C_{1-20}$-aliphatic. In certain embodiments $R_C$ is $C_{1-6}$-alkyl. In certain embodiments $R_C$ is methyl. In certain embodiments $R_C$ is ethyl. In certain embodiments $R_C$ is propyl. In certain embodiments $R_C$ is butyl. In certain embodiments, $R_C$ is an unsubstituted and unbranched $C_{1-20}$-heteroaliphatic. In certain embodiments $R_C$ is $C_{1-6}$-heteroalkyl. In certain embodiments, $R_C$ is —CH$_2$CH(OH)$R_E$.

In certain embodiments, $R_D$ is hydrogen. In certain embodiments, $R_D$ is an unsubstituted and unbranched $C_{1-20}$-aliphatic. In certain embodiments $R_D$ is $C_{1-6}$-alkyl. In certain embodiments $R_D$ is methyl. In certain embodiments $R_D$ is ethyl. In certain embodiments $R_D$ is propyl. In certain embodiments $R_D$ is butyl. In certain embodiments, $R_D$ is an unsubstituted and unbranched $C_{1-20}$-heteroaliphatic. In certain embodiments $R_D$ is $C_{1-6}$-heteroalkyl. In certain embodiments, $R_D$ is —CH$_2$CH(OH)$R_E$.

In certain embodiments, $R_C$ and $R_D$ are both the same. In certain embodiments, each of $R_C$ and $R_D$ are independently hydrogen, or $C_1$-$C_6$ alkyl. In certain embodiments, $R_C$ and $R_D$ are both hydrogen. In certain embodiments, $R_C$ and $R_D$ are both $C_1$-$C_6$ alkyl. In certain embodiments, $R_C$ and $R_D$ are both hydroxyalkyl. In certain embodiments, $R_C$ and $R_D$ are both aminoalkyl. In certain embodiments, $R_C$ and $R_D$ are different.

In certain embodiments, $R_E$ is hydrogen. In certain embodiments, $R_E$ is an unsubstituted and unbranched $C_{1-20}$-aliphatic. In certain embodiments $R_E$ is $C_{1-6}$-alkyl. In certain embodiments $R_E$ is methyl. In certain embodiments $R_E$ is ethyl. In certain embodiments $R_E$ is propyl. In certain embodiments $R_E$ is butyl. In certain embodiments, $R_E$ is an unsubstituted and unbranched $C_{1-20}$-heteroaliphatic. In certain embodiments $R_E$ is $C_{1-6}$-heteroalkyl.

Particular exemplary compounds include:

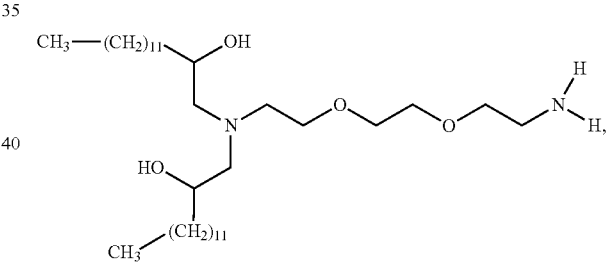

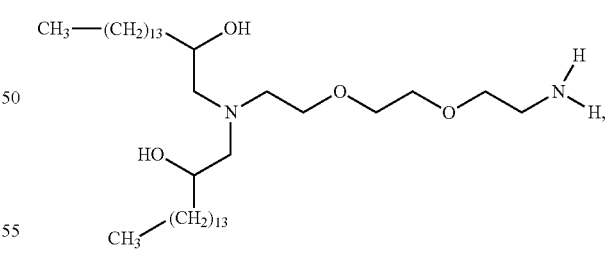

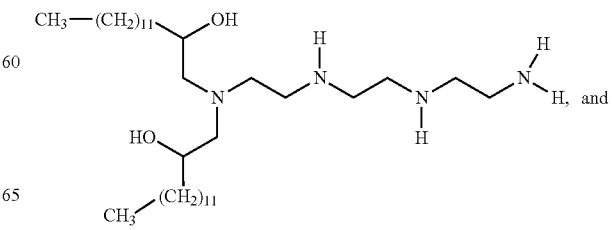

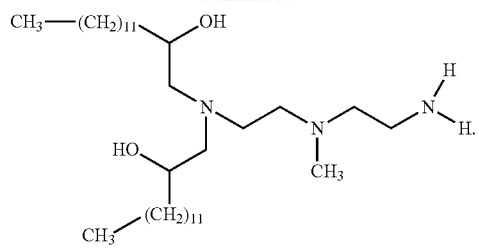

In certain embodiments, the aminoalcohol lipidoid compound of the present invention is of the formula:

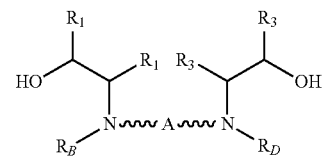

wherein:

A is a substituted or unsubstituted, branched or unbranched, cyclic or acyclic $C_{2-20}$ alkylene, optionally interrupted by 1 or more heteroatoms independently selected from O, S and N, or A is a substituted or unsubstituted, saturated or unsaturated 4-6-membered ring;

$R_1$ and $R_3$ are, independently, hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen and at least one occurrence of $R_3$ is hydrogen;

$R_B$ and $R_D$ are, independently, hydrogen, a substituted, unsubstituted, branched or unbranched $C_{1-20}$-aliphatic, or a substituted, unsubstituted, branched or unbranched $C_{1-20}$-heteroaliphatic or —$CH_2CH(OH)R_E$;

$R_B$ and $R_D$ together may optionally form a cyclic structure; and $R_E$ is a substituted, unsubstituted, branched or unbranched $C_{1-20}$ aliphatic or a substituted, unsubstituted, branched or unbranched $C_{1-20}$ heteroaliphatic; or a pharmaceutically acceptable salt thereof.

In certain embodiments, each

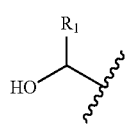

is independently

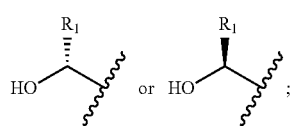

and each

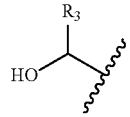

is independently

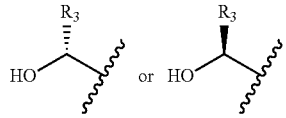

In certain embodiments, A is an unsubstituted, unbranched, and acyclic $C_{2-20}$ alkylene. In certain embodiments, A is a substituted or unsubstituted, branched or unbranched, cyclic or acyclic $C_{2-20}$ alkylene, optionally interrupted by 1 or more nitrogen atoms. In certain embodiments A is a substituted, unbranched, and acyclic $C_{2-10}$ alkylene, optionally interrupted by 1 oxygen atom. In certain embodiments, A is of the formula

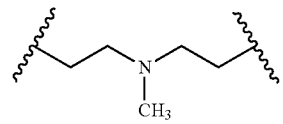

In certain embodiments, A is a substituted or unsubstituted, branched or unbranched, cyclic or acyclic $C_{2-20}$ alkylene, optionally interrupted by 1 or more oxygen atoms. In certain embodiments A is an unsubstituted, unbranched, and acyclic $C_{2-10}$ alkylene, optionally interrupted by 1 or more oxygen atoms. In certain embodiments A is an unsubstituted, unbranched, and acyclic $C_{2-10}$ alkylene, optionally interrupted by 2 oxygen atoms. In certain embodiments, A is of the formula

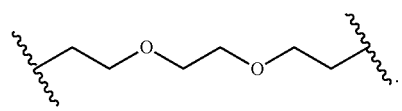 [SMILES: *CCOCCOCC*]

In certain embodiments, A is of the formula

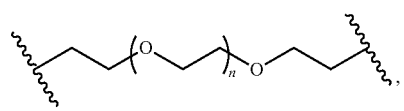

wherein n is an integer between 1 and 10, inclusive. In certain embodiments, A is a substituted or unsubstituted, branched or unbranched, cyclic or acyclic $C_{2-20}$ alkylene, optionally interrupted by 1 or more nitrogen atoms. In certain embodiments A is an unsubstituted, unbranched, and acyclic $C_{2-10}$ alkylene, optionally interrupted by 1 or more nitrogen atoms. In certain embodiments A is an unsubstituted, unbranched, and acyclic $C_{2-10}$ alkylene, optionally interrupted by 2 nitrogen atoms. In certain embodiments, A is of the formula

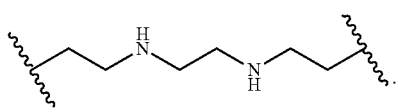

In certain embodiments, A is of the formula

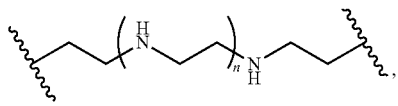

wherein n is an integer between 1 and 10, inclusive.

In certain embodiments, A is selected from the following formulae:

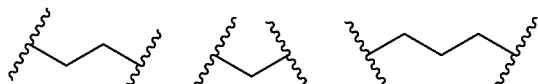

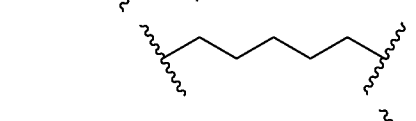

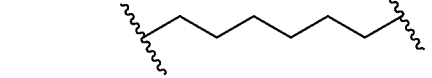

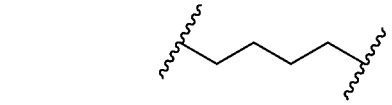

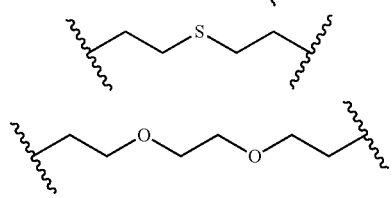

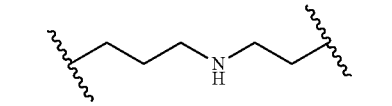

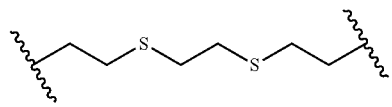

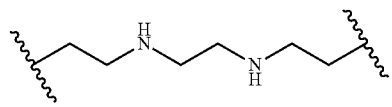

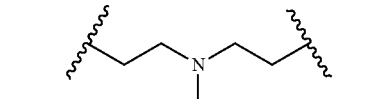

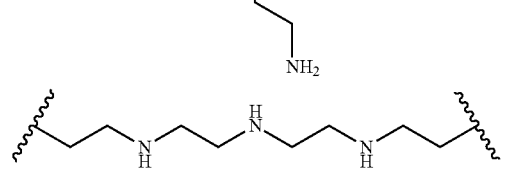

-continued

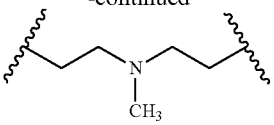

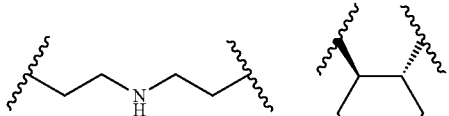
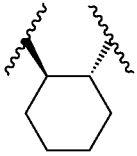

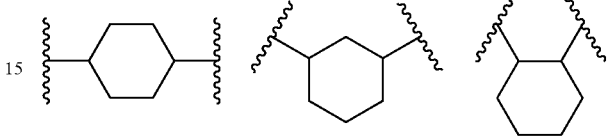

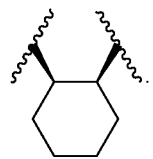

In certain embodiments, $R_1$ and $R_3$ are hydrogen. In certain embodiments, $R_1$ and $R_3$ are, independently, an unsubstituted and unbranched, $C_{1-20}$-aliphatic or $C_{1-20}$ heteroaliphatic moiety. In some embodiments, $R_1$ and $R_3$ are, independently, an unsubstituted and unbranched, $C_{10-12}$-aliphatic group. In some embodiments, $R_1$ and $R_3$ are

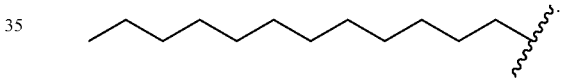

In some embodiments, $R_1$ and $R_3$ are, independently, an unsubstituted and unbranched, $C_{13}$ heteroaliphatic group. In some embodiments, $R_1$ and $R_3$ are

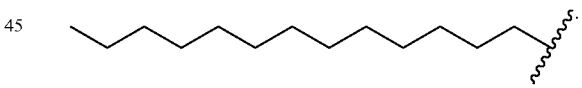

In some embodiments, $R_1$ and $R_3$ are, independently, an unsubstituted and unbranched, $C_{14}$ heteroaliphatic group. In some embodiments, $R_1$ and $R_3$ are

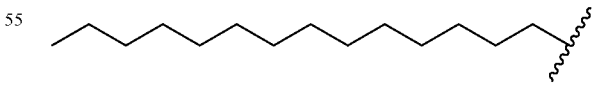

In certain embodiments, $R_1$ and $R_3$ are, independently, selected from the following formulae:

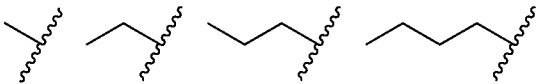

-continued

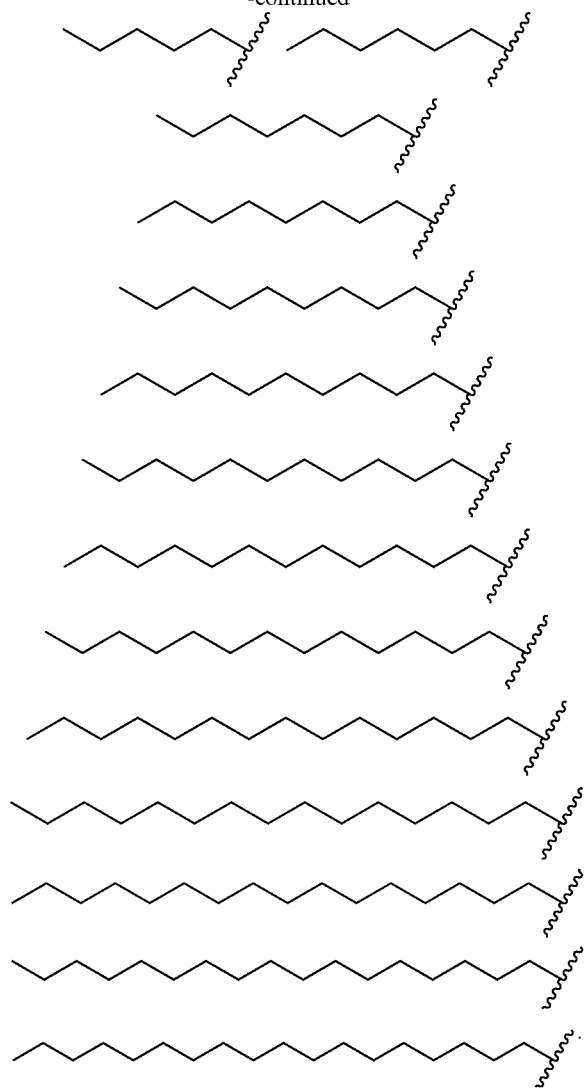

In certain embodiments, $R_1$ and $R_3$ are, a $C_{1-20}$ alkenyl moiety, optionally substituted. In certain embodiments, $R_1$ and $R_3$ are, independently, selected from the following formulae:

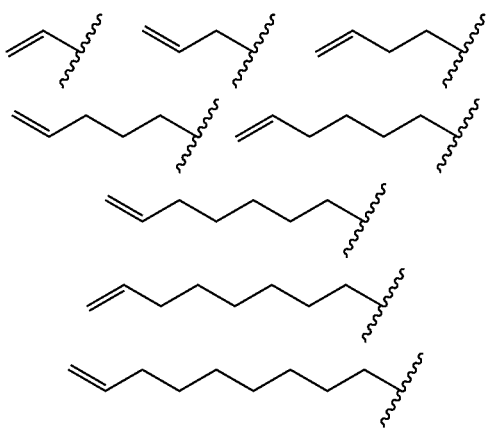

-continued

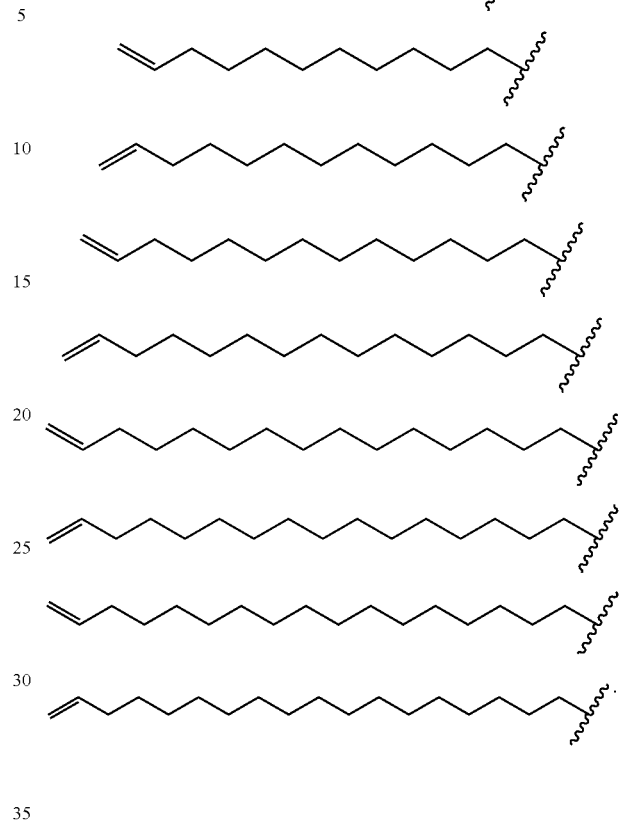

It will be appreciated by one of ordinary skill in the art that the above substituents may have multiple sites of unsaturation, and could be so at any position within the substituent.

In certain embodiments, $R_1$ and $R_3$ are:

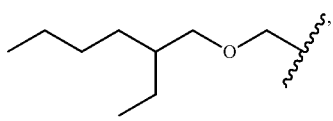

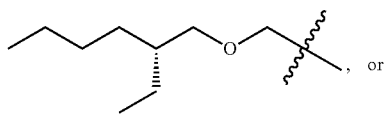, or

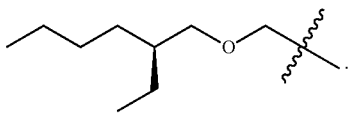

In certain embodiments, $R_1$ and $R_3$ are, independently, selected from the following formulae:

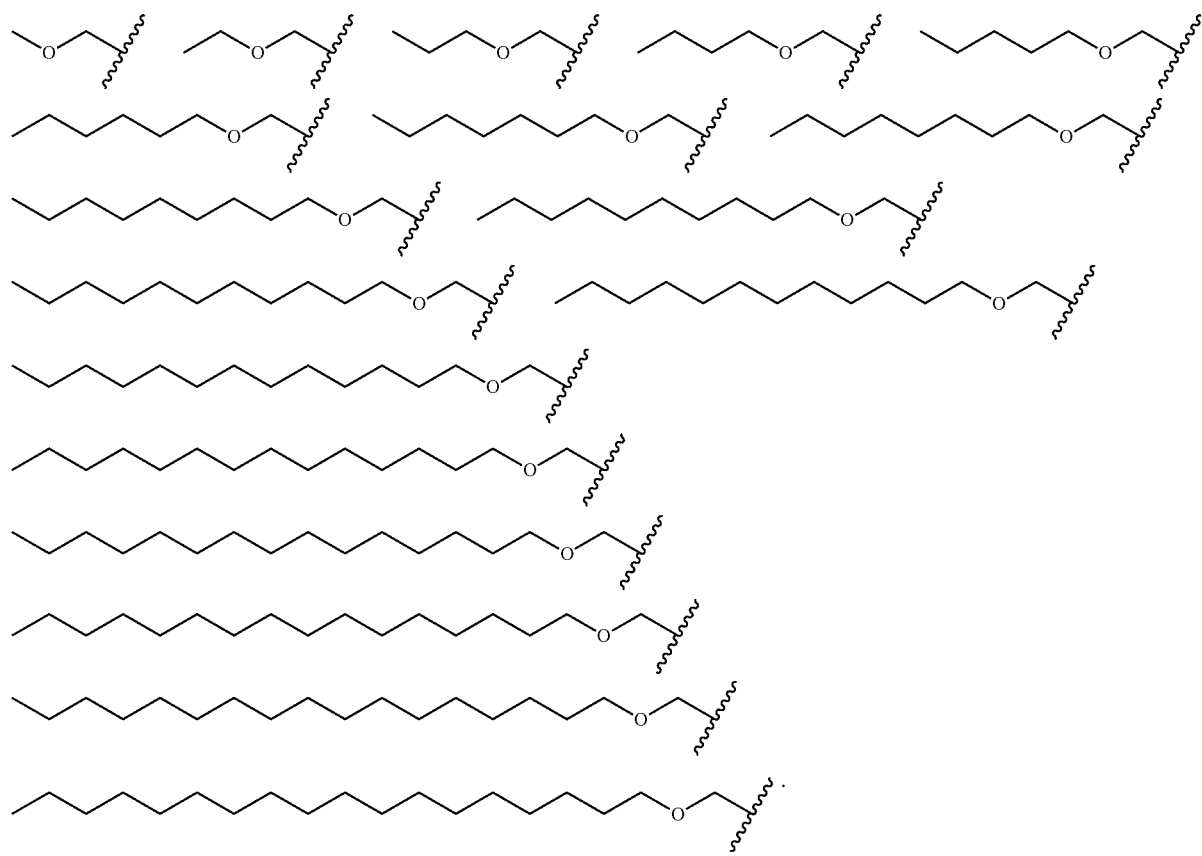

In certain embodiments, $R_1$ and $R_3$ are fluorinated. In certain embodiments $R_1$ and $R_3$ are a fluorinated aliphatic moiety. In certain embodiments $R_1$ and $R_3$ are perfluorinated. In certain embodiments $R_1$ and $R_3$ are a perfluorinated aliphatic moiety. In certain embodiments, $R_1$ and $R_3$ are a perfluorinated $C_{1-20}$ alkyl group. In certain embodiments, $R_1$ and $R_3$ are selected from the following formulae:

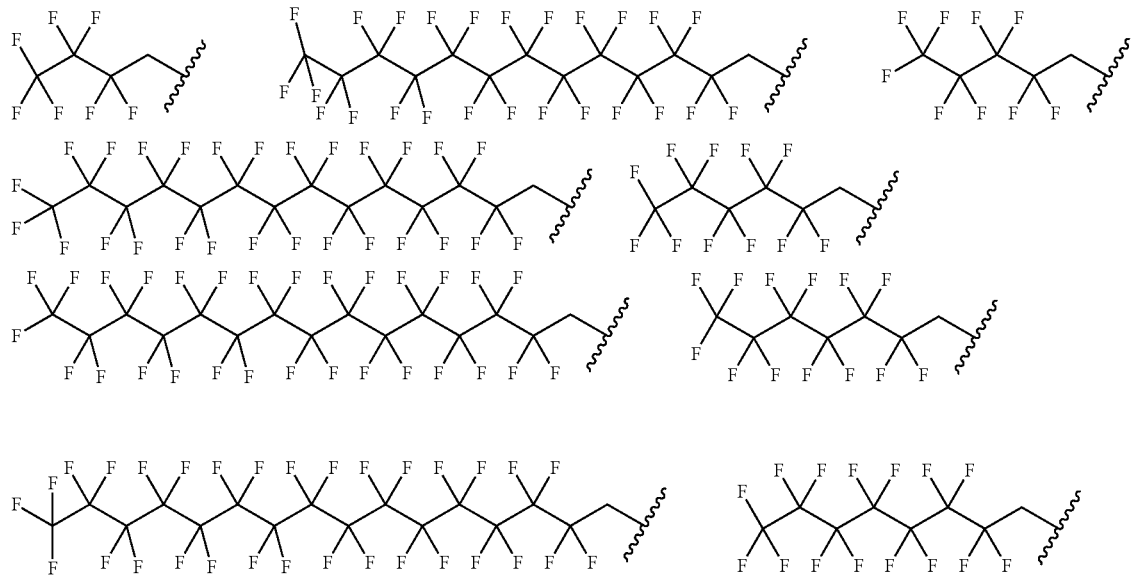

-continued

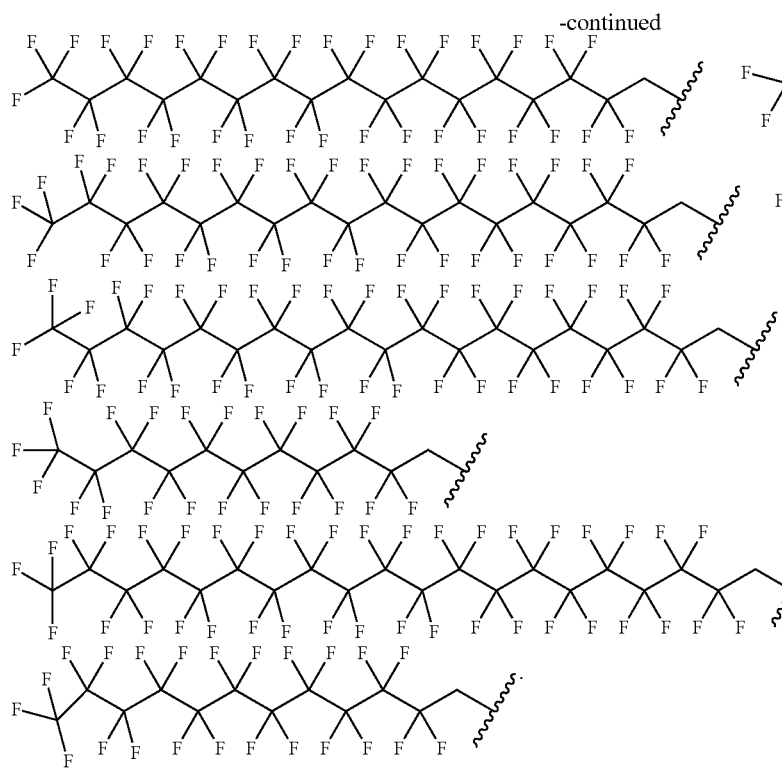

In certain embodiments, $R_1$ and $R_3$ are, independently, selected from the following formulae:

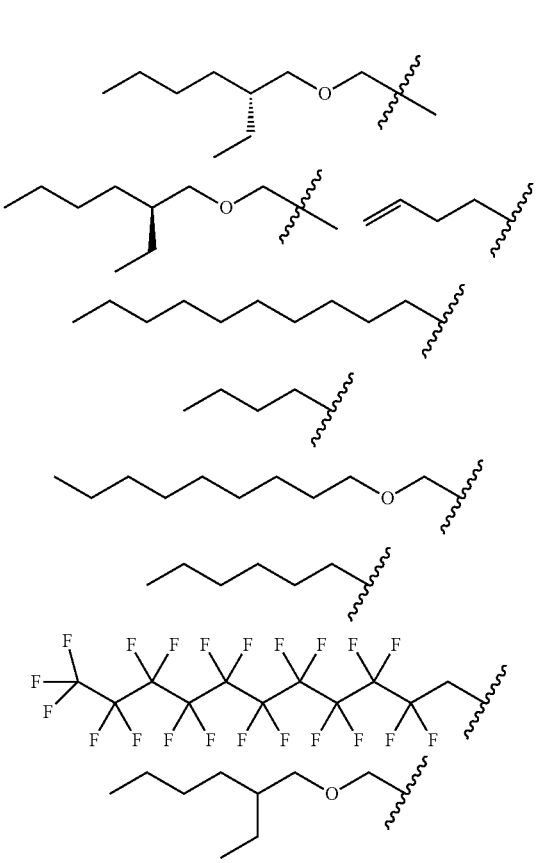

-continued

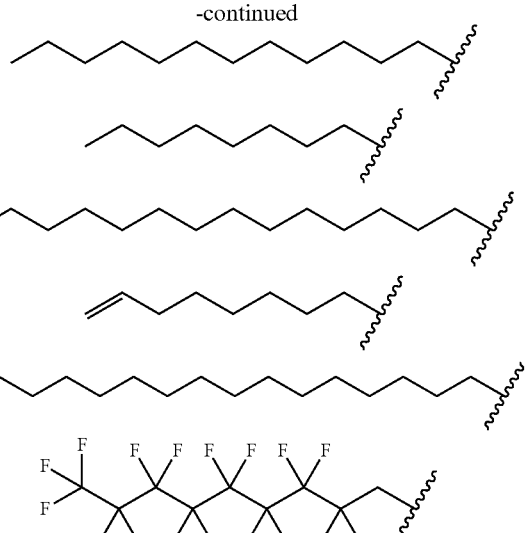

In certain embodiments, $R_1$ and $R_3$ are both the same. In certain embodiments, each of $R_1$ and $R_3$ are independently hydrogen, or $C_1$-$C_6$ alkyl. In certain embodiments, $R_1$ and $R_3$ are both hydrogen. In certain embodiments, $R_1$ and $R_3$ are both $C_1$-$C_6$ alkyl. In certain embodiments, $R_1$ and $R_3$ are both hydroxyalkyl. In certain embodiments, $R_1$ and $R_3$ are both aminoalkyl. In certain embodiments, $R_1$ and $R_3$ are different.

In certain embodiments, $R_B$ is hydrogen. In certain embodiments, $R_B$ is an unsubstituted and unbranched $C_{1-20}$-aliphatic. In certain embodiments $R_B$ is $C_{1-6}$-alkyl. In certain embodiments $R_B$ is methyl. In certain embodiments $R_B$ is ethyl. In certain embodiments $R_B$ is propyl. In certain embodiments $R_B$ is butyl. In certain embodiments, $R_B$ is an unsubstituted and unbranched $C_{1-20}$-heteroaliphatic. In certain embodiments $R_B$ is $C_{1-6}$-heteroalkyl. In certain embodiments, $R_B$ is —CH$_2$CH(OH)R$_E$.

In certain embodiments, $R_D$ is hydrogen. In certain embodiments, $R_D$ is an unsubstituted and unbranched $C_{1-20}$-aliphatic. In certain embodiments $R_D$ is $C_{1-6}$-alkyl. In certain embodiments $R_D$ is methyl. In certain embodiments $R_D$ is ethyl. In certain embodiments $R_D$ is propyl. In certain embodiments $R_D$ is butyl. In certain embodiments, $R_D$ is an unsubstituted and unbranched $C_{1-20}$-heteroaliphatic. In certain embodiments $R_D$ is $C_{1-6}$-heteroalkyl. In certain embodiments, $R_D$ is —CH$_2$CH(OH)R$_E$.

In certain embodiments, $R_B$ and $R_D$ are both the same. In certain embodiments, each of $R_B$ and $R_D$ are independently hydrogen, or $C_1$-$C_6$ alkyl. In certain embodiments, $R_B$ and $R_D$ are both hydrogen. In certain embodiments, $R_B$ and $R_D$ are both $C_1$-$C_6$ alkyl. In certain embodiments, $R_B$ and $R_D$ are both hydroxyalkyl. In certain embodiments, $R_B$ and $R_D$ are both aminoalkyl. In certain embodiments, $R_B$ and $R_D$ are different.

In certain embodiments, $R_E$ is hydrogen. In certain embodiments, $R_E$ is an unsubstituted and unbranched $C_{1-20}$-aliphatic. In certain embodiments $R_E$ is $C_{1-6}$-alkyl. In certain embodiments $R_E$ is methyl. In certain embodiments $R_E$ is ethyl. In certain embodiments $R_E$ is propyl. In certain embodiments $R_E$ is butyl. In certain embodiments, $R_E$ is an unsubstituted and unbranched $C_{1-20}$-heteroaliphatic. In certain embodiments $R_E$ is $C_{1-6}$-heteroalkyl.

Particular exemplary compounds include:

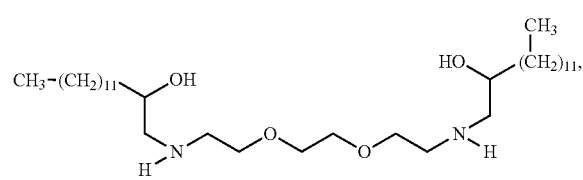

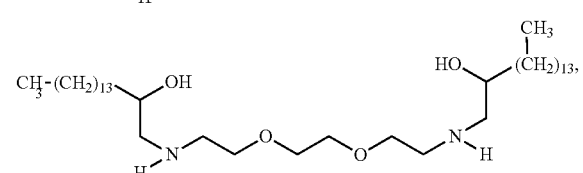

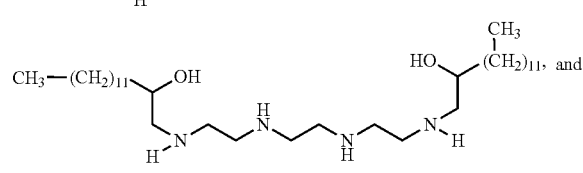

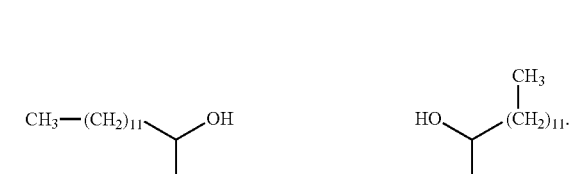

In certain embodiments, each

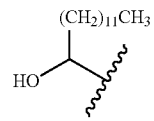

is independently

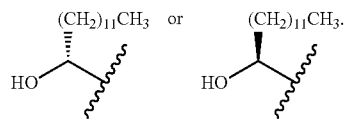

In certain embodiments, the aminoalcohol lipidoid compound of the present invention is of the formula:

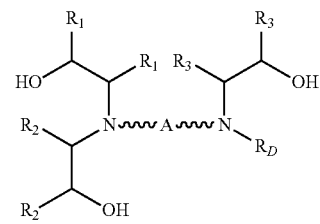

wherein:

A is a substituted or unsubstituted, branched or unbranched, cyclic or acyclic $C_{2-20}$ alkylene, optionally interrupted by 1 or more heteroatoms independently selected from O, S and N, or A is a substituted or unsubstituted, saturated or unsaturated 4-6-membered ring;

$R_1$, $R_2$, and $R_3$ are, independently, hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen, at least one occurrence of $R_2$ is hydrogen and at least one occurrence of $R_3$ is hydrogen;

$R_D$ is hydrogen, a substituted, unsubstituted, branched or unbranched $C_{1-20}$-aliphatic, or a substituted, unsubstituted, branched or unbranched $C_{1-20}$-heteroaliphatic or —CH$_2$CH(OH)R$_E$; and $R_E$ is a substituted, unsubstituted, branched or unbranched $C_{1-20}$ aliphatic or a substituted, unsubstituted, branched or unbranched $C_{1-20}$ heteroaliphatic; or a pharmaceutically acceptable salt thereof.

In certain embodiments, each

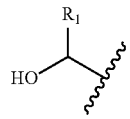

is independently

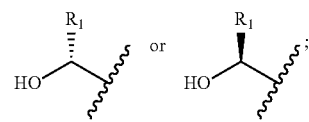

each

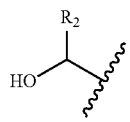

is independently

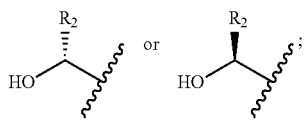

and each

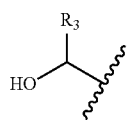

is independently

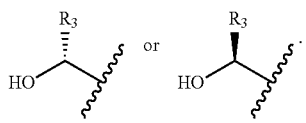

In certain embodiments, A is an unsubstituted, unbranched, and acyclic $C_{2-20}$ alkylene. In certain embodiments, A is a substituted or unsubstituted, branched or unbranched, cyclic or acyclic $C_{2-20}$ alkylene, optionally interrupted by 1 or more nitrogen atoms. In certain embodiments A is a substituted, unbranched, and acyclic $C_{2-10}$ alkylene, optionally interrupted by 1 oxygen atom. In certain embodiments, A is of the formula

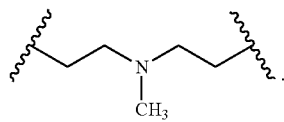 [SMILES: *CCN(C)CC*]

In certain embodiments, A is a substituted or unsubstituted, branched or unbranched, cyclic or acyclic $C_{2-20}$ alkylene, optionally interrupted by 1 or more oxygen atoms. In certain embodiments A is an unsubstituted, unbranched, and acyclic $C_{2-10}$ alkylene, optionally interrupted by 1 or more oxygen atoms. In certain embodiments A is an unsubstituted, unbranched, and acyclic $C_{2-10}$ alkylene, optionally interrupted by 2 oxygen atoms. In certain embodiments, A is of the formula

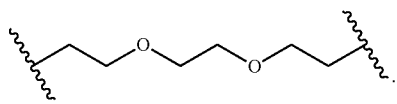 [SMILES: *CCOCCOCC*]

In certain embodiments, A is of the formula

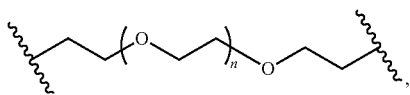

wherein n is an integer between 1 and 10, inclusive. In certain embodiments, A is a substituted or unsubstituted, branched or unbranched, cyclic or acyclic $C_{2-20}$ alkylene, optionally interrupted by 1 or more nitrogen atoms. In certain embodiments A is an unsubstituted, unbranched, and acyclic $C_{2-10}$ alkylene, optionally interrupted by 1 or more nitrogen atoms. In certain embodiments A is an unsubstituted, unbranched, and acyclic $C_{2-10}$ alkylene, optionally interrupted by 2 nitrogen atoms. In certain embodiments, A is of the formula

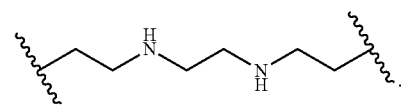 [SMILES: *CCNCCNCC*]

In certain embodiments, A is of the formula

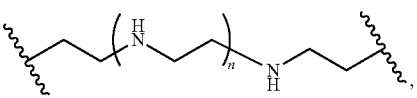

wherein n is an integer between 1 and 10, inclusive.

In certain embodiments, A is selected from the following formulae:

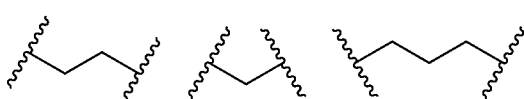
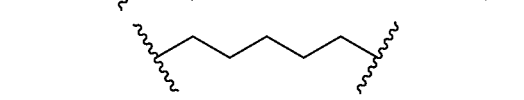
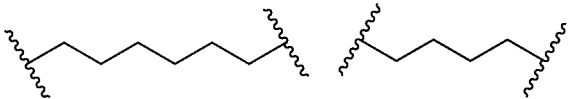
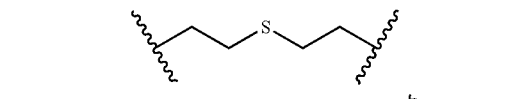
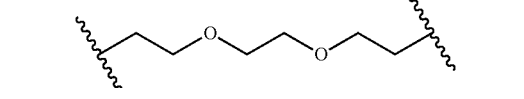
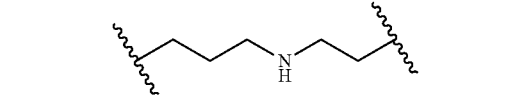
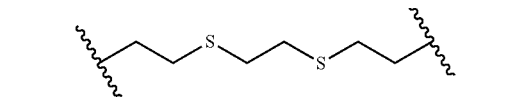

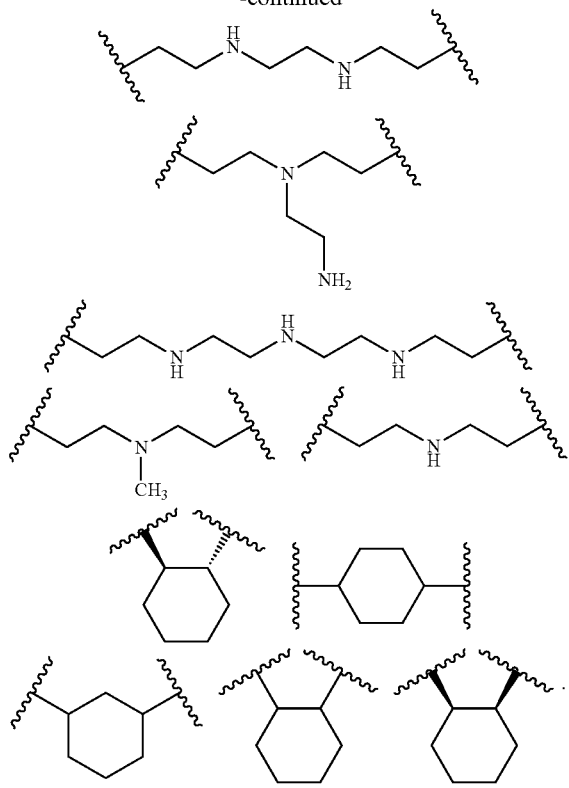

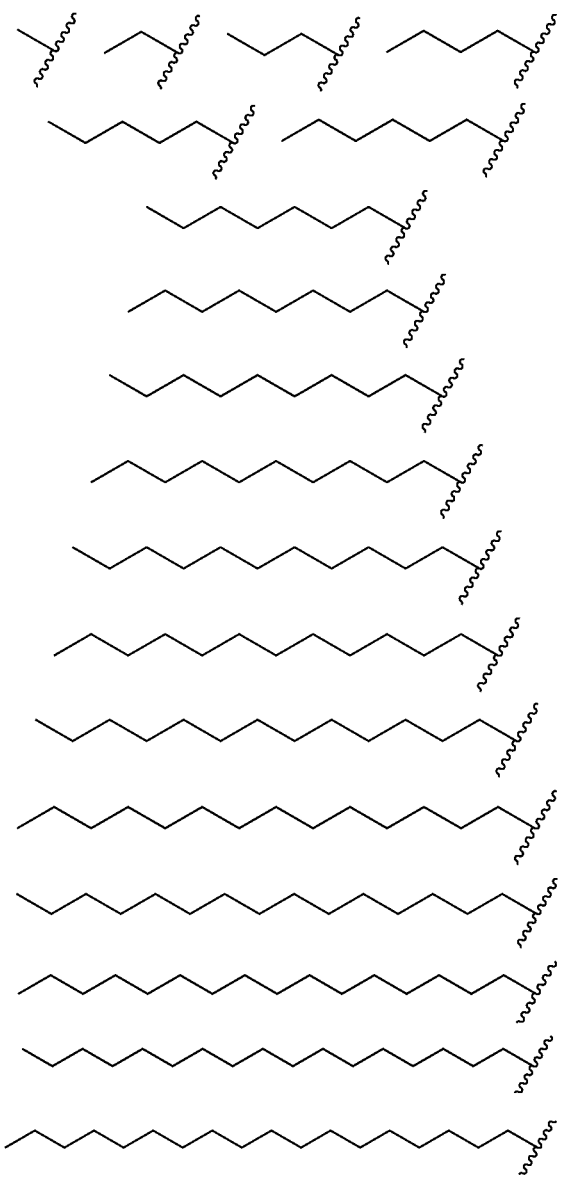

In certain embodiments, $R_1$, $R_2$ and $R_3$ are hydrogen. In certain embodiments, $R_1$, $R_2$ and $R_3$ are, independently, an unsubstituted and unbranched, $C_{1-20}$ aliphatic or $C_{1-20}$ heteroaliphatic moiety. In some embodiments, $R_1$, $R_2$ and $R_3$ are, independently, an unsubstituted and unbranched, $C_{12}$-aliphatic group. In some embodiments, $R_1$, $R_2$ and $R_3$ are

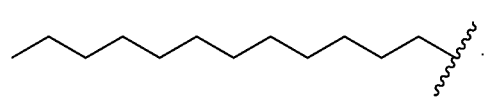 [SMILES: *CCCCCCCCCCCC]

In some embodiments, $R_1$, $R_2$ and $R_3$ are, independently, an unsubstituted and unbranched, $C_{13}$ heteroaliphatic group. In some embodiments, $R_1$, $R_2$ and $R_3$ are

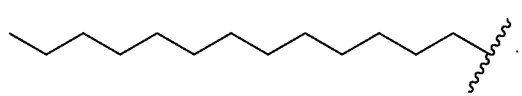 [SMILES: *CCCCCCCCCCCCC]

In some embodiments, $R_1$, $R_2$ and $R_3$ are, independently, an unsubstituted and unbranched, $C_{14}$ heteroaliphatic group. In some embodiments, $R_1$, $R_2$ and $R_3$ are

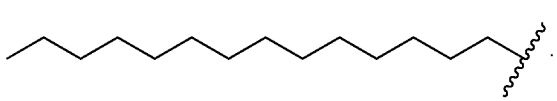 [SMILES: *CCCCCCCCCCCCCC]

In certain embodiments, $R_1$, $R_2$ and $R_3$ are, independently, selected from the following formulae:

In certain embodiments, $R_1$, $R_2$, and $R_3$ are, a $C_{1-20}$ alkenyl moiety, optionally substituted. In certain embodiments, $R_1$, $R_2$, and $R_3$ are, independently, selected from the following formulae:

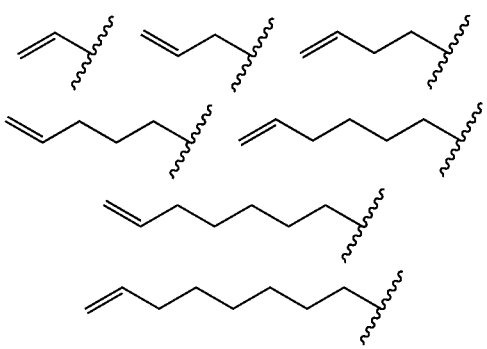

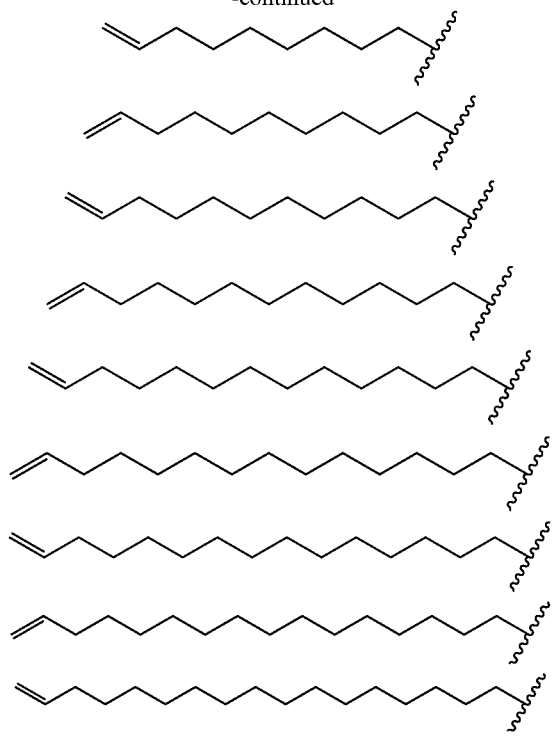
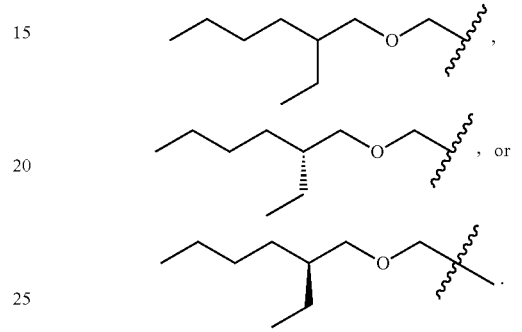
It will be appreciated by one of ordinary skill in the art that the above substituents may have multiple sites of unsaturation, and could be so at any position within the substituent.
In certain embodiments, $R_1$, $R_2$, and $R_3$ are:
In certain embodiments, $R_1$, $R_2$, and $R_3$ are, independently, selected from the following formulae:
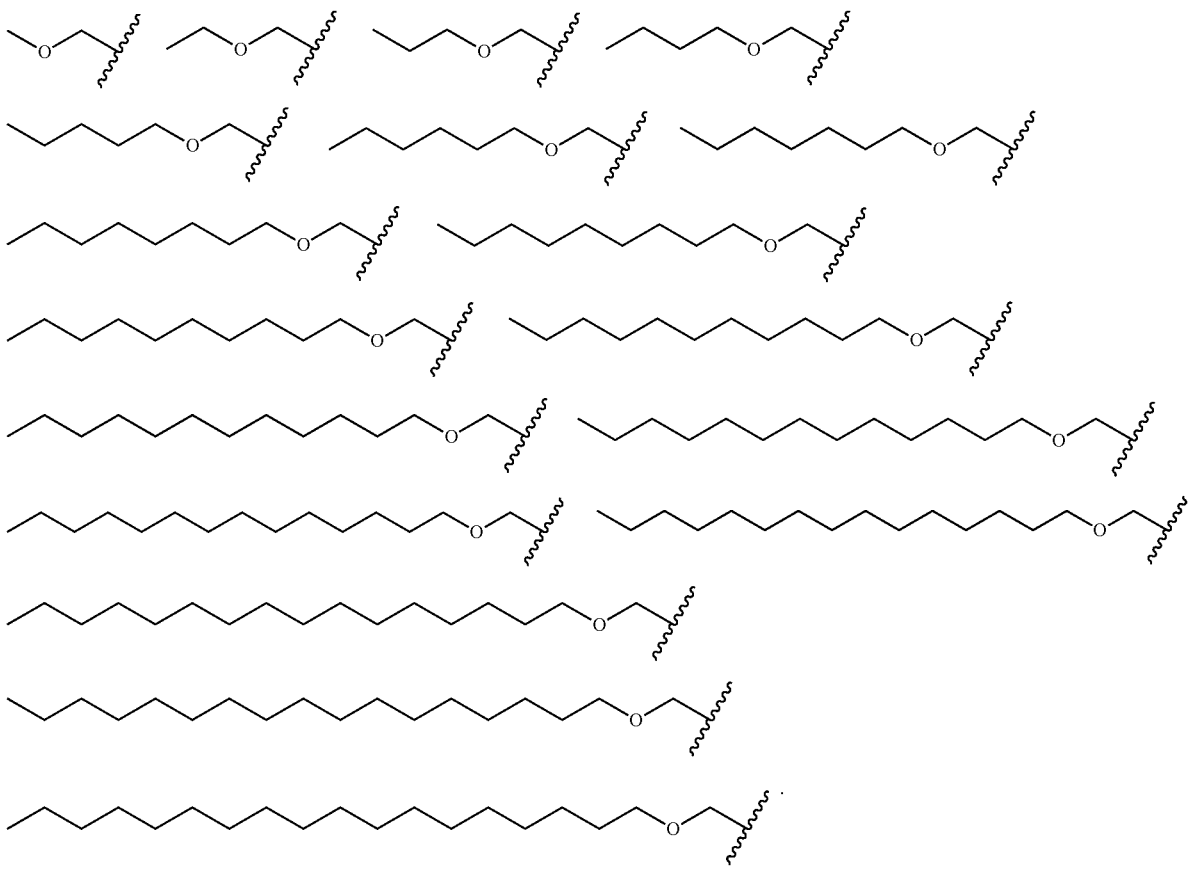

In certain embodiments, $R_1$, $R_2$ and $R_3$ are fluorinated. In certain embodiments $R_1$, $R_2$ and $R_3$ are a fluorinated aliphatic moiety. In certain embodiments $R_1$, $R_2$ and $R_3$ are perfluorinated. In certain embodiments $R_1$, $R_2$ and $R_3$ are a perfluorinated aliphatic moiety. In certain embodiments, $R_1$, $R_2$ and $R_3$ are a perfluorinated $C_{1-20}$ alkyl group. In certain embodiments, $R_1$, $R_2$ and $R_3$ are selected from the following formulae:

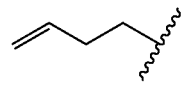

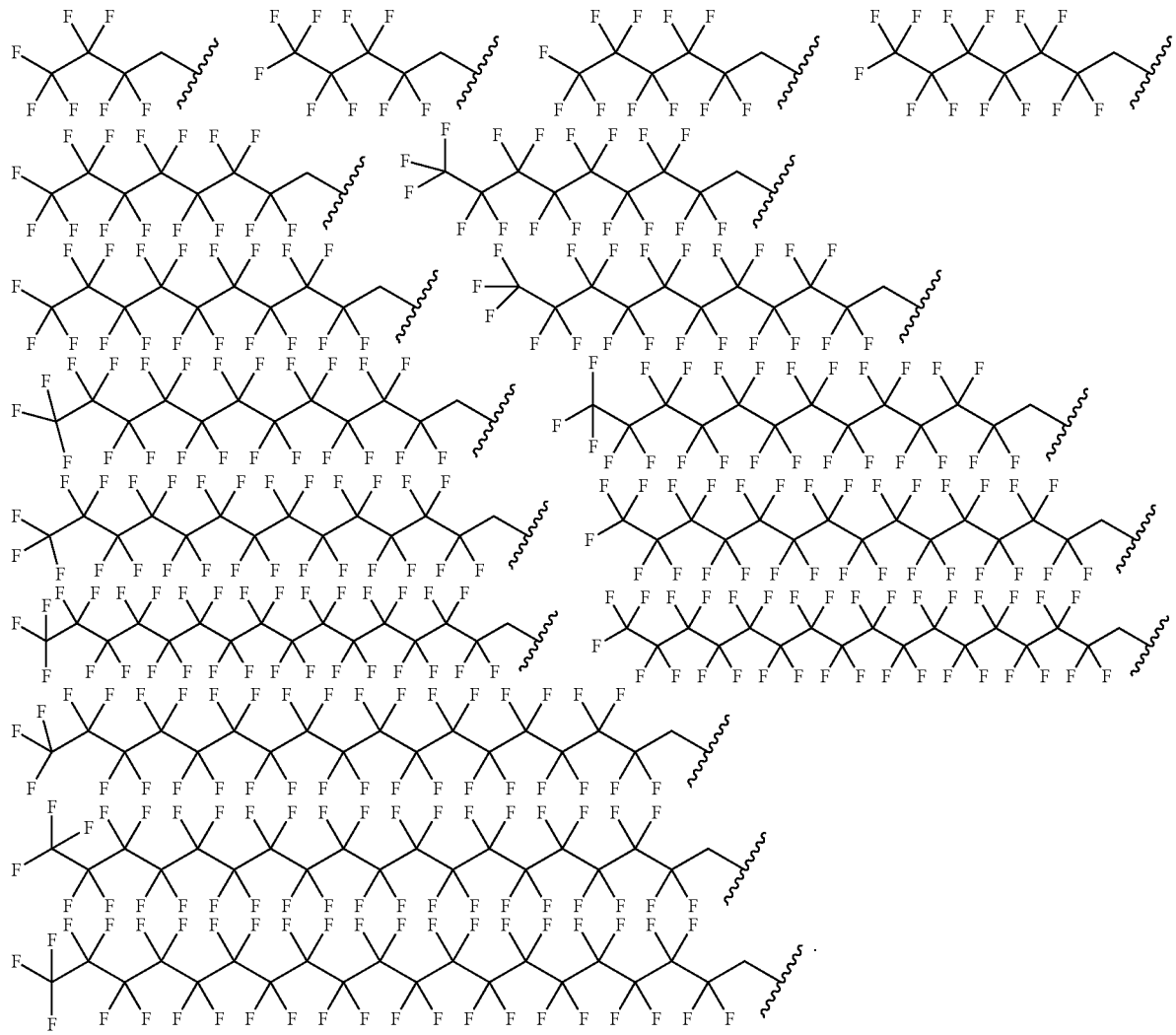

In certain embodiments, $R_1$, $R_2$, and $R_3$ are, independently, selected from the following formulae:

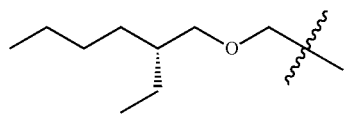

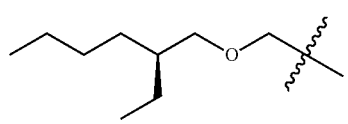

-continued

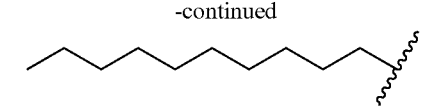

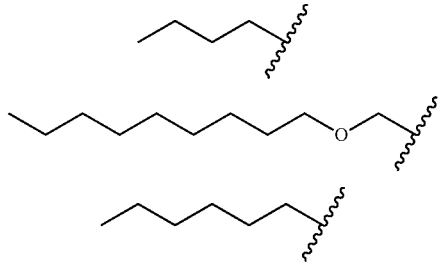

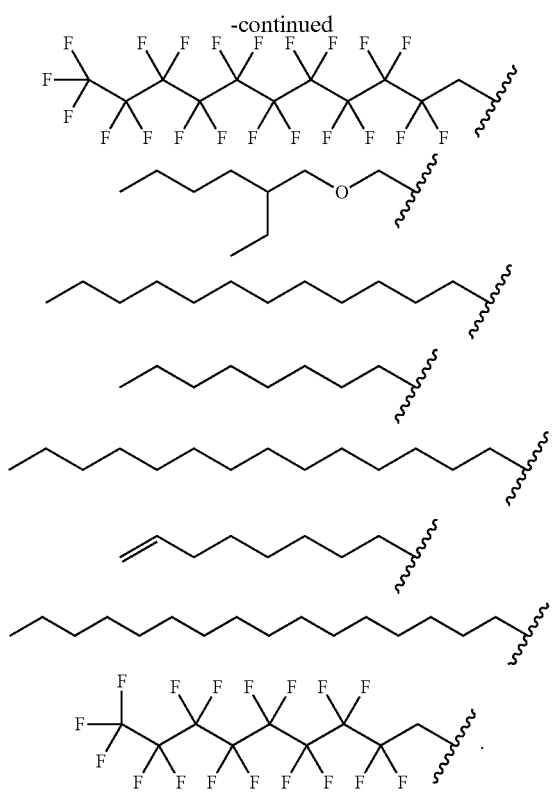

In certain embodiments, $R_1$, $R_2$, and $R_3$ are all the same. In certain embodiments, at least two of $R_1$, $R_2$, and $R_3$ are the same. In certain embodiments, $R_1$, $R_2$, and $R_3$ are all different.

In certain embodiments, $R_D$ is hydrogen. In certain embodiments, $R_D$ is an unsubstituted and unbranched $C_{1-20}$-aliphatic. In certain embodiments $R_D$ is $C_{1-6}$-alkyl. In certain embodiments $R_D$ is methyl. In certain embodiments $R_D$ is ethyl. In certain embodiments $R_D$ is propyl. In certain embodiments $R_D$ is butyl. In certain embodiments, $R_D$ is an unsubstituted and unbranched $C_{1-20}$-heteroaliphatic. In certain embodiments $R_D$ is $C_{1-6}$-heteroalkyl. In certain embodiments, $R_D$ is —CH$_2$CH(OH)R$_E$.

In certain embodiments, $R_E$ is hydrogen. In certain embodiments, $R_E$ is an unsubstituted and unbranched $C_{1-20}$-aliphatic. In certain embodiments $R_E$ is $C_{1-6}$-alkyl. In certain embodiments $R_E$ is methyl. In certain embodiments $R_E$ is ethyl. In certain embodiments $R_E$ is propyl. In certain embodiments $R_E$ is butyl. In certain embodiments, $R_E$ is an unsubstituted and unbranched $C_{1-20}$-heteroaliphatic. In certain embodiments $R_E$ is $C_{1-6}$-heteroalkyl.

Particular exemplary compounds include:

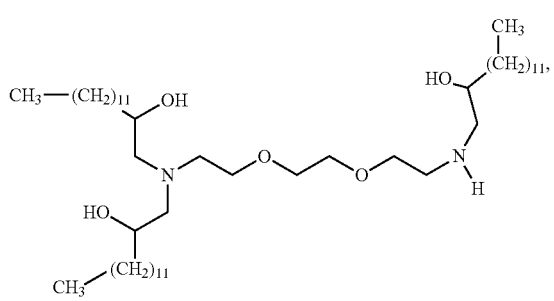

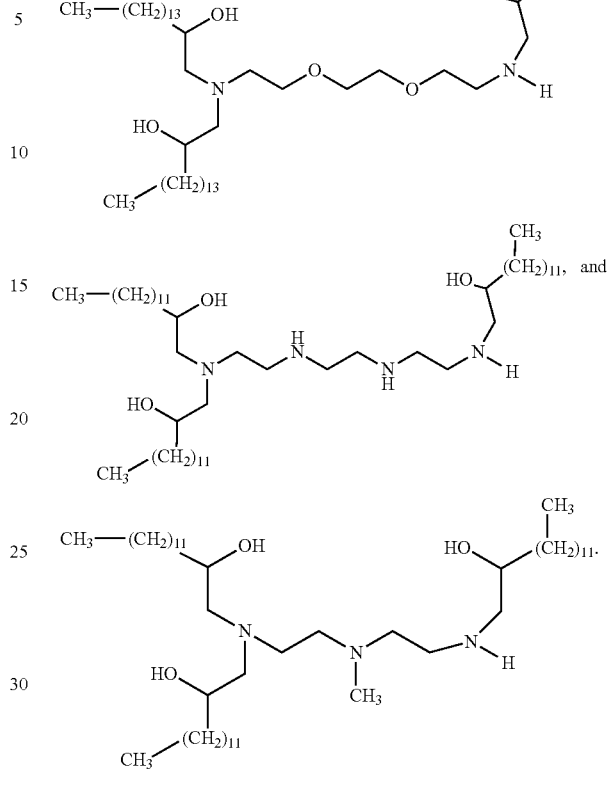

In certain embodiments, each

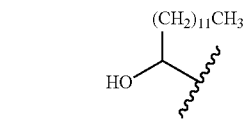

is independently

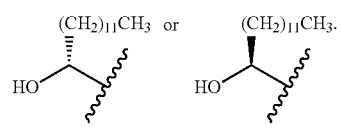

In certain embodiments, the aminoalcohol lipidoid compound of the present invention is of the formula:

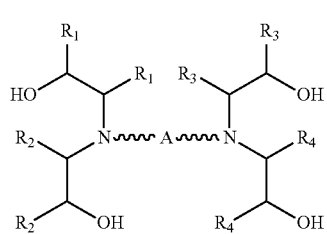

wherein:

A is a substituted or unsubstituted, branched or unbranched, cyclic or acyclic $C_{2-20}$ alkylene, optionally interrupted by 1 or more heteroatoms independently selected from O, S and N, or A is a substituted or unsubstituted, saturated or unsaturated 4-6-membered ring; and $R_1$, $R_2$, $R_3$, and $R_4$ are, independently, hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen, at least one occurrence of $R_2$ is hydrogen, at least one occurrence of $R_3$ is hydrogen and at least one occurrence of $R_4$ is hydrogen; or a pharmaceutically acceptable salt thereof.

In certain embodiments, each

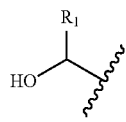

is independently

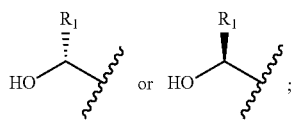

each

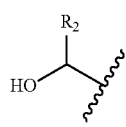

is independently

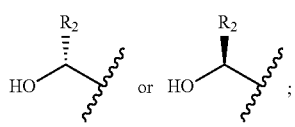

each

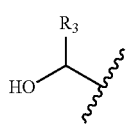

is independently

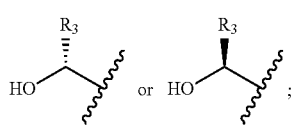

and each

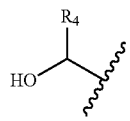

is independently

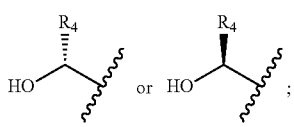

In certain embodiments, A is an unsubstituted, unbranched, and acyclic $C_{2-20}$ alkylene. In certain embodiments, A is a substituted or unsubstituted, branched or unbranched, cyclic or acyclic $C_{2-20}$ alkylene, optionally interrupted by 1 or more nitrogen atoms. In certain embodiments A is a substituted, unbranched, and acyclic $C_{2-10}$ alkylene, optionally interrupted by 1 oxygen atom. In certain embodiments, A is of the formula

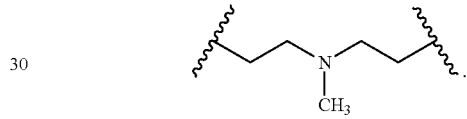

In certain embodiments, A is a substituted or unsubstituted, branched or unbranched, cyclic or acyclic $C_{2-20}$ alkylene, optionally interrupted by 1 or more oxygen atoms. In certain embodiments A is an unsubstituted, unbranched, and acyclic $C_{2-10}$ alkylene, optionally interrupted by 1 or more oxygen atoms. In certain embodiments A is an unsubstituted, unbranched, and acyclic $C_{2-10}$ alkylene, optionally interrupted by 2 oxygen atoms. In certain embodiments, A is of the formula

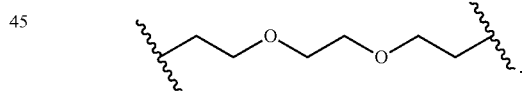

In certain embodiments, A is of the formula

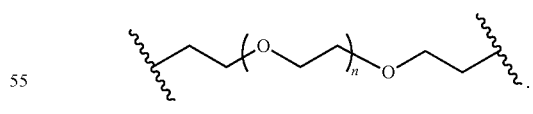

wherein n is an integer between 1 and 10, inclusive. In certain embodiments, A is a substituted or unsubstituted, branched or unbranched, cyclic or acyclic $C_{2-20}$ alkylene, optionally interrupted by 1 or more nitrogen atoms. In certain embodiments A is an unsubstituted, unbranched, and acyclic $C_{2-10}$ alkylene, optionally interrupted by 1 or more nitrogen atoms. In certain embodiments A is an unsubstituted, unbranched, and acyclic $C_{2-10}$ alkylene, optionally interrupted by 2 nitrogen atoms. In certain embodiments, A is of the formula

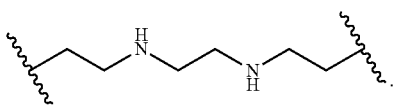 [SMILES: *CCNCCNCC*]

In certain embodiments, A is of the formula

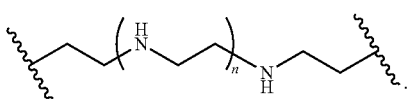

wherein n is an integer between 1 and 10, inclusive.

In certain embodiments, A is selected from the following formulae:

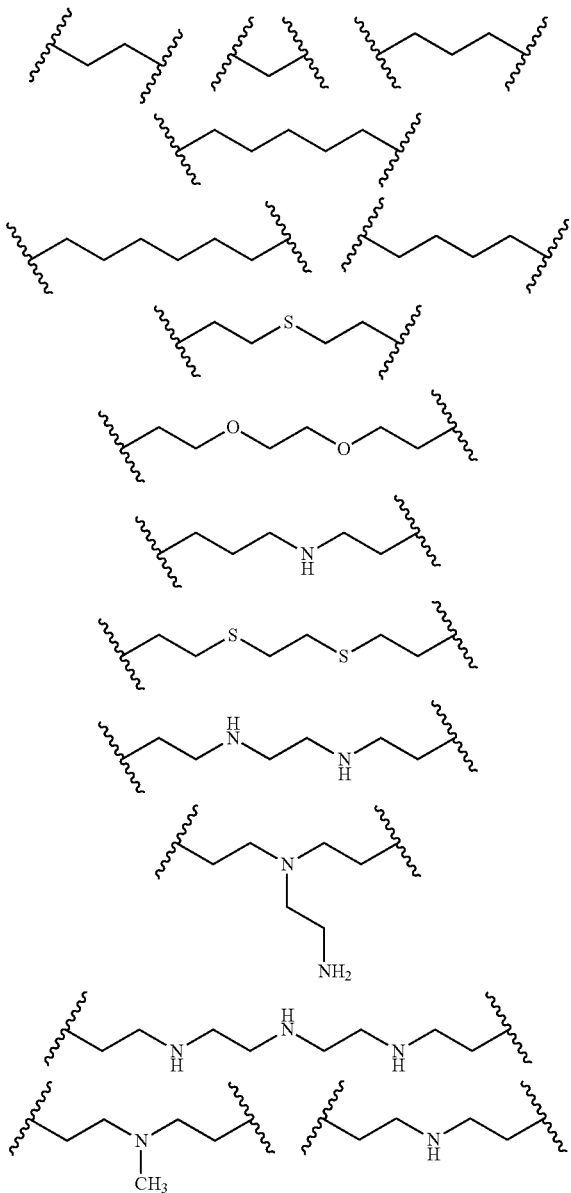

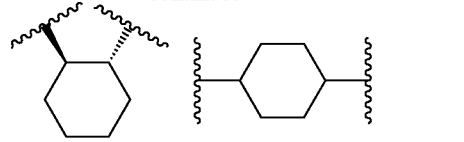

In certain embodiments, $R_1$, $R_2$, $R_3$ and $R_4$ are hydrogen. In certain embodiments, $R_1$, $R_2$, $R_3$ and $R_4$ are, independently, an unsubstituted and unbranched, $C_{1-20}$-aliphatic or $C_{1-20}$ heteroaliphatic moiety. In some embodiments, $R_1$, $R_2$, $R_3$ and $R_4$ are, independently, an unsubstituted and unbranched, $C_{12}$-aliphatic group. In some embodiments, $R_1$, $R_2$, $R_3$ and $R_4$ are

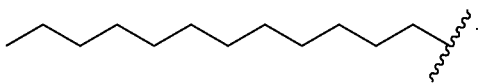

In some embodiments, $R_1$, $R_2$, $R_3$ and $R_4$ are, independently, an unsubstituted and unbranched, $C_{13}$ heteroaliphatic group. In some embodiments, $R_1$, $R_2$, $R_3$ and $R_4$ are

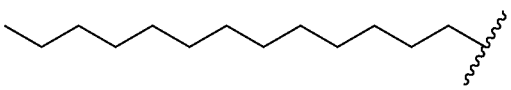

In some embodiments, $R_1$, $R_2$, $R_3$ and $R_4$ are, independently, an unsubstituted and unbranched, $C_{14}$ heteroaliphatic group. In some embodiments, $R_1$, $R_2$, $R_3$ and $R_4$ are

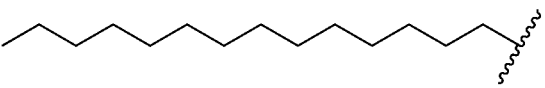

In certain embodiments, $R_1$, $R_2$, $R_3$ and $R_4$ are, independently, selected from the following formulae:

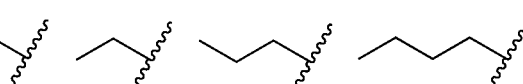
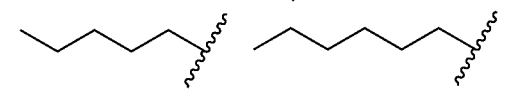
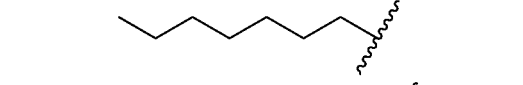
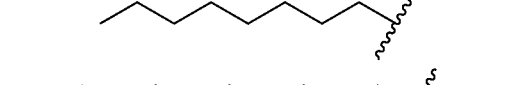
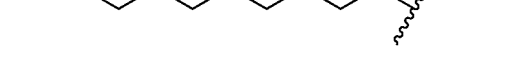

-continued

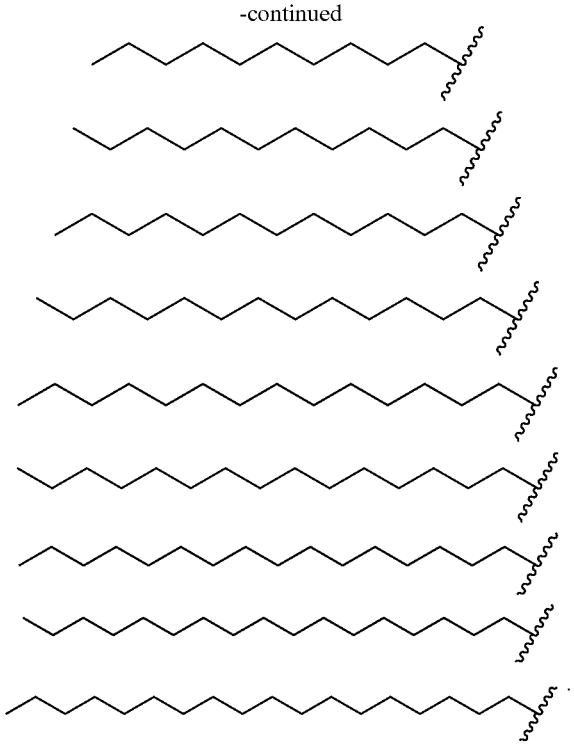

In certain embodiments, $R_1$, $R_2$, $R_3$, and $R_4$ are, a $C_{1-20}$ alkenyl moiety, optionally substituted. In certain embodiments, $R_1$, $R_2$, $R_3$, and $R_4$ are, independently, selected from the following formulae:

-continued

It will be appreciated by one of ordinary skill in the art that the above substituents may have multiple sites of unsaturation, and could be so at any position within the substituent.

In certain embodiments, $R_1$, $R_2$, $R_3$, and $R_4$ are:

In certain embodiments, $R_1$, $R_2$, $R_3$, and $R_4$ are, independently, selected from the following formulae:

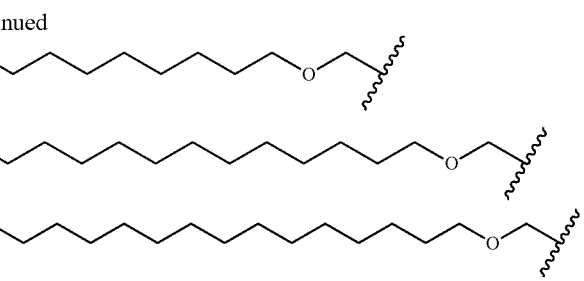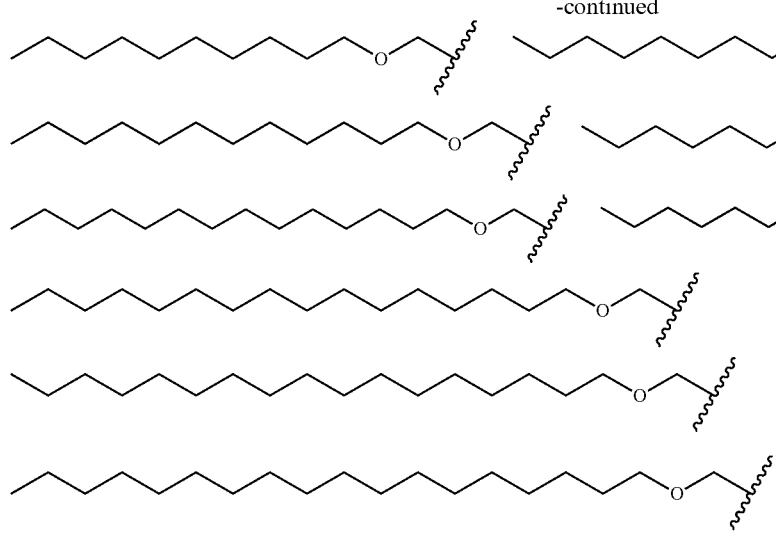

In certain embodiments, $R_1$, $R_2$, $R_3$, and $R_4$ are fluorinated. In certain embodiments $R_1$, $R_2$, $R_3$, and $R_4$ are a fluorinated aliphatic moiety. In certain embodiments $R_1$, $R_2$, $R_3$, and $R_4$ are perfluorinated. In certain embodiments $R_1$, $R_2$, $R_3$, and $R_4$ are a perfluorinated aliphatic moiety. In certain embodiments, $R_1$, $R_2$, $R_3$, and $R_4$ are a perfluorinated $C_{1-20}$ alkyl group. In certain embodiments, $R_1$, $R_2$, $R_3$, and $R_4$ are selected from the following formulae:

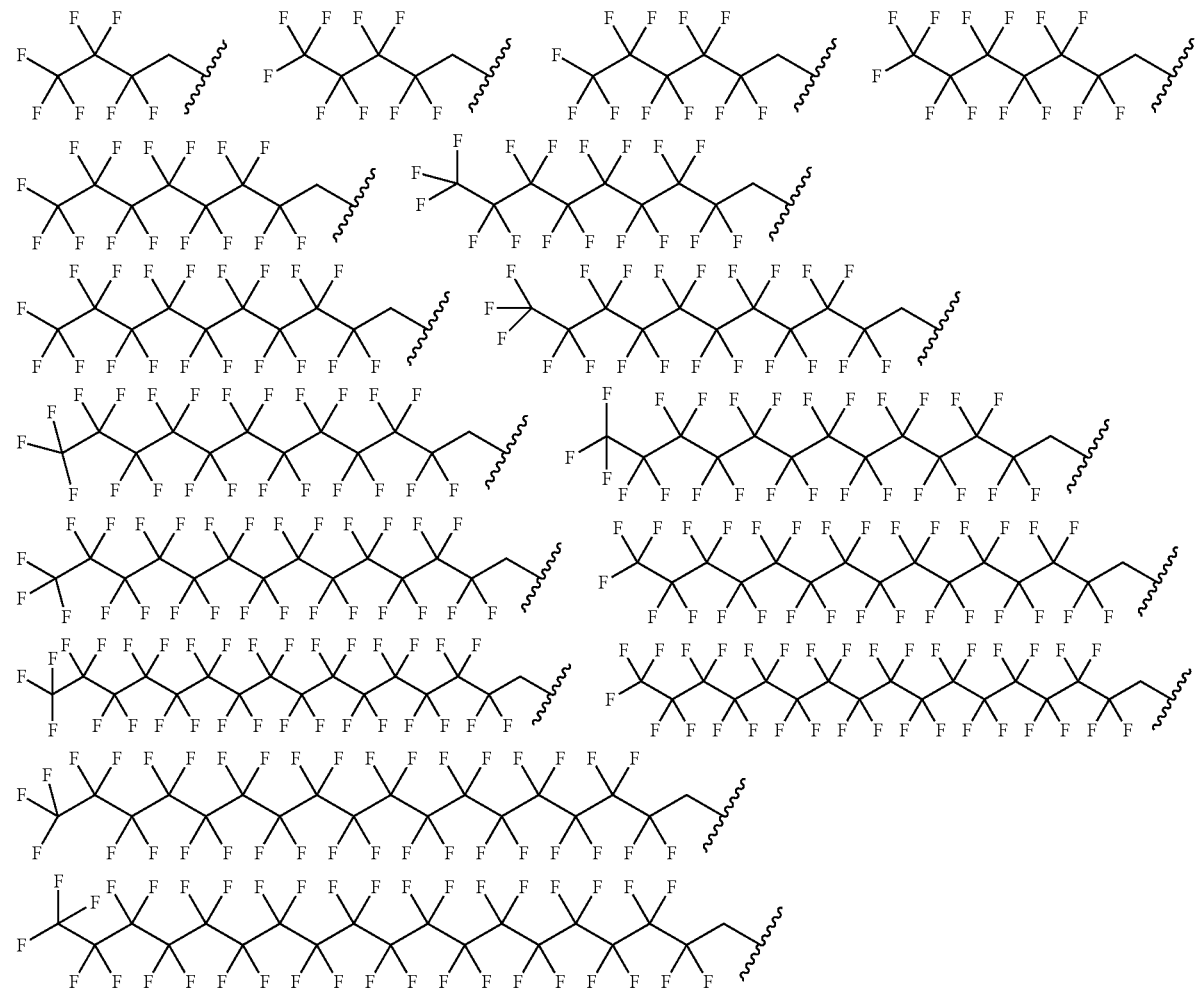

-continued

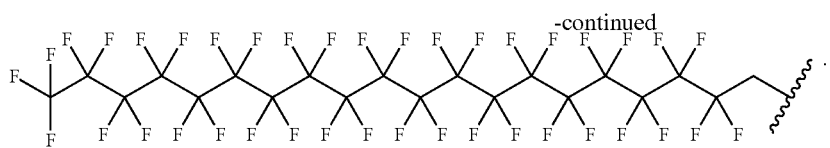

In certain embodiments, $R_1$, $R_2$, $R_3$, and $R_4$ are, independently, selected from the following formulae:

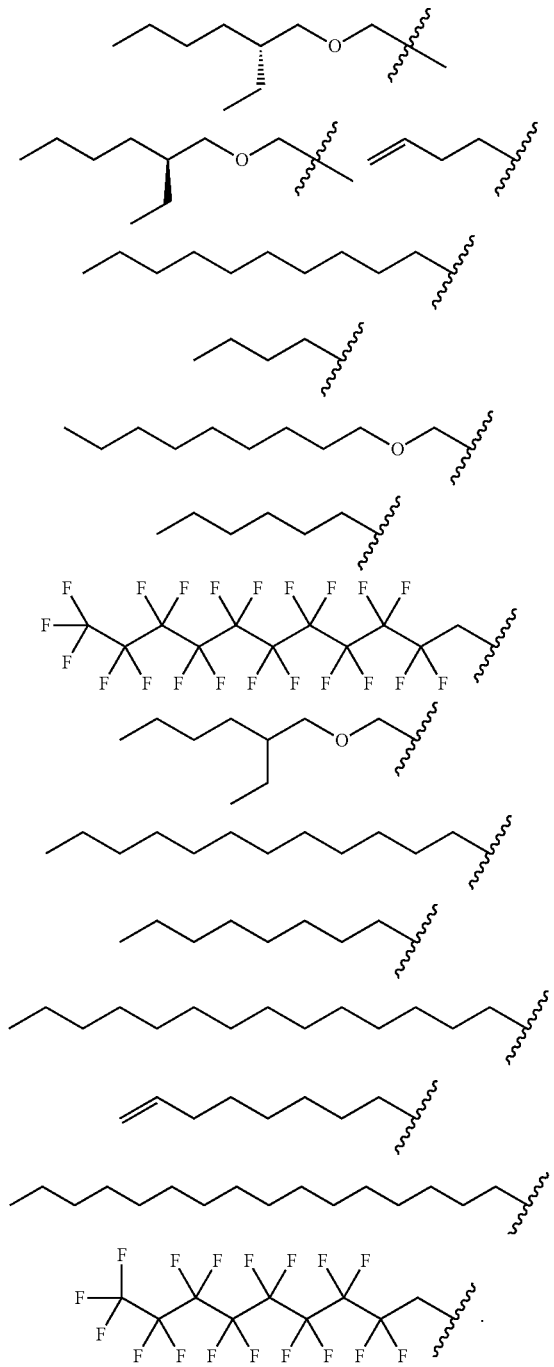

In certain embodiments, $R_1$, $R_2$, $R_3$, and $R_4$ are all the same. In certain embodiments, at least two of $R_1$, $R_2$, $R_3$, and $R_4$ are the same. In certain embodiments, at least three of $R_1$, $R_2$, $R_3$, and $R_4$ are the same. In certain embodiments, $R_1$, $R_2$, $R_3$, and $R_4$ are all different.

Particular exemplary compounds include:

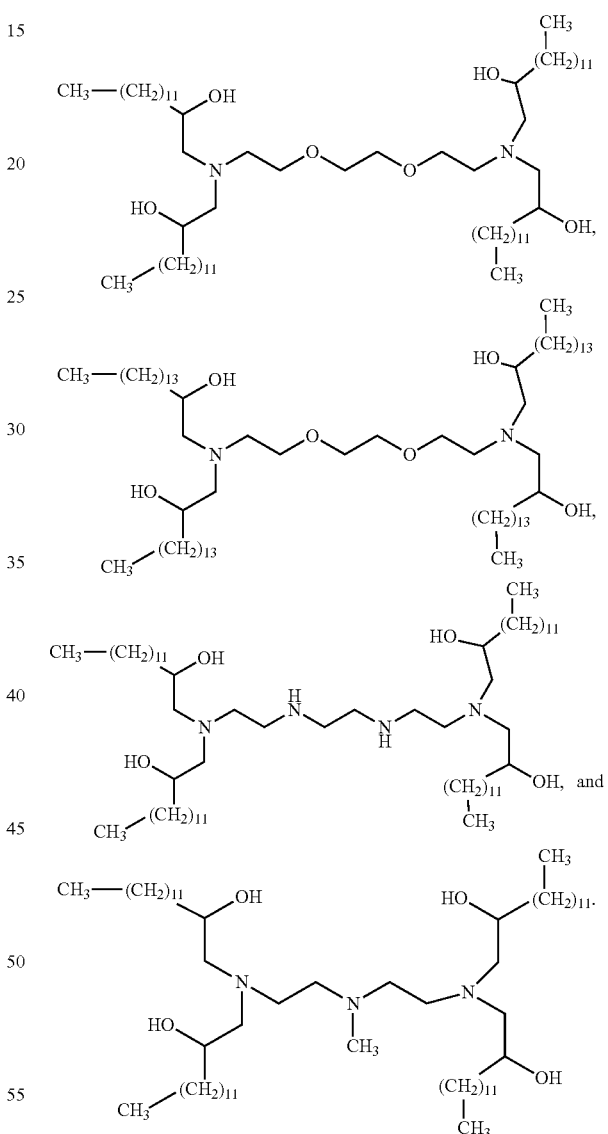

In certain embodiments, each

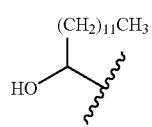

is independently

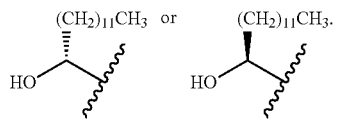

In certain embodiments the aminoalcohol lipidoid compound or composition containing a mixture of aminoalcohol lipidoid compounds is prepared by reacting amine 120 with the epoxide-terminated compound C14. In certain embodiments, the aminoalcohol lipidoid compound C14-120 is one of the formulae below:

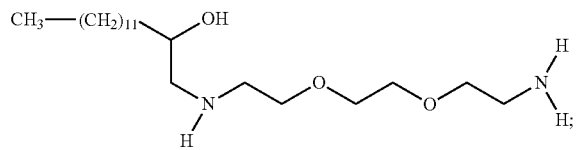

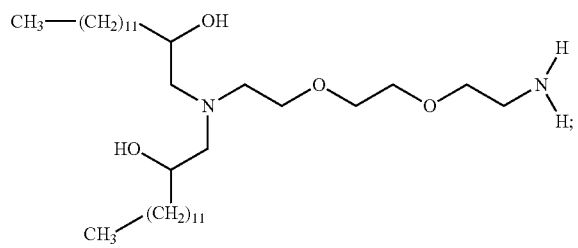

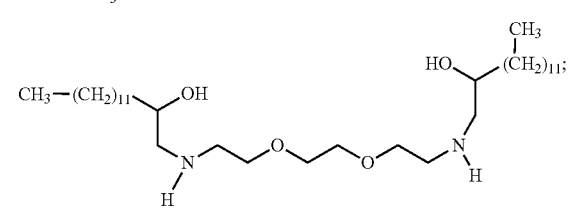

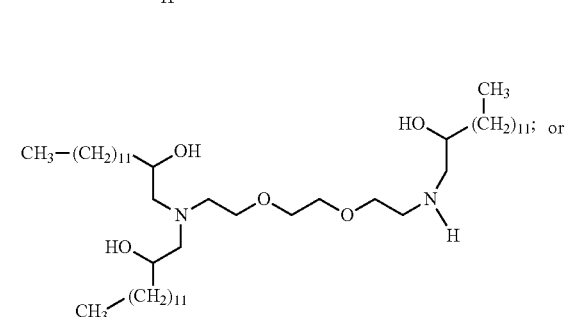

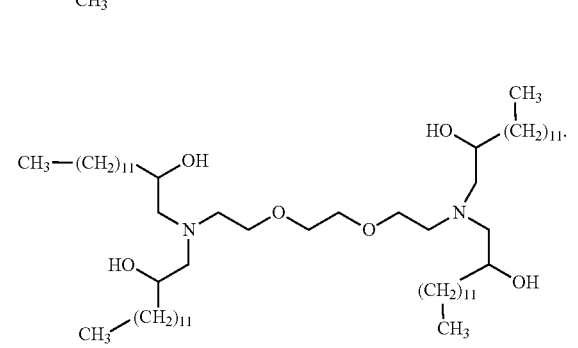

In certain embodiments, each

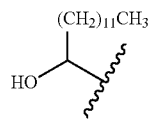

is independently

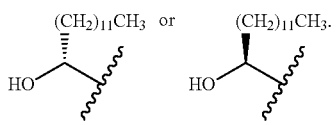

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 120 with the epoxide-terminated compound C16. In certain embodiments, the aminoalcohol lipidoid compound C16-120 is of one of the formulae below:

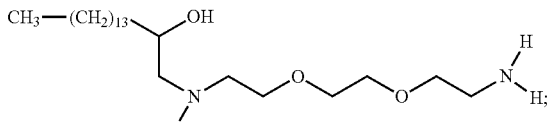

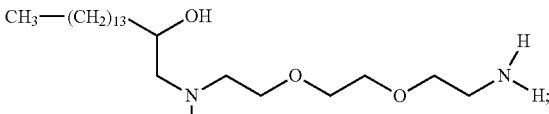

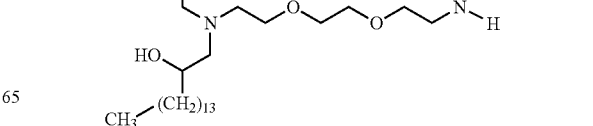

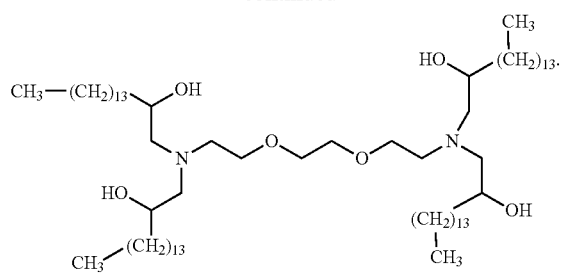

In certain embodiments, each

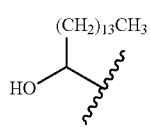

is independently

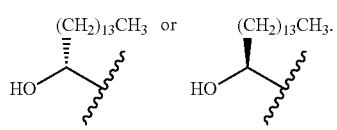

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 98 with the epoxide-terminated compound C14. In certain embodiments, the aminoalcohol lipidoid compound C14-98 is of one of the formulae below:

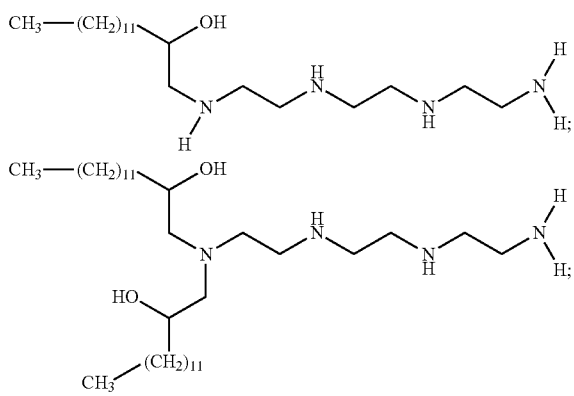

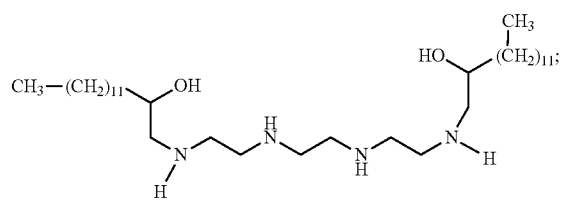

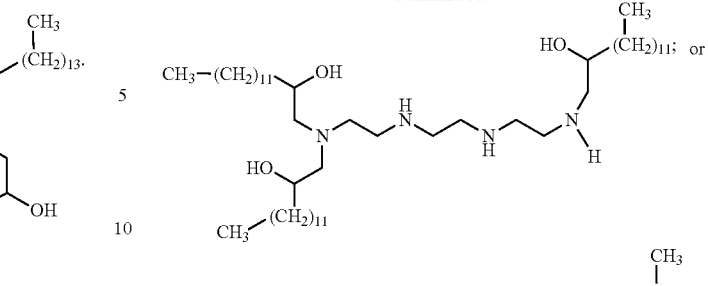

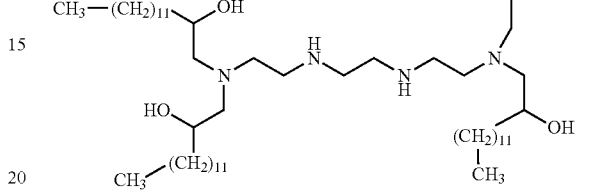

In certain embodiments, each

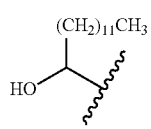

is independently

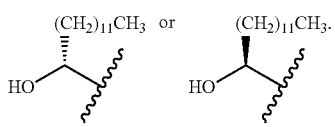

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 113 with the epoxide-terminated compound C14. In certain embodiments, the aminoalcohol lipidoid compound C14-113 is of one of the formulae below:

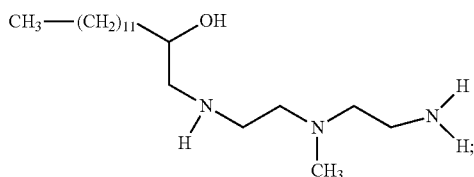

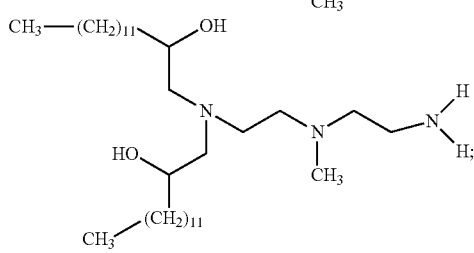

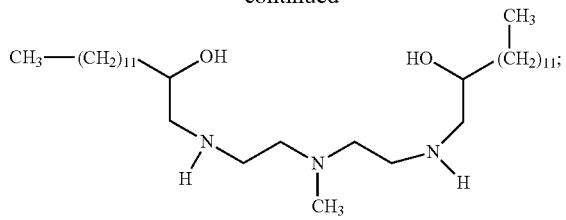

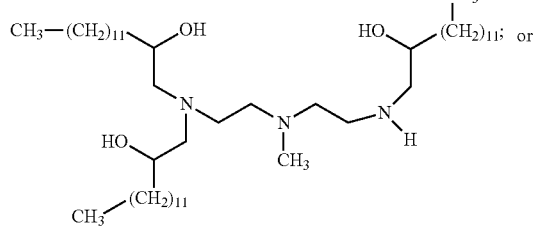

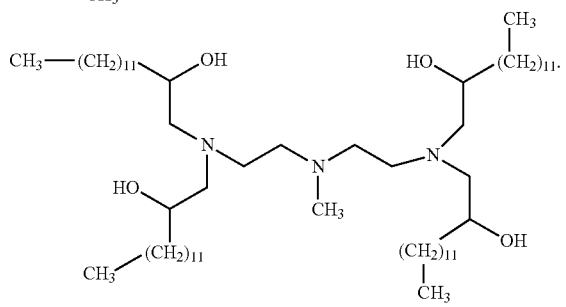

In certain embodiments, each

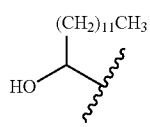

is independently

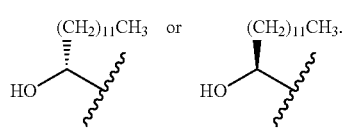

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 96 with the epoxide-terminated compound C18. In certain embodiments, the aminoalcohol lipidoid compound is of one of the formulae below:

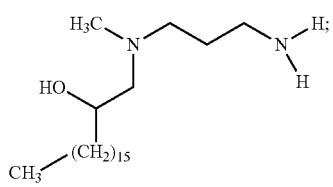

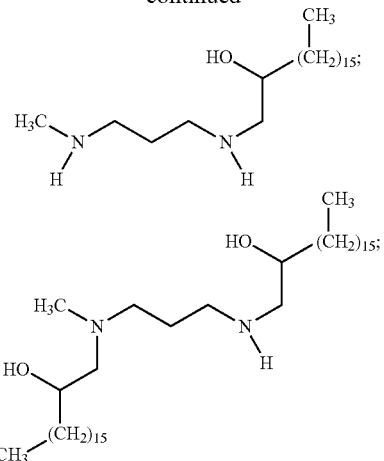

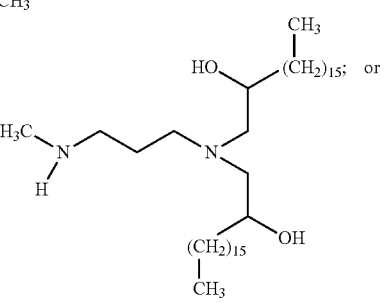

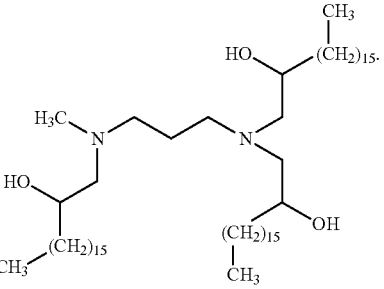

In certain embodiments, each

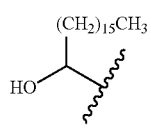

is independently

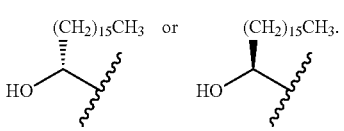

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 96 with the epoxide-terminated compound C14. In certain embodiments, the aminoalcohol lipidoid compound C14-96 is of one of the formulae below:

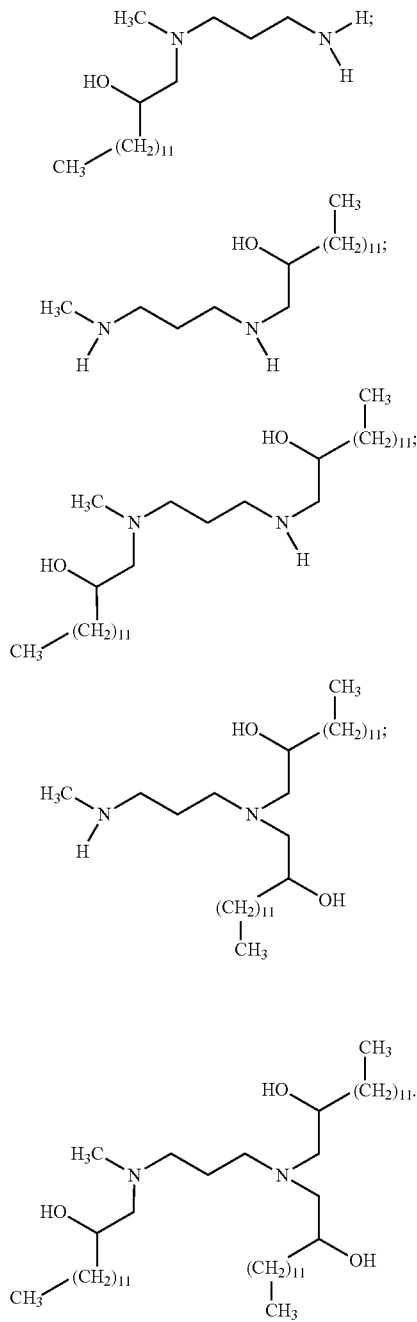

In certain embodiments, each

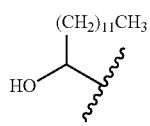

is independently

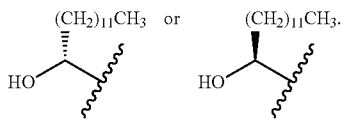

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 110 with the epoxide-terminated compound C14. In certain embodiments, the aminoalcohol lipidoid compound C14-110 is of one of the formulae below:

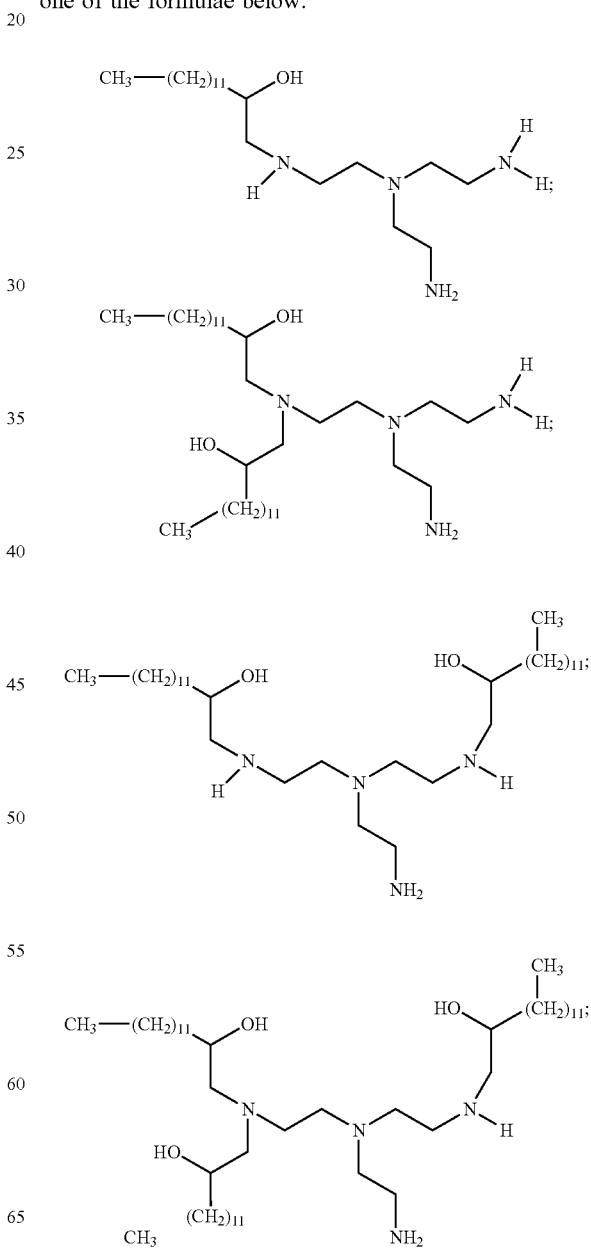

-continued

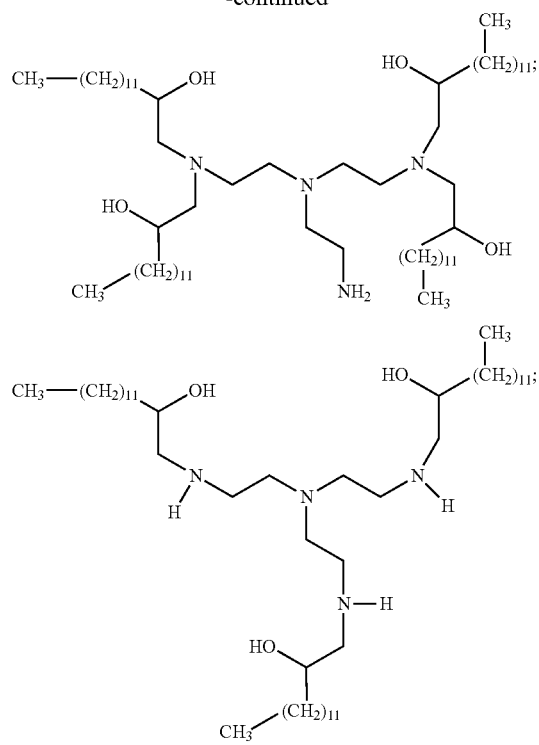

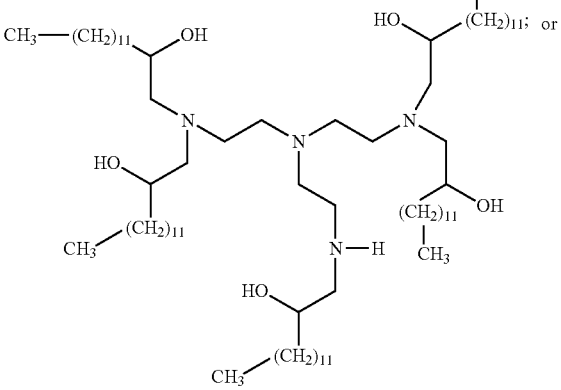

-continued

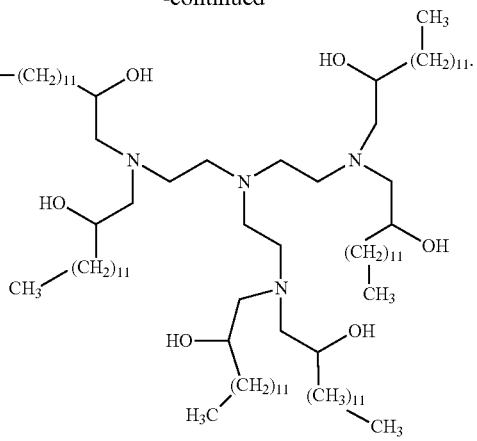

In certain embodiments, each

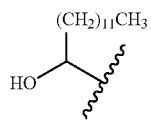

is independently

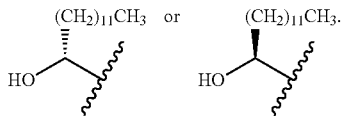

In certain embodiments the aminoalcohol lipidoid composition, is a composition containing one or more of the above aminoalcohol lipidoid compounds.

In certain embodiments, the aminoalcohol lipidoid compound of the present invention is of the formula:

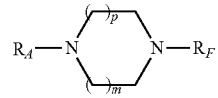

wherein:
p is an integer between 1 and 3, inclusive;
m is an integer between 1 and 3, inclusive;
$R_A$ is hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

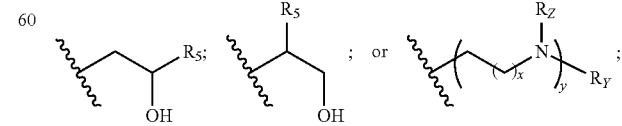

$R_F$ is hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

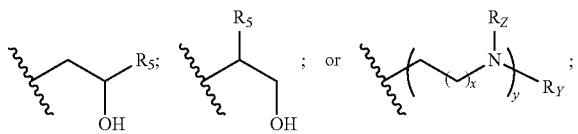

each occurrence of $R_5$ is independently hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; or substituted or unsubstituted heteroaryl;

wherein, at least one of $R_A$, $R_F$, $R_Y$, and $R_Z$ is

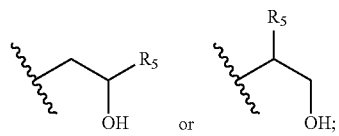

each occurrence of x is an integer between 1 and 10, inclusive;

each occurrence of y is an integer between 1 and 10, inclusive;

each occurrence of $R_Y$ is hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

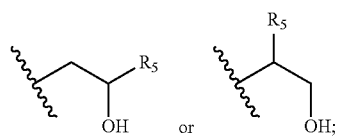

each occurrence of $R_Z$ is hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

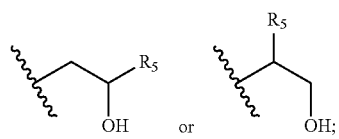

or a pharmaceutically acceptable salt thereof.

In certain embodiments, $R_A$ is hydrogen. In certain embodiments, $R_A$ is hydrogen. In certain embodiments, $R_A$ is substituted or unsubstituted, cyclic or acyclic, branched or unbranched $C_{1-20}$ aliphatic. In certain embodiments, $R_A$ is $C_1$-$C_6$ aliphatic. In certain embodiments, $R_A$ is $C_1$-$C_6$ alkyl. In certain embodiments, $R_A$ is substituted or unsubstituted, cyclic or acyclic, branched or unbranched $C_{1-20}$ heteroaliphatic. In certain embodiments, $R_A$ is substituted or unsubstituted aryl. In certain embodiments, $R_A$ is substituted or unsubstituted heteroaryl. In certain embodiments, $R_A$ is

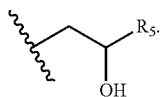

In certain embodiments, each

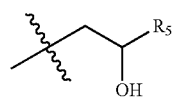

is independently

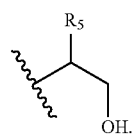

In certain embodiments, $R_A$ is

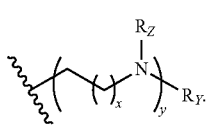

In certain embodiments, $R_A$ is

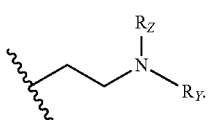

In certain embodiments $R_A$ is

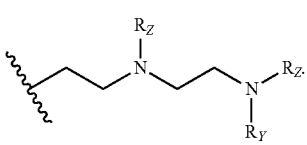

In certain embodiments $R_A$ is

In certain embodiments $R_A$ is

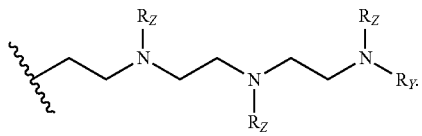

In certain embodiments, $R_F$ is hydrogen. In certain embodiments, no $R_F$ is hydrogen. In certain embodiments, $R_F$ is substituted or unsubstituted, cyclic or acyclic, branched or unbranched $C_{1-20}$ aliphatic. In certain embodiments, $R_F$ is $C_1$-$C_6$ aliphatic. In certain embodiments, $R_F$ is $C_1$-$C_6$ alkyl. In certain embodiments, $R_F$ is substituted or unsubstituted, cyclic or acyclic, branched or unbranched $C_{1-20}$ heteroaliphatic. In certain embodiments, $R_F$ is substituted or unsubstituted aryl. In certain embodiments, $R_F$ is substituted or unsubstituted heteroaryl. In certain embodiments, $R_F$ is

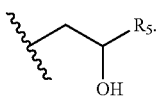

In certain embodiments, each

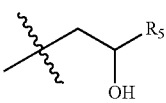

is

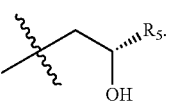

In certain embodiments, each

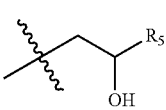

is

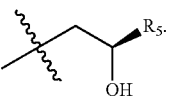

In certain embodiments, $R_F$ is

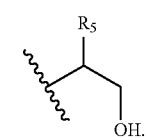

In certain embodiments, $R_F$ is

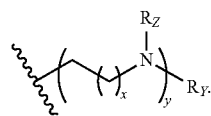

In certain embodiments $R_F$ is

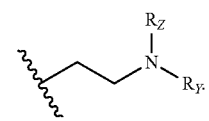

In certain embodiments $R_F$ is

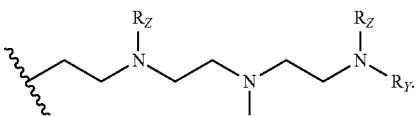

In certain embodiments $R_F$ is

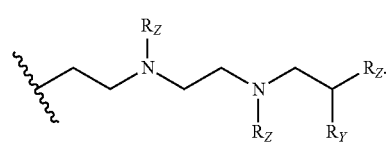

In certain embodiments $R_F$ is

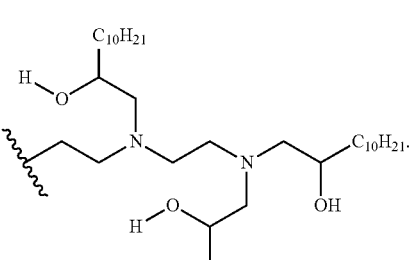

In certain embodiments, no $R_A$ is hydrogen and no $R_F$ is hydrogen. In certain embodiments, $R_A$ is

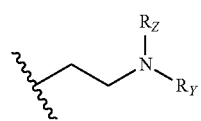
and R$_F$ is
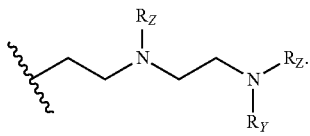
In certain embodiments, R$_A$ is
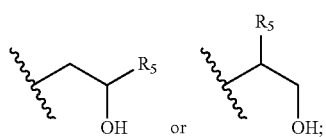
and R$_F$ is
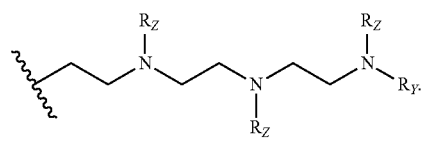
In certain embodiments, each
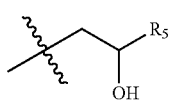
is
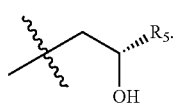
In certain embodiments, each
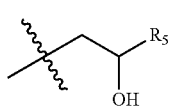
is
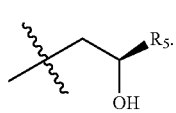
In certain embodiments, R$_A$ is
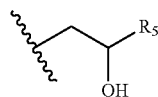
and R$_F$ is
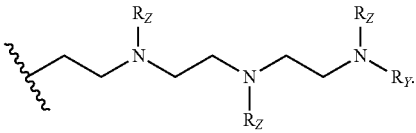
In certain embodiments, each
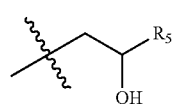
is
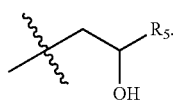
In certain embodiments, each
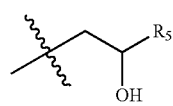
is
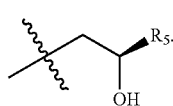
In certain embodiments, R$_A$ is
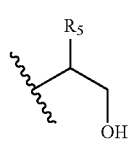
and R$_F$ is
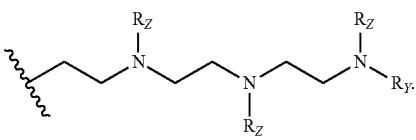

In certain embodiments, $R_A$ is

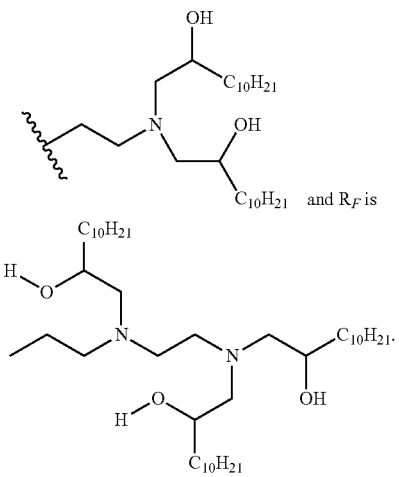 and $R_F$ is

In certain embodiments, each

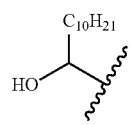

is

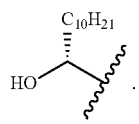

In certain embodiments, each

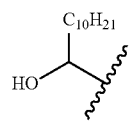

is

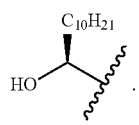

In certain embodiments, m is 1. In certain embodiments, m is 2. In certain embodiments, m is 3.

In certain embodiments, p is 1. In certain embodiments, p is 2. In certain embodiments, p is 3.

In certain embodiments, $R_5$ is hydrogen. In certain embodiments, $R_5$ is substituted or unsubstituted, cyclic or acyclic, branched or unbranched $C_{1-20}$ aliphatic. In certain embodiments, $R_5$ is $C_8$-$C_{16}$ aliphatic. In certain embodiments, $R_5$ is $C_8$-$C_{16}$ alkyl. In some embodiments, $R_5$ is an unsubstituted and unbranched, $C_{10-12}$-aliphatic group. In some embodiments, $R_5$ is

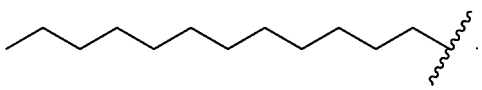 [SMILES: *CCCCCCCCCCCC]

In some embodiments, $R_5$ is

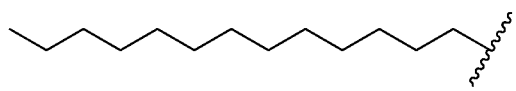

In some embodiments, $R_5$ is

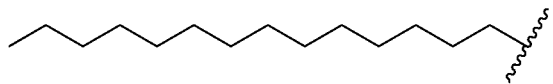

In certain embodiments, $R_5$ is selected from the following formulae:

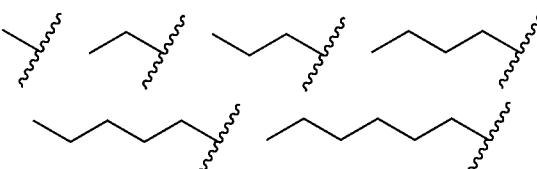
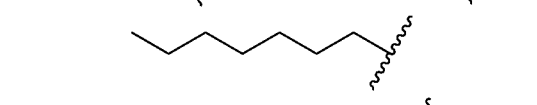
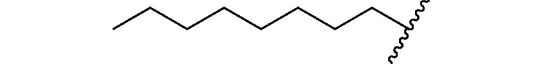
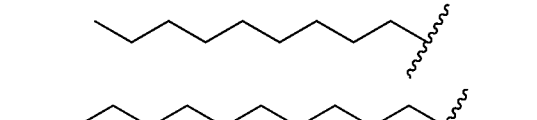
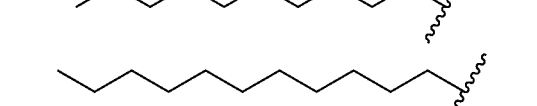
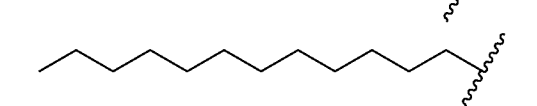
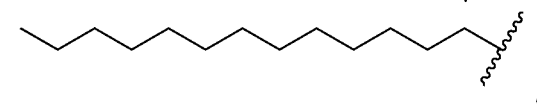
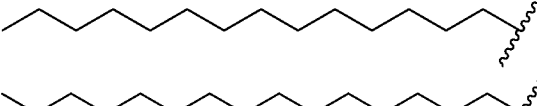

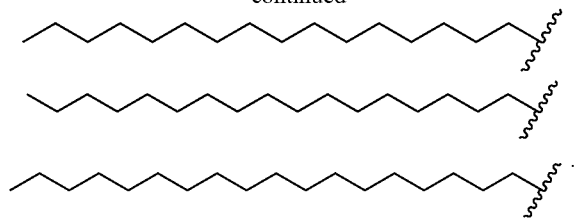

In certain embodiments, R$_5$ is a C$_{1-20}$ alkenyl moiety, optionally substituted. In certain embodiments, R$_5$ is selected from the following formulae:

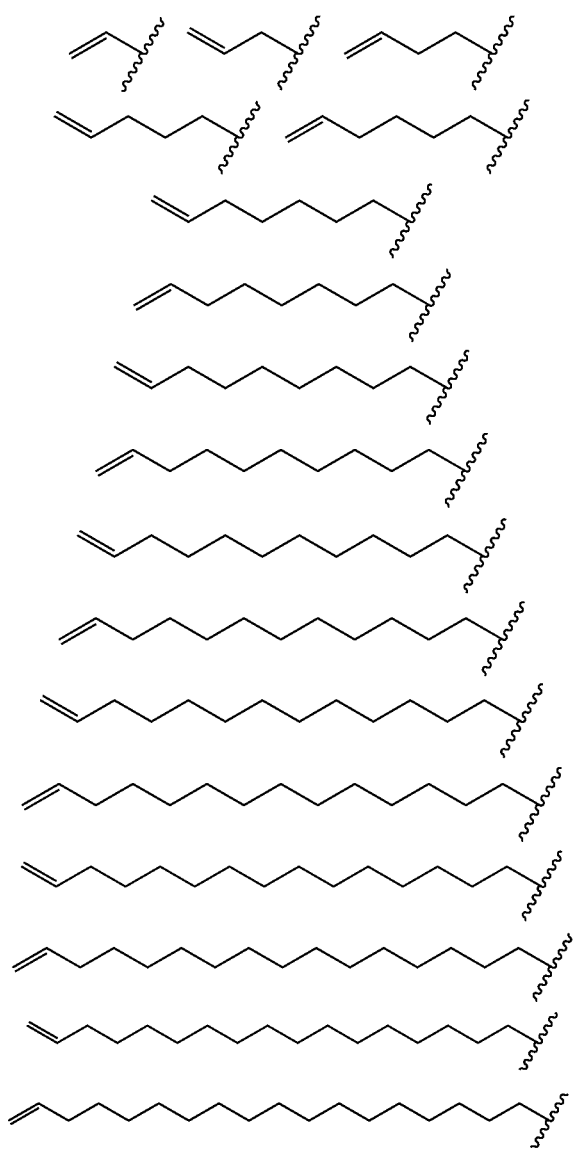

In certain embodiments, R$_5$ is substituted or unsubstituted, cyclic or acyclic, branched or unbranched C$_{1-20}$ heteroaliphatic. In some embodiments, R$_5$ is an unsubstituted and unbranched, C$_{13}$ heteroaliphatic group. In some embodiments, R$_5$ is an unsubstituted and unbranched, C$_{14}$ heteroaliphatic group. In certain embodiments, R$_5$ is:

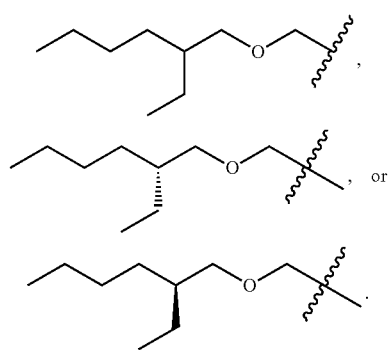

In certain embodiments, R$_5$ is, independently, selected from the following formulae:

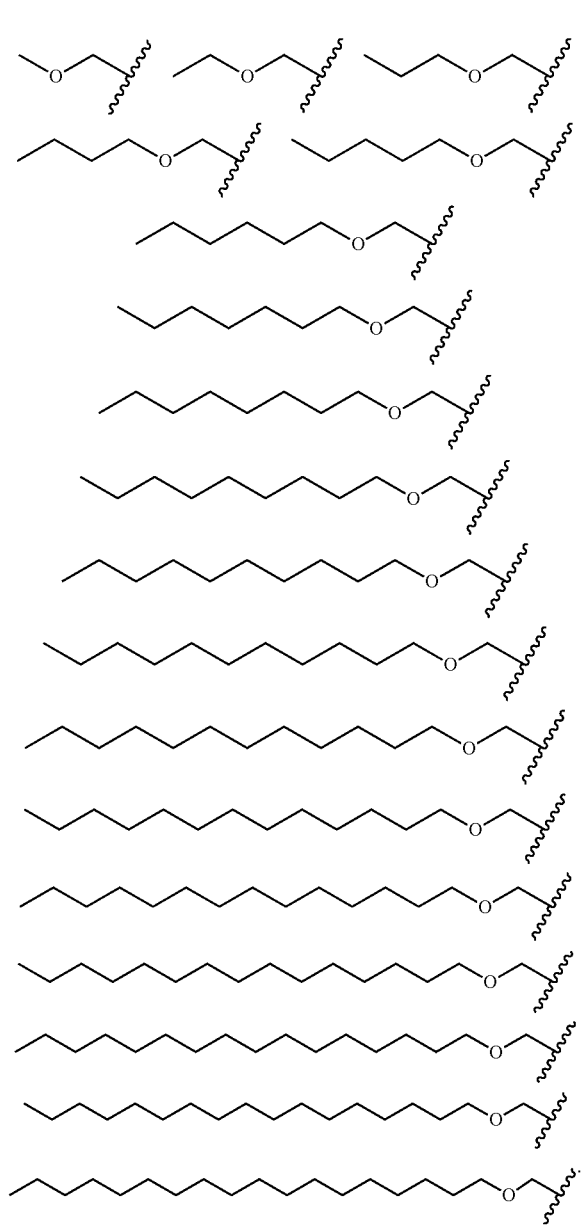

It will be appreciated by one of ordinary skill in the art that the above substituents may have multiple sites of unsaturation, and could be so at any position within the substituent.

In certain embodiments, $R_5$ is substituted or unsubstituted aryl. In certain embodiments, $R_5$ is or substituted or unsubstituted heteroaryl.

In certain embodiments, $R_5$ is fluorinated. In certain embodiments $R_5$ is a fluorinated aliphatic moiety. In certain embodiments $R_5$ is perfluorinated. In certain embodiments $R_5$ is a perfluorinated aliphatic moiety. In certain embodiments, $R_5$ is a perfluorinated $C_{1-20}$ alkyl group. In certain embodiments, $R_5$ is selected from the following formulae:

In certain embodiments, $R_5$ is selected from the following formulae:

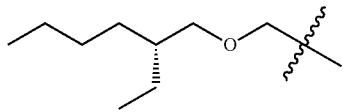

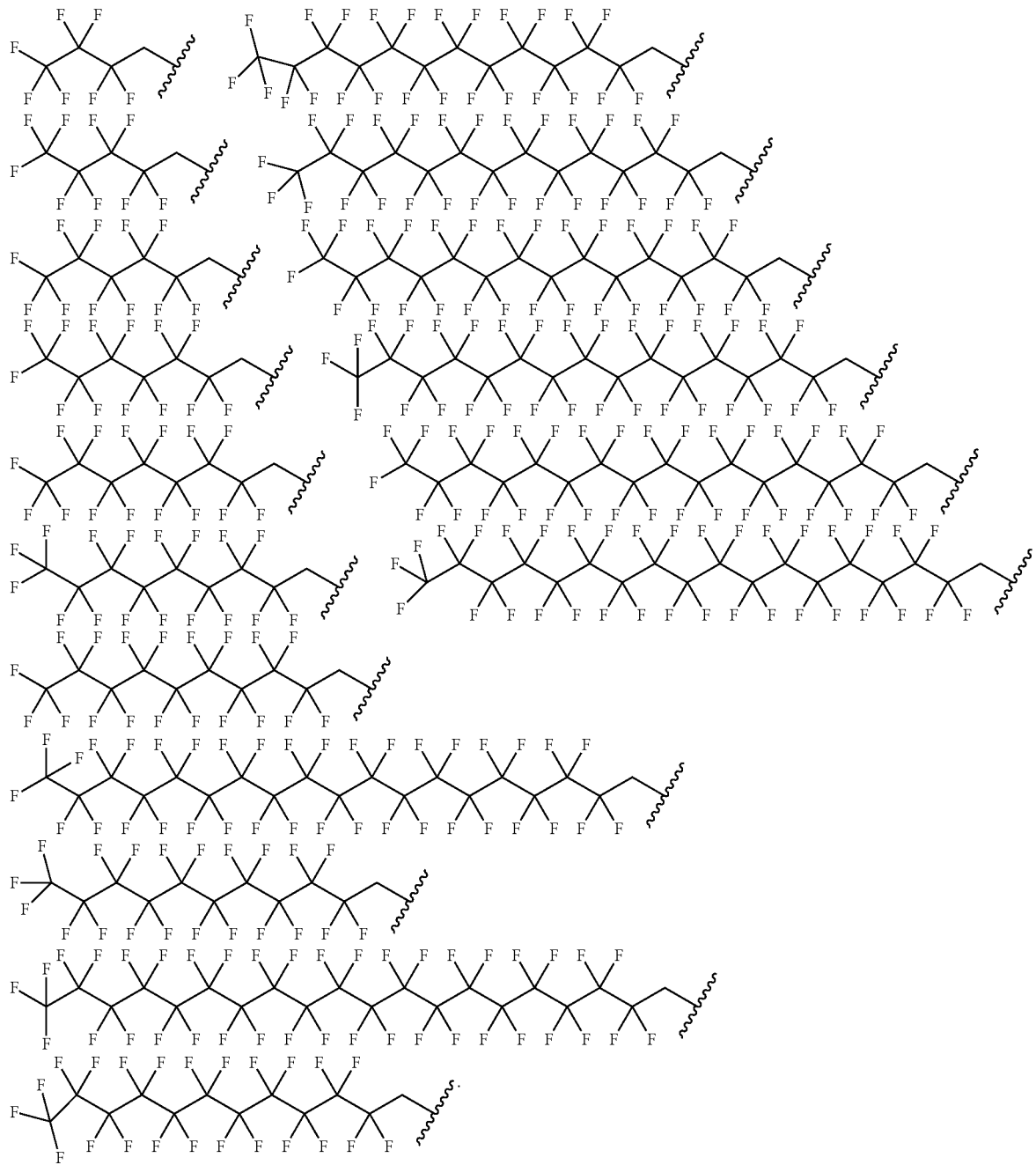

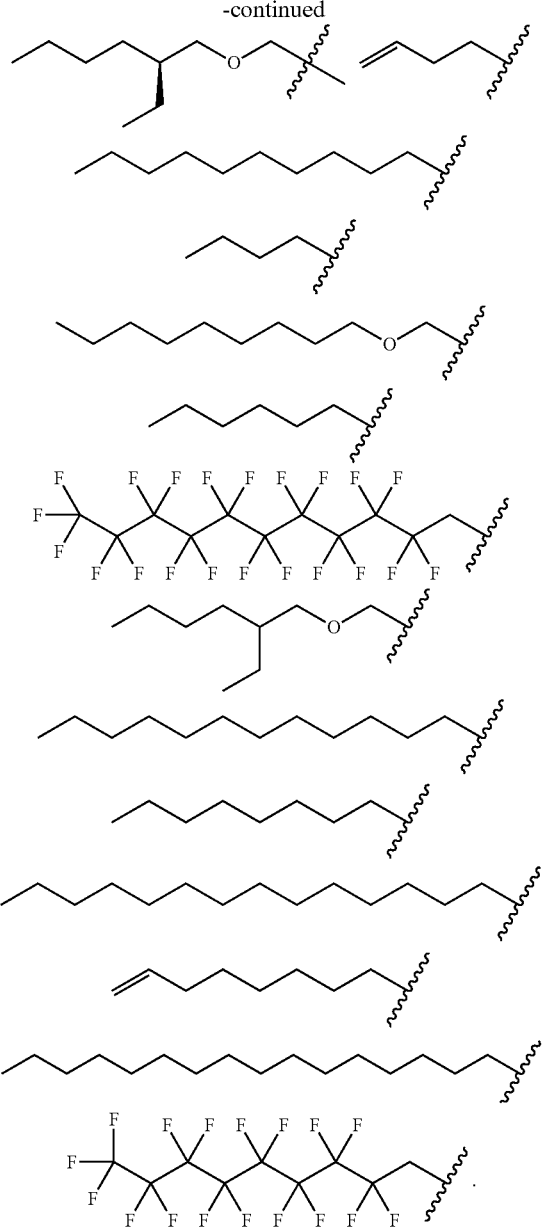

In certain embodiments, each $R_5$ is independently hydrogen, or $C_1$-$C_6$ alkyl. In certain embodiments, each $R_5$ is hydrogen. In certain embodiments, $R_1$ and $R_3$ each $R_5$ is $C_1$-$C_6$ alkyl. In certain embodiments, each $R_5$ is hydroxyalkyl. In certain embodiments, each $R_5$ is aminoalkyl. In certain embodiments, two $R_5$ variables are the same. In certain embodiments, three $R_5$ variables are the same. In certain embodiments, each $R_5$ variable is different from the other.

In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10.

In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, y is 10.

In certain embodiments, x is 1 and y is 2. In certain embodiments, x is 1 and y is 3. In certain embodiments, x is 1 and y is 4. In certain embodiments, x is 1 and y is 5. In certain embodiments, x is 2 and y is 2. In certain embodiments, x is 2 and y is 3.

In certain embodiments, $R_Y$ is hydrogen. In certain embodiments, $R_Y$ is substituted or unsubstituted, cyclic or acyclic, branched or unbranched $C_{1-20}$ aliphatic. In certain embodiments, $R_Y$ is $C_1$-$C_6$ alkyl. In certain embodiments, $R_Y$ is substituted or unsubstituted, cyclic or acyclic, branched or unbranched $C_{1-20}$ heteroaliphatic. In certain embodiments, $R_Y$ is substituted or unsubstituted aryl. In certain embodiments, $R_Y$ is substituted or unsubstituted heteroaryl. In certain embodiments, $R_Y$ is

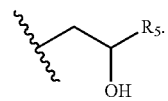

In certain embodiments, each

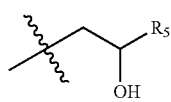

is independently

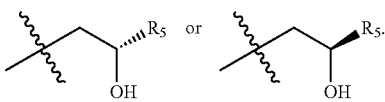

In certain embodiments, $R_Y$ is

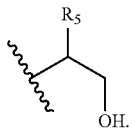

In certain embodiments, $R_Z$ is hydrogen. In certain embodiments, $R_Z$ is substituted or unsubstituted, cyclic or acyclic, branched or unbranched $C_{1-20}$ aliphatic. In certain embodiments, $R_Y$ is $C_1$-$C_6$ alkyl. In certain embodiments, $R_Z$ is substituted or unsubstituted, cyclic or acyclic, branched or unbranched $C_{1-20}$ heteroaliphatic. In certain embodiments, $R_Z$ is substituted or unsubstituted aryl. In certain embodiments, $R_Z$ is substituted or unsubstituted heteroaryl. In certain embodiments, $R_Z$ is

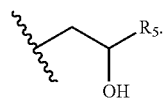

In certain embodiments, each

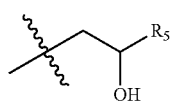

is independently
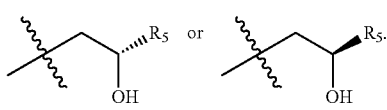
In certain embodiments, $R_Z$ is
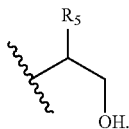
Particular exemplary compounds include:
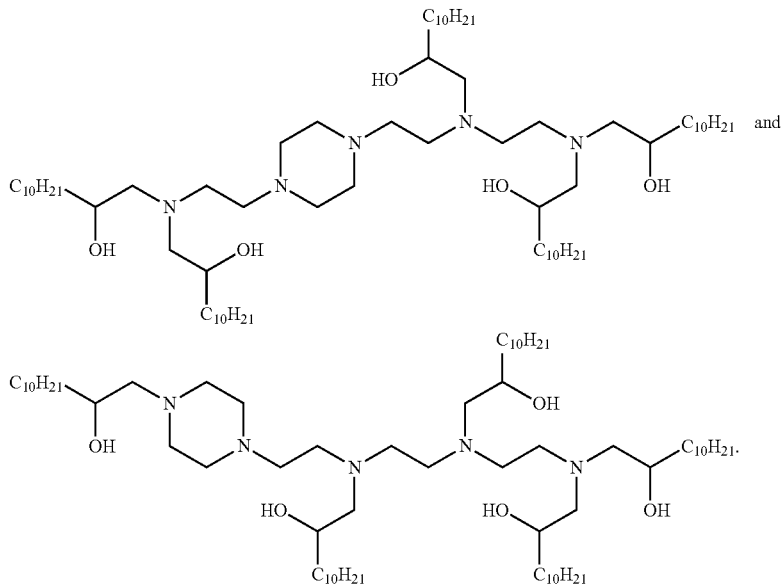
In certain embodiments, the aminoalcohol lipidoid compounds of the present invention comprises a mixture of formulae:
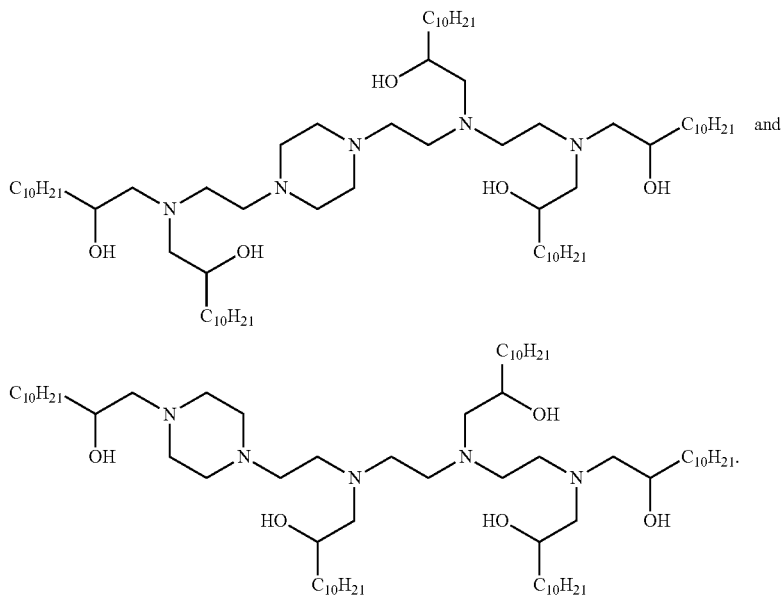

In certain embodiments, each

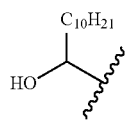

is independently

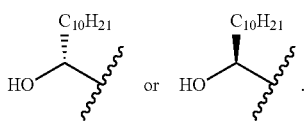

In certain embodiments, the aminoalcohol lipidoid compound of the present invention is of the formula:

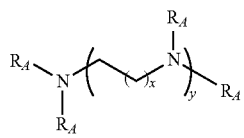

wherein:

each occurrence of $R_A$ is independently hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

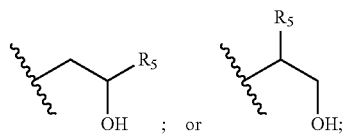

wherein at least one $R_A$ is

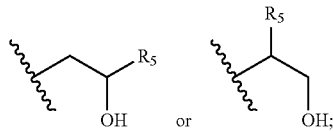

each occurrence of $R_5$ is independently hydrogen; substituted or unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; or substituted or unsubstituted heteroaryl;

each occurrence of x is an integer between 1 and 10, inclusive;
each occurrence of y is an integer between 1 and 10, inclusive;
or a pharmaceutically acceptable salt thereof.

In certain embodiments, $R_A$ is hydrogen. In certain embodiments, no $R_A$ is hydrogen. In certain embodiments, at least one $R_A$ is hydrogen. In certain embodiments, $R_A$ is substituted or unsubstituted, cyclic or acyclic, branched or unbranched $C_{1-20}$ heteroaliphatic. In certain embodiments, $R_A$ is substituted or unsubstituted aryl. In certain embodiments, $R_A$ is substituted or unsubstituted heteroaryl. In certain embodiments, two $R_A$'s together may form a cyclic structure. In certain embodiments, at least one $R_A$ is

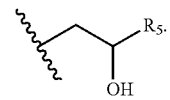

In certain embodiments, each

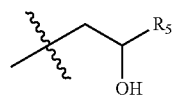

is

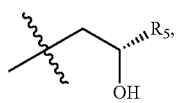

In certain embodiments, each

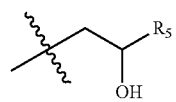

is independently

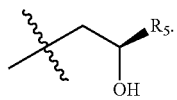

In certain embodiments, at least one $R_A$ is

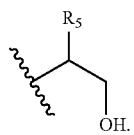

In certain embodiments, $R_A$ is substituted or unsubstituted, cyclic or acyclic, branched or unbranched $C_{1-20}$ aliphatic. In certain embodiments, at least one $R_A$ is an alkenyl group. In certain embodiments, at least one $R_A$ is

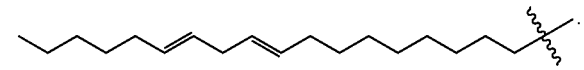 [SMILES: *CCCCCCCC/C=C/C/C=C/CCCCC]

In certain embodiments, at least one $R_A$ is

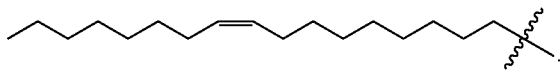 [SMILES: *CCCCCCCC/C=C\CCCCCCC]

In certain embodiments, at least one $R_A$ is

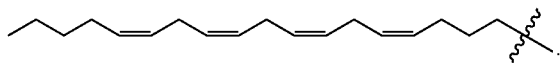

In certain embodiments, at least one $R_A$ is

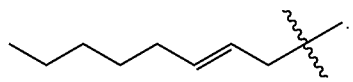 [SMILES: *C/C=C/CCCCC]

In certain embodiments, at least one $R_A$ is

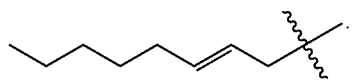 [SMILES: *C/C=C/CCCCC]

In certain embodiments, at least one $R_A$ is

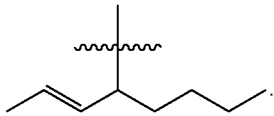 [SMILES: *C(/C=C/C)CCCC]

In certain embodiments, at least one $R_A$ is an alkynyl group. In certain embodiments, at least one $R_A$ is

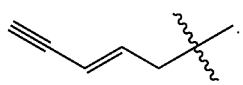 [SMILES: *C/C=C/C#C]

In certain embodiments, at least one $R_A$ is a substituted or unsubstituted, cyclic or acyclic, branched or unbranched $C_{1-20}$ heteroaliphatic group. In certain embodiments, at least one $R_A$ is a heteroaliphatic group. In certain embodiments, at least one $R_A$ is

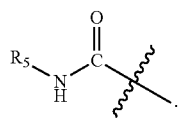

In certain embodiments, at least one $R_A$ is

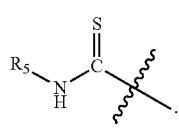

In certain embodiments, at least one $R_A$ is

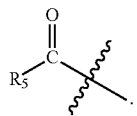

In certain embodiments, at least one $R_A$ is

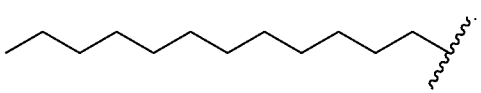 [SMILES: *CCCCCCCCCCCC]

In certain embodiments, two $R_A$ variables are the same. In certain embodiments, three $R_A$ variables are the same. In certain embodiments, each $R_A$ variable is different from the other.

In certain embodiments, $R_5$ is hydrogen. In certain embodiments, $R_5$ is substituted or unsubstituted, cyclic or acyclic, branched or unbranched $C_{1-20}$ aliphatic. In certain embodiments, $R_5$ is $C_8$-$C_{16}$ aliphatic. In certain embodiments, $R_5$ is $C_8$-$C_{16}$ alkyl. In some embodiments, $R_5$ is an unsubstituted and unbranched, $C_{10-12}$-aliphatic group. In some embodiments, $R_5$ is

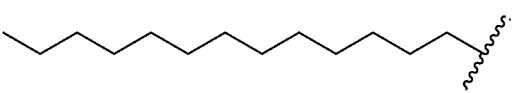 [SMILES: *CCCCCCCCCCCCC]

In some embodiments, $R_5$ is

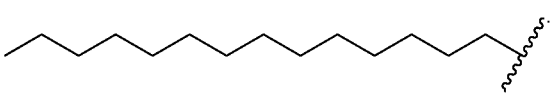 [SMILES: *CCCCCCCCCCCCCC]

In some embodiments, $R_5$ is

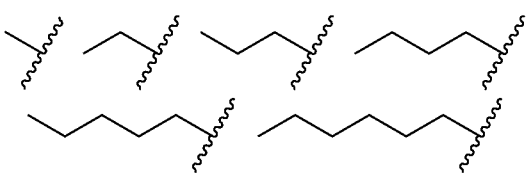

In certain embodiments, $R_5$ is selected from the following formulae:

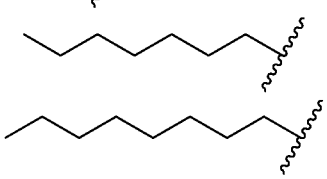

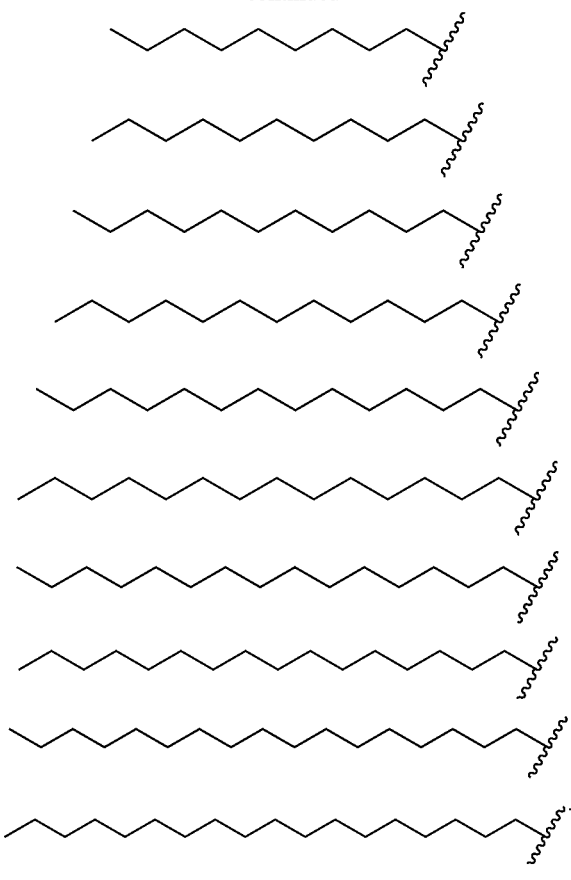

In certain embodiments, $R_5$ is a $C_{1-20}$ alkenyl moiety, optionally substituted. In certain embodiments, $R_5$ is selected from the following formulae:

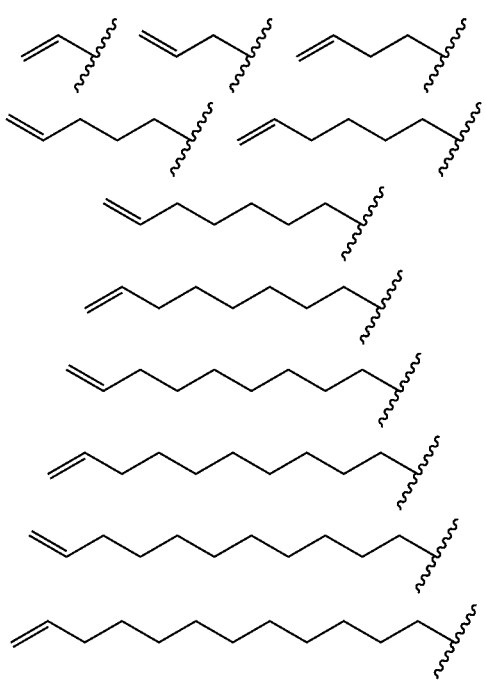

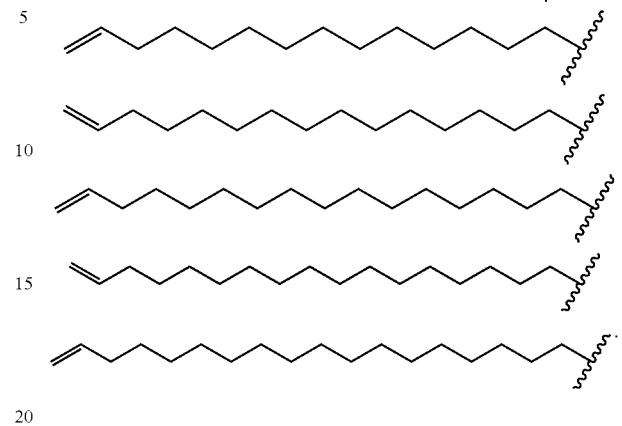

In certain embodiments, $R_5$ is substituted or unsubstituted, cyclic or acyclic, branched or unbranched $C_{1-20}$ heteroaliphatic. In some embodiments, $R_5$ is an unsubstituted and unbranched, $C_{13}$ heteroaliphatic group. In some embodiments, $R_5$ is an unsubstituted and unbranched, $C_{14}$ heteroaliphatic group. In certain embodiments, $R_5$ is:

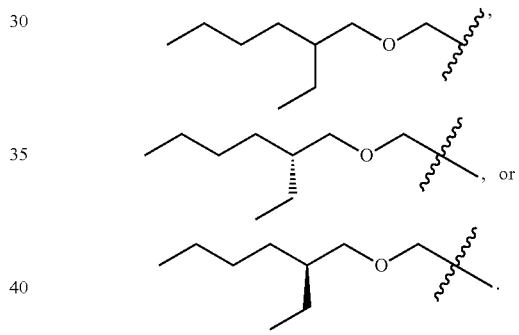

In certain embodiments, $R_5$ is, independently, selected from the following formulae:

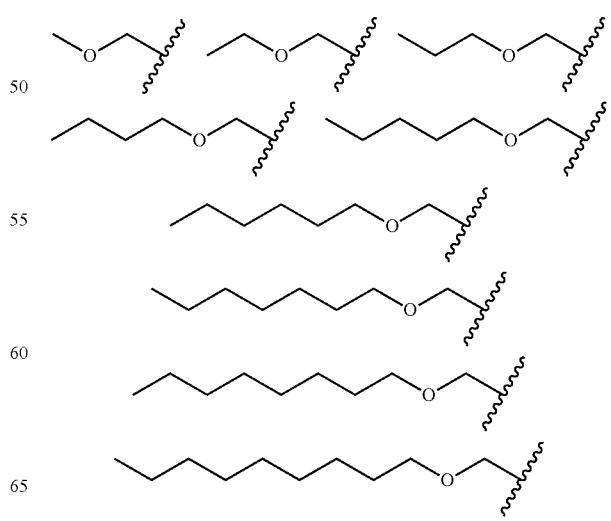

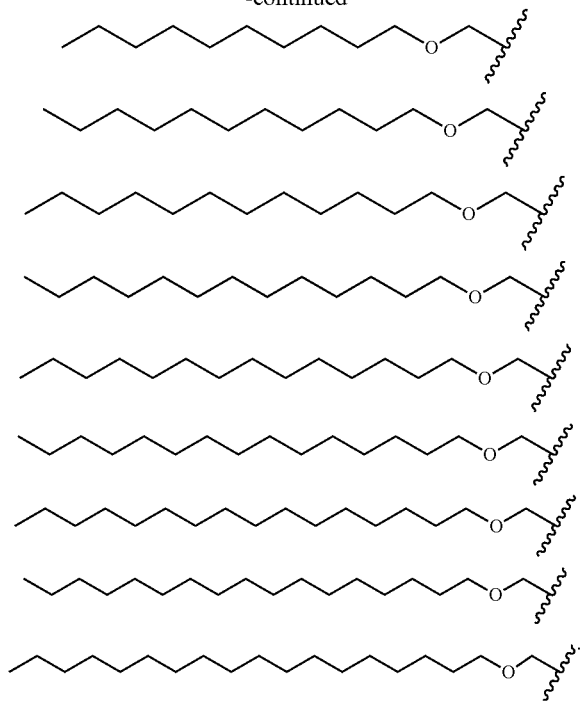

It will be appreciated by one of ordinary skill in the art that the above substituents may have multiple sites of unsaturation, and could be so at any position within the substituent.

In certain embodiments, $R_5$ is substituted or unsubstituted aryl. In certain embodiments, $R_5$ is or substituted or unsubstituted heteroaryl. In certain embodiments, $R_5$ is

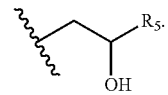

In certain embodiments, each

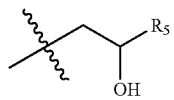

is independently

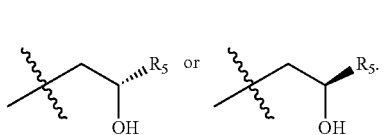

In certain embodiments, $R_5$ is

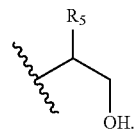

In certain embodiments, $R_5$ is fluorinated. In certain embodiments $R_5$ is a fluorinated aliphatic moiety. In certain embodiments $R_5$ is perfluorinated. In certain embodiments $R_5$ is a perfluorinated aliphatic moiety. In certain embodiments, $R_5$ is a perfluorinated $C_{1-20}$ alkyl group. In certain embodiments, $R_5$ is selected from the following formulae:

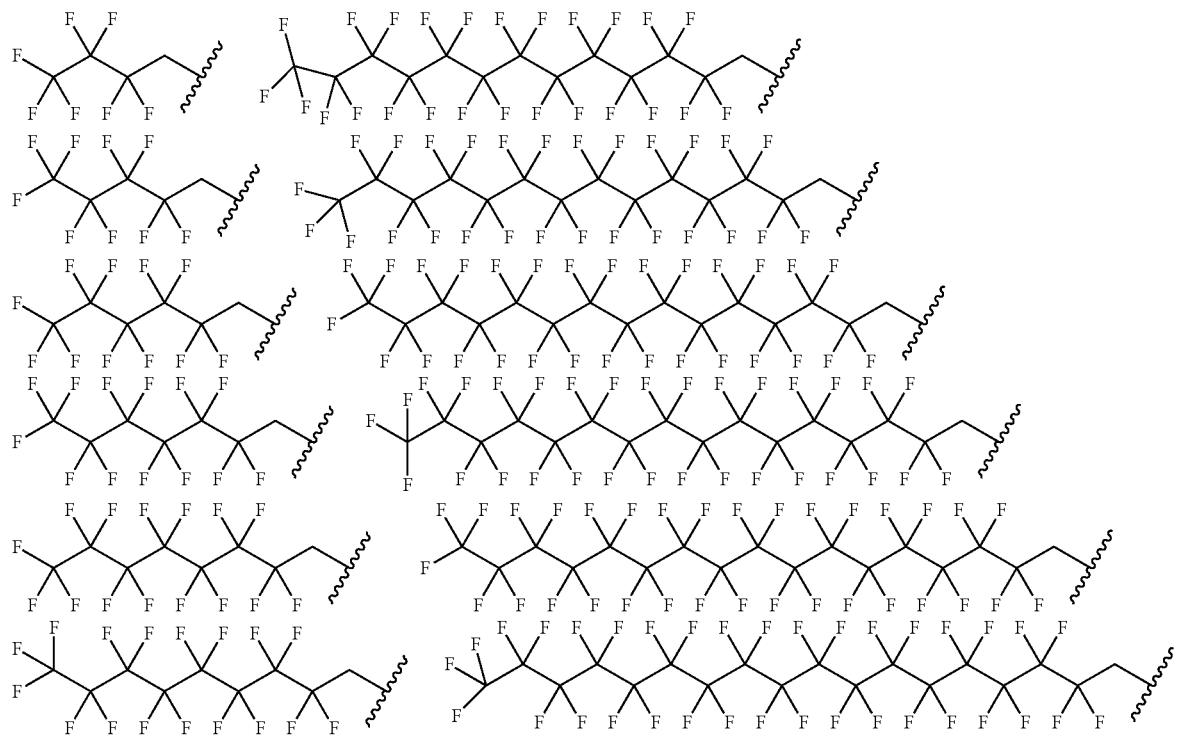

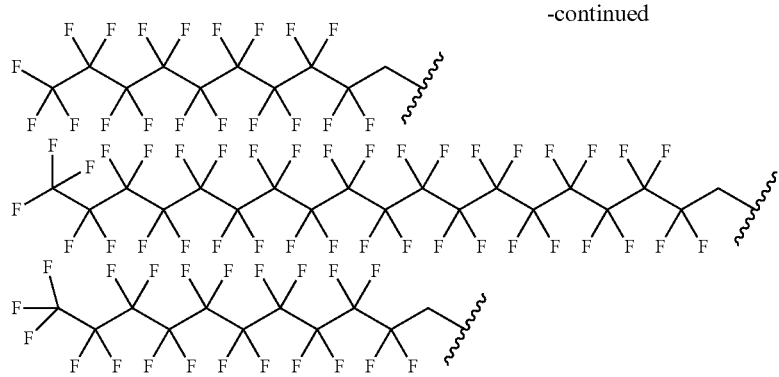

In certain embodiments, R$_5$ is selected from the following formulae:

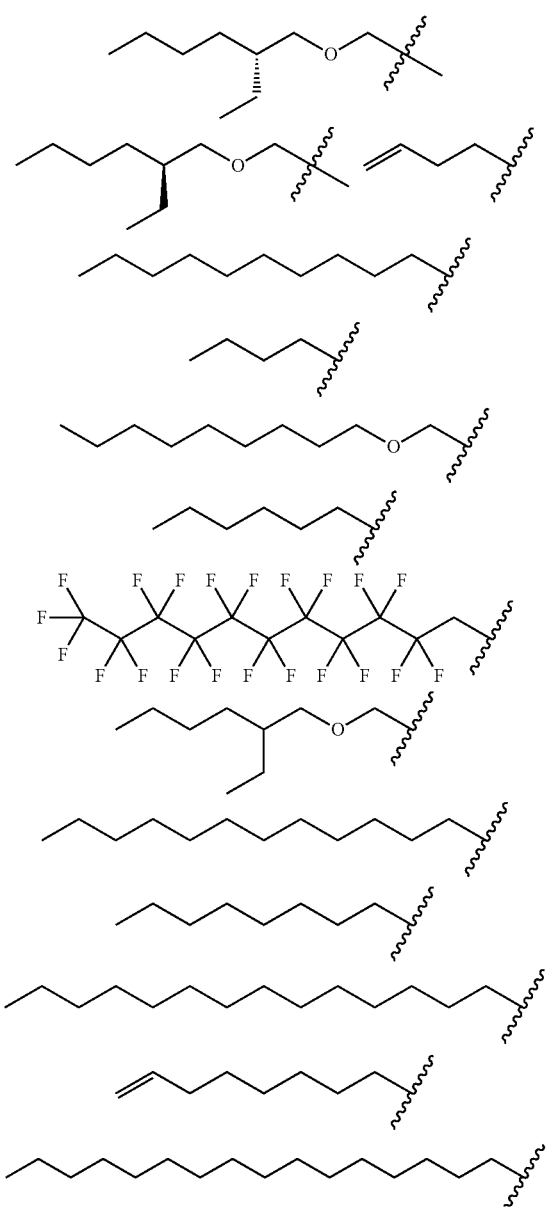

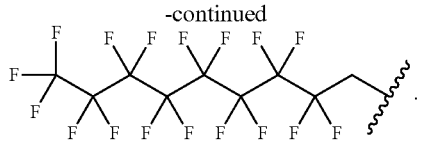

In certain embodiments, each R$_5$ is independently hydrogen, or C$_1$-C$_6$ alkyl. In certain embodiments, each R$_5$ is hydrogen. In certain embodiments, R$_1$ and R$_3$ each R$_5$ is C$_1$-C$_6$ alkyl. In certain embodiments, each R$_5$ is hydroxyalkyl. In certain embodiments, each R$_5$ is aminoalkyl. In certain embodiments, two R$_5$ variables are the same. In certain embodiments, three R$_5$ variables are the same. In certain embodiments, each R$_5$ variable is different from the other.

In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10.

In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, y is 10.

In certain embodiments, an aminoalcohol lipidoid compound or composition containing aminoalcohol lipidoid compound(s) is prepared by reacting an amine of one of the formulae:

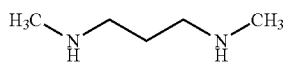

62

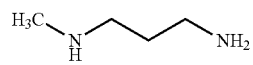

96

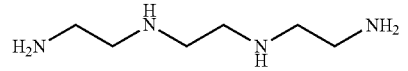

98

99

100

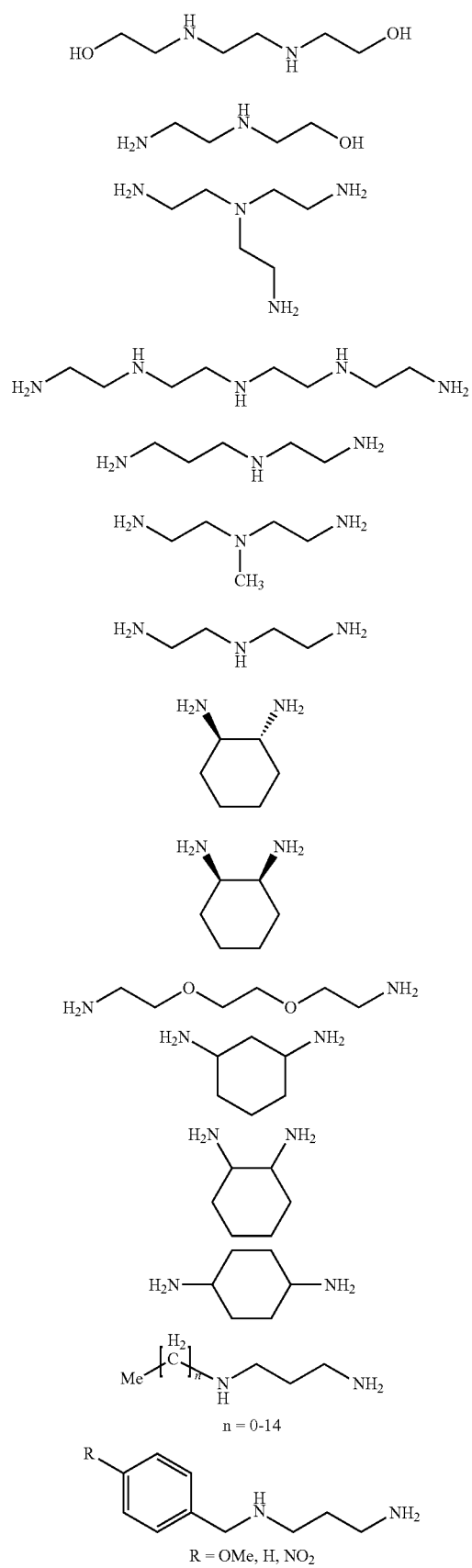
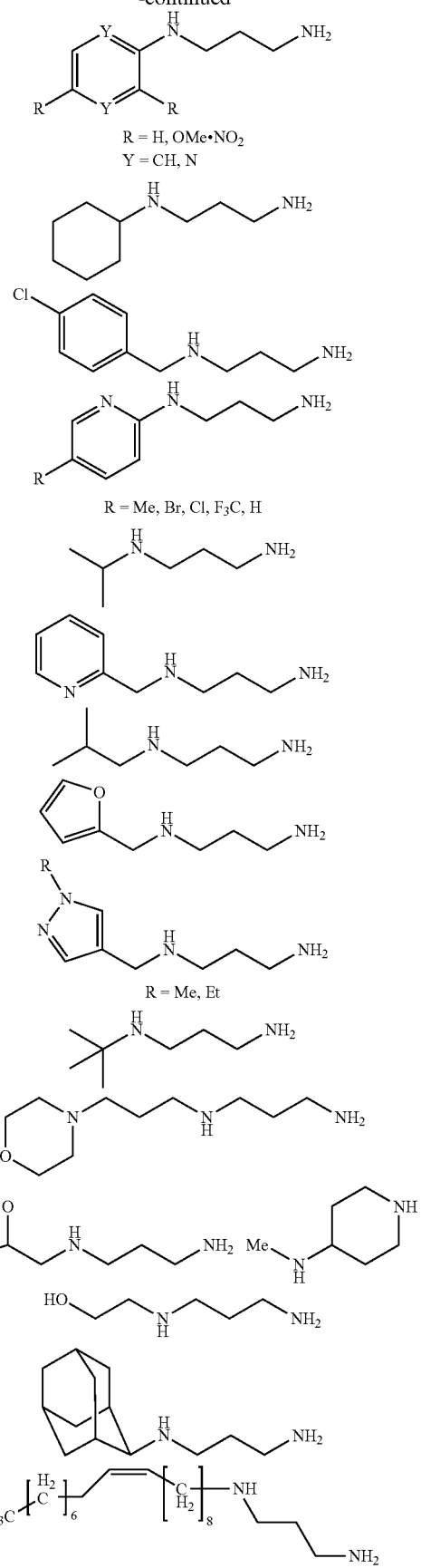

117
-continued
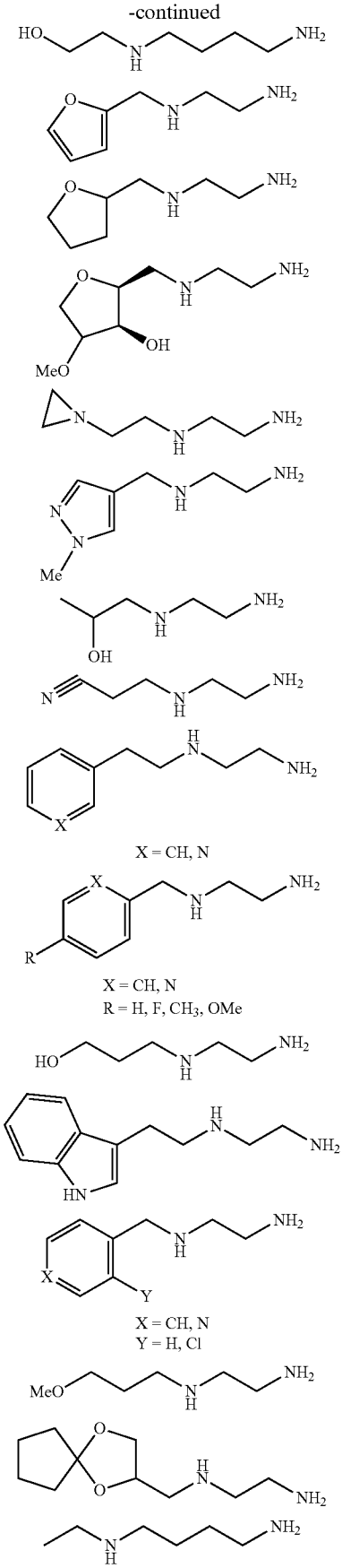
118
-continued
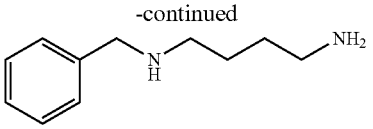
with an epoxide-containing compound of one of the formulae:
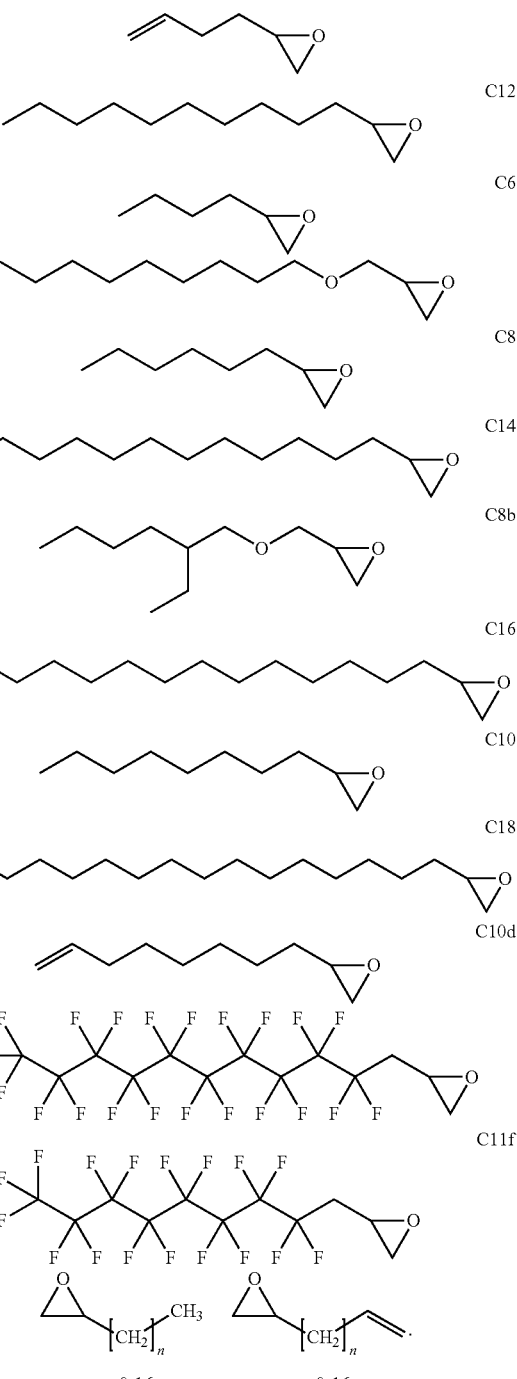
In certain embodiments, the epoxide-terminated compounds are of the formula:

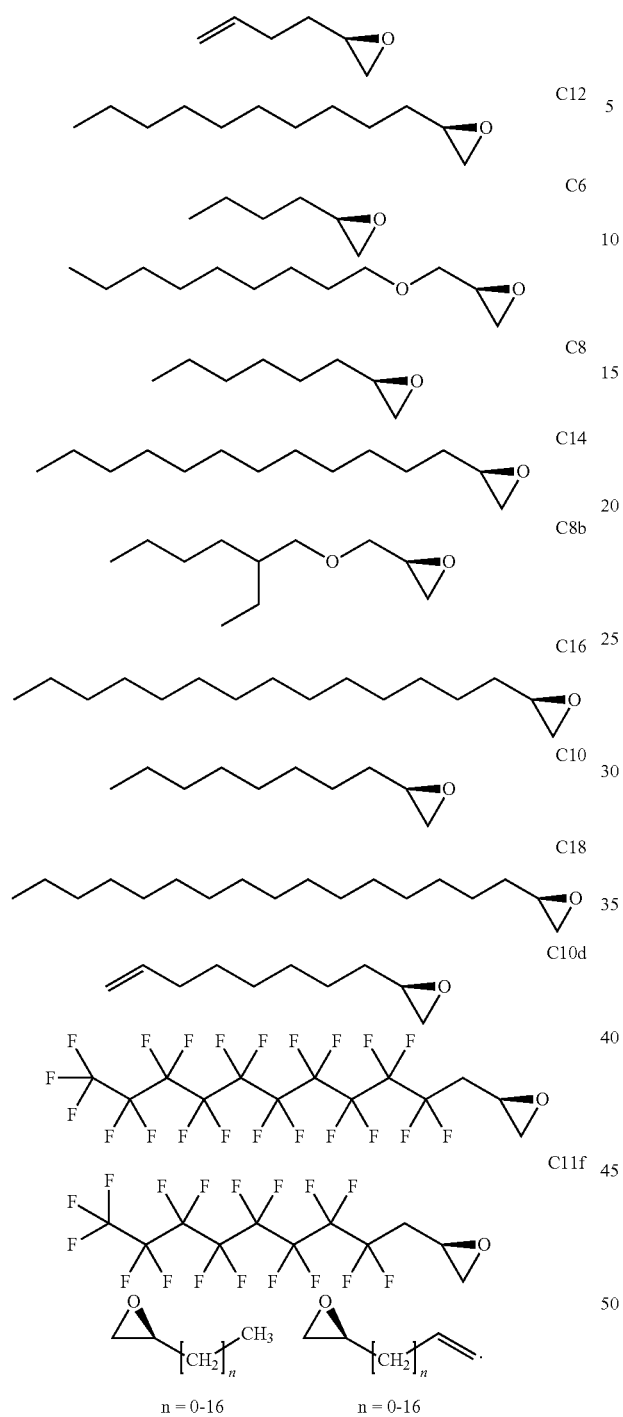
In certain embodiments, the epoxide-containing compound is of the formula:
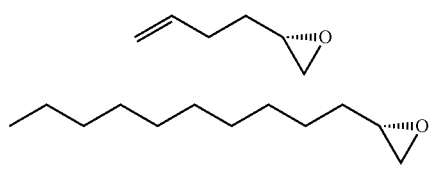
In certain embodiments, the epoxide contains one or more chiral centers, such as those shown below for amine C8b:
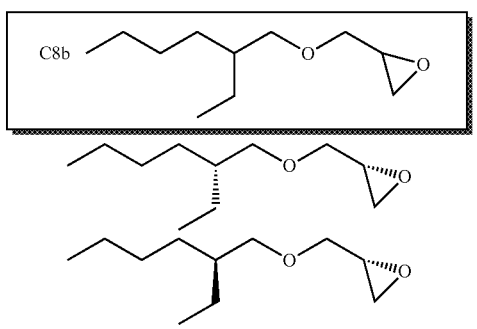

121

-continued

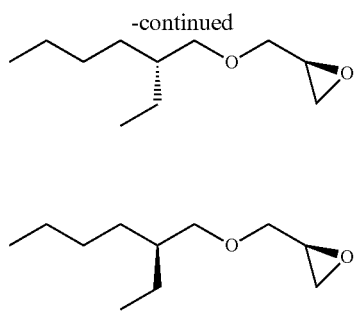

In certain embodiments, one equivalent of an amine is reacted with one equivalent of an epoxide-terminated compound. In certain embodiments, one equivalent of an amine is reacted with one, two, three, four, five, six or more equivalents of an epoxide-terminated compound. In certain embodiments, the amount of epoxide-terminated compound is limiting to prevent the functionalization of all amino groups. The resulting aminoalcohol lipidoid or aminoalcohol lipidoid composition in these instances contain secondary amino groups and/or primary amino groups. Aminoalcohol lipidoid compounds having secondary amines are particular useful in certain instances. In certain embodiments, amine-containing aminoalcohol lipidoid compounds that have not been fully functionalized are futher reacted with another electrophile (e.g., terminal epoxide, alkyl halide, etc.). Such further functionalization of the amines of the aminoalcohol lipidoid compound results in aminoalcohol lipidoid compounds with different epoxide-compound derived tails. One, two, three, four, five, or more tails may be different from the other tails of the aminoalcohol lipidoid compounds.

In certain embodiments, it will be appreciated by one skilled in the art that the amine and the epoxide will react at the unsubstituted carbon of the epoxide resulting in an aminoalcohol lipidoid compound as shown in the following schemes.

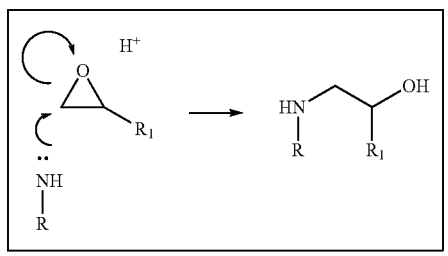

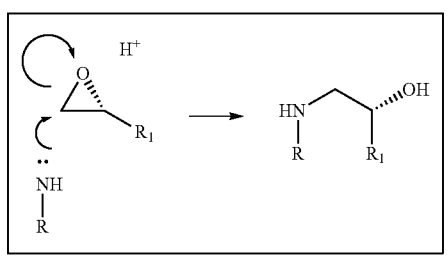

122

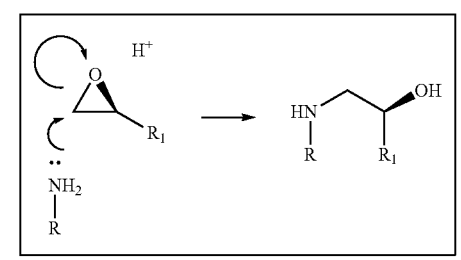

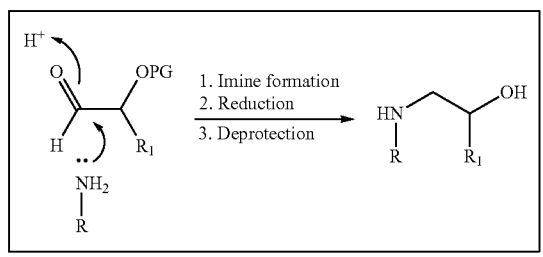

In certain embodiments, the epoxide is stereochemically pure (e.g., enantiomerically pure). In certain embodiments, the amine is stereochemically pure (e.g., enantiomerically pure). In certain embodiments, the lipidoid is prepared from the reductive amination of an imine which derived from the condensation of an amine and an aldehyde. The compounds of the invention can have an enantiomeric excess or a diastereomeric excess up to and including 2%, 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100%.

In other embodiments, it will be appreciated by one skilled in the art that the amine and the epoxide will react at the substituted carbon of the epoxide resulting in an aminoalcohol lipidoid compound as shown in the following scheme.

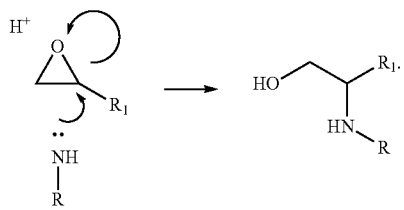

While the above reaction may be less preferred, it is likely to occur at least to some degree and may be more favored under certain reaction conditions. An aminoalcohol lipidoid compound may have amines that have reacted in one or both manners.

In certain embodiments, the amine and epoxide-terminated compound are reacted together neat. In other embodiments, the reaction is done in a solvent (e.g., THF, $CH_2Cl_2$, MeOH, EtOH, $CHCl_3$, hexanes, toluene, benzene, $CCl_4$, glyme, diethyl ether, etc.). In certain embodiments, the reaction mixture is heated. In certain embodiments, the reaction mixture is heated to temperature ranging from 30° C.-100° C. In another embodiment, the reaction mixture is heated to approximately 90° C. The reaction may also be catalyzed. For example, the reaction may be catalyzed by the addition of an acid, base, or metal (e.g., Lewis acid). The reaction may be allowed to proceed for hours, days, or weeks. In certain embodiments, the reaction is allowed to proceed for 1-7 days. In certain embodiments, the reactions were run from about 1 to about 3 days. The resulting composition may be used with or without purification. In certain embodiments, the lipidoids are subsequently subjected to an alkylation step (e.g., reaction with methyl iodide) to form quaternary amine salts. Optionally, various salt forms of the lipidoids may be prepared. In certain embodiments, the salts are pharmaceutically acceptable salts.

In certain embodiments the aminoalcohol lipidoid compound or composition containing a mixture of aminoalcohol lipidoid compounds is prepared by reacting amine 200 with an epoxide-terminated compound. In certain embodiments, the amine 200-derived aminoalcohol lipidoid compounds (i.e., C12-200) and its various possible isomers are of the formulae below:

5 Tails

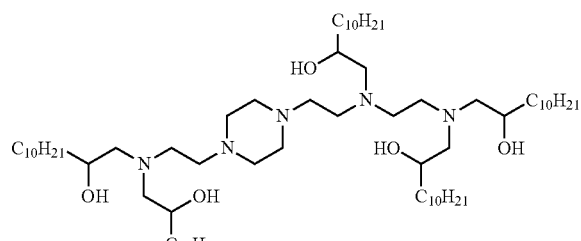

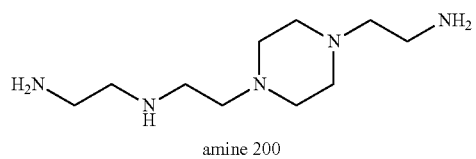 [SMILES: NCCNCCN1CCN(CCN)CC1]

amine 200

4 Tails

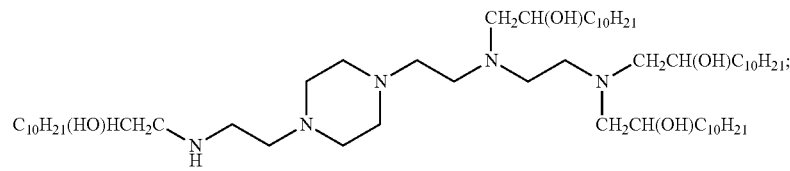

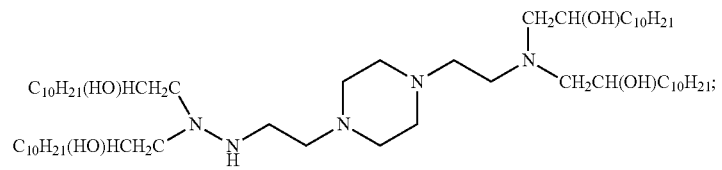

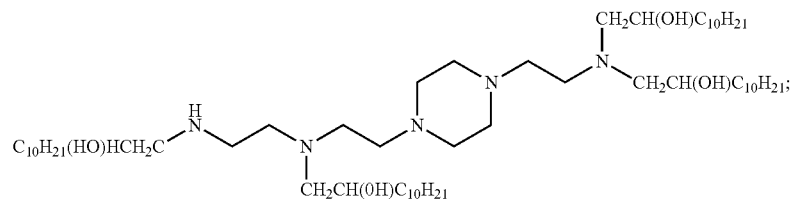

3 Tails

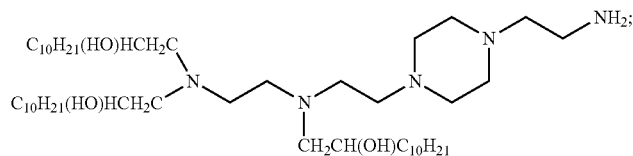

-continued
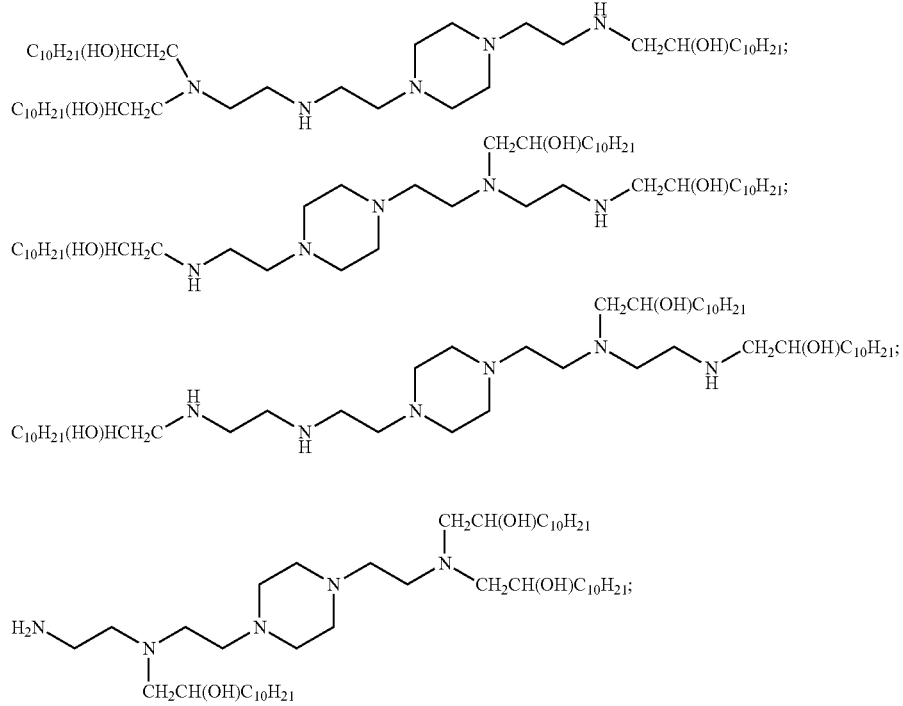
2 Tails
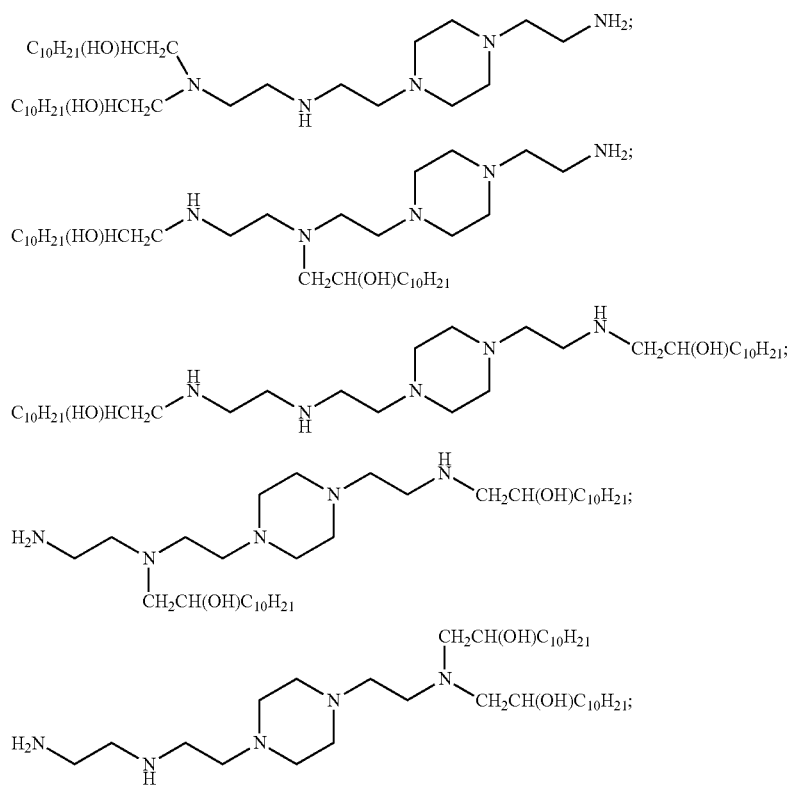

1 Tail

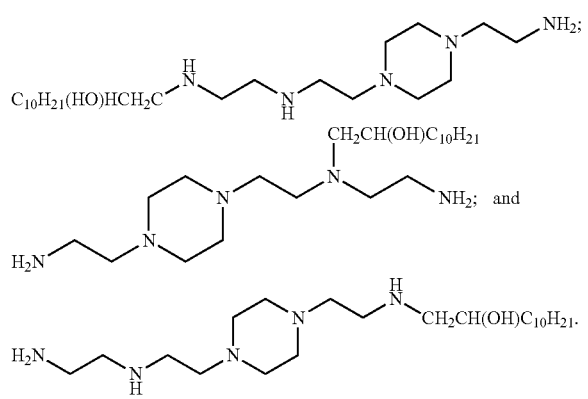

In certain embodiments, each

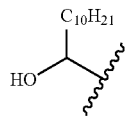

is independently

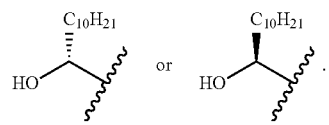

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 205

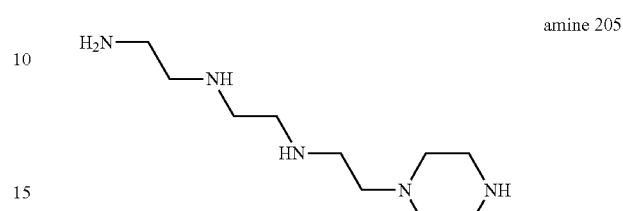

with an epoxide-terminated compound C12. In certain embodiments, the amine 205-derived aminoalcohol lipidoid compounds (i.e., C12-205) and its various possible isomers are of the formulae below:

5 Tails

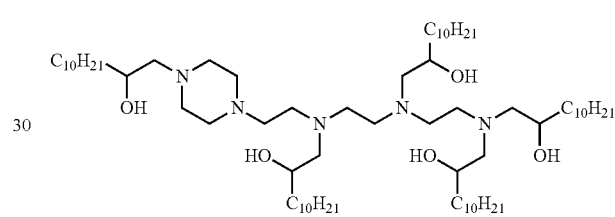

4 Tails

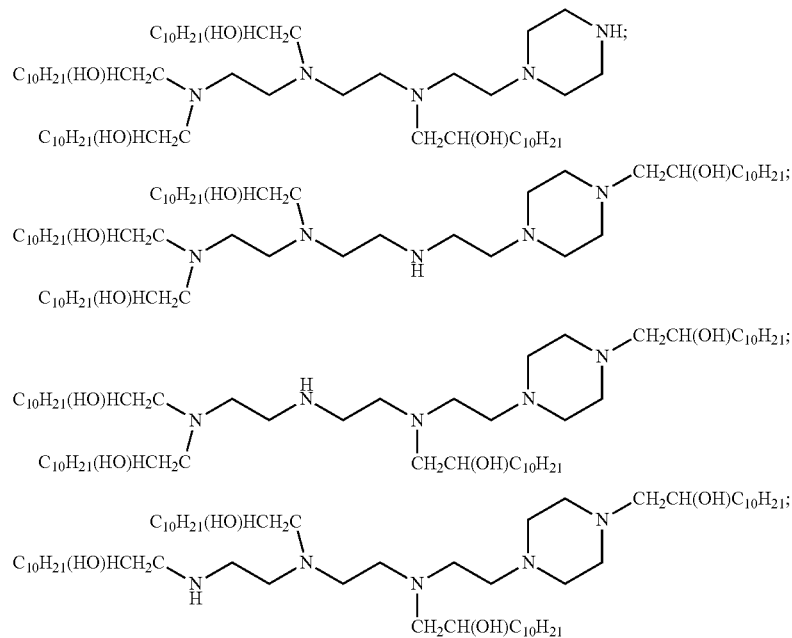

3 Tails
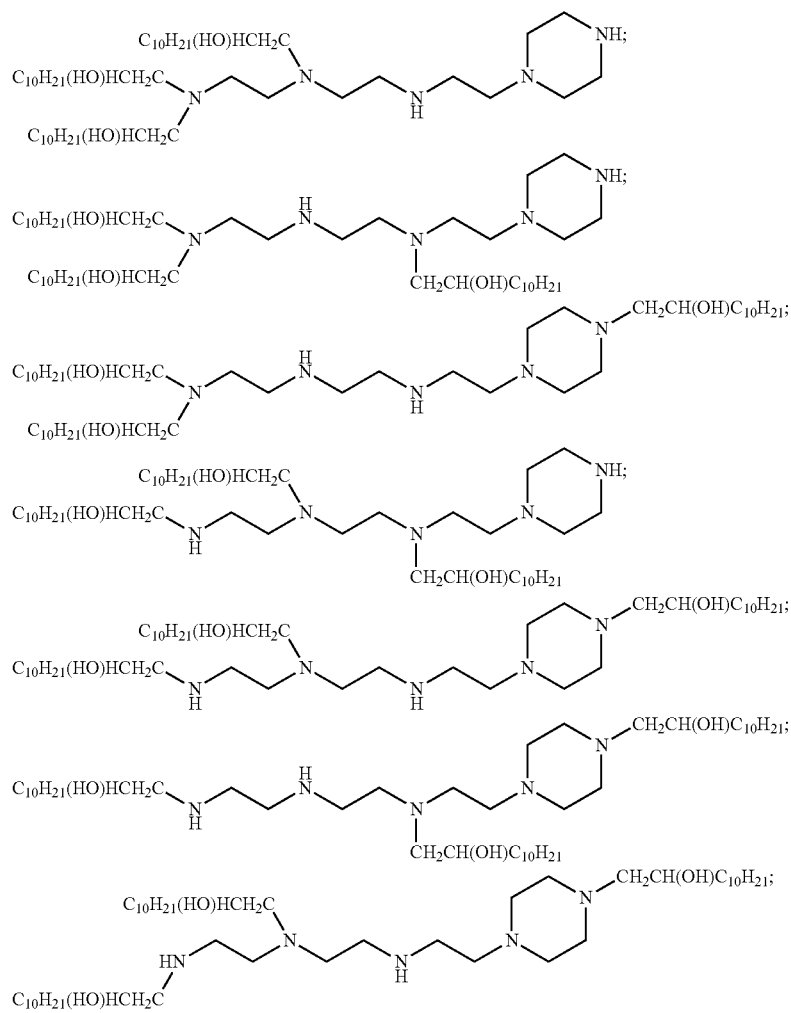
2 Tails
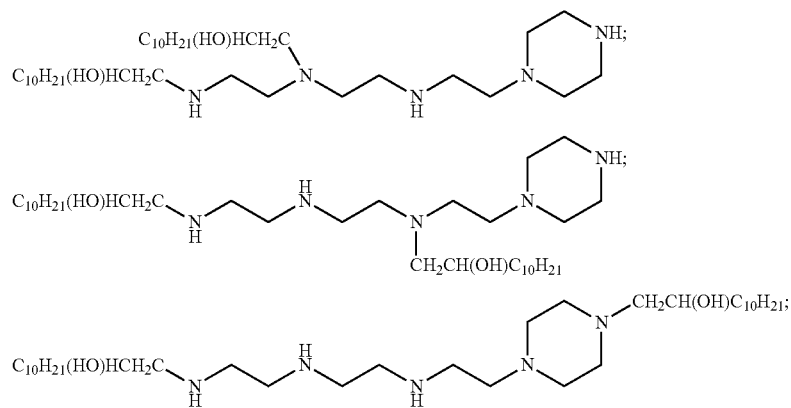

-continued

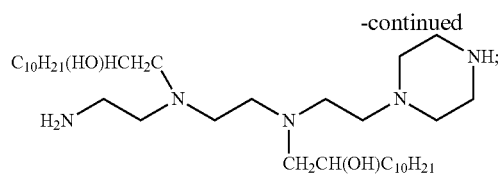

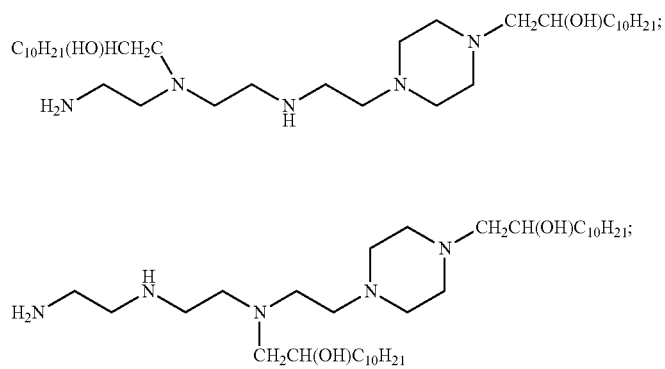

1 Tail

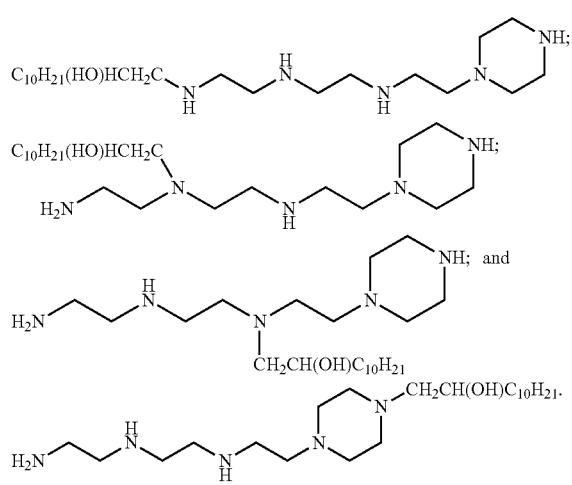

In certain embodiments, each

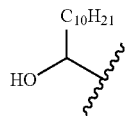

is independently

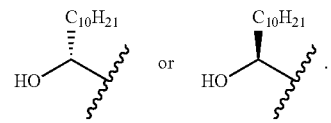

In certain embodiments the aminoalcohol lipidoid composition, is a composition containing one or more of the above aminoalcohol lipidoid compounds.

In certain embodiments, the aminoalcohol lipidoid is of the formula

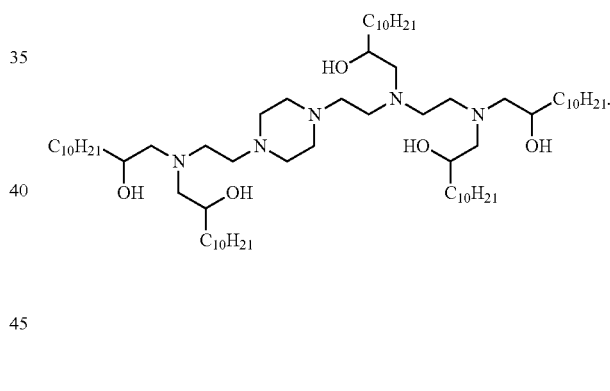

In certain embodiments, the aminoalcohol lipidoid compound is of the formula

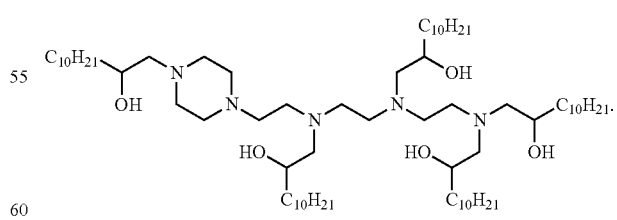

In certain embodiments, the aminoalcohol lipidoid compound is a mixture of

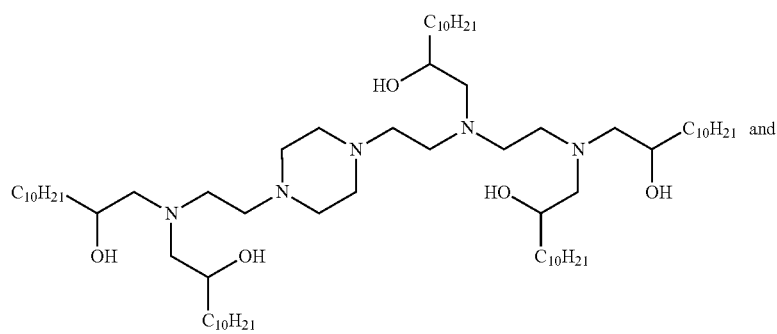

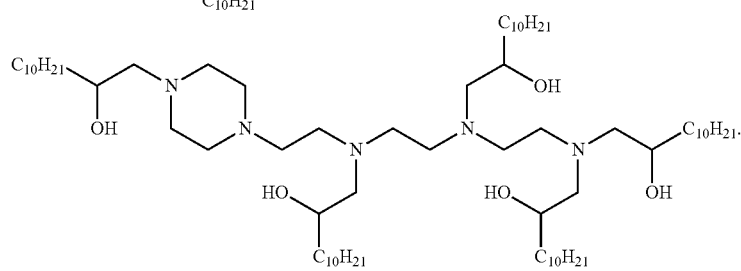

In certain embodiments, each

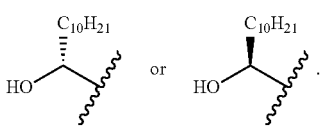

is independently

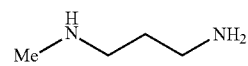

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 96 amine 96

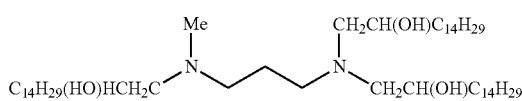

with an epoxide-terminated compound C16. In certain embodiments, the amine 96-derived aminoalcohol lipidoid compounds (i.e., C16-96) and its various possible isomers are of the formulae below:

3 Tails

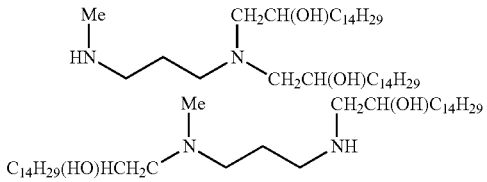

2 Tails

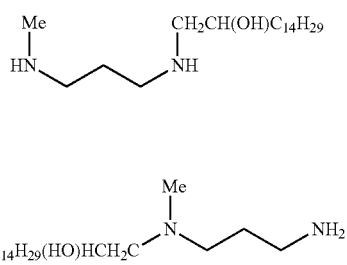

1 Tail

In certain embodiments the aminoalcohol lipidoid compound or composition containing a mixture of aminoalcohol lipidoid compounds is prepared by reacting amine 210

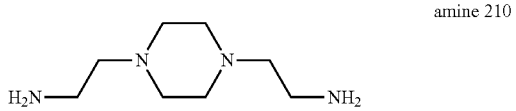

amine 210 with the epoxide-terminated compound C12. In a similar manner as illustrated above, one skilled in the art will readily be able to determine the various possible 210-derived aminoalcohol lipidoid compounds (i.e., C12-210) isomeric structures that are possible from this reaction.

In certain embodiments the aminoalcohol lipidoid composition, is a composition containing one or more of the above aminoalcohol lipidoid compounds.

In certain embodiments the aminoalcohol lipidoid compound or composition containing a mixture of aminoalcohol lipidoid compounds is prepared by reacting amine 220

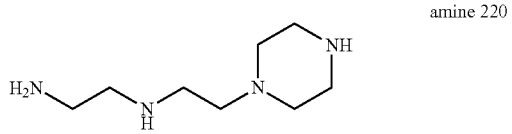 [SMILES: NCCNCCN1CCNCC1]

amine 220 with the epoxide-terminated compound C12. In a similar manner as illustrated above, one skilled in the art will readily be able to determine the various possible 220-derived aminoalcohol lipidoid compounds (i.e., C12-220) isomeric structures that are possible from this reaction.

In certain embodiments the aminoalcohol lipidoid composition, is a composition containing one or more of the above aminoalcohol lipidoid compounds.

In certain embodiments, the aminoalcohol lipidoid compound or composition containing a mixture of aminoalcohol lipidoid compounds is prepared by reacting amine 111

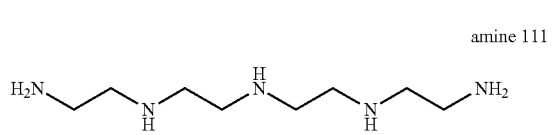 [SMILES: NCCNCCNCCNCCN]

amine 111 with the epoxide-terminated compound C12. In a similar manner as illustrated above, one skilled in the art will readily be able to determine the various possible 111-derived aminoalcohol lipidoid compounds (i.e., C12-111) isomeric structures that are possible from this reaction.

In certain embodiments the aminoalcohol lipidoid composition, is a composition containing one or more of the above aminoalcohol lipidoid compounds.

2. Synthesis of Aminoalcohol Lipidoid Compounds

The inventive aminoalcohol lipidoid compounds may be prepared by any method known in the art. Preferably the aminoalcohol lipidoid compounds are prepared from commercially available starting materials, such as terminal-epoxide compounds, interior epoxide compounds, and amines. In another embodiment, the aminoalcohol lipidoid compounds are prepared from easily and/or inexpensively prepared starting materials. As would be appreciated by one of skill in the art, the inventive aminoalcohol lipidoid compounds can be prepared by total synthesis starting from commercially available starting materials. A particular aminoalcohol lipidoid compound may be the desired final product of the synthesis, or a mixture of aminoalcohol lipidoid compounds may be the desired final product.

In certain embodiments, the inventive aminoalcohol lipidoid compound is prepared by reacting an amine with an epoxide-terminated compound. An exemplary reaction scheme is shown in FIG. 1.

Any amine containing between one, two, and five amine functionalities is useful in preparing inventive aminoalcohol lipidoid compounds. Primary amines useful in this invention include, but are not limited to, methylamine, ethylamine, isopropylamine, aniline, substituted anilines, ethanolamine, decylamine, undecylamine, dodecylamine, tetradecylamine, hexadecylamine, and octadecylamine. The amine may be a bis(primary amine) including, but not limited to, ethylenediamine, 1,3 diaminopropane, 1,4 diamino butane, 1,5 diaminopentane, 1,6 diaminohexane, 2,2' (ethylenedioxy)bis (ethylamine). The amine may be a bis(secondary amine). Secondary amines useful in this invention include, but are not limited to dipropylamine and methylpentylamine. The amine may include both primary and secondary amines including, but not limited to, (2-aminoethyl) ethanolamine, diethylenetriamine and triethylenetetramine. Preferably, the amine is commercially available. In certain embodiments, the amine is stereochemically pure (e.g., enantiomerically pure).

In certain embodiments, the amine used in the synthesis of the aminoalcohol lipidoid compound is of the formula:

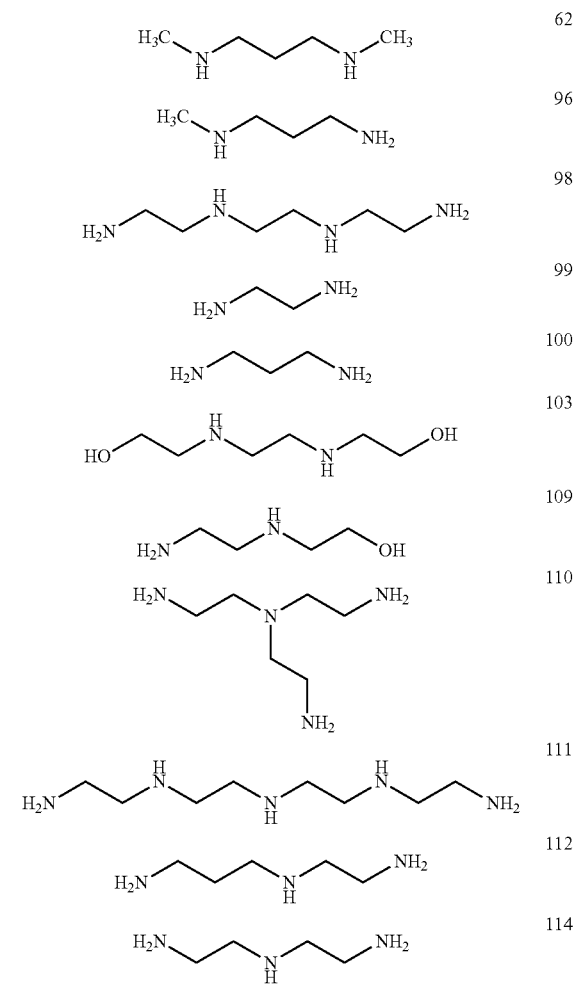

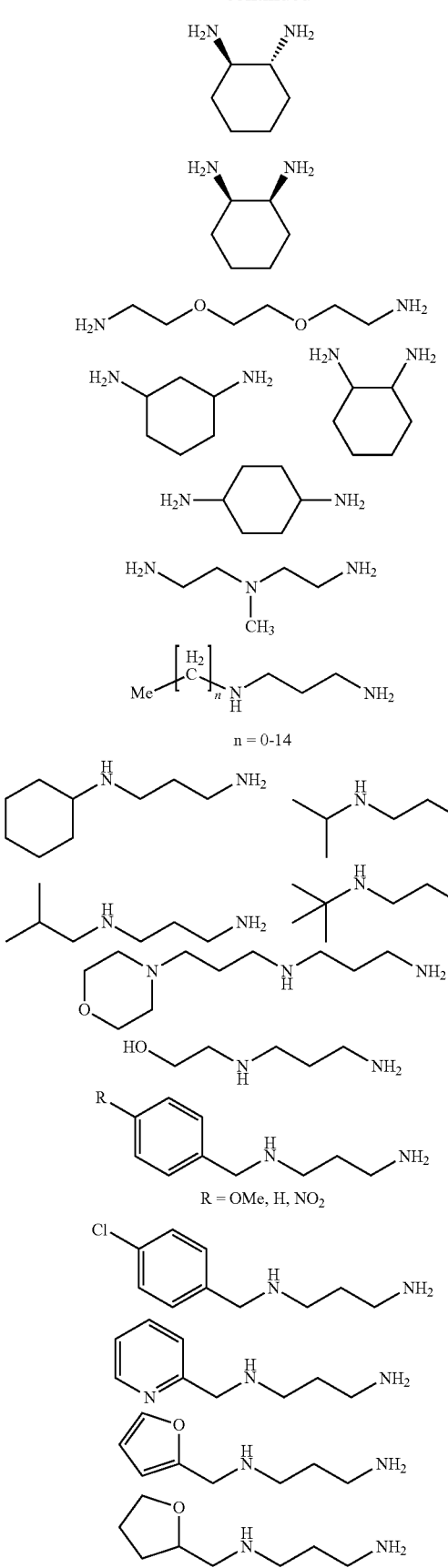
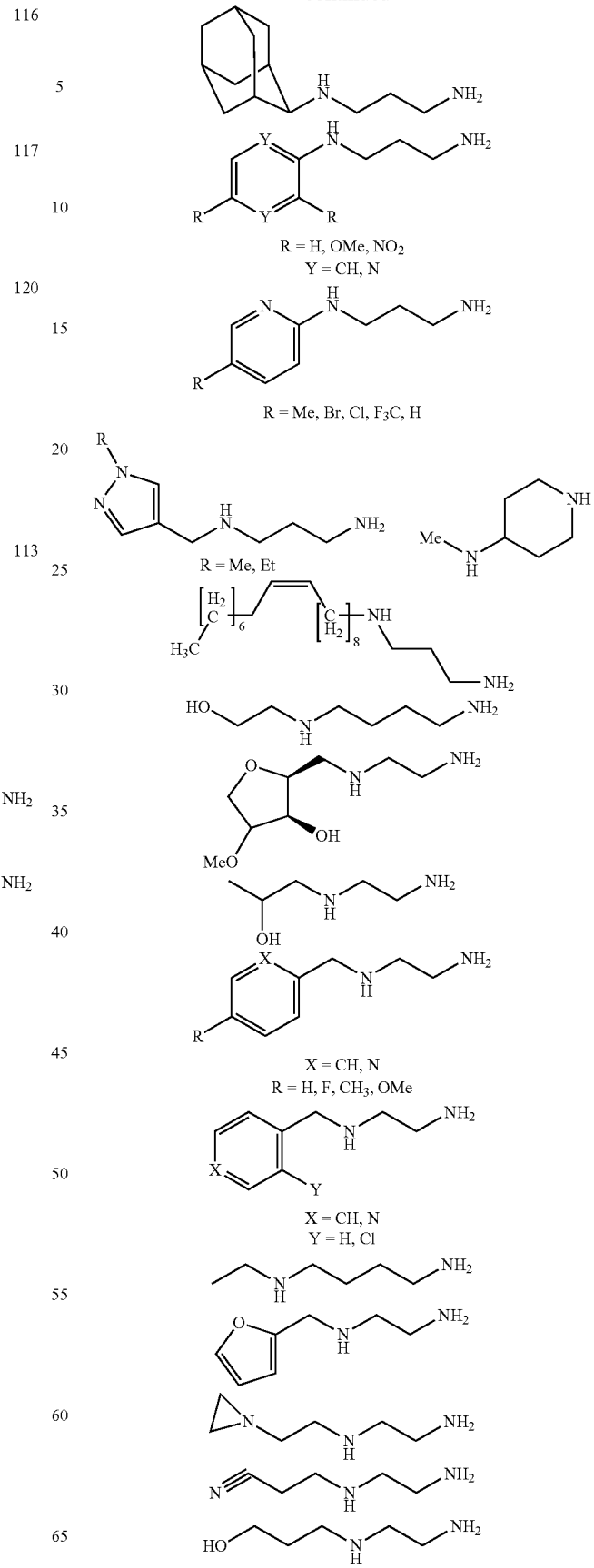

Epoxide-terminated compounds that are useful in the present invention include any epoxide-terminated compounds that are racemic or stereoisomers thereof, all of varying chain lengths and feature unique functional groups having varying degrees of saturation. In certain embodiments, the epoxide is stereochemically pure (e.g., enantiomerically pure). In certain embodiments, the epoxide contains one or more chiral centers. In certain embodiments, the epoxide-terminated compounds are of the formula:

In certain embodiments, the epoxide-terminated compounds are of the formula:

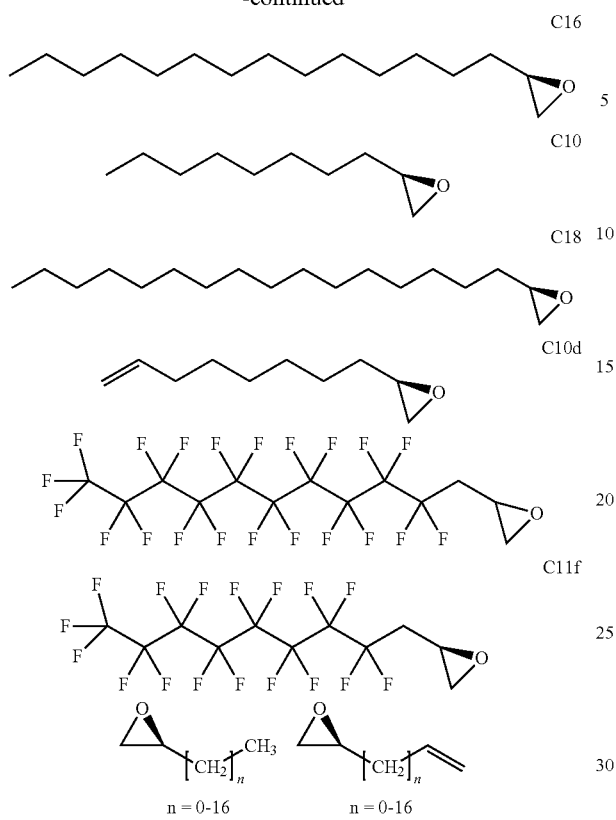

In certain embodiments, the epoxide-terminated compounds are of the formula:

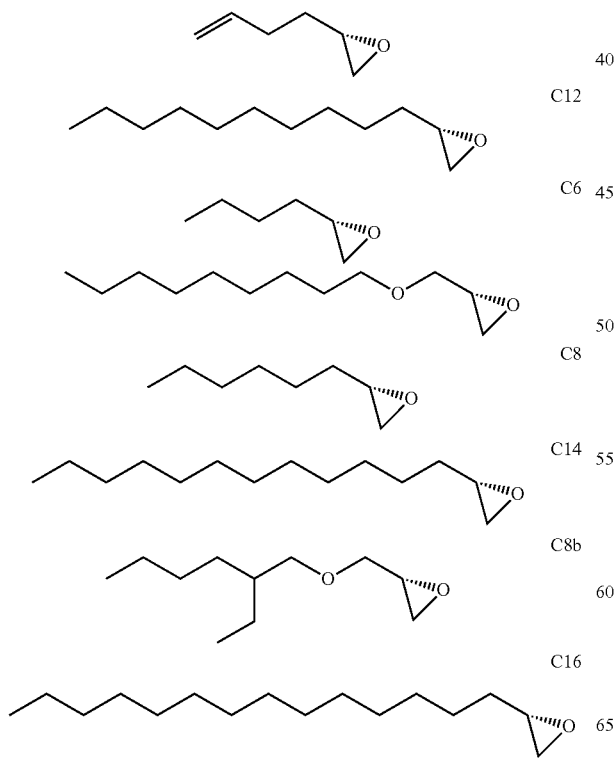

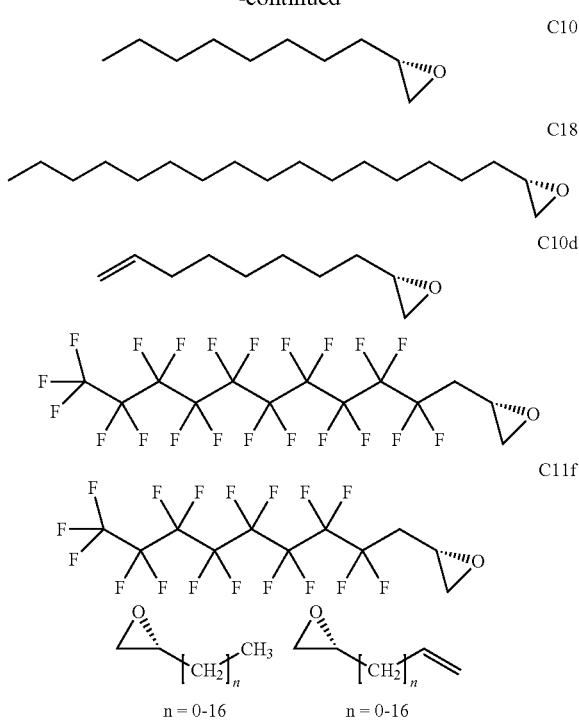

In certain embodiments, the epoxide contains one or more chiral centers, such as those shown below:

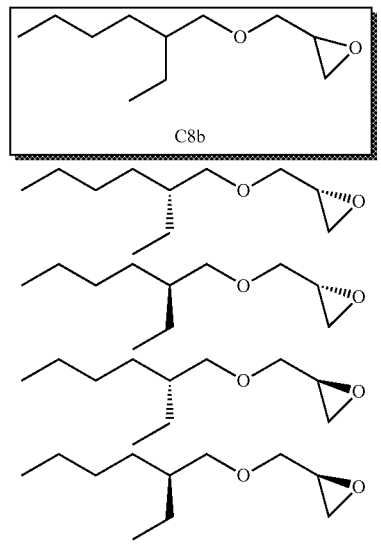

In certain embodiments, the enantiomeric epoxide

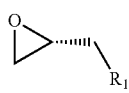

is resolved from the racemic mixture of epoxides using hydrolytic kinetic resolution (HKR) catalyzed with the (R,R)-HKR catalyst of the formula:

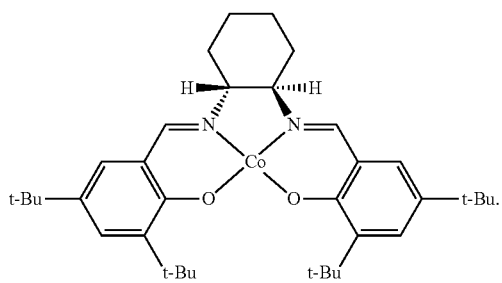

In further embodiments, the enantiomeric epoxide

is resolved from the racemic mixture of epoxides using hydrolytic kinetic resolution (HKR) catalyzed with the (S,S)-HKR catalyst of the formula:

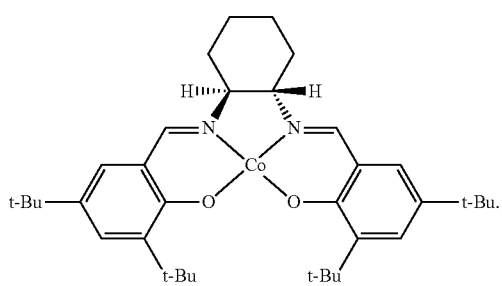

In certain embodiments, the aminoalcohol lipidois of the invention are prepared from a process comprising steps of:

(a) converting the epoxide primary alcohol of the formula:

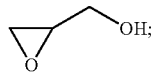

into the corresponding protected primary alcohol derivative of the formula:

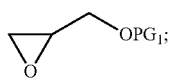

(b) reacting the protected primary alcohol derivative of the formula:

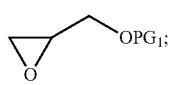

with a carbon-based nucleophile to produce the secondary alcohol of the formula:

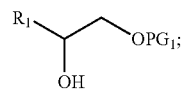

(c) converting the secondary alcohol of the formula:

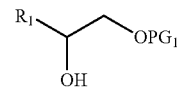

into the corresponding protected secondary alcohol derivative of the formula

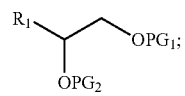

(d) deprotecting the protected secondary alcohol derivative of the formula

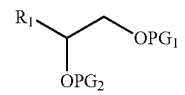

into the corresponding primary alcohol of the formula

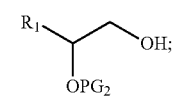

(e) oxidizing the primary alcohol of the formula

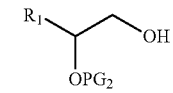

into the corresponding aldehyde of the formula

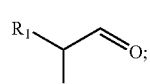

(f) condensing the aldehyde of the formula:

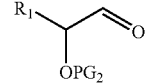

with an amine of the formula:

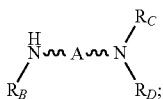

to produce an imine of the formula:

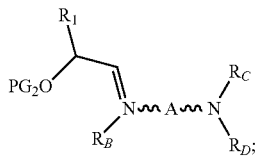

and (g) reducing an imine of the formula:

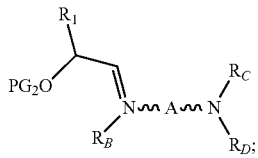

to produce the corresponding amine of the formula:

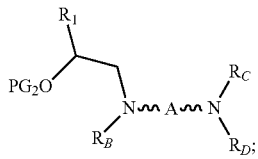

wherein $R_1$ is hydrogen, a substituted, unsubstituted, branched or unbranched $C_{1-20}$-aliphatic or a substituted, unsubstituted, branched or unbranched $C_{1-20}$ heteroaliphatic, wherein at least one occurrence of $R_1$ is hydrogen; $R_B$, $R_C$, and $R_D$ are, independently, hydrogen, a substituted, unsubstituted, branched or unbranched $C_{1-20}$-aliphatic, or a substituted, unsubstituted, branched or unbranched $C_{1-20}$-heteroaliphatic or —CH$_2$CH(OH)R$_E$; $R_B$ and $R_D$ together may optionally form a cyclic structure; $R_C$ and $R_D$ together may optionally form a cyclic structure; $R_E$ is a substituted, unsubstituted, branched or unbranched $C_{1-20}$ aliphatic or a substituted, unsubstituted, branched or unbranched $C_{1-20}$ heteroaliphatic; and PG$_1$ and PG$_2$ are O-protecting groups as described herein.

In certain embodiments, the epoxide primary alcohol of step (a) is

and the amine of step (f) is

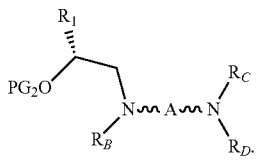

In certain embodiments, the epoxide primary alcohol of step (a) is

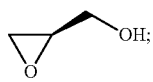

and the amine of step (f) is

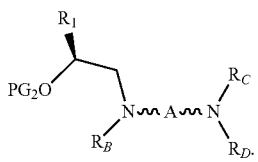

The chiral epoxides useful in the invention can be obtained from a variety of sources which are familiar to those skilled in the art of organic synthesis. In some embodiments, the chiral epoxides useful in the invention can be obtained commercially. In some embodiments, the chiral epoxides useful in the invention can be synthesized according to methods known to those of skill in the art, such as, but not limited to the Sharpless epoxidation of primary and secondary allylic alcohols into 2,3-epoxyalcohols (Katsuki, et al., *J. Am. Chem. Soc.* 1980, 102, 5974; Hill, et al., *Org. Syn.*, Coll. Vol. 7, p. 461 (1990); Vol. 63, p. 66 (1985) and Katsuki, et al., *Org. React.* 1996, 48, 1-300; incorporated herein by reference.) In some embodiments, the chiral epoxides useful in the invention are obtained from the resolution of racemic epoxides. In some embodiments, the chiral epoxides useful in the invention are obtained by the separation of enantiomers or diastereoisomers on chiral columns.

In certain embodiments, the reaction is performed neat without the use of a solvent. In other embodiments, a solvent is used for the reaction. Both or one of the starting amine or epoxide-terminated compound is dissolved in an organic solvent (e.g., THF, CH$_2$Cl$_2$, MeOH, EtOH, CHCl$_3$, hexanes, toluene, benzene, CCl$_4$, glyme, diethyl ether, etc.). The resulting solutions are combined, and the reaction mixture is heated to yield the desired aminoalcohol lipidoid compound. In certain embodiments, the reaction mixture is heated to a temperature ranging from 25° C. to 100° C., preferably at approximately 90° C. The reaction may also be catalyzed. For example, the reaction may be catalyzed by the addition of an acid, base, or metal. The reagents may be allowed to react for hours, days, or weeks. Preferably, the reaction is allowed to proceed from overnight (e.g., 8-12 hours) to 7 days.

The synthesized aminoalcohol lipidoid compounds may be purified by any technique known in the art including, but not limited to, precipitation, crystallization, chromatography, distillation, etc. In certain embodiments, the aminoalcohol lipidoid compound is purified through repeated precipitations in organic solvent (e.g., diethyl ether, hexane, etc.). In certain embodiments, the aminoalcohol lipidoid compound is isolated as a salt. The aminoalcohol lipidoid compound is reacted with an acid (e.g., an organic acid or inorganic acid) to form the corresponding salt. In certain embodiments, the tertiary amine is alkylated to form a quaternary ammonium salt of the aminoalcohol lipidoid compound. The tertiary amines may be alkylated with any alkylating agent, for example, alkyl halides such as methyl iodide may be used to from the quaternary amino groups. The anion associated with the quaternary amine may be any organic or inorganic anion. Preferably, the anion is a pharmaceutically acceptable anion.

In certain embodiments, the reaction mixture results in a mixture of isomers with varying numbers and positions of epoxide-derived compound tails. Such mixtures of products or compounds may be used as is, or a single isomer, or compound, may be purified from the reaction mixture. When an amine is not exhaustively alkylated, the resulting primary, secondary, or tertiary amines may be further reacted with another aminoalcohol lipidoid compound, epoxide-terminated compound, or other electrophile. The resulting aminoalcohol lipidoid compound may then be optionally purified.

In certain embodiments, a desired aminoalcohol lipidoid compound is prepared by traditional total synthesis. In certain embodiments, a commercially available amine is the starting material. One or more amino groups of the amine are optionally protected. The unprotected amino groups are reacted with an epoxide-terminated compound. The product is optionally purified. Protecting groups are removed, and the free amino groups are optionally reacted with another aminoalcohol lipidoid compound, epoxide-terminated compound, or other electrophile. Such a sequence may be repeated depending on the desired complexity of the inventive product being prepared. The final product may then be optionally purified.

In one embodiment, a library of different aminoalcohol lipidoid compounds is prepared in parallel. A different amine and/or epoxide-terminated compound is added to each vial in a set of vials or to each well of a multi-well plate used to prepare the library. The array of reaction mixtures is incubated at a temperature and length of time sufficient to allow formation of the aminoalcohol lipidoid compounds to occur. In one embodiment, the vials are incubated at approximately 90° C. overnight. In certain embodiments, the vials are incubated from 1 to 7 days at approximately 90° C. In certain embodiments, the vials are incubated from 3 to 4 days at approximately 90° C. In certain embodiments, the vials are incubated from 1 to 2 days at approximately 90° C. The aminoalcohol lipidoid compounds may then be isolated and purified using techniques known in the art. The aminoalcohol lipidoid compounds may then be screened using high-throughput techniques to identify aminoalcohol lipidoid compounds with a desired characteristic (e.g., solubility in water, solubility at different pH, ability to bind polynucleotides, ability to bind heparin, ability to bind small molecules, ability to bind protein, ability to form microparticles, ability to increase tranfection efficiency, etc.). In certain embodiments the aminoalcohol lipidoid compounds may be screened for properties or characteristics useful in gene therapy (e.g., ability to bind polynucleotides, increase in transfection efficiency).

3. Polynucleotide Complexes

The ability of cationic compounds to interact with negatively charged polynucleotides through electrostatic interactions is well known. Cationic lipids such as Lipofectamine have been prepared and studied for their ability to complex and transfect polynucleotides. The interaction of the lipid with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive $\zeta$-potential, more preferably the $\zeta$-potential is between 0 and +30.

The aminoalcohol lipidoid compounds of the present invention possess tertiary amines. Although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the inventive aminoalcohol lipidoid compounds under conditions suitable to form polynucleotide/lipidoid complexes. The lipidoid is preferably at least partially protonated so as to form a complex with the negatively charged polynucleotide. In certain embodiments, the polynucleotide/lipidoid complexes form particles that are useful in the delivery of polynucleotides to cells. In certain embodiments, multiple aminoalcohol lipidoid molecules may be associated with a polynucleotide molecule. The complex may include 1-100 aminoalcohol lipidoid molecules, 1-1000 aminoalcohol lipidoid molecules, 10-1000 aminoalcohol lipidoid molecules, or 100-10,000 aminoalcohol lipidoid molecules.

In certain embodiments, the complex may form a particle. In certain embodiments, the diameter of the particles ranges from 10-500 micrometers. In certain embodiments, the diameter of the particles ranges from 10-1200 micrometers. In certain embodiments, the diameter of the particles ranges from 50-150 micrometers. In certain embodiments, the diameter of the particles ranges from 10-500 nm, more preferably the diameter of the particles ranges from 10-1200 nm, and most preferably from 50-150 nm. The particles may be associated with a targeting agent as described below. In certain embodiments, the diameter of the particles ranges from 10-500 μm, more preferably the diameter of the particles ranges from 10-1200 μm, and most preferably from 50-150 μm. The particles may be associated with a targeting agent as described below.

4. Polynucleotide

The polynucleotide to be complexed, encapsulated by the inventive aminoalcohol lipidoid compounds, or included in a composition with the inventive aminoalcohol lipidoid compounds may be any nucleic acid including, but not limited to, RNA and DNA. In certain embodiments, the polynucleotide is DNA. In certain embodiments, the polynucleotide is RNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553.

In certain embodiments, the polynucleotide is a dsRNA (double-stranded RNA).

In certain embodiments, the polynucleotide is an siRNA (short interfering RNA).

In certain embodiments, the polynucleotide is an shRNA (short hairpin RNA).

In certain embodiments, the polynucleotide is an miRNA (micro RNA). micro RNAs (miRNAs) are genomically encoded non-coding RNAs of about 21-23 nucleotides in length that help regulate gene expression, particularly during development (see, e.g., Bartel, 2004, *Cell,* 116:281; Novina and Sharp, 2004, *Nature,* 430:161; and U.S. Patent Publication 2005/0059005; also reviewed in Wang and Li, 2007, *Front. Biosci.,* 12:3975; and Zhao, 2007, *Trends Biochem. Sci.,* 32:189; each of which are incorporated herein by reference).

In certain embodiments, the polynucleotide is an antisense RNA.

In some embodiments, a dsRNA, siRNA, shRNA, miRNA and/or antisense RNA can be designed and/or predicted using one or more of a large number of available algorithms To give but a few examples, the following resources can be utilized to design and/or predict dsRNA, siRNA, shRNA, and/or miRNA: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.,* 22:326; Naito et al., 2006, *Nucleic Acids Res.,* 34:W448; Li et al., 2007, *RNA,* 13:1765; Yiu et al., 2005, *Bioinformatics,* 21:144; and Jia et al., 2006, *BMC Bioinformatics,* 7: 271; each of which is incorporated herein by reference).

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluorori- bose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391:806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1): 31-44, 1999; Crooke "Evaluating the mechanism of action of antiproliferative antisense drugs" *Antisense Nucleic Acid Drug Dev.* 10(2):123-126, discussion 127, 2000; *Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the internet (www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.*

6:251-281, 1998; and Phillips et al. *Vaccine* 10:151-158, 1992; each of which is incorporated herein by reference).

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

5. Particles

The aminoalcohol lipidoid compounds of the present invention may also be used to form drug delivery devices. The inventive aminoalcohol lipidoid compounds may be used to encapsulate agents including polynucleotides, small molecules, proteins, peptides, metals, organometallic compounds, etc. The inventive aminoalcohol lipidoid compounds have several properties that make them particularly suitable in the preparation of drug delivery devices. These include: 1) the ability of the lipid to complex and "protect" labile agents; 2) the ability to buffer the pH in the endosome; 3) the ability to act as a "proton sponge" and cause endosomolysis; and 4) the ability to neutralize the charge on negatively charged agents. In certain embodiments, the aminoalcohol lipidoid compounds are used to form particles containing the agent to be delivered. These particles may include other materials such as proteins, carbohydrates, synthetic polymers (e.g., PEG, PLGA), and natural polymers.

In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

6. Methods of Preparing Particles

The inventive particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

7. Micelles and Liposomes

The aminoalcohol lipidoid compounds of the invention may be used to prepare micelles or liposomes. Many techniques for preparing micelles and liposomes are known in the art, and any method may be used with the inventive aminoalcohol lipidoid compounds to make micelles and liposomes. In addition, any agent including polynucleotides, small molecules, proteins, peptides, metals, organometallic compounds, etc. may be included in a micelle or liposome. Micelles and liposomes are particularly useful in delivering hydrophobic agents such as hydrophobic small molecules.

In certain embodiments, liposomes (lipid or aminoalcohol lipidoid compound vesicles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion).

See Walde, P. "Preparation of Vesicles (Liposomes)" In *Encyclopedia of Nanoscience and Nanotechnology*; Nalwa, H. S. Ed. American Scientific Publishers: Los Angeles, 2004; Vol. 9, pp. 43-79; Szoka et al. "Comparative Properties and Methods of Preparation of Lipid Vesicles (Liposomes)" *Ann. Rev. Biophys. Bioeng.* 9:467-508, 1980; each of which is incorporated herein. The preparation of lipsomes involves preparing the aminoalcohol lipidoid compounds for hydration, hydrating the aminoalcohol lipidoid compounds with agitation, and sizing the vesicles to achieve a homogenous distribution of liposomes. Aminoalcohol lipidoid compounds are first dissolved in an organic solvent to assure a homogeneous mixture of aminoalcohol lipidoid compounds. The solvent is then removed to form a lipidoid film. This film is thoroughly dried to remove residual organic solvent by placing the vial or flask on a vaccuum pump overnight. Hydration of the lipidoid film/cake is accomplished by adding an aqueous medium to the container of dry lipidoid and agitating the mixture. Disruption of LMV suspensions using sonic energy typically produces small unilamellar vesicles (SUV) with diameters in the range of 15-50 nm Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm In certain embodiments, the polynucleotide is an RNA molecule (e.g., an RNAi molecule). In other embodiments, the polynucleotide is a DNA molecule. In certain embodiments, the aminoalcohol lipidoid is C14-120. In certain embodiments, the aminoalcohol lipidoid is C16-120. In certain embodiments, the aminoalcohol lipidoid is C14-98. In certain embodiments, the aminoalcohol lipidoid is C14-113. In certain embodiments, the aminoalcohol lipidoid is C18-96. In certain embodiments, the aminoalcohol lipidoid is C14-96. In certain embodiments, the aminoalcohol lipidoid is C14-110. In certain embodiments, the amount of aminoalcohol lipidoid compound in the liposome ranges from 30-80 mol %, preferably 40-70 mol %, more preferably 60-70 mol %. These liposomes may be prepared using any method known in the art. In certain embodiments (e.g., liposomes containing RNAi molecules), the liposomes are prepared by lipid extrusion.

Certain aminoalcohol lipidoid compounds can spontaneously self assemble around certain molecules, such as DNA and RNA, to form liposomes. In some embodiments, the application is the delivery of polynucleotides. Use of these aminoalcohol lipidoid compounds allows for simple assembly of liposomes without the need for additional steps or devices such as an extruder.

The following scientific papers described other methods for preparing liposomes and micelles: Narang et al. "Cationic Lipids with Increased DNA Binding Affinity for Non-viral Gene Transfer in Dividing and Nondividing Cells" *Bioconjugate Chem.* 16:156-68, 2005; Hofland et al. "Formation of stable cationic lipid/DNA complexes for gene transfer" *Proc. Natl. Acad. Sci. USA* 93:7305-7309, July 1996; Byk et al. "Synthesis, Activity, and Structure—Activity Relationship Studies of Novel Cationic Lipids for DNA Transfer" *J. Med. Chem.* 41(2):224-235, 1998; Wu et al. "Cationic Lipid Polymerization as a Novel Approach for Constructing New DNA Delivery Agents" *Bioconjugate Chem.* 12:251-57, 2001; Lukyanov et al. "Micelles from lipid derivatives of water-soluble polymers as delivery systems for poorly soluble drugs" *Advanced Drug Delivery Reviews* 56:1273-1289, 2004; Tranchant et al. "Physico-chemical optimisation of plasmid delivery by cationic lipids" *J. Gene Med.* 6:S24-S35, 2004; van Balen et al. "Liposome/Water Lipophilicity: Methods, Information Content, and Pharmaceutical Applications" *Medicinal Research Rev.* 24(3):299-324, 2004; each of which is incorporated herein by reference.

8. Agent

The agents to be delivered by the system of the present invention may be therapeutic, diagnostic, or prophylactic agents. Any chemical compound to be administered to an individual may be delivered using the inventive complexes, picoparticles, nanoparticles, microparticles, micelles, or liposomes. The agent may be a small molecule, organometallic compound, nucleic acid, protein, peptide, polynucleotide, metal, an isotopically labeled chemical compound, drug, vaccine, immunological agent, etc.

In certain embodiments, the agents are organic compounds with pharmaceutical activity. In another embodiment of the invention, the agent is a clinically used drug. In certain embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryp-* tococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni, and the like. These antigens may be in the form of whole killed organisms, peptides, proteins, glycoproteins, carbohydrates, or combinations thereof.

9. Targeting Agents

The inventive complexes, liposomes, micelles, microparticles, picoparticles and nanoparticles may be modified to include targeting agents since it is often desirable to target a particular cell, collection of cells, or tissue. A variety of targeting agents that direct pharmaceutical compositions to particular cells are known in the art (see, for example, Cotten et al. *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

10. Pharmaceutical Compositions

Once the complexes, micelles, liposomes, or particles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis and Characterization of 1,2-Aminoalcohols

These lipidoids were synthesized by combining amines and epoxides in a glass vial equipped with a stirbar and heated to 90° C., as shown in FIG. 1. The amines chosen contain between two and five amine functionalities, while the epoxides are racemic, of varying chain lengths and feature unique functional groups and varying degrees of saturation (FIG. 2). The reaction times varied from 24-72 hours at this temperature. Mixtures generally remained clear throughout the reaction and became noticeably viscous as the reaction progressed. Upon cooling, many became waxy solids. The extent of the reaction could be controlled by the number of equivalents of epoxide added to the reaction mixture. For example, in the examples shown, amine 114 has a maximum of five points for substitution. Addition of five equivalents of epoxide would yield an amine core with five alkane chains linked by a 1,2-aminoalcohol. Addition of four equivalents of epoxide would yield only four chains linked by the same structure. This was verified by thin layer chromatography (TLC), which showed primarily one product existing in the crude reaction mixtures set up as described.

Figure 4:
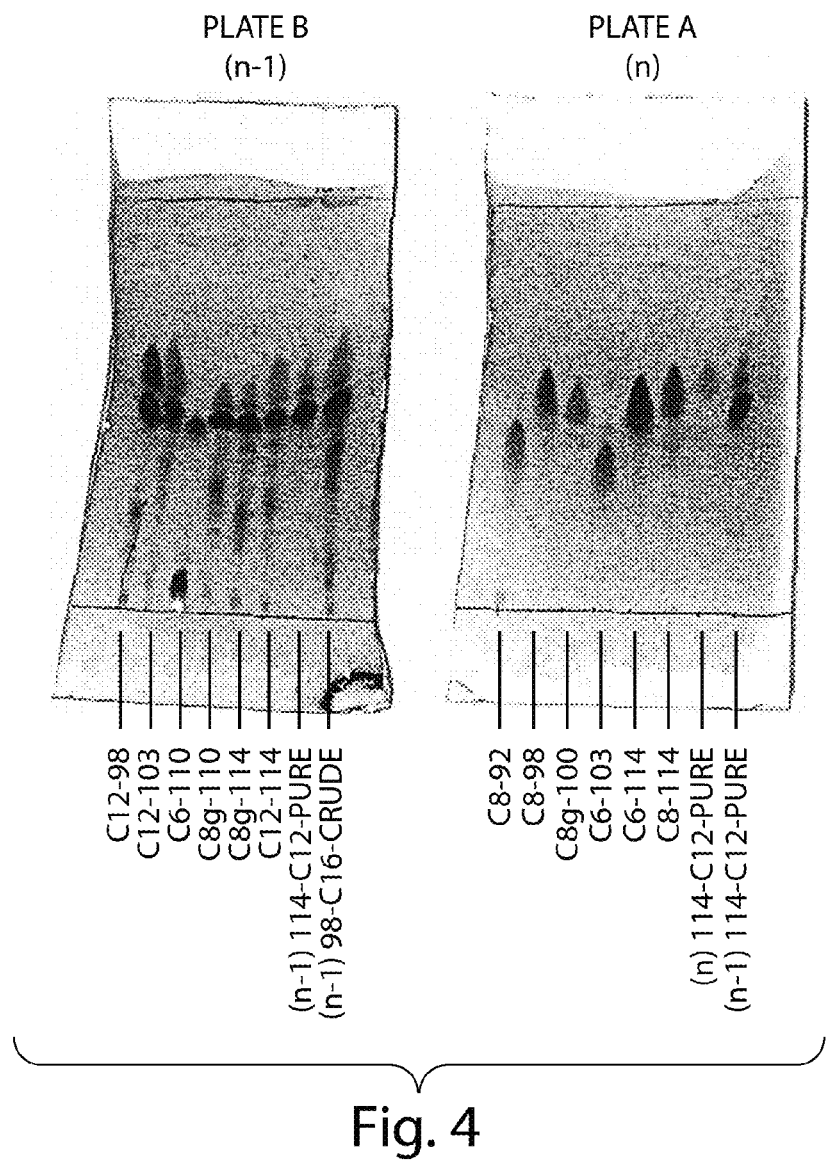
FIG. 4 depicts thin layer chromatography (TLC) plates of selected compounds from the aminoalcohol lipidoid library. Plate "A" depicts fully substituted amines, while Plate "B" depicts n−1 substituted amines.

To verify the identity of the molecules, a few test reactions were set up and purified by silica gel chromatography. The components of the crude reaction mixture were separated and tested by NMR and mass spectrometry. Again, in the case of amine 114, three products were identified: three, four and five tailed products. The molecular weight was confirmed by mass spectrometry, and the structure was verified by NMR (FIG. 3, which shows characterization data of epoxide lipidoids derived from amine 114). These isolated compounds were then used as standards versus selected members of the library for TLC analysis. Reactions set up to fully substitute the amine had similar $R_f$ and staining profiles to the fully substituted standard. Reactions set up to occupy n–1 positions of the amine had similar $R_f$ and staining profiles to n–1 standard (FIG. 4).

Example 2

In Vitro Screening for RNA Delivery

Figure 5:
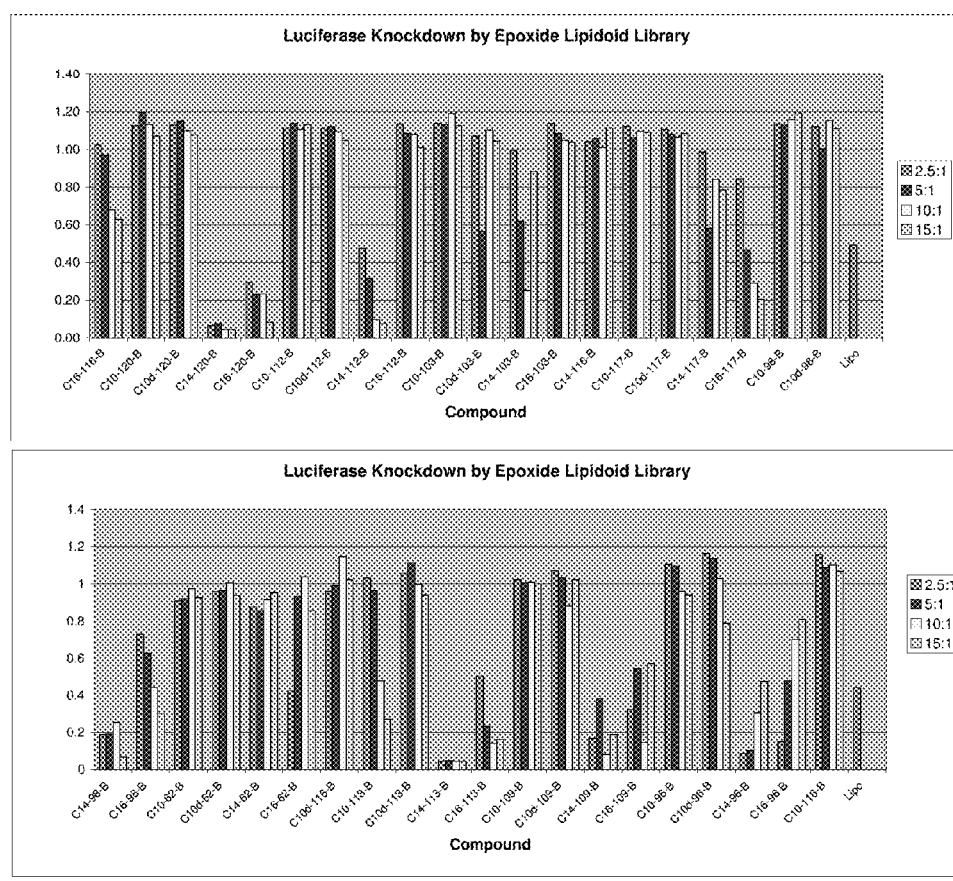
FIG. 5 depicts Firefly luciferase knockdown results relative to untreated cells from complexing RNA (50 ng) with various aminoalcohol lipidoids (at various wt/wt ratios) and incubated with HeLa cells.

Epoxide lipidoids were tested for their ability to deliver siRNA to a HeLa cell line that stably expresses both firefly and *Renilla luciferase*. Efficacy was determined by complexing the lipidoid with siRNA specific for firefly luciferase, adding this mixture to cells and measuring the subsequent ratio of firefly to *Renilla* expression. This procedure was performed in 96-well microtiter plates to enable high throughput testing of the materials. In this assay, reduction of both firefly and *Renilla* expression indicates toxicity, while reduction of only firefly expression is an indication of specific knockdown due to siRNA. Initial screening results of selected members of the library are shown in FIG. 5. Many members of this sampling showed some ability to transfect cells and give rise to some knockdown of firefly luciferase. Of these the best performers were generally lipidoids derived from epoxides of 14 carbons or longer coupled with monomers of three or more amine functional groups. A few show nearly complete ablation of firefly expression, even at the lowest dose of lipidoid tested.

Example 3

RNA Encapsulation Efficiency

Formulation for in vitro experiments is a simple mixing of RNA with lipidoid at a set ratio in buffer prior to addition to cells. In vivo formulation requires the addition of extra ingredients to facilitate circulation throughout the body. To test the ability of these lipidoids to form particles suitable for in vivo work, we followed a standard formulation procedure utilized in the lab. These particles consisted of 42% lipidoid, 48% cholesterol and 10% PEG. After formation of the particle, RNA was added and allowed to integrate with the complex. The encapsulation efficiency was determined using a standard Ribogreen assay. As shown in the table below, these particles were on the order of 100 nm after extrusion, with some achieving encapsulation efficiency of over 90%.

Particle Size and Entrapment Efficiency of Selected Epoxide Lipidoids

| Compound | Size (nm) | Entrapment (%) |
|---|---|---|
| C14-120-B | 95.2 | 92.75 |
| C16-120-B | 128.4 | 67.22 |
| C14-98-B | 126.9 | 44.84 |
| C14-113-B | 92.7 | 96.42 |

Example 4

Figure 6:
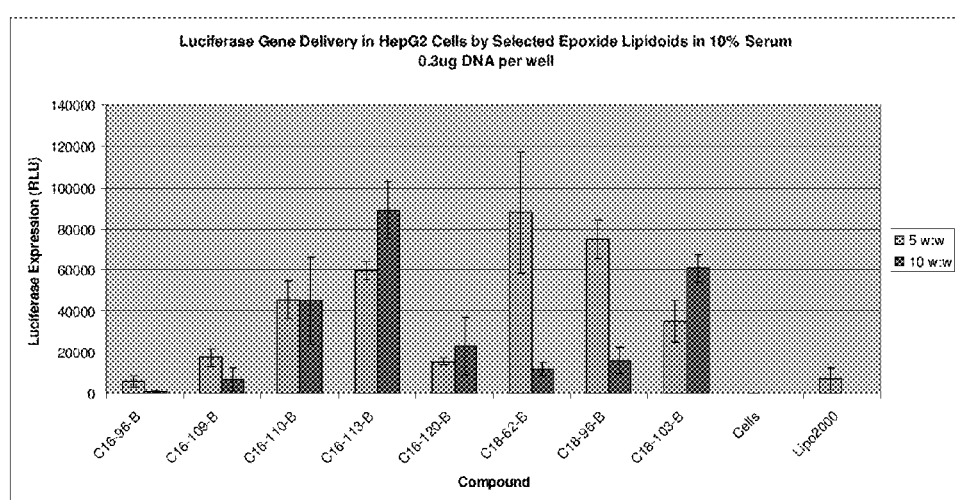
FIG. 6 depicts luciferase gene delivery results (Luciferase Expression, "RLU") in HepG2 cells for various epoxide lipidoid compounds in 10% serum and 0.3 μg of DNA per well.

HepG2 cells were seeded at a density of 15,000 cells per well into opaque white 96-well plates (Corning-Costar, Kennebunk, Me.) 24 hours prior to transfection to allow for growth and confluence. Working dilutions of lipidoids were made in 25 mM sodium acetate (pH 5) at a concentration of 0.5 mg/ml. For gene delivery experiments pCMV-Luc firefly luciferase DNA (ElimBiopharmaceuticals, South San Francisco, Calif.) was used. Lipidoid:DNA complexes were formed by electrostatic interaction between positively charged lipidoid molecules and negatively charged nucleic acids. By varying the volume of lipidoid solution added to a constant amount of DNA, varying weight:weight ratios of lipidoid to DNA were tested. Lipidoid solution (75 µl) was added to DNA solution (75 µl) and mixed well. Mixtures were then incubated at room temperature for 20 minutes to allow for complexation. These complexes (30 µl) were then added to serum containing medium (200 µl) and mixed well. Growth medium was then removed from the cells and lipidoid:DNA complex containing medium was immediately added. Total DNA loading was 300 ug DNA per well. Lipofectamine 2000 transfection was performed as described by the vendor. Complexes were allowed to incubate with cells for 48 hours. Luciferase expression was then quantified by Bright-Glo assay (Promega, Madison, Wis.). Briefly, 48 hours post-transfection, the lipidoid:DNA complex containing growth medium was removed from cells using a 12-channel aspirating wand. 200 ul of a 1:1 mixture of Bright-Glo reagent and non-phenol red containing DMEM was added to each well of the 96-well plate with cells. After 10 minute incubation at room temperature, luminescence was measured using a luminometer. (n=3). Exemplary results are depicted in FIG. 6.

Example 5

Lipidoid-based siRNA formulations comprised lipidoid, cholesterol, polyethylene glycol-lipid (PEG-lipid) and siRNA. Stock solutions of Lipidoid, mPEG2000-DMG MW 2660 (synthesized by Alnylam), and cholesterol MW 387 (Sigma-Aldrich) were prepared in ethanol and mixed to yield a molar ratio of 42:10:48. Mixed lipids were added to 200 mM sodium acetate buffer pH 5.2 to yield a solution containing 35% ethanol, resulting in spontaneous formation of empty lipidoid nanoparticles. Resulting nanoparticles were extruded through an 80 nm membrane (three passes). siRNA in 35% ethanol and 50 mM sodium acetate pH 5.2 was added to the nanoparticles at 10:1 (wt/wt) total lipids:siRNA and incubated at 37° C. for 30 min. Ethanol removal and buffer exchange of siRNA-containing lipidoid nanoparticles was achieved by dialysis against PBS using a 3,500 MWCO membrane. Particle size was determined using a Malvern Zetasizer NanoZS (Malvern). siRNA content and entrapment efficiency was determined by Ribogreen assay.

Figure 7:
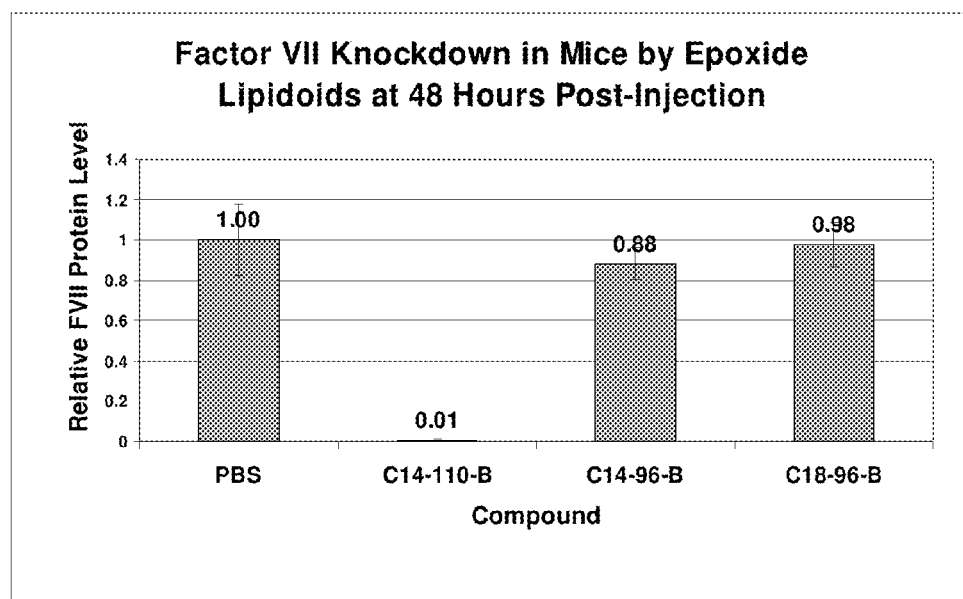
FIG. 7 depicts Factor VII Knockdown in vivo results and characterization of C57BL/6 mice 48 hours after administration (via tail vein injection at a volume of 0.01 ml/g) of (a) phosphate buffered saline; (b) 1.75 mg/kg entrapped siRNA in lipidoid formulation; and (c) 4 mg/kg entrapped siRNA in lipidoid formulation.
Figure 8:
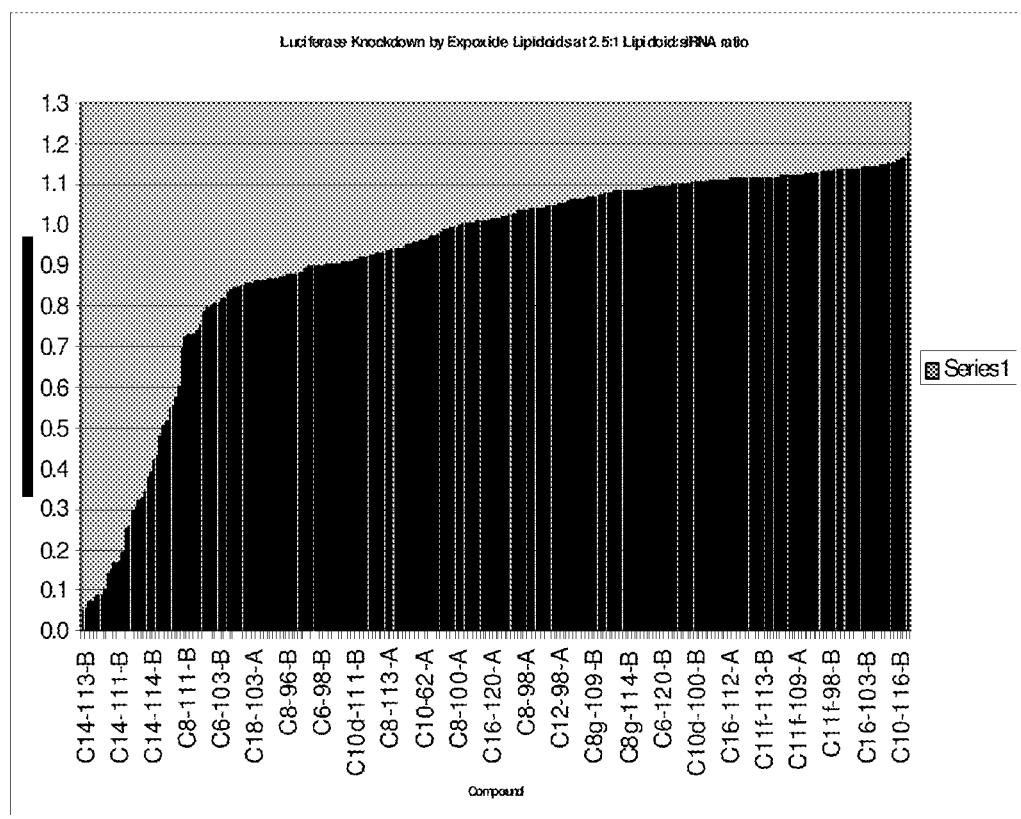
FIG. 8 depicts luciferase knockdown results (measured by relative luceriferase expression, % control) for a library of aminoalcohol lipidoid compounds wherein the ratio of aminoalcohol lipidoid compound to siRNA is 2.5:1 (w/w).
Figure 9:
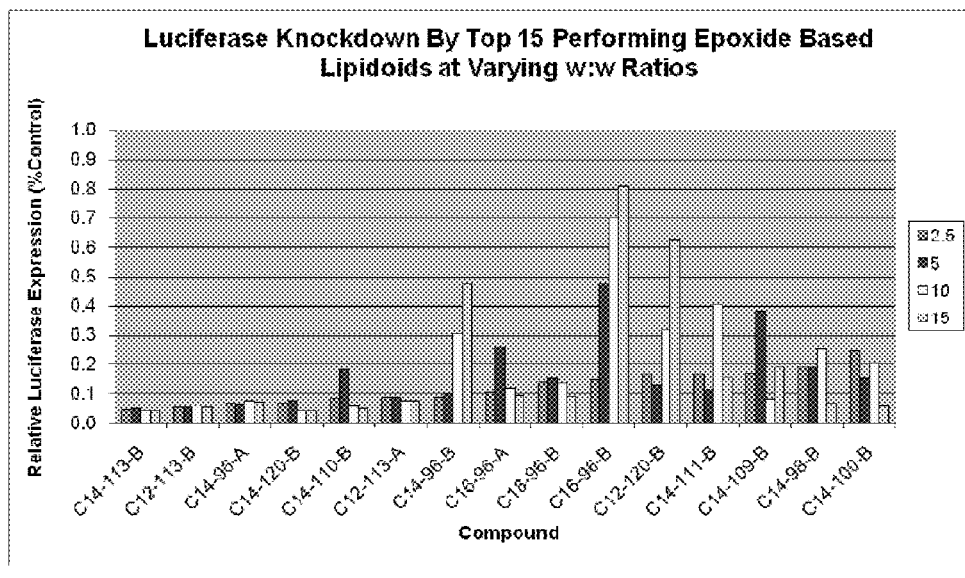
FIG. 9 depicts the luciferase knockdown results (measured by relative luceriferase expression, % control) for fifteen aminoalcohol lipidoid compounds having >90% knockdown wherein the ratio of aminoalcohol lipidoid compound to siRNA is 2.5:1 (w/w).
Figure 10:
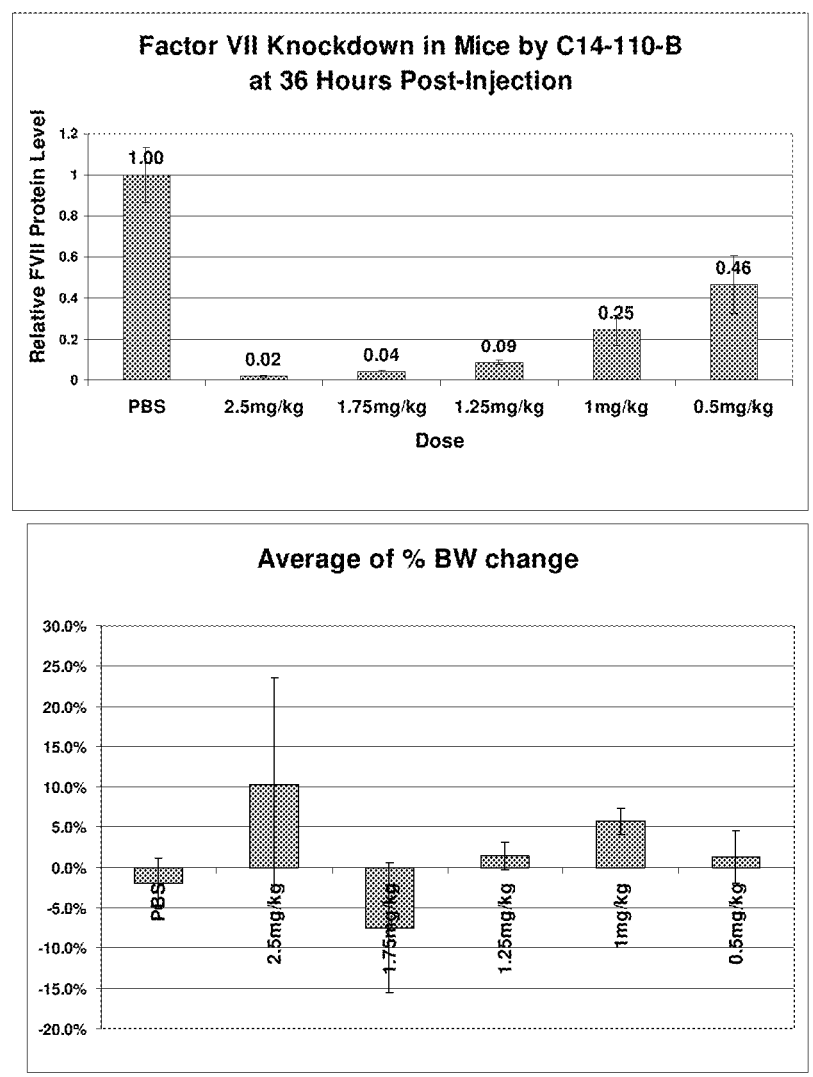
FIG. 10 depicts: (a) dose (mg/kg) response results (measured by Factor VII knockdown in mice by aminoalcohol lipidoid C14-110 36 hours post-injection) wherein the ratio of aminoalcohol lipidoid compound to siRNA is 10:1 (w/w), the ratio of aminoalcohol lipidoid compound:cholesterol:PEG is 42:48:10, and 44% entrapment of 91 nm particles; and (b) average of % BW change.

C57BL/6 mice (Charles River Labs) received either saline or siRNA in lipidoid formulations via tail vein injection at a volume of 0.01 ml/g. Mice were dosed at either 1.75 or 4 mg/kg entrapped siRNA. At 48 hours after administration, animals were anesthetized by isofluorane inhalation and blood was collected into serum separator tubes by retroorbital bleed. Serum levels of Factor VII protein were determined in samples using a chromogenic assay (Biophen FVII, Aniara Corporation) according to the manufacturer's protocols. A standard curve was generated using serum collected from saline-treated animals. Exemplary results are depicted in FIG. 7.

Example 6

In Vitro Screening of Epoxide Library

Figure 11:
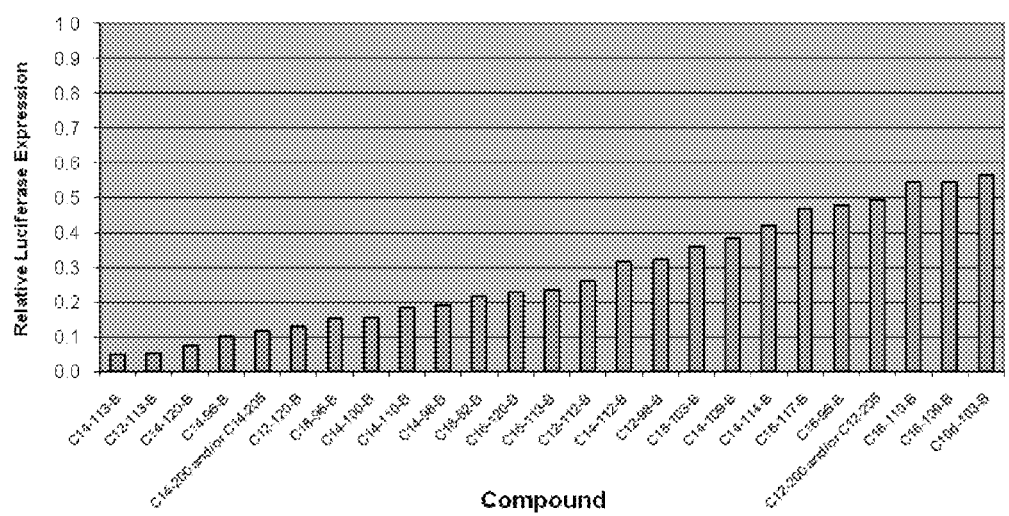
FIG. 11 depicts in vitro screening results as luciferase knockdown in HeLa cells by 25 epoxide-based lipidoids at 5:1 w/w ratio.

Compounds of the epoxide-based lipidoid library were synthesized according to the procedures described herein. The compounds were then screened for siRNA delivery efficacy to a cancer cell line, using a Hela-derived cell line genetically engineered to express luciferase reporter proteins. In these experiments, the ability of each material to facilitate sequence-specific gene silencing was evaluated by comparison of protein levels in treated groups to untreated controls. For each compound, delivery experiments were performed using varying weight ratios of lipidoid: siRNA. In the original disclosure, knockdown results for the entire library were shown. An abbreviated data set is shown in FIG. 11 demonstrating the results for the top 25 performing compounds in the in vitro screen, including C16-96-B, C14-200 and/or C14-205, and C12-200 and/or C12-205.

Example 7

In Vivo Screening of Top Performing Epoxide Lipidoids

To test siRNA delivery efficacy in vivo, a mouse model for liver delivery was used. Factor VII, a hepatocyte-specific blood clotting factor, served as a model protein for knockdown studies. Once produced by hepatocytes, Factor VII is released into the bloodstream, and a baseline level of expression can be determined by simple blood draw and quantification of protein levels by colorimetric assay. By delivering anti-Factor VII siRNA to hepatocytes, knockdown of this model protein can be achieved and a percentage of silencing can be determined by comparison to an untreated control.

Figure 12:
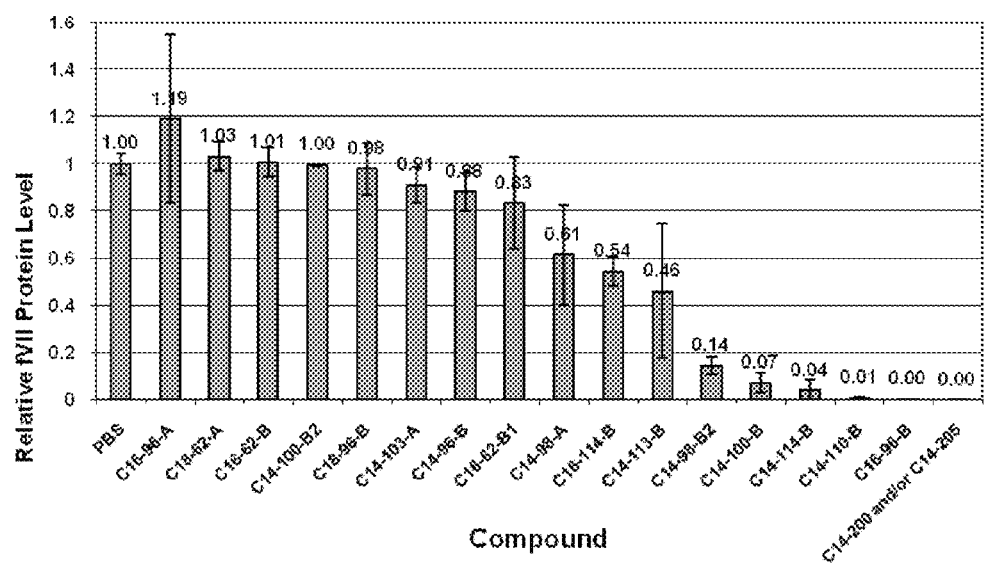
FIG. 12 depicts in vivo screening results as Factor VII knockdown 48 hours post-injection of formulated epoxide lipidoids in mice.

Following the in vitro screen, compounds were purified as detailed in Part 1 (see Example 14). For in vivo testing, the compounds were formulated with cholesterol and a PEG-lipid for serum stability and siRNA packaging. In these experiments, lipidoids were formulated at a 42:48:10 molar ratio of lipidoid:cholesterol:PEG. The weight ratio of total lipids (lipidoid+cholesterol+PEG) to siRNA was 10:1. After each formulation, the particles were characterized for size and siRNA entrapment efficiency using dynamic light scattering and Ribogreen assay, respectively. The total dose of siRNA administered in the initial screen varies from group to group due to the differences in entrapment efficiency of the lipidoid particles. In all experiments, the dose of siRNA administered to each mouse is consistent according to body weight. The knockdown results from the in vivo screen are shown in FIGS. 12. B1 and B2 nomenclature signify different compounds visualized by TLC and isolated during purification. As shown, C14-11-B and C16-96-B were the lead compounds from the initial screen. It should be noted that while some compounds did not show efficacy in this screen, a simple adjustment of formulation composition may greatly improve the results.

Example 8

Figure 13A:
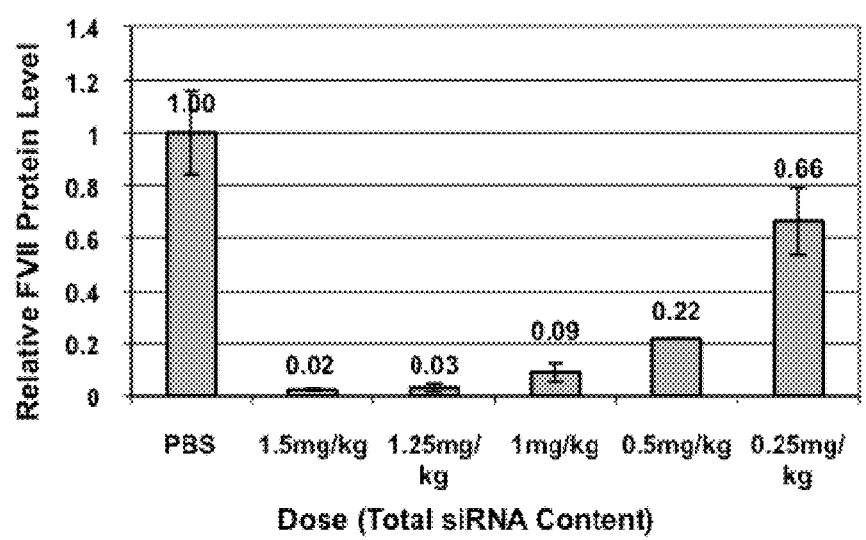
FIG. 13*a* depicts dose response results for C16-96B as Factor VII knockdown 48 hours post-injection of formulation C16-96-B in mice.
Figure 13B:
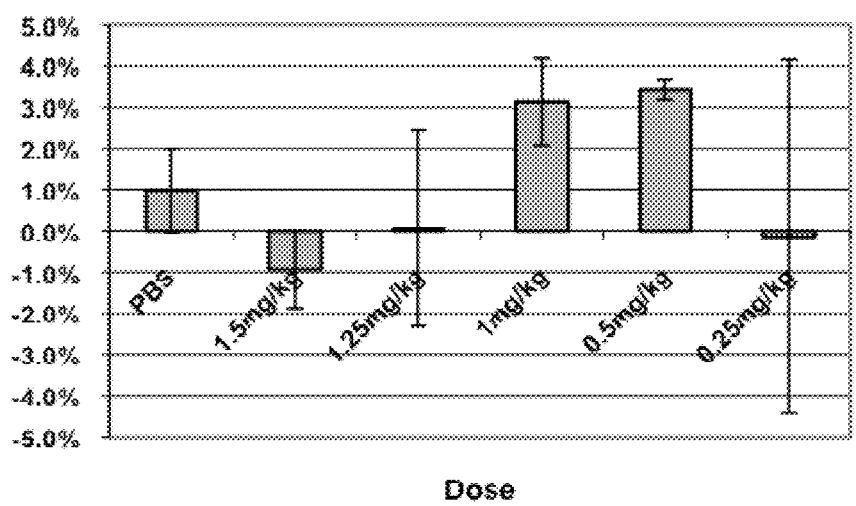
FIG. 13*b* depicts corresponding mice body weight loss and/or gain during the experimental that provided the results in FIG. 13.
Figure 14A:
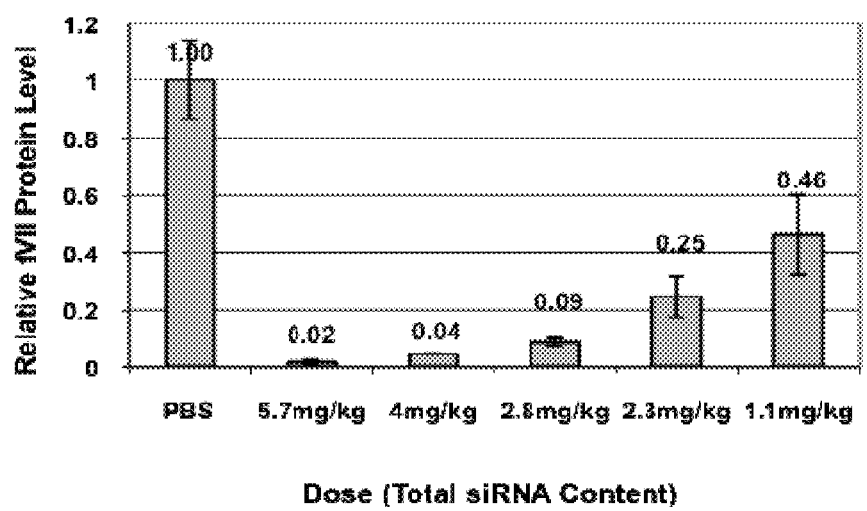
FIG. 14*a* depicts dose response results for C14-110B as Factor VII knockdown 72 hours post-injection of formulation C14-110-B in mice.
Figure 14B:
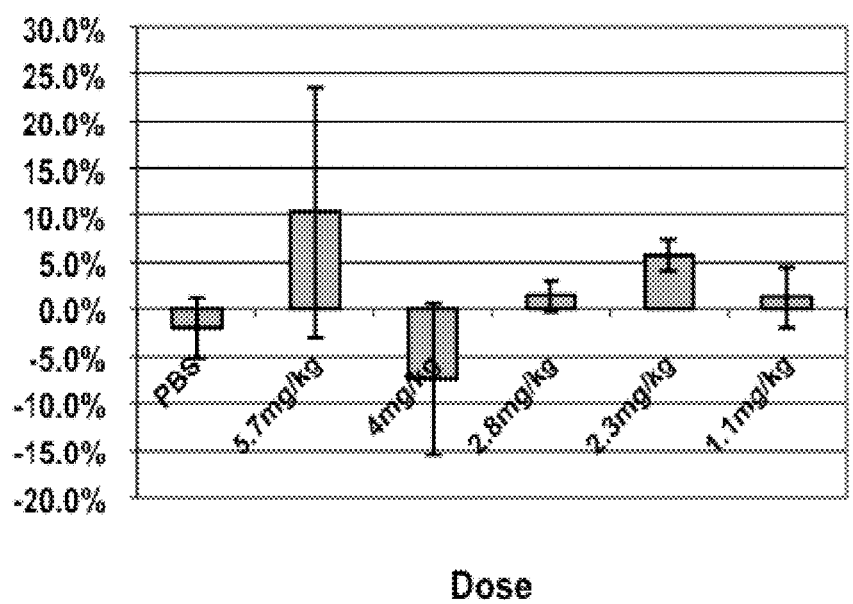
FIG. 14*b* depicts corresponding mice body weight loss and/or gain during the experiment that provided the results in FIG. 14*a*.

Following the initial in vivo screening experiments, two compounds were used to conduct a dose response. In these experiments and all subsequent experiments, the siRNA dose is based on total siRNA content in the formulation, not entrapped siRNA. The dose response results are shown in FIG. 13a and FIG. 14a. In addition to Factor VII measurement, the change in mouse body weight is recorded and a loss in weight is generally considered formulation induced toxicity (See FIG. 13b and FIG. 14b). Tables 1 and 2 tabulate the formulation parameters and characterization data from these experiments.

TABLE 1

Formulation parameters and characterization data for C16-96-B dose response formulation

| Formulation | | | Characterization | |
| --- | --- | --- | --- | --- |
| Lipidoid | Lipid:Chol:PEG | Total Lipid:siRNA | Entrapment | Size |
| C16-96-B | 65:29:6 | 10:1 | 81% | 107.8 nm |

TABLE 2

Formulation parameters and characterization data for C14-110-B dose response formulation

| Formulation | | | Characterization | |
| --- | --- | --- | --- | --- |
| Lipidoid | Lipid:Chol:PEG | Total Lipid:siRNA | Entrapment | Size |
| C14-110-B | 42:48:10 | 10:1 | 44% | 115 nm |

Example 9

Figure 15:
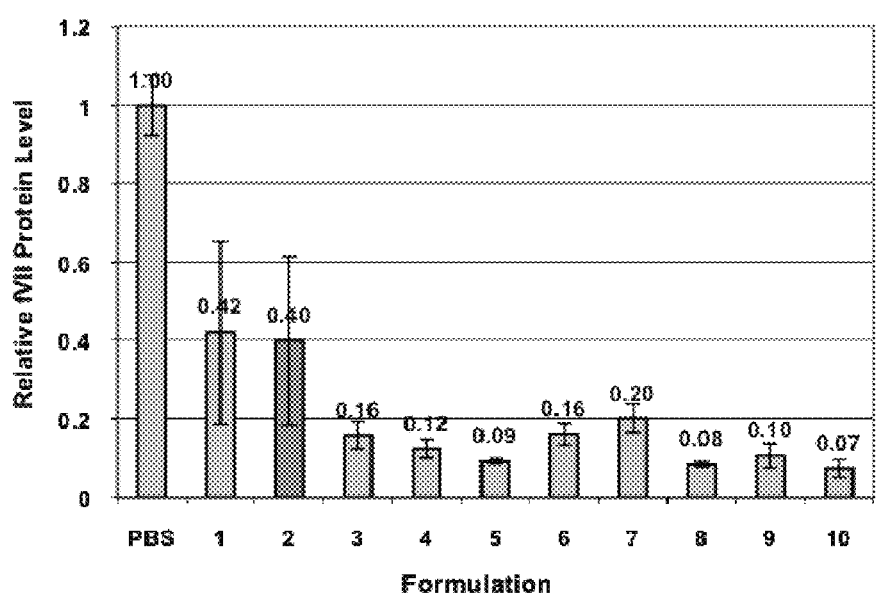
FIG. 15 depicts C16-96-B formulation optimization as Factor VII knockdown 48 hours post-injection of formulation C16-96-B in mice at 1 mg/kg dose.

After completing the dose response, C16-96-B was chosen for further investigation and optimization. In the next experiments, the percent composition of the formulations was varied to observe the effect of composition on particle size, entrapment, and efficacy. The compositions investigated are shown in Table 3. FIG. 15 shows the knockdown results from the formulations tested. Where the formulation in red was the previous best, it is shown that efficacy can be improved by formulating particles at different compositions.

TABLE 3

Formulation parameters and characterization data for C16-96-B formulation optimization experiment

| Formulation Parameters | | | | | |
| --- | --- | --- | --- | --- | --- |
| Formulation | Lipidoid | Chol | PEG | Total Lipid:siRNA | Entrapment |
| 1 | 63 | 31 | 6 | 8.5:1 | 80% |
| 2 | 65 | 29 | 6 | 8.5:1 | 80% |
| 3 | 67 | 27 | 6 | 8.5:1 | 80% |
| 4 | 69 | 25 | 6 | 8.5:1 | 84% |
| 5 | 71 | 23 | 6 | 8.5:1 | 85% |
| 6 | 63 | 33 | 4 | 8.5:1 | 85% |
| 7 | 65 | 31 | 4 | 8.5:1 | 85% |
| 8 | 67 | 29 | 4 | 8.5:1 | 84% |
| 9 | 69 | 27 | 4 | 8.5:1 | 83% |
| 10 | 71 | 25 | 4 | 8.5:1 | 85% |

Example 10

Figure 16:
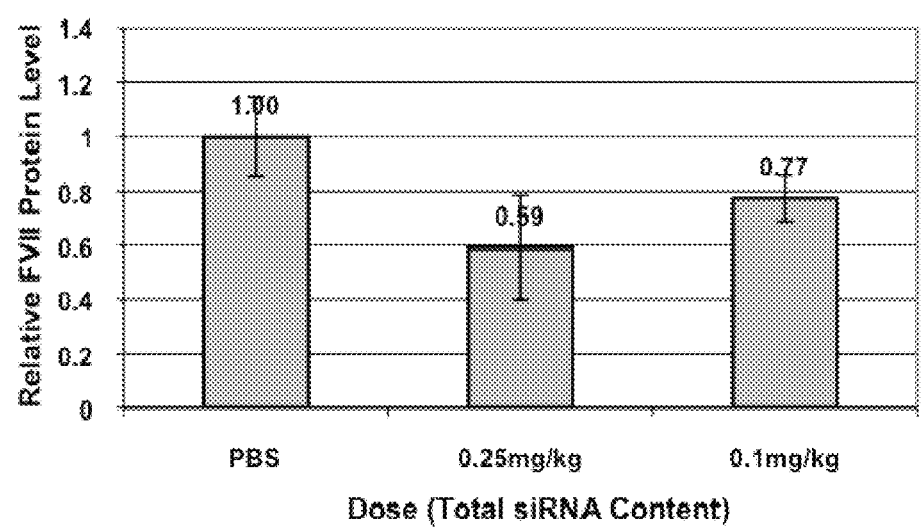
FIG. 16 depicts C16-96-B dose response as Factor VII knockdown 48 hours post-injection of formulation C16-96-B in mice.

A second dose response was conducted with the new percent composition parameters. The knockdown results and particle formulation/characteristics are shown in FIG. 16 and Table 4, respectively. By formulating at this composition, approximately 40% knockdown was achieved at a dose of 0.25 mg/kg. Using this result as the new benchmark, the library was revisited and previously untested materials were screened at 0.25 mg/kg in attempt to find other compounds which could give similar or better results.

TABLE 4

| Formulation | | | Characterization | |
| --- | --- | --- | --- | --- |
| Lipidoid | Lipid:Chol:PEG | Total Lipid:siRNA | Entrapment | Size |
| C16-96-B | 71:23:6 | 20:1 | 83% | 205 nm |

Example 11

In the revisited in vivo screen, compound C12-200 and/or C12-205 was identified as giving nearly complete silencing at a dose of 0.25 mg/kg. As depicted in FIG. 12, the slightly longer tailed version of this compound, C12-200 and/or C12-205 was previously identified as a highly efficient delivery agent, showing complete silencing at a much higher dose of 7.5 mg/kg total siRNA. It is quite possible that this compound could facilitate complete silencing at much lower doses, but this has not yet been fully explored as the focus has been on C12-200 and/or C12-205. Following the discovery of the efficacy of this compound, the characterization experiments detailed in Part 1 (see Example 14) were initiated.

Figure 17A:
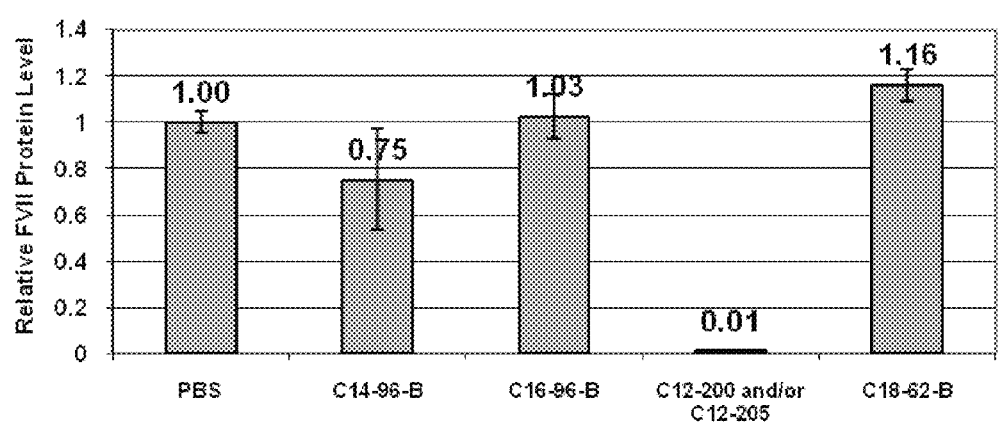
FIG. 17*a* depicts additional in vivo screening and discovery of C12-200 and/or C12-205 as Factor VII knockdown 48 hours post-injection of formulated lipidoids in mice at 0.25 mg/kg dose.
Figure 17B:
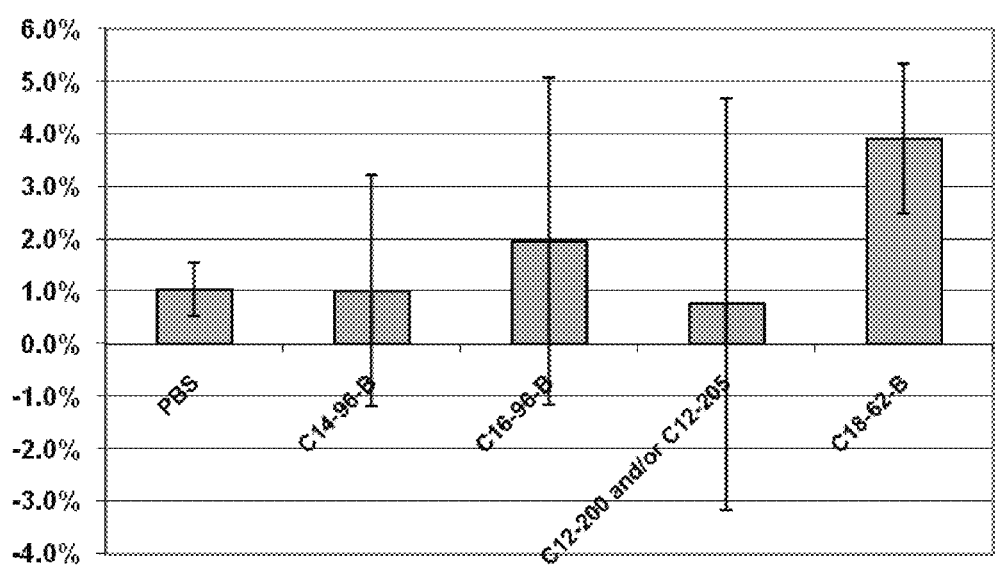
FIG. 17*b* depicts additional in vivo screening and discovery of C12-200 and/or C12-205 and corresponding mice body weight loss and/or gain during the experiment that provided the results in FIG. 17*a*.

The knockdown and body weight change results of this screen are depicted in FIG. 17b, and Table 5 tabulates the formulation parameters and characteristics. FIG. 17a depicts knockdown results for a second batch of C16-96-B. In previous experiments, this compound had resulted in approximately 40% knockdown at a dose of 0.25 mg/kg. From mass spec analysis, it was shown that this batch is two-tailed as opposed to the more efficacious three-tailed version that had been used in the previous studies.

TABLE 5

Formulation parameters and characterization data for revisited in vivo screening
Formulation Parameters

| Formulation | Lipid | Chol | PEG | Total Lipid:siRNA | Entrapment (%) | Size (nm) |
|---|---|---|---|---|---|---|
| C14-96-B | 73.1 | 21.3 | 5.6 | 8.5 | 87 | 81.7 |
| C16-96-B | 71.0 | 23.0 | 6.0 | 8.5 | 55 | 170.2 |
| C12-200 and/or C12-205 | 45.0 | 45.5 | 9.5 | 8.5 | 36 | 167 |
| C18-62-B | 52.7 | 39.1 | 8.2 | 8.5 | 86 | 227.4 |

Example 12

Figure 18A:
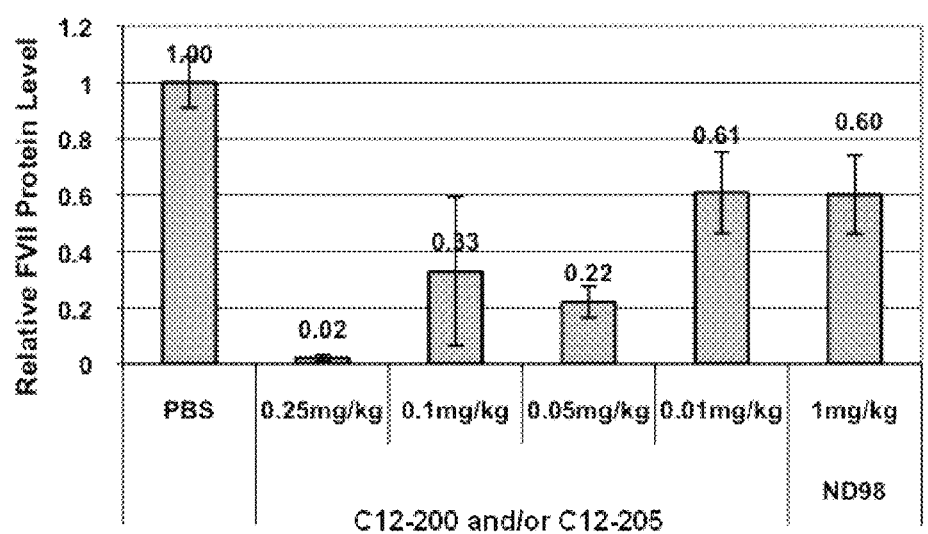
FIG. 18*a* depicts dose response results for C12-200 and/or C12-205 and ND98 comparison as Factor VII knockdown 48 hours post-injection of formulated C12-200 and/or C12-205 in mice.
Figure 18B:
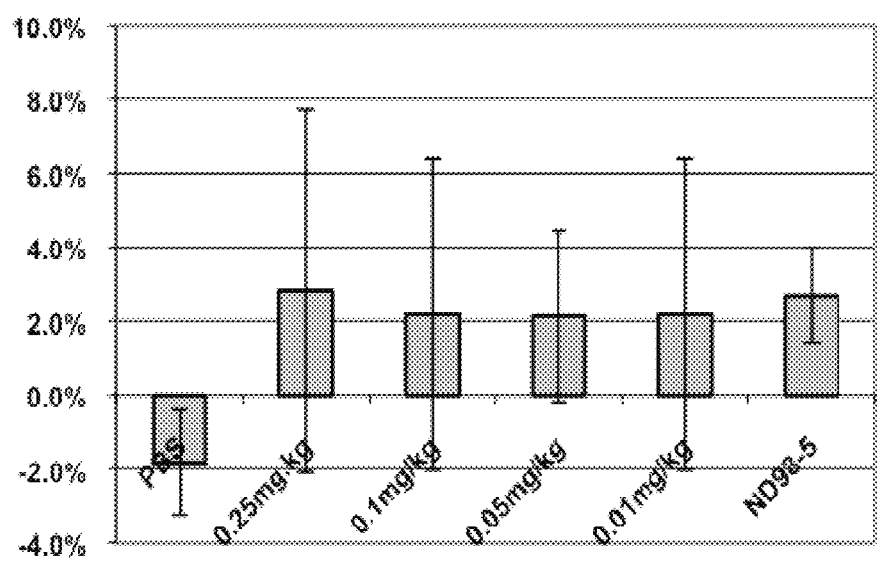
FIG. 18*b* depicts corresponding mice body weight loss and/or gain during the experiment that provided the results in FIG. 18*a*.

A low-dose response was performed on C12-200 and/or C12-205. The knockdown and body weight loss results are shown in FIG. 18a and FIG. 18b. The results show that efficient knockdown is achieved and extremely low doses of siRNA. In comparison to ND98, our previous best compound from the original lipidoid library, comparable knockdown can be achieved with 100-fold lower doses of siRNA. The formulation parameters and characterization data are shown in Table 6.

TABLE 6

Formulation parameters and characterization data for C12-200 and/or C12-205 and ND 98 formulations
Formulation Parameters

| Formulation | Lipid | Chol | PEG | Total Lipid:siRNA | Entrapment(%) | Size (nm) |
|---|---|---|---|---|---|---|
| C12-200 and/or C12-205 | 48.2 | 42.8 | 8.9 | 8.5 | 45 | 154.1 |
| ND98 | 42.0 | 48.0 | 10.0 | 8.5 | 99 | 83.9 |

Example 13

Figure 19:
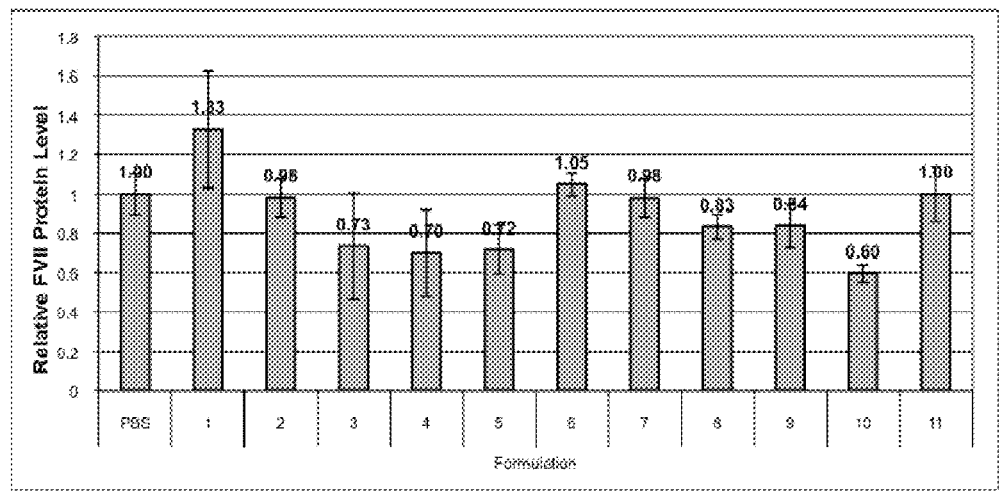
FIG. 19 depicts formulation optimization of C12-200 and/or C12-205 as Factor VII knockdown 48 hours post-injection of formulated C12-200 and/or C12-205 in mice at 0.01 mg/kg dose.

To further improve delivery efficacy, the percent composition of the C12-200 and/or C12-205 formulation was modified incrementally. These formulations were screened at a dose of 0.01 mg/kg to identify formulations which may perform better than the previous compositions. The results of these experiments are shown in FIG. 19 along with the formulation parameters and characteristics in Table 7. As expected, more efficacious delivery can be achieved by tuning the composition of the formulation. This optimization work is currently ongoing, along with synthesis of longer and shorter tailed versions of the C12-200 and/or C12-205 structure.

TABLE 7

Formulation parameters and characterization data for C12-200 and/or C12-205 formulations
Formulation Parameters

| Formulation | Lipid | Chol | PEG | Total Lipid:siRNA | Entrapment (%) | Size (nm) |
|---|---|---|---|---|---|---|
| 1 | 65.0 | 25.0 | 10.0 | 8.5 | 0 | 129 |
| 2 | 60.0 | 30.0 | 10.0 | 8.5 | 1 | 128 |
| 3 | 55.0 | 35.0 | 10.0 | 8.5 | 16 | 156 |
| 4 | 50.0 | 40.0 | 10.0 | 8.5 | 30 | 136 |
| 5 | 45.0 | 45.0 | 10.0 | 8.5 | 46 | 140 |
| 6 | 40.0 | 50.0 | 10.0 | 8.5 | 44 | 168 |
| 7 | 35.0 | 55.0 | 10.0 | 8.5 | 40 | 154 |
| 8 | 50.0 | 45.0 | 5.0 | 8.5 | 29 | 157 |

TABLE 7-continued

Formulation parameters and characterization data for C12-200 and/or C12-205 formulations
Formulation Parameters

| Formulation | Lipid | Chol | PEG | Total Lipid:siRNA | Entrapment (%) | Size (nm) |
|---|---|---|---|---|---|---|
| 9 | 45.0 | 50.0 | 5.0 | 8.5 | 34 | 154 |
| 10 | 40.0 | 55.0 | 5.0 | 8.5 | 27 | 159 |
| 11 | 35.0 | 60.0 | 5.0 | 8.5 | 34 | 155 |

Example 14

Part 1

Lipidoids Based on Amine 111

Amine 111 (tetraethylenepentamine, or TEPA) is represented as the linear polyamine of the following structure:

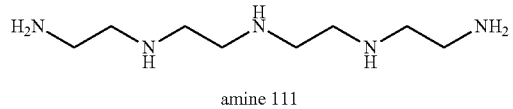 [SMILES: NCCNCCNCCNCCN]

amine 111

The expected products of the reaction between amine 111 and the 12 carbon terminal epoxide C12 are illustrated as follows.

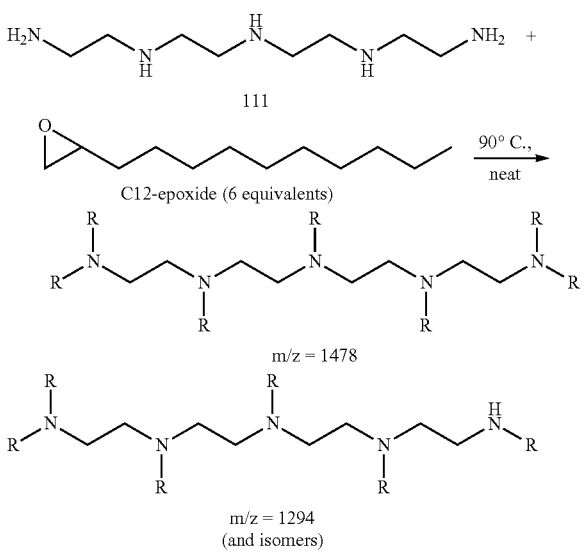

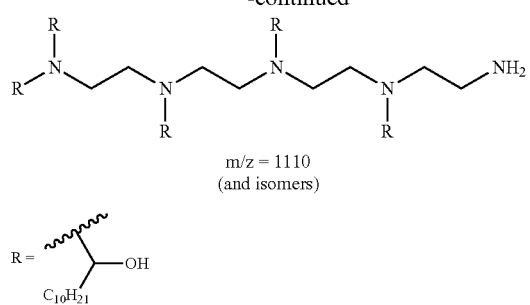

m/z = 1110
(and isomers)

R = 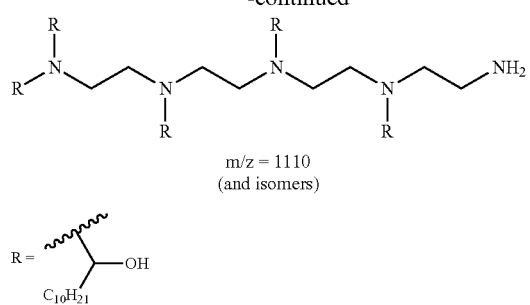 (structure with OH and C₁₀H₂₁)

This reaction was performed, and the crude reaction mixture was separated based on the assumption that the order of product elution from polar silica gel would be: a) 7 tail (max substitution on 111 amine); b) 6 tail isomers (the isomers corresponding to 6 epoxides having reacted with the 111 amine); c) 5 tail isomers, and so on. It was expected that the MALDI-MS spectra of the crude reaction mixture would reveal peaks corresponding to the m/z ratios of these compounds (calculated [M+H$^+$] for the expected 7 tail, 6 tail, and 5 tail products: 1481, 1295, and 1111, respectively). Material was isolated from the crude reaction mixture that, based on TLC analysis, was assumed to be the mixture of 6 tail isomers. This "purified" material performed quite well in the in vivo anti-Factor VII transfection assay.

Figure 20A:
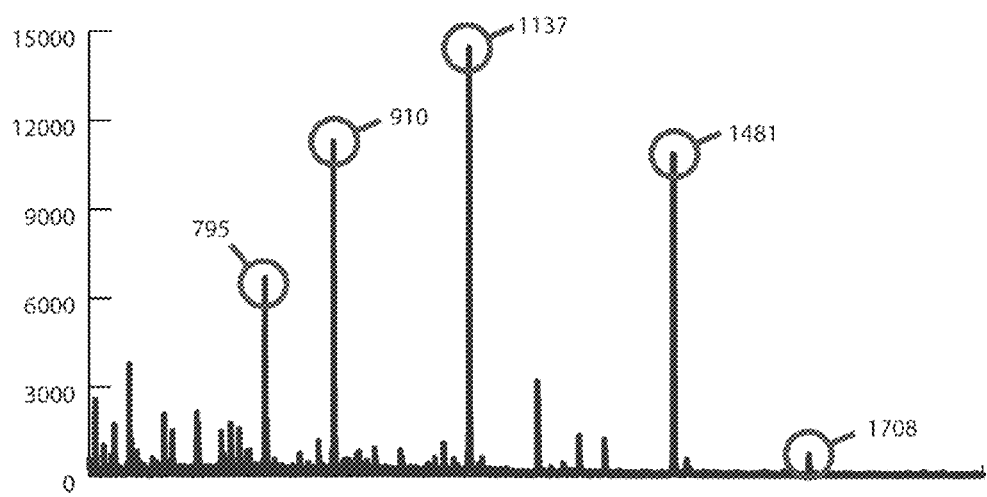
FIG. 20*a* depicts a MALDI-TOF mass spectra (intensity vs. m/z ratio) of the crude reaction mixture of technical grade 111 amine and C12 epoxide.
Figure 20B:
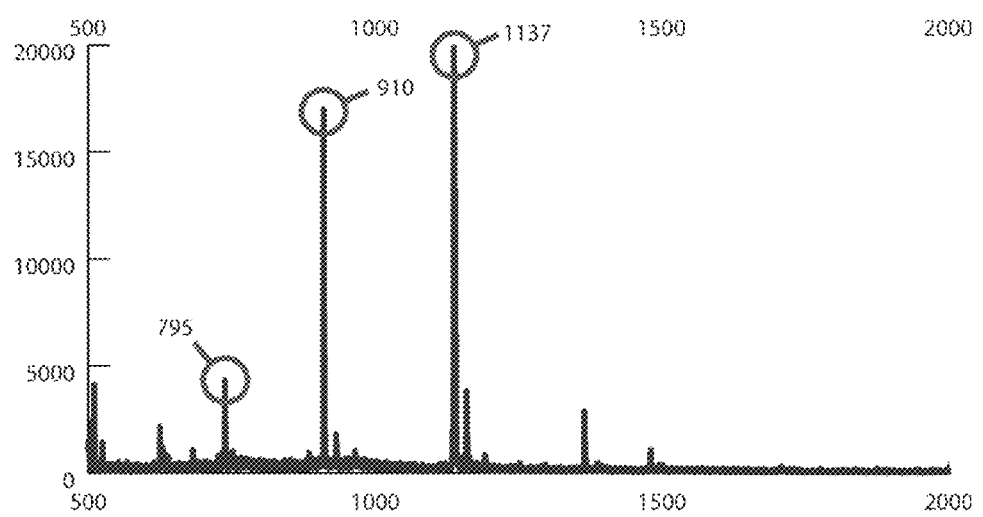
FIG. 20*b* depicts a MALDI-TOF mass spectra (intensity vs. m/z ratio) of the "purified" product from the crude reaction mixture of technical grade 111 amine and C12 epoxide (from FIG. 20*a*).

MALDI-MS spectra (see FIG. 20a) of the crude reaction mixture and of the purified "6 tail" material suggested compounds (see FIG. 20b). Technical grade tetraethlenepentamine (TEPA) is a mixture of compounds with similar boiling points; some of these compounds are of the following formulae:

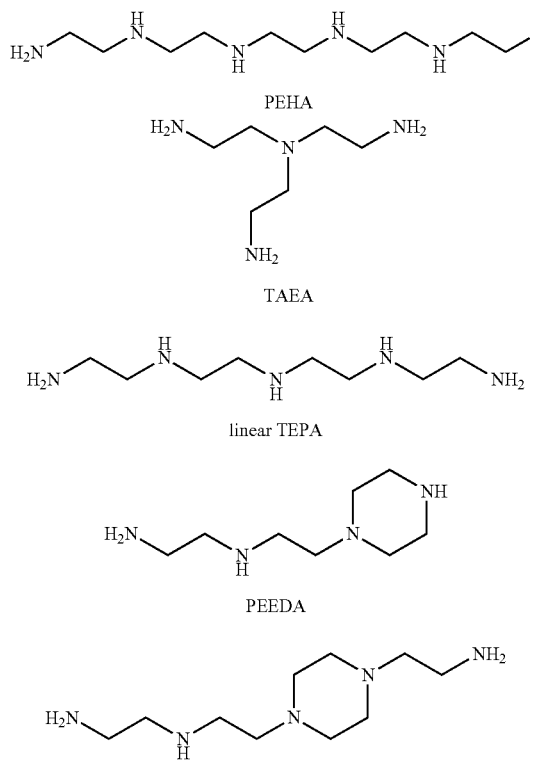

PEHA

TAEA linear TEPA

PEEDA

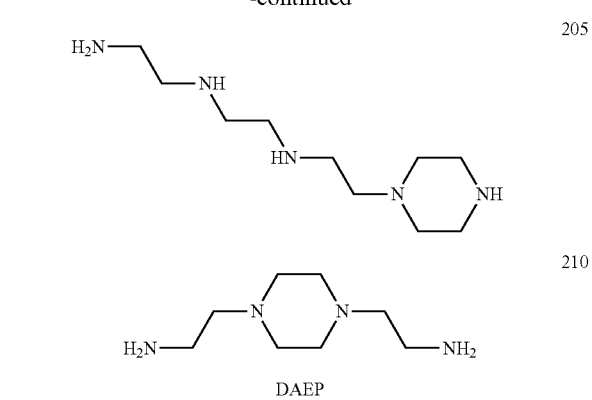

205

DAEP

210

Reaction of the C12 epoxide with these compounds accounts for most of the intense peaks in the MALDI mass spectra of the crude reaction mixture (FIG. 20a). The m/z ratios observed for the "purified" material (FIG. 20b) are consistent with amine 200 or 205 reacting with 5 equivalents of epoxide (calculated m/z for [M+H$^+$] 1137. found 1137) and with amine 210 or 220 reacting with 4 equivalents of epoxide (calculated m/z for [M+H$^+$]910. found 910). The structures of these compounds are illustrated as follows:

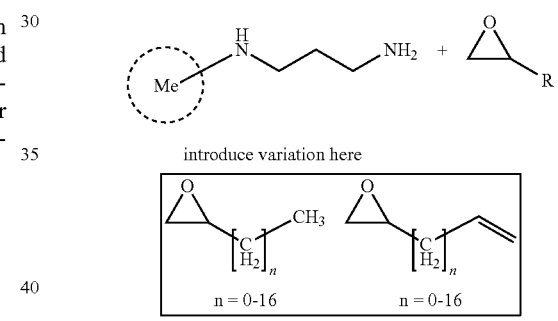

introduce variation here n = 0-16    n = 0-16

Figure 21A:
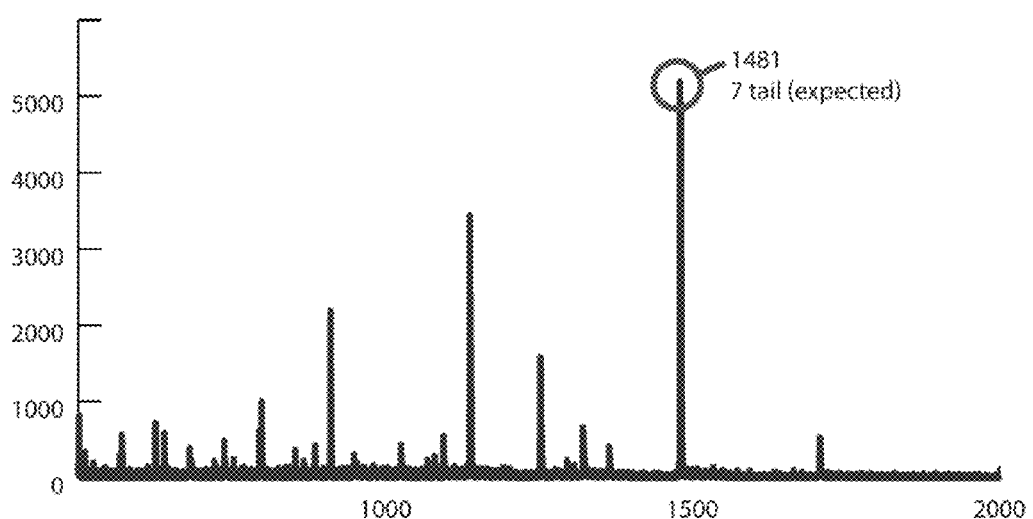
FIG. 21*a* depicts a MALDI-TOF mass spectra (intensity vs. m/z ratio) of the crude reaction mixture of technical grade 111 amine and C12 epoxide.
Figure 21B:
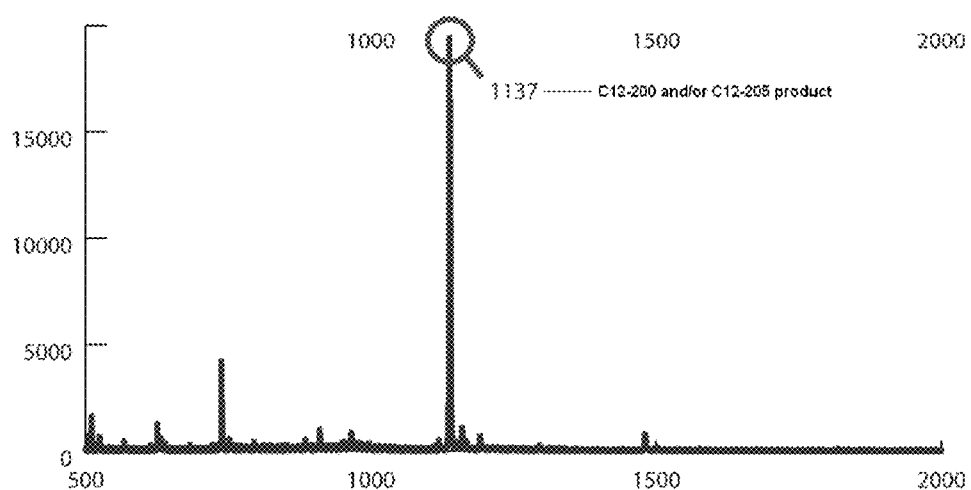
FIG. 21b depicts a MALDI-TOF mass spectra (intensity vs. m/z ratio) of the "purified" product from the crude reaction mixture of technical grade 111 amine and C12 epoxide (from FIG. 21a).
Figure 22:
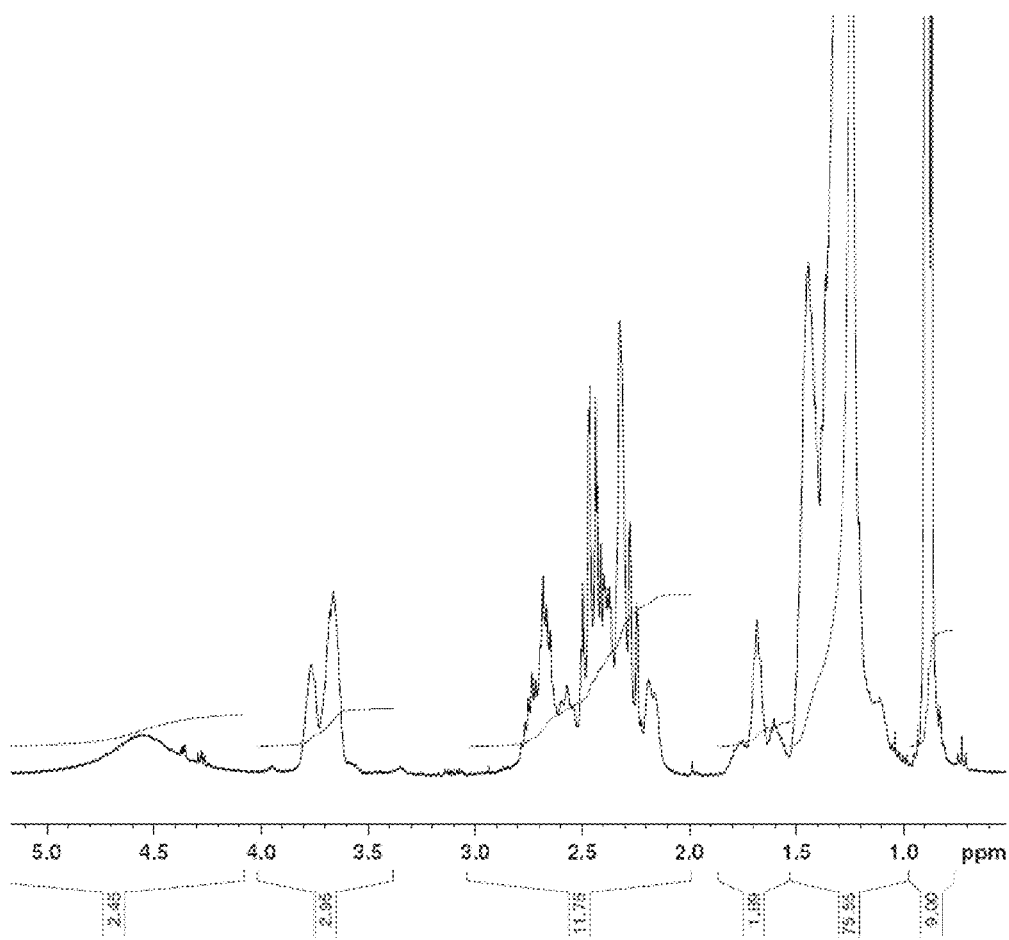
FIG. 22 depicts an $^1$H NMR (400 MHz) spectrum of C12-200 and/or C12-205 (chloroform, room temperature).

To determine if this result was reproducible, an epoxide ring opening reaction was performed using the C12 epoxide and two different batches of amine 111. MALDI-MS was performed on each crude reaction mixture. In the reaction between the C12 epoxide and an older batch of 111 amine, an array of compounds were observed that were also observed in the original crude reaction mixture (see FIG. 20a). The MALDI spectrum of the crude reaction mixture using the C12 epoxide and a newer batch of amine 111 (see FIG. 21a) contains predominant peaks with m/z ratios of 1481 (linear amine 111 and 7 epoxide tails) and 1137 (consistent with amine 200 or 205 with 5 epoxide tails). The peak at m/z 910 in this spectrum was small. This might be a result of batch to batch differences in the 111 amine. Purification of the second reaction allowed isolation of a highly pure sample of the m/z 1137 material; we have designated this material "C12-200 and/or C12-205". The $^1$H NMR spectrum of C12-200 and/or C12-205 is consistent with the proposed structure (see FIG. 22).

We are developing a library of materials based on the reaction of amines 200, 205, 210, and 220 and related amine structures with epoxides of varying length as depicted below:

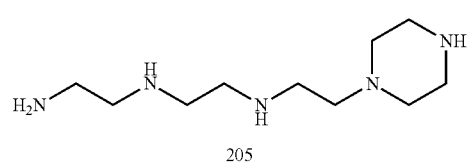

205

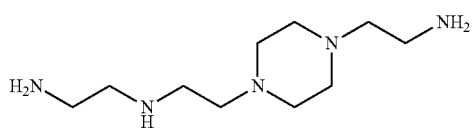

200

+

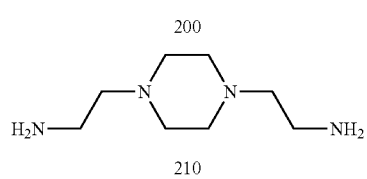

210

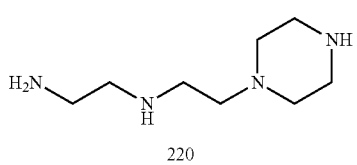

220

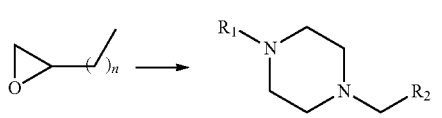

n = 0-16     R1, R2 = alkyl, alkenyl, alkynyl, polyamines, hydrogen

These amines are being prepared in pure form using techniques familiar to one skilled in the art. We also propose a library of materials derived from free-based commercially available 111 amine pentahydrochloride according to the following scheme:

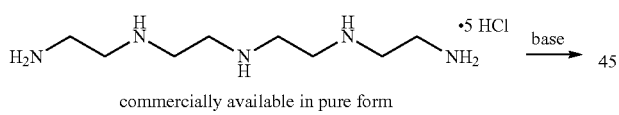

commercially available in pure form

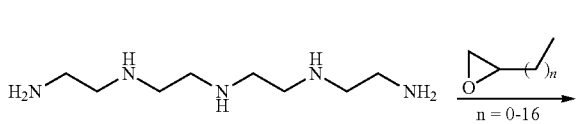

the actual linear pentamine having the following structure:

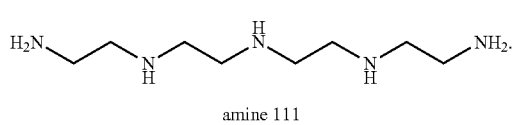 [SMILES: NCCNCCNCCNCCN]

amine 111

Example 15

Part 2

Lipidoids Based on Amine 96

This Example describes the synthesis of a library of structures that are variations of the amino alcohols lipidoid derived from the reaction of amine 96 with a C16 epoxide as follows:

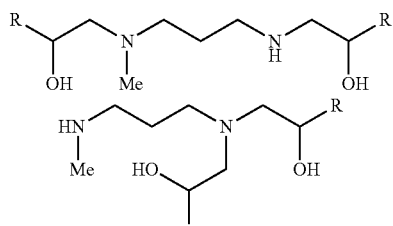

R = $C_{14}H_{29}$ based upon the core 96 amine First, variations at the position of the methyl group are achieved according to the following scheme:

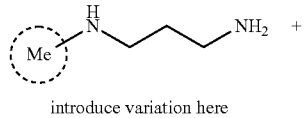

introduce variation here

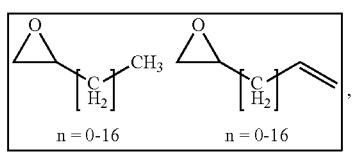

n = 0-16     n = 0-16 by reacting the terminal epoxides with an assortment of commercially available amines as depicted below.

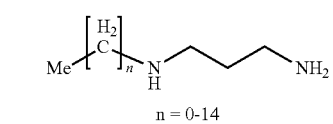

n = 0-14

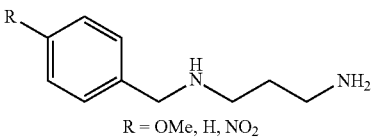

R = OMe, H, $NO_2$

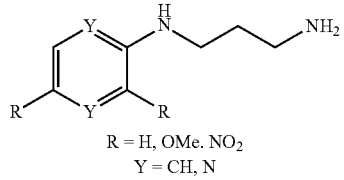

R = H, OMe, $NO_2$
Y = CH, N

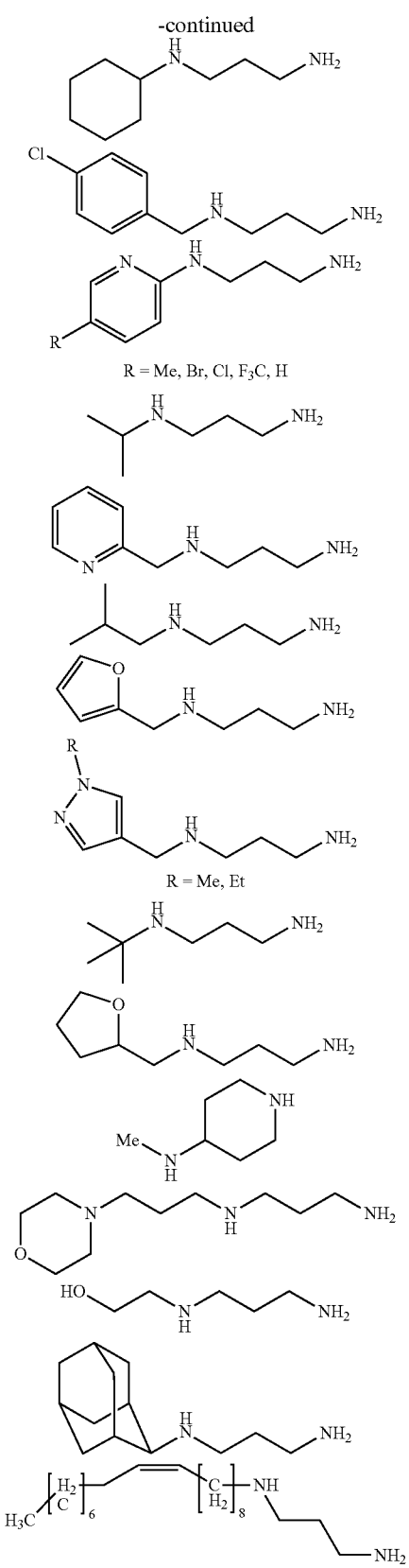
Based on this strategy, the resulting library would contain approximately 800 possible amino alcohols of varying structure.
Similar amine starting materials are available wherein the length of the carbon chain between the two amines is longer or shorter than amine 96 as depicted below.
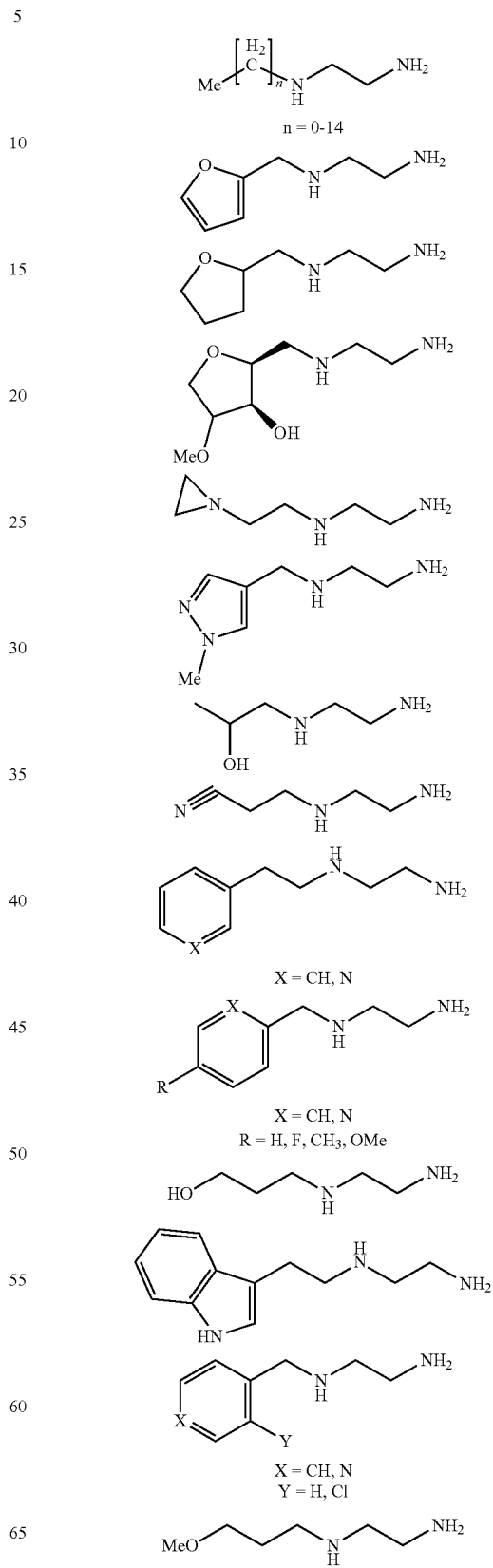

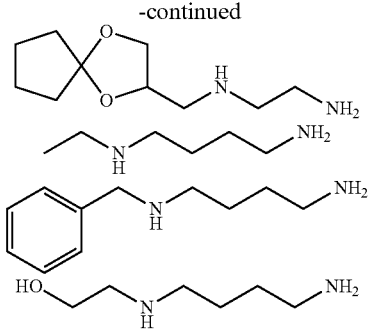

A library of compounds resulting from the reaction of these amines with the various terminal epoxides would provide an additional ~700 amino alcohol lipidoids.

A protection/deprotection synthetic strategy could provide multiple variations, where the two core amines are functionalized with different alkyl epoxides according to the following scheme:

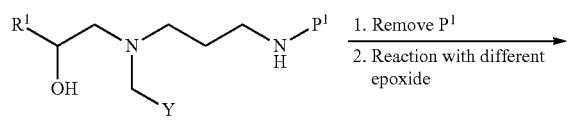

P is protecting group
Y are aforementioned variations

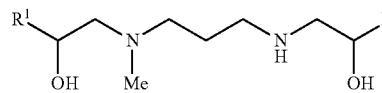

This strategy could allows for substitution at one amine position with a functional group other than an epoxide (e.g., alkyl halide, isothiocyanate, chloroformate, acid halide) generating two different functional groups on the same amine core as follows:

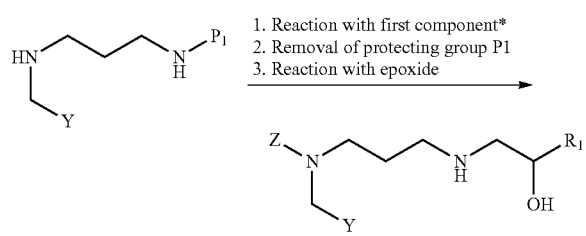

wherein the first component can be any of the following or similar derivatives:

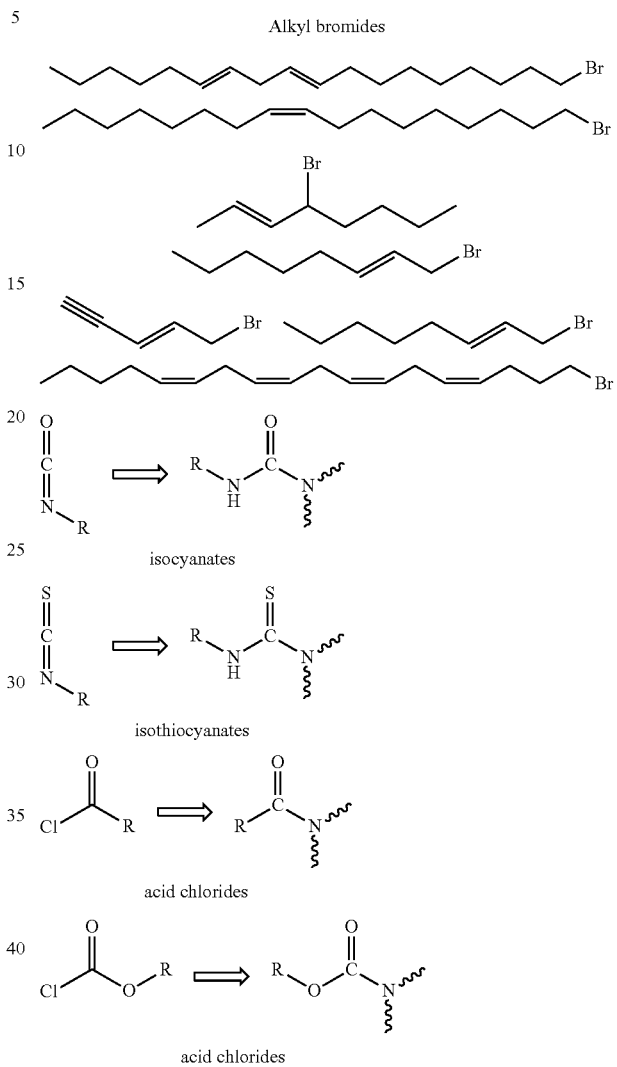

The following is an exemplary scheme illustrates general synthetic procedures to generate various compounds having two different functional groups on the same amine core as follows:

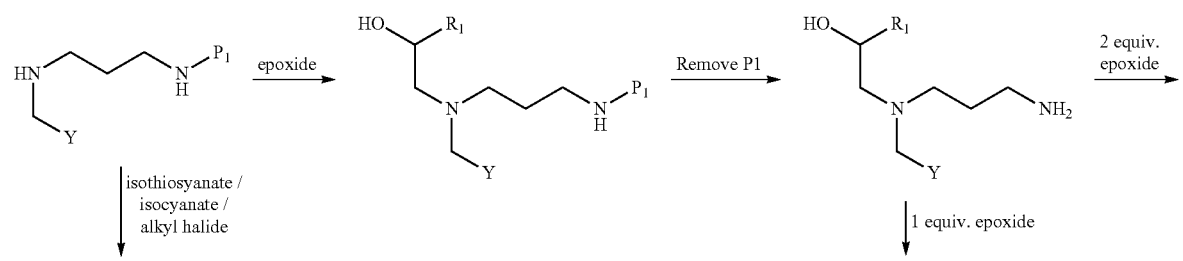

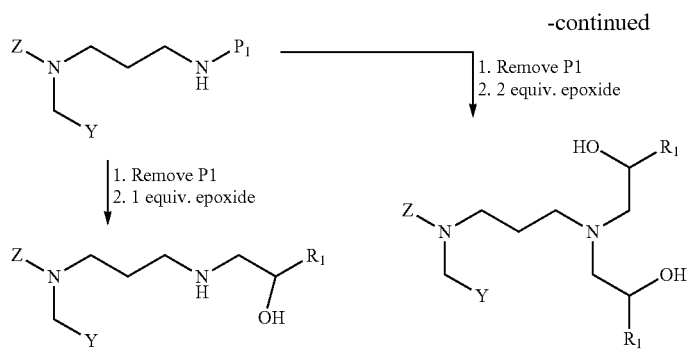

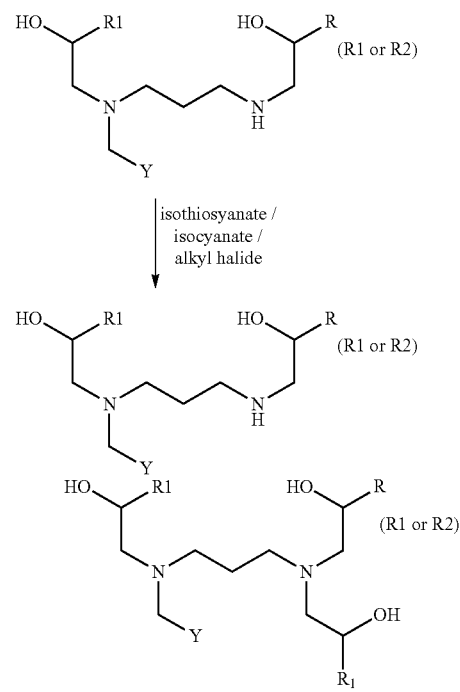

wherein, Y is an aryl, heteroaryl, alkyl group (unreactive with epoxides, isocyanates, isothiocyanates and/or alkyl halides); and Z represents fragment from isocyanate, isothiocyante, alkyl halide, having the following exemplary structures:

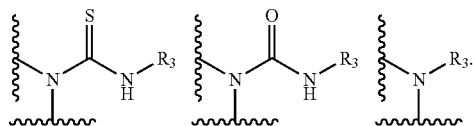

Various multi-step sequences could be used to introduce additional hydroxyl groups near the amine core at positions different from those generated through epoxide ring opening as follows:

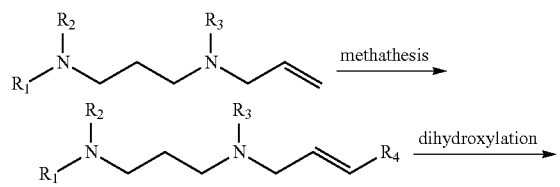

Similar routes could provide the means to generate both hydroxyl groups and additional unsaturation as follows:

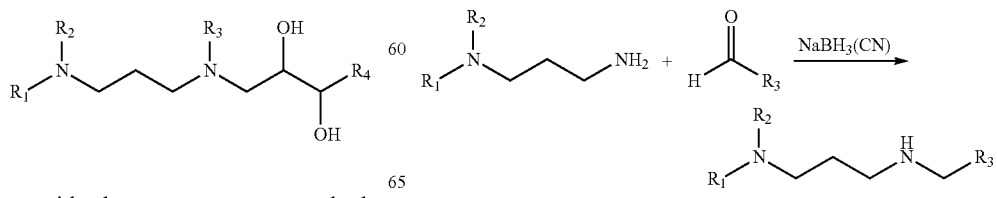

Reductive amination as a first step after differential protection of the amine core provides access to a multitude of commercially available aldehydes and perhaps a way to introduce multiple hydroxyl groups through reductive amination using simple carbohydrates (a known procedure) as follows:

-continued for example:

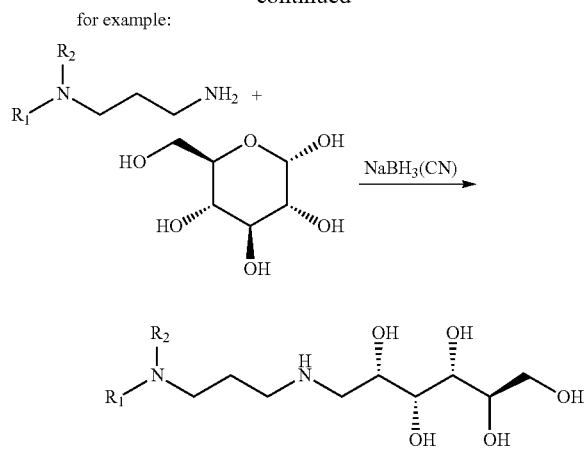

Example 16

Synthesis of 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200 and/or C12-205)

A 250 mL glass pressure vessel was charged with 2-decyloxirane (20.0 grams, 109 mmoles), tetraethylenepentamine (Sigma-Aldrich technical grade, 2.93 grams, 15.5 mmoles) and a magnetic stir bar. The vessel was sealed and immersed in a silicone oil bath at 90° C. The reaction mixture was stirred vigorously for ~72 hours at 90° C. The pressure vessel was then removed from the oil bath, allowed to cool to room temperature, then opened with caution. ~9 grams of the resulting viscous, slightly yellow oil were purified via chromatography on silica gel (gradient elution from dichloromethane to 83.5:16.3:1.5 dichloromethane/methanol/aqueous ammonium hydroxide). Fractions containing the desired compound were pooled and concentrated by rotary evaporation. The resulting yellow oil was dissolved in ~15 mL of ethyl acetate; decolorizing charcoal was added to this mixture. The solution was warmed to 68° C. and then filtered through Celite; the filtrate was concentrated by rotary evaporation; residual solvent was removed under reduced pressure overnight affording ~1.3 grams of a pale yellow viscous oil. The starting material may contain inseparable isomer N1-(2-aminoethyl)-N2-(2-(piperazin-1-yl)ethyl)ethane-1,2-diamine; and the product may contain an inseparable isomer 1,1'-(2-((2-hydroxydodecyl)(2-((2-hydroxydodecyl)(2-(4-(2-hydroxydodecyl)piperazin-1-yl)ethyl)amino)ethyl)-amino)-ethylazanediyl)-didodecan-2-ol.

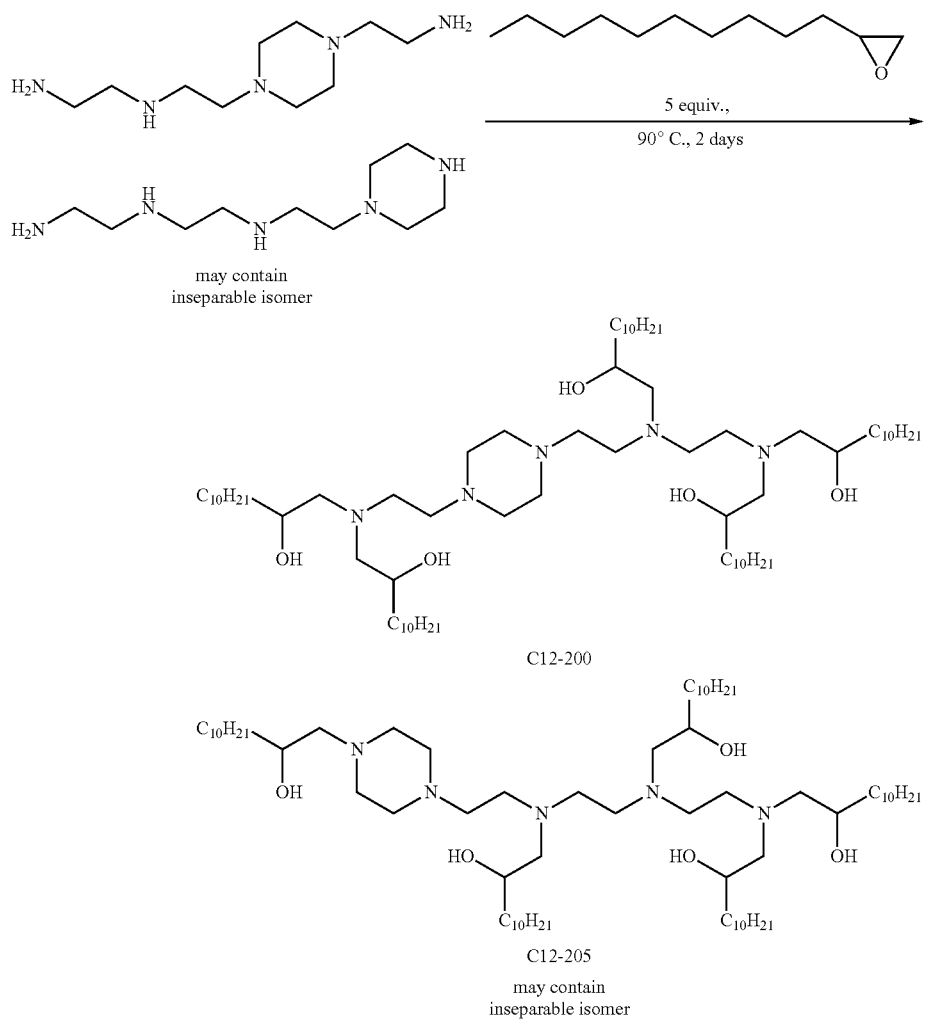

Example 17

Amino Alcohol Lipidoids Prepared from Chiral Epoxides

Antimicrobial lipidoids (e.g., C12-200, C16-96) can be prepared by reacting lipophilic, racemic terminal epoxides with low molecular weight polyamines. This approach is illustrated directly below with amine 200 and a generic terminal epoxide. There are two problems with this approach that complicate the isolation of pure products: the use of racemic epoxides, and addition of amines to the second carbon atom (C2) in the epoxide chain. In the following Examples, we report: a) the issues that may arise from the use of racemic epoxides can be avoided through the use of stereochemically pure terminal epoxides; and b) side products that may arise from additions at C2 of the epoxide can be avoided through an alternate synthetic route involving reductive amination.

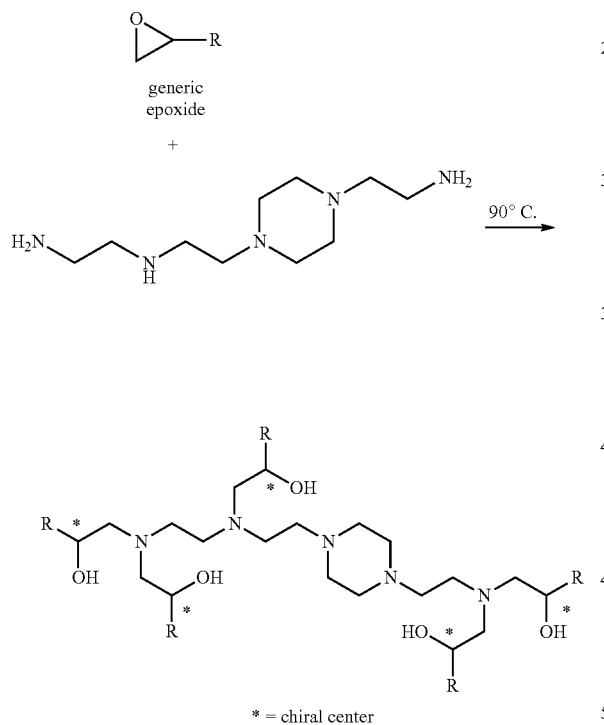

\* = chiral center

Reactions of Racemic Epoxides

The epoxides used in the initial library synthesis were purchased from commercial sources as racemic mixtures: each epoxide contained an equal proportion of the R and S enantiomer. Achiral amines are equally likely to react with either stereoisomer. The effect of using racemic epoxides can be illustrated by considering the simple case of the reaction between an amine with one reactive site (e.g., piperidine) and a racemic epoxide (illustrated directly below). In this case, two aminoalcohol lipidoid products are generated: the R and S enantiomers. In theory, these products are separable through chromatography on a chiral stationary phase; in practice, developing and scaling up a method to perform this separation is difficult and expensive.

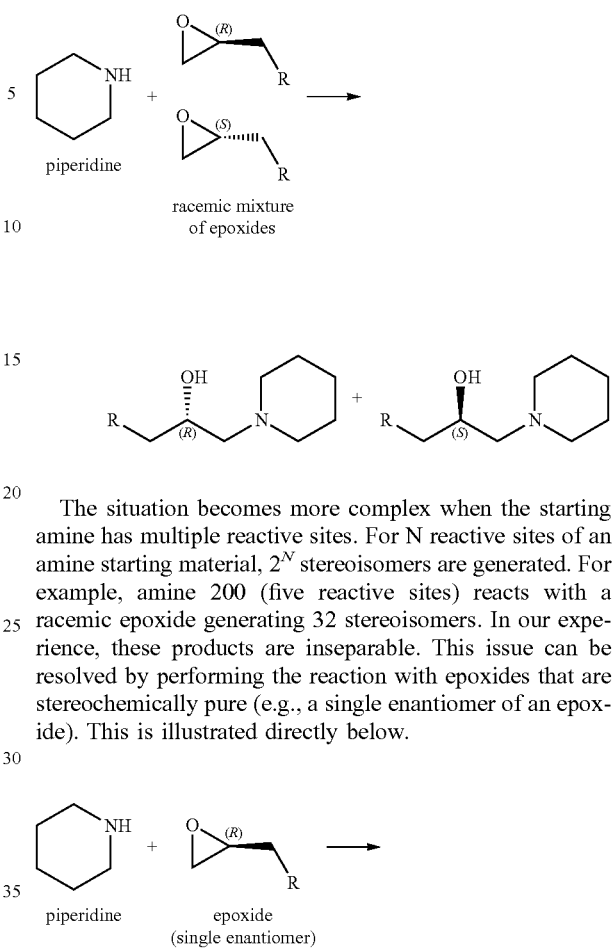

The situation becomes more complex when the starting amine has multiple reactive sites. For N reactive sites of an amine starting material, $2^N$ stereoisomers are generated. For example, amine 200 (five reactive sites) reacts with a racemic epoxide generating 32 stereoisomers. In our experience, these products are inseparable. This issue can be resolved by performing the reaction with epoxides that are stereochemically pure (e.g., a single enantiomer of an epoxide). This is illustrated directly below.

A few terminal epoxides are commercially available as single enantiomers, but the cost of these compounds is prohibitive. Racemic epoxides can be resolved (separated into constituent enantiomers) by several means, including chromatography on a chiral stationary phase. We resolved the epoxides using a chemical method known as hydrolytic kinetic resolution (HKR). Efficient HKR of racemic epoxides can be achieved using a procedure described by Jacobsen (Schaus, et al., *J. Am. Chem. Soc.* 2002, 124, 1307-1315; which is incorporated herein by reference). The process is illustrated directly below. A chiral catalyst and water are added to a solution containing the racemic epoxide. In the presence of the chiral catalyst, the rate of hydrolysis of one epoxide enantiomer is much greater than the rate of hydrolysis for the other enantiomer. This allows selective hydrolysis of the unwanted epoxide enantiomer (to a 1,2-diol). The 1,2-diol can be separated from the epoxide by removing the epoxide through distillation under reduced pressure.

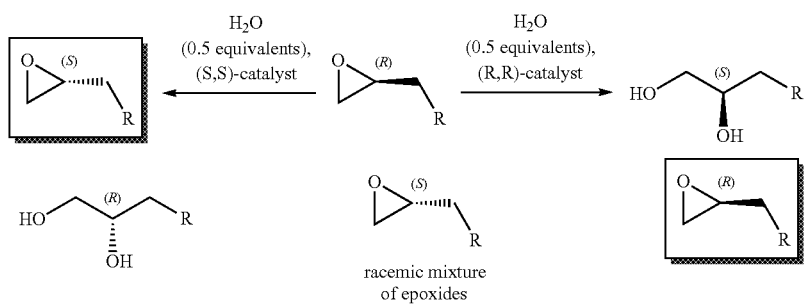

Step 1. The Resolution of Epoxydodecane by HKR

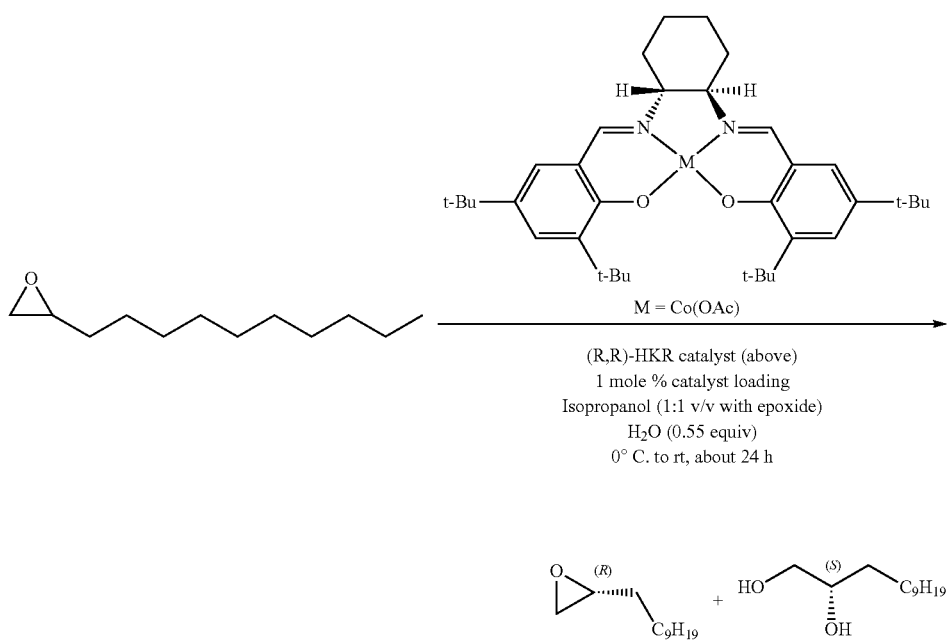

(R)-(+)-1,2-epoxydodecane. An oven-dried round bottom flask containing a magnetic stir bar was charged with the (R,R)-HKR catalyst (Schaus, et al., *J. Am. Chem. Soc.* 2002, 124, 1307-1315); CAS Number 176763-62-5, 1.31 g, 2.17 mmol Dichloromethane (34 mL) and then glacial acetic acid (1.30 mL) were added to the flask. The resulting solution was stirred vigorously for 1.5 h; during this time the color of the mixture changed from dark red to brown. The solvent was removed by rotary evaporation until the material appeared dry. 1,2-epoxydodecane (40.0 g, 217 mmol) then isopropyl alcohol (reagent grade, 47 mL) were added to the flask containing the oxidized catalyst and a magnetic stir bar. The flask was immersed in an ice bath. $H_2O$ (2.15 mL, 119 mmol, 0.55 equiv relative to epoxide) was added dropwise to the stirred mixture. The flask was sealed with a rubber septum and the solution was allowed to warm to room temperature. After stirring for 2 days, the reaction mixture was diluted with ~200 mL of hexanes. The resulting solution was filtered through paper to remove the white precipitate (1,2-diol). The filtrate was concentrated by rotary evaporation. The resulting dark red oily liquid was dissolved in ~150 mL of hexanes and filtered in order to remove a substantial amount of white crystalline precipitate (diol). The filtrate was transferred into a 250 mL round bottom flask and concentrated by rotary evaporation. The desired product was isolated by distillation under vacuum (literature: 124° C./15 mm Hg). The desired product (14.3 grams, 71.5% of theoretical yield) was collected as a clear oil. The product was determined to be 100% ee by chiral chromatography of the 2-napthylenethiol derivative.

Step 2. The Synthesis of (R)—C12-200

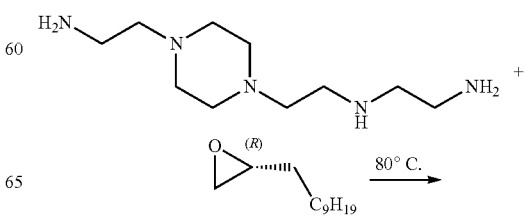

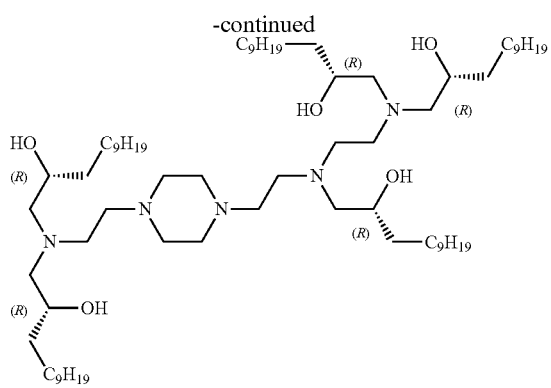

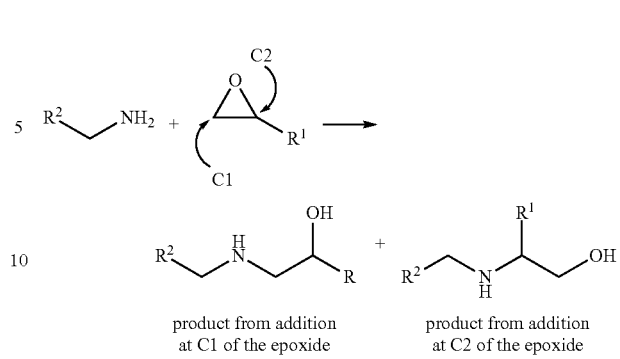

product from addition at C1 of the epoxide product from addition at C2 of the epoxide (R)—C12-200. Amine 200 (640 mg, 2.97 mmol) and (R)-1,2-epoxydodecane (2.27 g, 12.1 mmol) were added to a vial containing a magnetic stir bar. The vial was sealed and warmed on a 80° C. reaction block for 5 days. The reaction mixture was allowed to cool to room temperature, and the desired product was isolated by chromatography on silica gel (gradient elution from $CH_2Cl_2$ to 175:22:3 $CH_2Cl_2$/ MeOH/$NH_4$OH (aq.)). Fractions were pooled and concentrated affording (R)—C12-200 (665 mg) as a pale yellow oil. $^1$H NMR (600 MHz, $CDCl_3$): δ 4.37 (br s, —OH, 4H), 3.63 (app. br s, 3H), 3.56 (app. br s, 2H), 2.84-2.21 (m, 30H), 1.43-1.26 (m, 90H), 0.88 (t, J=7.0 Hz, 15H); MALDI-TOF-MS m/z: calcd for $C_{70}H_{146}N_5O_5$ [M+H$^+$] 1137.1. found 1137.6.

Example 18

In Vivo Transfection with Chiral Amino Alcohol Lipidoids

Preliminary in vivo transfections using anti-Factor VII siRNA formulated with were performed using (R)—C12-200 and (S)—C12-200 in mice. At 0.01 mg/kg siRNA dosing, approximately 50% reduction of systemic Factor VII was achieved using either the R or S forms of C12-200; there difference between these results and those obtained using C12-200 (the lipidoid prepared using amine 200 and racemic C12 epoxide) were insignificant.

Example 19

Synthesis of Amino Alcohol Lipidoids by the Reductive Amination Approach

The first carbon atom in a terminal epoxide is the preferred site of attack during nucleophilic addition. 2D-NMR analysis of amino alcohol lipidoids shows that the majority of addition occurs at C1 of the epoxide, as illustrated directly below. Nevertheless, a trace amount of addition at C2 does occur. 2D-NMR analysis of compounds (S)—C12-205 and (R)—C12-200 suggest that roughly 10% of the lipid "tails" are the result of amine attack at C2 of the epoxide. These regioisomeric tails are likely distributed randomly throughout the entire population of lipid tails in the material. Efforts to limit this side reaction with the epoxides have not been successful. To avoid this side reaction, we proposed and executed an alternate synthetic strategy.

A retrosynthetic analysis of this strategy is presented directly below. The desired product is C (as illustrated directly below), from addition of amine A to C1 of epoxide B. D is the undesired constitutional isomer formed when amine A attacks C2 of epoxide B. Reductive amination of aldehyde fragment E with amine A and a reducing agent (giving F), followed by removal of the protecting group on the secondary alcohol, should generate product C. This route does not generate undesired structure D. This approach has two advantages: it does not generate the side product from reaction at C2 of the epoxide (e.g., D, directly below), and avoids the generation of a mixture of stereoisomers. To demonstrate that this strategy is feasible, we prepared a substrate analogous to E and reacted this component with an amine, ultimately generating the desired product (analogous to C).

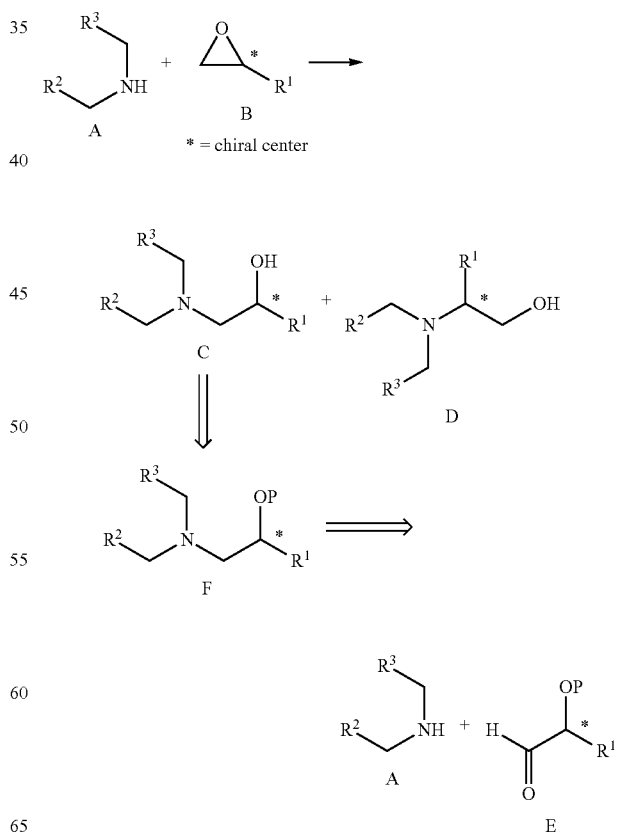

Synthesis of (S)—C12-205 by Reductive Amination Approach

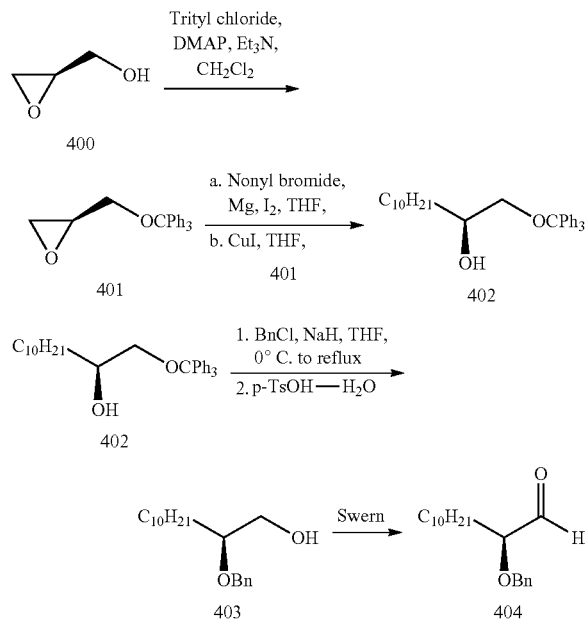

Step 1. Synthesis of Fragment 404 for the Reductive Amination Approach (S)-2-((trityloxy)methyl)oxirane (401)

Trityl protected glycidol derivative 401 was prepared as described previously (Schweizer, et al., Synthesis 2007, 3807-3814; which is incorporated herein by reference.) A solution of (R)-glycidol (5.0 g, 61 mmol) in CH$_2$Cl$_2$ (30 mL) was added by syringe to a stirred solution of trityl chloride (18.6 g, 66.8 mmol) and triethylamine (16.9 mL, 122 mmol) in CH$_2$Cl$_2$ (67 mL) in an ice bath under argon. DMAP (742 mg, 6.08 mmol) was added to the reaction mixture following addition of the glycidol. The reaction was allowed to warm to room temperature. After 14 hours, the reaction mixture was diluted with 300 mL saturated aqueous NH$_4$Cl. The mixture was further diluted to ~1 L with water to dissolve precipitated salts. The product was extracted from the quenching solution with Et$_2$O (3×); combined ethereal layers were washed with brine, dried over MgSO$_4$, filtered through paper, and concentrated by rotary evaporation to a white solid. The crude product was purified by recrystallization from boiling MeOH (200 mL) affording the desired product 401 (14.1 g, 73%) as white crystals. NMR analysis of this material was consistent with that reported in the literature. (Schweizer, et al., *Synthesis* 2007, 3807-3814.)

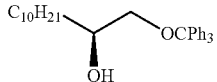

(S)-2-(benzyloxy)dodecan-1-ol (403).

A 60 wt. % suspension of NaH in mineral oil (2.01 g, 50.3 mmol) was added to an oven-dried round bottom flask containing a magnetic stir bar. THF (120 mL) was added to the flask by syringe under Ar, and the flask was submerged in an ice bath. Crude 402 (14.9 g, 33.5 mmol) was dissolved in anhydrous THF (50 mL) and was added slowly to the stirred suspension of NaH. The reaction mixture was allowed to warm to room temperature. Benzyl chloride (5.8 mL, 50 mmol) was added to the reaction mixture. The flask was fitted with a reflux condenser, and the mixture was warmed to reflux under Ar overnight. After the reaction mixture had cooled, NH$_4$Cl (sat. aq., ~300 mL) was added slowly to quench residual NaH. The suspension was transferred into a separatory funnel using H$_2$O (300 mL) and Et$_2$O (200 mL). The organic layer was extracted with additional Et$_2$O; ethereal layers were dried over MgSO$_4$, filtered through paper, and concentrated to a yellow oil. This material was purified by chromatography on silica (gradient elution from hexanes to EtOAc); desired fractions were pooled and concentrated affording 15 g of a slightly yellow oil. This oil was dissolved in 1:1 MeOH/THF (100 mL). p-TsOH.H$_2$O (572 mg) was added to the mixture; the solution was stirred for 6 hours. The reaction mixture was concentrated onto Celite by rotary evaporation and purified by chromatography on silica gel (gradient elution from hexanes to ethyl acetate). Fractions containing the desired product were pooled and concentrated affording 403 (5.44 g, 66%) as a clear oil. $^1$H NMR (400 MHz, CDCl$_3$): δ 7.39-7.29 (m, 5H), 4.64 (d, J=11.6 Hz, 1H), 4.55 (d, J=11.6 Hz, 1H), 3.74-3.67 (m, 1H), 3.60-3.49 (m, 2H), 1.93-1.90 (m, 1H), 1.68-1.60 (m, 1H), 1.53-1.45 (m, 1H), 1.40-1.40 (m, 16H), 0.89 (t, J=6.9 Hz, 3H).

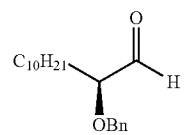

(S)-2-(benzyloxy)dodecanal (404)

CH$_2$Cl$_2$ (10 mL) and oxalyl chloride (1.72 mL, 20.3 mmol) were added to an oven-dried 2-neck round bottom flask containing a magnetic stir bar under Ar. The flask was immersed in a dry ice/acetone bath. A solution of DMSO (2.88 mL, 40.6 mmol) in CH$_2$Cl$_2$ (10 mL) was added to the stirred solution of oxalyl chloride slowly. 403 (5.4 g, 18.5 mmol) was dissolved in CH$_2$Cl$_2$ and added dropwise, over a period of 15 minutes, to the cold, stirred reaction mixture. After stirring for 2 hours, Et$_3$N (12.9 mL, 18.46 mmol) was added to the reaction mixture, which was then allowed to warm to room temperature. The mixture was diluted with Et$_2$O (~300 mL) and water. The ether layer was washed with sat. aq. NaHCO$_3$, 1M aq. HCl, and brine. The Et$_2$O layer was then dried over MgSO$_4$, filtered through paper, and concentrated by rotary evaporation. The crude product was purified by chromatography on silica (gradient elution from hexanes to 1:1 EtOAc/hexanes); fractions containing the desired product were pooled and concentrated affording 404 (3.58 g, 67%) as a clear, slightly viscous oil. $^1$H NMR (400 MHz, CDCl$_3$): δ 9.66 (d, J=1.9 Hz, 1H), 7.37-7.31 (m, 5H), 4.69 (d, J=11.7 Hz, 1H), 4.55 (d, J=11.7 Hz, 1H), 3.78-3.75 (m, 1H), 1.68 (dd, J=14.3, 7.2 Hz, 2H), 1.49-1.35 (m, 2H), 1.25 (br s, 14H), 0.89 (t, J=6.7, 3H)

Step 2. Reductive Amination Pure Form of (S)—C12-205

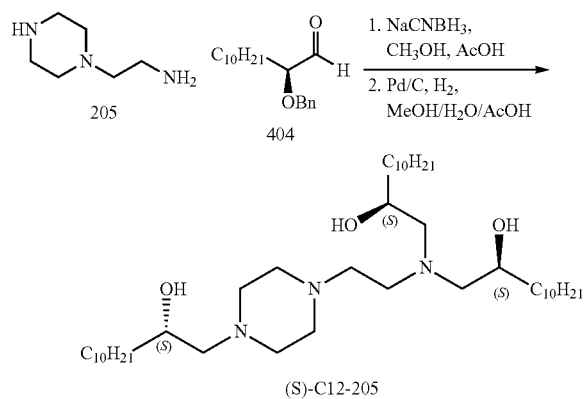

1-(2-aminoethyl)piperazine (205, 39 μL, 0.3 mmol) was added to a vial containing a magnetic stir bar. MeOH (10 mL) and the aldehyde 404 (971 mg, 3.34 mmol) were added to the vial. NaCNBH$_3$ (188 mg, 3 mmol) was then added to the mixture. Glacial AcOH was added dropwise to the stirred solution until the pH (as measured using indicator strips) was approximately 5.5. The mixture bubbled during the addition of the AcOH. The mixture was stirred for 4 days, whereupon it was diluted with 1M NaOH (aq.) and CH$_2$Cl$_2$. The aqueous layer was extracted an additional time with CH$_2$Cl$_2$. The combined organic layers were washed with brine, dried over MgSO$_4$, filtered through paper and concentrated. The desired intermediate was purified by chromatography on silica (CH$_2$Cl$_2$ to 10% MeOH/CH$_2$Cl$_2$) affording a yellow oil (83 mg). This oil was dissolved in 25 mL 7:2:1 MeOH/H$_2$O/AcOH. A portion of 10 wt. % Pd/C was added to the solution. The reaction mixture was stirred under H$_2$ (slightly above atmospheric pressure) for 8 hours. The reaction mixture was filtered through Celite to remove the Pd/C and then concentrated to a film. Mass spectral analysis of this material indicated that it was the pure, desired product (S)—C12-205. MALDI-TOF-MS m/z: calcd for C$_{42}$H$_{88}$N$_3$O$_3$ [M+H$^+$], 682.7. found 682.9.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of formula:

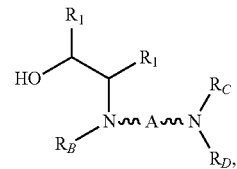

wherein:
A is substituted or unsubstituted, branched or unbranched, acyclic C$_{2-20}$ alkylene, wherein the alkylene is interrupted by 1 or more heteroatoms independently selected from O, S and N;
one occurrence of R$_1$ is substituted or unsubstituted, branched or unbranched, C$_{2-20}$-aliphatic, and the other occurrence of R$_1$ is hydrogen; and
R$_B$, R$_C$, and R$_D$ are, independently, hydrogen or unsubstituted, branched or unbranched C$_{1-20}$-aliphatic;
or R$_B$ and R$_D$ together form a cyclic structure;
or R$_C$ and R$_D$ together form a cyclic structure;
or a pharmaceutically acceptable salt thereof.

2. The compound of claim 1, wherein R$_B$, R$_C$, and R$_D$ are all hydrogen.

3. The compound of claim 1, wherein R$_B$, R$_C$, and R$_D$ are all C$_1$-C$_6$ alkyl.

4. The compound of claim 1, wherein each of R$_B$, R$_C$, and R$_D$ are hydrogen or methyl.

5. The compound of claim 1, wherein one occurrence of R$_1$ is selected from the group consisting of:

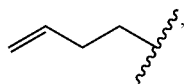

187

-continued

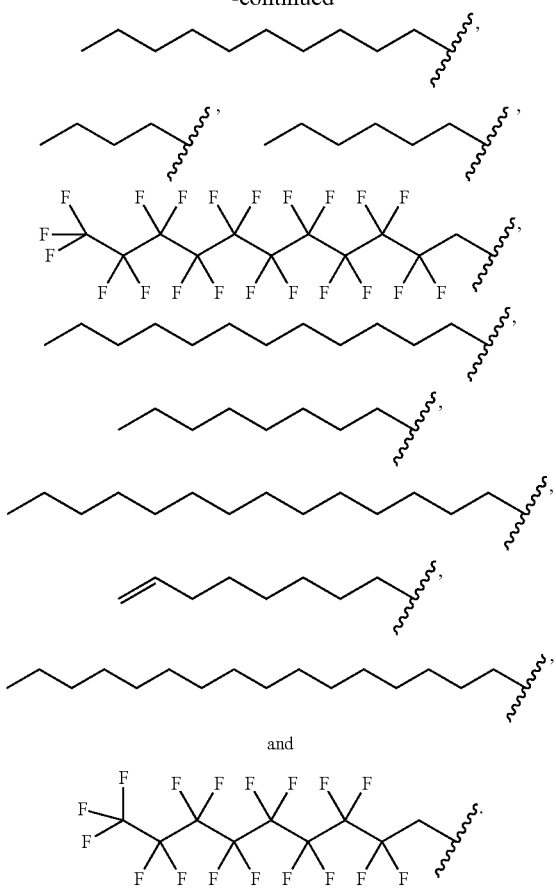

6. The compound of claim 1, wherein one occurrence of $R_1$ is unsubstituted, acyclic, branched or unbranched $C_2$-$C_{20}$ aliphatic.

7. The compound of claim 1, wherein one occurrence of $R_1$ is substituted, acyclic, branched or unbranched $C_2$-$C_{20}$ aliphatic.

8. The compound of claim 1, wherein one occurrence of $R_1$ is substituted or unsubstituted, unbranched $C_2$-$C_{20}$ aliphatic.

9. The compound of claim 1, wherein one occurrence of $R_1$ is fluorinated $C_2$-$C_{20}$ aliphatic.

10. The compound of claim 1, wherein one occurrence of $R_1$ is substituted or unsubstituted, cyclic or acyclic, branched or unbranched $C_{2\text{-}20}$ alkyl.

11. The compound of claim 1, wherein one occurrence of $R_1$ is selected from the group consisting of:

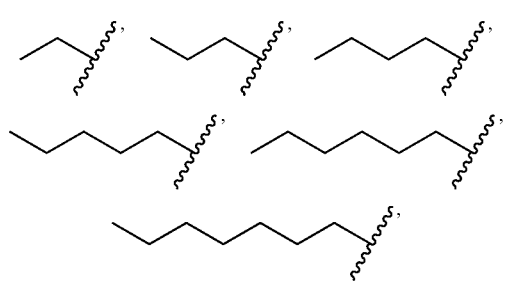

188

-continued

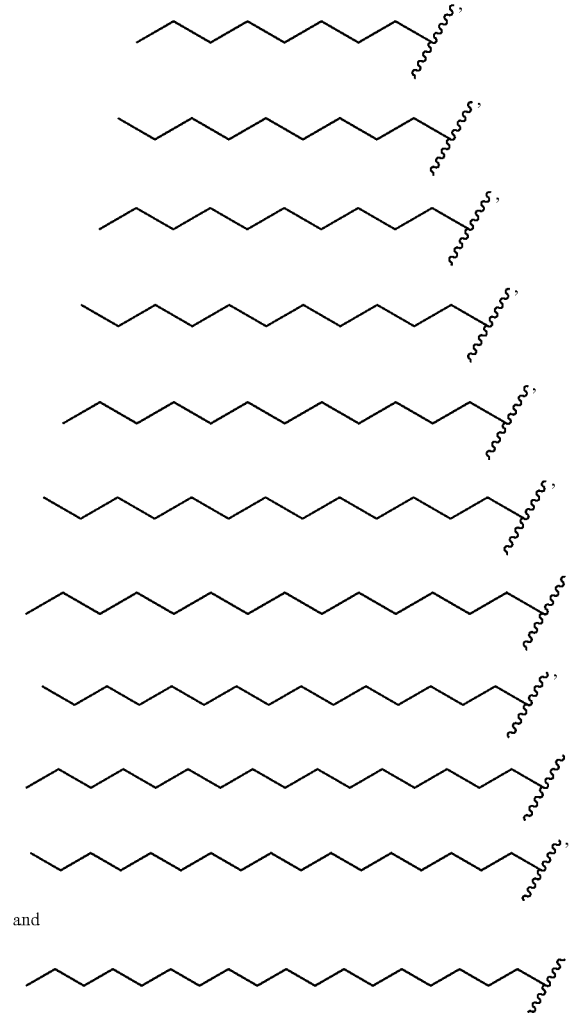

and

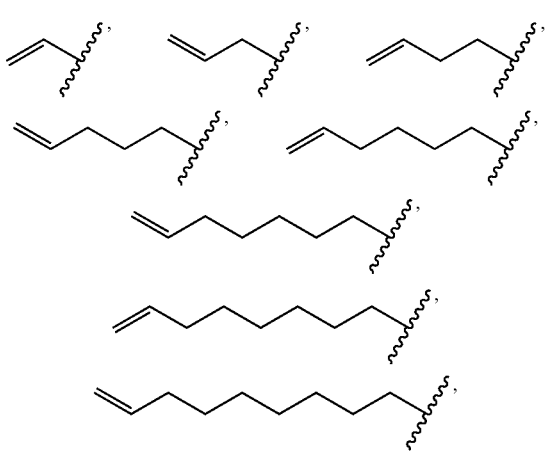

12. The compound of claim 1, wherein one occurrence of $R_1$ is substituted or unsubstituted, cyclic or acyclic, branched or unbranched $C_{2\text{-}20}$ alkenyl.

13. The compound of claim 1, wherein one occurrence of $R_1$ is selected from the group consisting of:

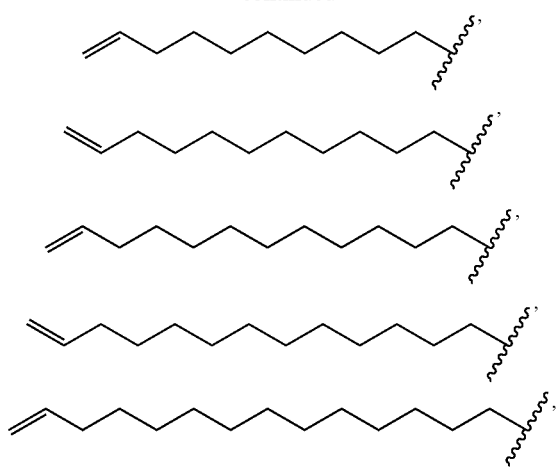
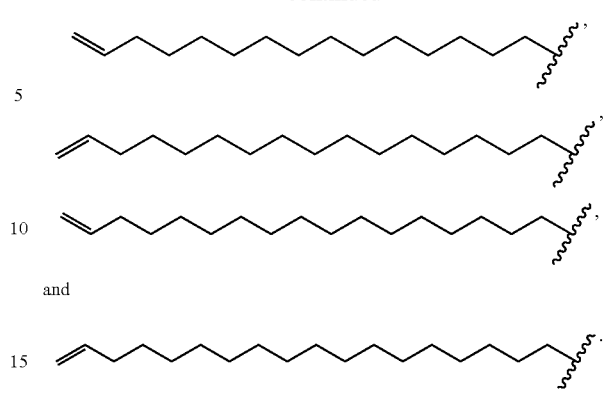
14. The compound of claim 1, wherein one occurrence of $R_1$ is selected from the group consisting of:
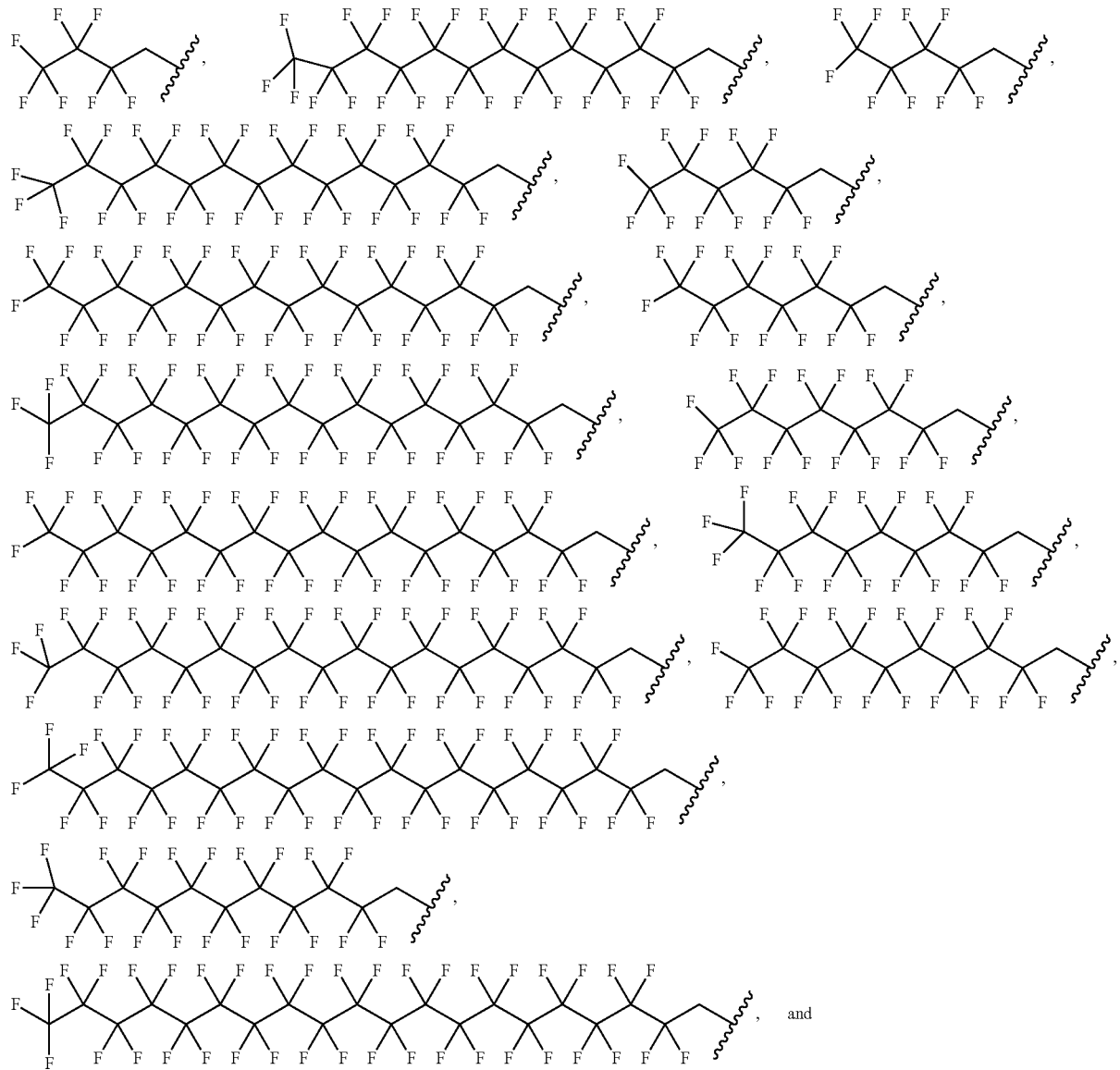

-continued

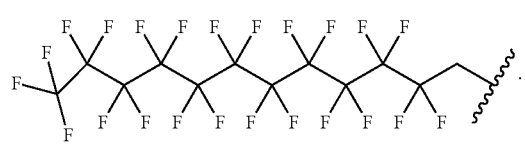

15. The compound of claim 1, wherein A is unsubstituted, unbranched, acyclic $C_{2-10}$ alkylene interrupted by 1 or more oxygen atoms.

16. The compound of claim 1, wherein A is unsubstituted, unbranched, acyclic $C_{2-10}$ alkylene interrupted by 1 or more nitrogen atoms.

17. The compound of claim 1, wherein A is selected from the group consisting of:

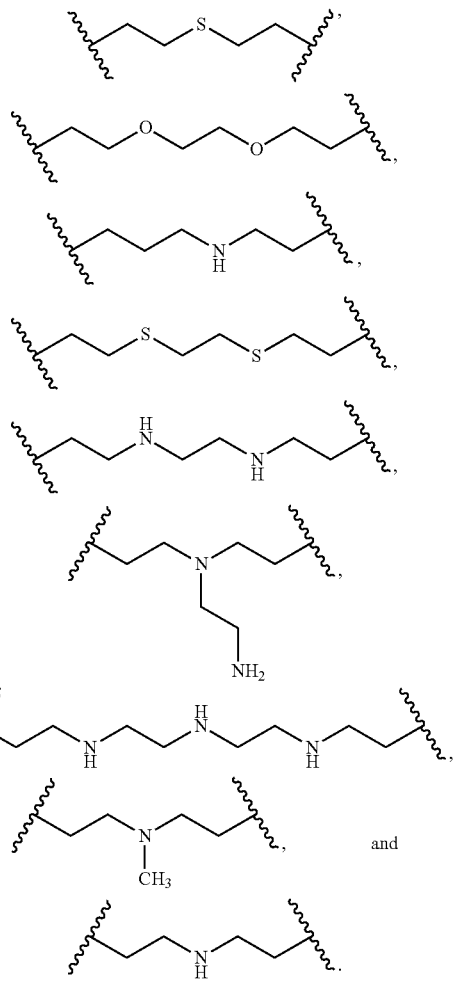

18. The compound of claim 1, wherein

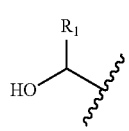

is

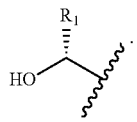

19. The compound of claim 1, wherein

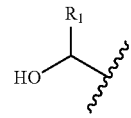

is

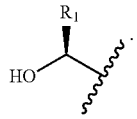

20. The compound of claim 1, wherein the compound is selected from the group consisting of:

and pharmaceutically acceptable salts thereof.

21. A pharmaceutical composition comprising a compound of claim 1; and a pharmaceutical agent.

22. The pharmaceutical composition of claim 21, wherein the pharmaceutical agent is selected from the groups consisting of polynucleotides, proteins, peptides, and small molecule drugs.

23. The compound of claim 1, wherein $R_B$, $R_C$, and $R_D$ are the same.

24. The pharmaceutical composition of claim 21, wherein the pharmaceutical agent is DNA or RNA.

25. The pharmaceutical composition of claim 21, wherein the pharmaceutical agent is dsRNA, siRNA, shRNA, miRNA, antisense RNA, or a polynucleotide that encodes a protein or peptide.

* * * * *